US008115936B2

(12) United States Patent
Ochiai et al.

(10) Patent No.: US 8,115,936 B2
(45) Date of Patent: Feb. 14, 2012

(54) LASER ULTRASONIC DETECTION DEVICE INCLUDING A LASER OSCILLATING DEVICE WHICH INCLUDES A SEED LASER OSCILLATING ELEMENT

(75) Inventors: Makoto Ochiai, Yokohama (JP);
Takahiro Miura, Yokohama (JP);
Hidehiko Kuroda, Yokohama (JP);
Fukashi Osakata, Fujisawa (JP);
Kentaro Tsuchihashi, Yokohama (JP);
Masahiro Yoshida, Chigasaki (JP);
Tetsuro Aikawa, Yokohama (JP);
Satoshi Okada, Ota-Ku (JP); Toru Onodera, Yokohama (JP); Akira Tsuyuki, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/766,517

(22) Filed: Apr. 23, 2010

(65) Prior Publication Data

US 2010/0199769 A1  Aug. 12, 2010

Related U.S. Application Data

(62) Division of application No. 11/480,959, filed on Jul. 6, 2006, now Pat. No. 7,728,967.

(30) Foreign Application Priority Data

| Jul. 7, 2005 | (JP) | 2005-199465 |
| Jul. 7, 2005 | (JP) | 2005-199466 |
| Jul. 7, 2005 | (JP) | 2005-199467 |
| Jul. 7, 2005 | (JP) | 2005-199469 |
| Jul. 7, 2005 | (JP) | 2005-199472 |
| Jul. 7, 2005 | (JP) | 2005-228801 |
| Feb. 28, 2006 | (JP) | 2006-052255 |

(51) Int. Cl.
*G01B 11/02* (2006.01)

(52) U.S. Cl. ..................................... 356/502; 356/237.2
(58) Field of Classification Search .................. 356/502, 356/506, 237.1–241.6, 399–401
See application file for complete search history.

(56) References Cited

U.S. PATENT DOCUMENTS 4,659,224 A * 4/1987 Monchalin .................... 356/502
(Continued)

FOREIGN PATENT DOCUMENTS

| JP | 2590283 | 12/1998 |
| JP | 2000-180418 | 6/2000 |
| JP | 2001-4599 | 1/2001 |
| JP | 2001-4600 | 1/2001 |
| JP | 2001-318081 | 11/2001 |
| JP | 2002-257793 | 9/2002 |

(Continued)

*Primary Examiner* — Tarifur Chowdhury
*Assistant Examiner* — Michael P Lapage
(74) *Attorney, Agent, or Firm* — Oblon, Spivak, McClelland, Maier & Neustadt, L.L.P.

(57) ABSTRACT

A laser maintenance apparatus including a laser system which includes an optical system for emitting, in a first irradiation condition, a generation laser beam for generating an ultrasonic wave in a portion of an object on which maintenance is to be performed, and including a laser source configured to generate and detect a detection laser beam which interacts with the ultrasonic wave generated by the laser light beam in the first condition. The laser maintenance apparatus also includes a light transmitting device for transmitting laser light emitted from the laser system, a laser irradiation device for irradiating laser light transmitted by the light transmitting device to the object portion, and a transporting/scanning mechanism for transporting the light transmitting device and the laser irradiation device to a portion near the object portion, and scanning over an arbitrary range at the object portion.

7 Claims, 71 Drawing Sheets

U.S. PATENT DOCUMENTS

| | | | |
|---|---|---|---|
| 4,696,062 A * | 9/1987 | LaBudde | 398/156 |
| 4,724,298 A | 2/1988 | Hawkins et al. | |
| 4,894,202 A | 1/1990 | Nagase et al. | |
| 4,966,459 A * | 10/1990 | Monchalin | 356/502 |
| 5,080,491 A * | 1/1992 | Monchalin et al. | 356/493 |
| 6,041,020 A * | 3/2000 | Caron et al. | 367/149 |
| 6,057,927 A * | 5/2000 | Levesque et al. | 356/432 |
| 6,084,202 A | 7/2000 | Okazaki et al. | |
| 6,891,912 B1 | 5/2005 | Lukic et al. | |
| 2003/0043867 A1 * | 3/2003 | Huber et al. | 372/34 |
| 2005/0162662 A1 * | 7/2005 | Sauerland et al. | 356/502 |
| 2006/0004243 A1 | 1/2006 | Shimizu et al. | |

FOREIGN PATENT DOCUMENTS

| | | |
|---|---|---|
| JP | 2005-040809 | 2/2005 |
| JP | 2005-40809 | 2/2005 |

* cited by examiner

ULTRASONIC WAVE SHAPE

LASER ULTRASONIC DETECTION DEVICE INCLUDING A LASER OSCILLATING DEVICE WHICH INCLUDES A SEED LASER OSCILLATING ELEMENT

CROSS-REFERENCE TO RELATED APPLICATIONS

This application is a divisional of and claims the benefit of priority of U.S. Ser. No. 11/480,959, filed Jul. 6, 2006, the entire contents of this application is incorporated herein by reference. U.S. Ser. No. 11/480,959 claims the benefit of priority from Japanese patent application Nos. JP 2005-228801, filed Jul. 7, 2005; JP 2006-52255, filed Feb. 28, 2006; JP 2005-199467, filed Jul. 7, 2005; JP 2005-199472, filed Jul. 7, 2005; JP 2005-199466, filed Jul. 7, 2005; JP 2005-199465, filed Jul. 7, 2005; and JP 2005-199469, filed Jul. 7, 2005.

BACKGROUND OF THE INVENTION

1. Field of the Invention

The present invention relates to a technical field of flaw detection and preventive maintenance by using an ultrasonic, preferably, laser, maintenance apparatus, wherein both laser nondestructive testing and laser prevention maintenance can be carried out, and particularly relates to an ultrasonic, i.e., laser-based (or merely, laser), maintenance apparatus capable of carrying out flaw testing and prevention maintenance without interchanging devices. The present invention also relates to a surface testing or inspecting, or processing technology utilizing laser such as laser-ultrasonics, which are related to the laser maintenance technology mentioned above.

2. Related Art

One way of ensuring continuous integrity of tubular structures in nuclear reactors is to nondestructively inspect (test) and measure whether there is no initiation of cracks in the structure or no material deterioration thereof and to employ reformation/processing for previously preventing cracking or deterioration of the structure.

In the following, description will be made regarding a bottom-mounted instrumentation tube which is a representative tubular structure in a nuclear reactor.

A bottom-mounted instrumentation tube is a guide tube for guiding, from the outside of the rector to the inside of the reactor, a sensor for measuring neutron flux at a portion near the nuclear reactor core of a pressurized water reactor, and penetrates the bottom of the reactor vessel to which it is welded. Neutron flux of the core is a parameter directly indicating the operating state of the nuclear reactor, and it is important to secure the integrity of bottom-mounted instrumentation tubes dealing with this measurement in the view point of safe operation of the plant.

Nondestructive testing devices for bottom-mounted instrumentation tubes have been proposed in Japanese Utility Model Registration No. 2590283 as shown in FIGS. 74 and 75. This device is a nondestructive testing device 3, capable of being raised and lowered, for testing bottom-mounted instrumentation tubes 2 positioned on the based within a nuclear reactor vessel 1 and has a slender tubular main body 4. Inside this main body of the nondestructive testing device 3 for bottom-mounted instrumentation tubes 2 are provided a guide device 6 having a test sensor 5 for testing the bottom-mounted instrumentation tubes at the tip thereof, a sensor insertion/extracting device 7 for inserting and extracting the test sensor 5 to and from the bottom-mounted instrumentation tubes, and a turning device 8 for turning the test sensor 5 in the bottom-mounted instrumentation tubes, and further, has a clamping device 9 for the bottom-mounted instrumentation tubes 2 at the top end of the main body 4.

On the other hand, laser technology can be used for testing/measuring material within nuclear reactors, such as detecting cracks in structures, measurement of crack size, stress measurement, material composition measurement, distance measurement, vibration measurement, shape measurement, temperature measurement, and so forth, or reforming/processing material within nuclear reactors, such as stress improvement of the material surface, solution treatment, cladding, removal of adhered matter, polishing, crack removal, crack sealing, welding, cutting, and so on, by using features thereof such as high energy density, peak power, coherence, coherent rectilinear propagation, and the like (e.g., Sano et al. "Underwater Maintenance Technology Using Laser for Nuclear Reactors", Welding Technology May 2005, P 78-82 (2005)").

In principle, such laser techniques are effectively utilized in cases wherein it is difficult to access to the materials, such as at high temperatures, at high positions, in high-dose radiation fields, at portions with complex shapes, and so on, or at portions where access is poor and remote non-contact techniques are required. There shows application can be effectively realized at portions where it is difficult to spatially send laser beams to the object portion, such as in narrow portions, on the inner side of shielding objects, on the inner face of piping by using optical fiber technology (Yoda et al.: "Transfer of 20 MW Laser Pulses by Optical Fiber and Applications Thereof" Laser Research Vol. 28, No. 5, P. 309-313 (2000)).

Particularly, a nondestructive test technique using laser technology is laser ultrasonics. This laser technology involves generating ultrasonic waves using distortion generated at the time of pulse laser beams being irradiated upon a structure material, and measuring the ultrasonic waves as vibrations signals using the interference effect of reception laser beams irradiated on a different point of the same structure material, and is known by way of, e.g., "Yamawaki: "Laser Ultrasonics and Non-Contact Material Evaluation", Welding Society Journal Vol. 64, No. 2, P. 104-108 (1995)". Ultrasonic waves generated and detected or received in this way can be used for various types of crack detection and material measurement for structures, in the same way as with ultrasonic waves generated and received with normal contact type devices.

Furthermore, as for a method for detecting flaws by using laser ultrasonics, a surface test device disclosed in Japanese Unexamined patent application Publication P 3735650 is already known. The surface test device disclosed in this publication relates to technology enabling a method for finding cracks in a structure material which is the subject of measurement, from reflection echoes of generated ultrasonic waves reflected off of cracks in the structure material, or irradiating laser so as to pin a crack found in the structure material between the generation and detection or reception position of the ultrasound, thereby measuring the depth of the crack from the generated ultrasonic propagation properties.

As for a nondestructive test technique of tubular structures within a reactor using laser ultrasonics, the laser irradiation device in Japanese Unexamined patent application Publication No. 2005-40809 is known. As shown in FIG. 76, two laser beams of ultrasonic wave generation laser beam (hereafter referred to as generation laser beam $L_1$) and ultrasonic wave reception laser beam (hereafter referred to as detection or reception laser beam $L_2$) are irradiated on a tubular structure which is the object of testing, and cracks in the subject part are detected using generated ultrasonic signals.

As described with Japanese Utility Model Registration No. 2590283, nondestructive testing devices for bottom-mounted instrumentation tubes are capable of readily realizing nondestructive tests of bottom-mounted instrumentation tubes using a test sensor of a known structure.

However, there is a case wherein, even in the event that no cracks are found in the structure material in the nondestructive test of the bottom-mounted instrumentation tubes, preventive maintenance may be desired for preventing cracks from initiating in the structure material in the future. For example, applying laser technology to preventive maintenance such as improving stress at the material surface of the structure material, is becoming very commonplace (laser peening technology), however, with the nondestructive testing device for bottom-mounted instrumentation tubes using the test sensor with the known structure, a laser maintenance apparatus must be prepared separately from the nondestructive testing device, and the devices must be exchanged each time test work or maintenance work is performed. Exchanging the nondestructive testing device and the laser maintenance apparatus for each task extends the work time in the perspective of the overall task from testing to preventive maintenance, causing the problem of increased costs.

On the other hand, with regard to laser ultrasonic flaw detection devices, while proposals have been made regarding the feasible base technology of using the basic device configuration and flaw detection method, for flaw detection testing of the inner cylinder face of bottom-mounted instrumentation tubes, no proposal has been made regarding an overall system of a nondestructive testing device for bottom-mounted instrumentation tubes combined with preventing maintenance using laser.

Furthermore, the present invention concerns with a laser irradiation device provided for the laser maintenance apparatus mentioned above.

That is, recently, the importance has increased for preventive maintenance technology which prevents premature deterioration of equipment or construction materials of, for example, a reactor construction in a nuclear power plant during a provision period, or in the event that deterioration occurs, maintenance technology such as repairs, maintenance, and prevention of advancing deterioration will be performed.

An optical fiber technology can also be effectively used even where it is difficult to spatially send laser beams to the object portion, such as in narrow portions, on the inner side of shielding objects, on the inner face of piping and so forth.

The surface testing technology uses the laser ultrasonic technology, in which ultrasonic waves are generated by using the distortion of an elastic region which occurs when a pulse laser light is irradiated on a material, and also detects the ultrasonic waves as an oscillating signal, using coherence effect of a reception laser light which is irradiated on the material, and for example is disclosed in the above mentioned publication.

According to this technology, the generated and detected ultrasonic waves can be used for various crack testing or material characterizations, similar to the ultrasonic waves sent or received with a normal contact-type element.

As shown in FIG. 76, with this technology an irradiation head formed with an optical system container, optical fiber, and so forth, is inserted into the cylinder portion of a narrow tube which is the test object, and the generation laser light (laser light for exciting ultrasonic waves) and the reception laser light (laser light for detecting ultrasonic waves) are both in the same direction of the cylinder as to the inner surface of the cylinder, and also toward the axis direction of the cylinder and are irradiated with positions shifted.

The generation laser light L1 excites ultrasonic waves at the sending point E, as shown in FIG. 77. The direct surface wave 104a which arrives at the detecting point R (irradiation position of the detection laser light L2) in a short propagation time detects a crack occurring in the circumference direction as to the axis direction of the cylinder CY.

The orbiting surface wave 104b which orbits the cylinder CY with a long propagation time and arrives at the detecting point R detects a crack occurring in the axis direction of the cylinder CY.

In the case that the test object with a crack is an inner surface of a cylinder as described above, there are several problems such as noise and crack depth measurement.

In other words, when the crack in the test object is on the inner surface of a cylinder, the space is relatively closed, and therefore, other mode ultrasonic signals such as shock waves from the generation laser light L1 is mixed as noise. Furthermore, in the case of measuring crack depth, the two laser lights which are the generation laser light L1 and the detection laser light L2 must be irradiated so as to sandwich the crack. However, if the positions for generation and detection or reception are only for irradiating from a distance in the same direction, as has been the case conventionally, the crack initiated in the axis direction of the test object cannot be sandwiched, and measuring the depth of the crack has been impossible.

Further, with the form of the irradiation head which contains the optical elements internally, depending on the form of the irradiation head, if the inner surface of the cylinder which is the test object has minute curved portions, the work of inserting into and removing from the cylinder which is the test object of the irradiation head becomes inefficient.

The present invention described above further concerns with a laser ultrasonic inspecting device for irradiating the laser to a test object without contact, and generating an ultrasonic wave, and a system including the inspecting device.

Heretofore, as for a flaw-inspecting method of a test object using an ultrasonic wave, the ultrasonic flaw detection method shown in FIG. 78 has been known. With this conventional method, first, a generation-side surface-wave probe 203a including a piezoelectric device is brought into contact with a test object 201 via a generation-side couplant 202a. In this state, an electric signal is applied to the generation-side surface-wave probe 203a from a transmitter 204, an ultrasonic wave is generated to the test object 201 from the surface-wave probe 203a, and a surface wave 205 is generated.

Then, the surface wave 205 is propagated over the surface of the test object 201 and reaches a reception-side surface-wave probe 203b including a piezoelectric device via a reception-side couplant 202b. This arriving signal is received at the reception-side surface-wave probe 203b and is converted into an electric signal by the piezoelectric device to be inputted to a flaw-detecting unit 206. The generation signal from the transmitter 204 is also inputted to this flaw-detecting unit 206, and the difference Δt between the generation time of the generation signal and the reception time of the reception signal, i.e., the time when the surface wave 205 is propagated over the surface of the test object 201 is measured.

When assuming that an interval L between the generation-side and reception-side surface-wave probes 203a and 203b and a sound velocity vs of the surface wave 205 are known, these have the relation that L=vs·Δt. Herein, assuming that the surface of the test object 201 includes a flaw 207 with an opening, which can be ignored, of a depth D, a part 205a of the surface wave 205 is steered around the flawed portion, and consequently, propagation time ΔtD is longer than the propagation time Δt in the case of no flaw.

Accordingly, upon measuring this propagation time ΔtD, the presence of the flaw 207 can be detected from comparison between propagation time L/vs to be measured essentially and the ΔtD, and also the depth D of the flaw can be calculated from the relation of D=(vs·ΔtD−L)/2.

FIG. 79 illustrates a conventional method of surface inspection using an ultrasonic wave. This method is for receiving flawed waves 208a and 208b at the opening end portion and the bottom portion of the flaw 207 based on the surface wave 205 generated to the test object 201 via the couplant 202a from the surface-wave probe 203 for both generation and reception by the surface-wave probe 203 again. With this method, arrival time Δta to the surface-wave probe 203 of the flawed wave 208a and arrival time Δtb to the surface-wave probe 203 of the flawed wave 208b have the relation that 2D=vs·(Δta−Δtb), the depth D of the flaw can be obtained by measuring Δta and Δtb at the flaw-detecting unit 206.

On the other hand, in recent years, a method for substituting with generation/reception of the surface wave 205 using laser light without using the surface-wave probe 203 and the couplant 202 has been proposed. This non-contact surface-wave generation method using laser light is for utilizing a phenomenon in which upon laser light having short pulse high energy being irradiated to a certain test object, thermal stress or evaporation (ablation) compressive force due to absorption of laser energy is generated near the laser light irradiation point, and the distortion due to the affect becomes a surface wave to propagate within the object.

Furthermore, another non-contact surface-wave detection method using laser light is a method for measuring fine vibration which the surface wave excites on the test object surface based on the variation (deflection) of the direction of movement of laser light, the phase modulation of the reflected light, the amount of frequency transition and the like by irradiating laser light to the test object 201 and receiving the reflected light. The above prior technology is disclosed, for example, in J. D. Aussel ("Generation Acoustic Waves by Laser: Theoretical and Experimental Study of the Emission Study of the Emission Source," Ultrasonics, vol. 24 (1988), 246-255 or C. Chenu ("Defect Detection by Surface Acoustic Waves Generated by a Multiple Beam Laser," Proc. of IEEE Ultrasonics Symposium (1995), 821-824)

However, with the above conventional ultrasonic flaw-inspection method, it is necessary to apply the couplants at the time of installing the surface-wave probes 203, 203a, and 203b in the test object, which leads to increase of processes of operation. Further, in the case in which the test object is small, or in the case in which the test object is in a narrow portion, it is difficult to install the surface-wave probes.

Moreover, the conventional non-contact flaw-inspection method using laser light provides a problem wherein the data obtaining time for obtaining more detailed data and inspecting a flaw improving resolution becomes huge. Accordingly, there poses a problem in which the capacity of a recording medium for recording obtained data and the flawed portion detection analysis time increase, and there also causes complex work for extracting necessary portions alone from the large quantity of data.

The present invention also includes a laser ultrasonic reception (detection) device related to the laser maintenance apparatus mentioned above, and more specifically, a laser ultrasonic reception device having monitoring functions of device condition, and optimizing functions of the device condition, for performing flaw detecting operations with a high degree of accuracy over a long period of time in a stable state.

Ultrasonic technology is an extremely effective means for detecting cracks or discontinuity occurring on a material surface or internal defects, or for performing material-characterization. With normal detecting operations, the ultrasonic waves is received by placing in contact a receiving element such as a piezoelectric element with a generation medium of the ultrasonic wave, but this can be substituted by using laser light and a receiving (detecting) optical system such as disclosed in Monchalin, J.-P., et al., "Optical detection of ultrasonic," IEEE Transactions on Ultrasonics, Ferroelectrics, and Frequency Control 33, 1986, pp. 485-499.

An ultrasonic reception method with laser light is in principle non-contact. The application is expected in cases wherein the measurement subject is in a high temperature state, or is placed in a high location, or is placed in a high radiation area, or is very small and in a complicated shape so that contact with testing equipment is difficult, or in industrial technological fields wherein the ability to approach in close proximity is poor and a remote non-contact measurement method is required.

The ultrasonic receiving technology by using laser is a technology in which an oscillating laser light with sufficiently longer pulses is irradiated on the receiving point compared to the generating time of ultrasonic waves or continuous oscillation, and the surface displacement of the receiving point induced by the ultrasonic waves is detected by using direct advancement or coherence, or the oscillating speed thereof such as disclosed in Choquet, M., et al., "Laser-ultrasonic inspection of the composite structure of an aircraft in a maintenance hanger," Review of Progress in Quantitative Nondestructive Evaluation, vol. 14, 1995, pp. 545-552.

As an optical system to use for the laser ultrasonic detection or reception method, a Michelson interference method, a Mach-Zehnder interference method, the Fabry-Perot method, a two-wave mixing method with a phase conjugation element, and a knife-edge method have been proposed such as disclosed in Yamawaki: "Laser Ultrasonics and Non-Contact Material Evaluation" Japan Welding Society Journal Vol. 64, No. 2, P 104-P 108 (1995). However, the method with which industrial applicability is particularly expected is the Fabry-Perot method.

Here, a typical conventional laser ultrasonic reception or detection method and device in which a pulse laser light and the Fabry-Perot method are combined will be described. FIG. 80 is a block diagram illustrating a configuration of a representative conventional laser ultrasonic reception device.

In FIG. 80, an ultrasonic signal US based on an arbitrary generating process or generating process arrives at an arbitrary point P on the surface of a measurement subject TP, and oscillation occurs at that portion. Now, a detection pulse laser light source PDL is appropriately synchronous with the ultrasonic signal US and emits the pulse laser light IL.

The seed laser light oscillated from the seed laser 401 which is set within the detection pulse laser light source PDL is injected into an optical amplifier 402 (MOPA: Master Oscillator Pulsed Amplifier) via a light isolator 405a and total reflection mirrors M1 and M2, and output is amplified in pulses. Herein, as the seed laser 401, a continuously oscillating Nd-YAG laser light source is used, which has a frequency stabilizing function with an output of approximately 10 mW-1 W. MOPA is to excite the optical amplification medium with a flash lamp which is driven by a power source 403 or a laser diode and is cooled with the coolant water W which circulates from the coolant water inlet Win to the coolant water outlet Wout.

The detection pulse laser light IL after amplification is injected into a first optical fiber 404 with a collimator lens L1, and is irradiated on the measurement point P on the measurement subject TP by a first pair of lenses L2 which is set within the irradiation head H. Here, when the reflected light which is reflected by the end face of each optical elements is injected in the seed laser 401 or the optical amplifier 402, optical noise is generated, and therefore optical isolators 405a and 405b may be placed in a position where reflective light can be prevented from mixing in to the seed laser 401 or the optical amplifier 402. Furthermore, an optical attenuator 406 may also be set for adjusting the light output which is irradiated on the measurement subject TP.

As shown in FIG. 81, the irradiated laser light L1 receives modulation to the optical frequency thereof only ±□Vd by the surface oscillation occurring to the ultrasonic signal US (Doppler shift), a portion of the scattered components thereof SL are collected with a second pair of lenses L3 which is set within the irradiation head H, and are injected into the Fabry-Perot interferometer FP via a second optical fiber 407 and a collimator lens L4. Here, a portion of the laser light SL to be injected into the Fabry-Perot interferometer FP is reflected with a partial generating mirror PM1, and the light amount thereof is measured with a reference optical detector 408.

The Fabry-Perot interferometer FP is a resonator comprising two partial reflection mirrors CPM1 and CPM2 which often have conjugated focal points, and the relationship indicated in FIG. 81 is established between the optical frequency of the incident light and the transiting light intensity. The horizontal axis in FIG. 81 indicates the optical frequency v and the vertical axis indicates in the light intensity I of the transiting light. As shown in FIG. 81, the Fabry-Perot interferometer FP has a peak with a specified optical frequency of the transiting optical intensity I thereof, and operates as an optical frequency narrow band filter which rapidly decays before and after the peak. The optical frequency causing the peak can be changed by adjusting the resonator (that is to say, the space between the mirrors CPM1 and CPM2) of the Fabry-Perot interferometer FP. Thus, from the measurement values of the incident light amount of the Fabry-Perot interferometer FP and the transiting light amount, if the mirrors CPM1 and CPM2 are drive-controlled by the piezoelectric element 409 so as to make the frequency where the slope of the curve shown in FIG. 81 is greatest (e.g., point A), to match the frequency of the pulse laser light IL, the optical frequency change ±v d from the ultrasonic signal US can be converted to a relatively great transiting light intensity change ±Id.

By detecting the light signal which has transited the Fabry-Perot interferometer FP with a light detector 410 via a lens 405, and processing with the frequency filter (a high pass filter is often used) 411 according to the ultrasonic frequency US, an electric signal according to the ultrasonic signal US can be obtained. The detected electric signal is appropriately signal-converted, signal-processed, displayed, and recorded with the signal processing device 412. For the light detector 408 or 410, a photodiode (PD), PIN-type photodiode (PIN-PD), or an avalanche photodiode (APD) is often used.

The output signal of the light detector 410 is separated and processed with the frequency filter 413 (often a low pass filter) for observing transiting light amount change and inputted into a piezoelectric element drive control device 414, and is supplied to the control of the resonator as described above.

Further, although the above description has been focused on the transiting light of the Fabry-Perot interferometer FP for simplification, an ultrasonic signal US can also be detected with the reflecting light from the Fabry-Perot interferometer FP by using similar operations as disclosed, for example, in Dewhurst, R. J., et al., "Modeling of confocal Fabry-Perot interferometer for the measurement of ultrasound," Meas. Sci. Technol. 5 (1994) pp. 655-662.

As shown in FIG. 82, it is known to irradiate the measuring object TP by the reception laser light IL using pair of lenses L6 set in the irradiation head H and optical fiber 415a, and a configuration to collect the scattered components SL on the measured object TP surface is also known. In this case, the scattered light SL which is generated from the measuring object TP side to the Fabry-Perot interferometer FP with the optical fiber 415a is separated from the light path of the reception laser light IL with a beam splitter 416a and is then guided to the Fabry-Perot interferometer FP via a coupling lens L7 and optical fiber 417a. In order to effectively perform the separating of the scattered light SL and ultrasonic reception laser light IL, a separated control with deflection using an optical element for deflecting control such as a wave plate and a polarized beam splitter may be adapted.

Furthermore, the laser ultrasonic detection or reception methods and devices of known technology are established as basic principles and can be sufficiently applied in a controlled environment such as a laboratory environment.

However, in a site environment such as a power plant or manufacturing line, when a conventional laser ultrasonic reception method and device as described above are used for a long time for defective flaw detecting or measurement work with ultrasonic waves, the following adverse effects are caused by position shifting of the optical elements due to temperature changes or oscillation in the device setting environment, and temperature changes of the coolant water used with the device, or time degradation of receiving laser excited by flash lamps used in a laser ultrasonic reception method and device:

(1) output decrease of seed laser light or oscillation abnormality, (2) output decrease of pulse laser light or occurrence of waveform distortion, (3) increase in optical fiber coupling loss, and (4) control unstable or control impossible of the resonator length of a Fabry-Perot interferometer.

In other words, there have been fatal problems such as the flaw detection operation becoming unstable and the flaw detection precision decreasing due to the adverse device states. Moreover, in order to secure a fixed device state over a long period of time, the conditions needed to be adjusted frequently and the operation became complicated and flaw detecting costs increased greatly. In order to enable flaw detection operations at a high degree of precision over a long period of time at a more stable state, it is necessary to monitor the above device state appropriately, and to reset the best conditions as needed.

The present invention also includes an ultrasonic inspecting device and an ultrasonic inspecting method for performing flaw detection using ultrasonic waves, preferably laser, related to the laser maintenance technology mentioned above according to the present invention.

With nondestructive tests using ultrasonic waves in a nuclear power plant, it is important to accurately record the storage date and time of testing data, the place of testing and the testing results. Additionally, in recent years, subjectivity of the test evaluation and the traceability of the test results have increased in importance.

In order to evaluate the overall safety of power plant equipment, a visual test (VT) or an ultrasonic test (UT) is performed as to the testing equipment which is an object for each periodic maintenance. In the event of such maintenance, a person holding certification for each method performs the tests according to the established examination procedures. Particularly with regard to UT, there are qualifications for testing performed based on the international standard ISO 9712 of the International Organization for Standardization (ISO) or the Japanese Society for Nondestructive Inspection standard NDIS 0601, and testers holding these certifications perform testing appropriate for each equipment according to the examination procedures determined in advance.

With UT, in addition to manual testing, recently a method wherein test data is stored with an automatic device, and the tester performs an evaluation, has become common. A report is created from the test results from the test performed by a tester according to the items required to be reported specified in, for example, "JIS Z 3060" after the tester returns to the office.

Now, the specification content of a general nature such as "constructor or manufacturer" or "process or product name", in addition to items necessary for each testing location such as "test date" or "examination number or code", "flaw detection range", "flaw detection data", and "pass/fail and standards thereof" are included for each testing location by the tester, and after the tester has personally signed the report, the test report is reported and submitted to the test client.

At this time, particularly in the case of storing test data with an automatic device, the stored test data is not analyzed at the site where the test was conducted, and the tester may return to the office, and after performing analysis may create, report, and submit the test report, similar to the procedure for manual testing.

The content to be included in the report may depend on ASME specifications or other specified confirmation function examinations, in addition to "JIS Z 3060" which is based on the testing technique or test object.

With the test method of performing analysis after returning to the office without analyzing the test data at the testing site, much labor is required, such as the tester recording the "flaw detection range" for each test location which is required to be recorded for example, and in the case of creating the test report, the tester including "flaw detection data", "flaw detection range", and numerous other items in the report.

Thus, a device has been proposed to store the size of the test object defect along with the "flaw detection location" thereof, for example, refer to Japanese Unexamined patent application Publication Publication No. HEI 6-265372

With the method of storing the size of the test object defect along with the "flaw detection location" thereof, information such as the test results and the "flaw detection location" thereof are automatically stored, as opposed to the "flaw detection location" information and the results thereof being recorded at the test site and later included in the report, and thus the workload on the tester to create the report is significantly lessened.

Furthermore, a method has been proposed to transfer the test data to an analysis computer from the test site using a communication system, for example, as disclosed in Japanese Unexamined patent application Publication No. 2002-296256.

According to the method using a communication system, the tester can make test determinations without going to the test site.

The above publications, however, do not describe the details relating to a recording method of test data, and in the case of recording a large amount of test data, from the perspective of test data traceability, in order to analyze the test data after the test or reviewing the test data several years later, accurate records of the test data is necessary such as testing date and time, the units tested, and flaw detection ranges or the like. In addition, tamper-proofing of the test data or test reports is also necessary.

The present invention still includes an improved technology of surface testing which can measure even a fine flaw depth with high precision without being influenced by noise and is particularly related to the laser maintenance technology according to the present invention.

Many techniques for flaw testing and measurement of material properties of a material surface layer often employ measuring of a surface wave serving as an elastic wave propagating along the surface of a material.

Such a flaw testing is performed by contacting a surface-wave probe to the surface of a test object via an ultrasonic propagation medium to transmit a surface wave, receiving a signal with this probe and determining the presence of a flaw by an echo from a flaw opening portion.

In addition, there is disclosed a technique for measuring a flaw depth by detecting the delay time of signal components passing through a flaw opening portion, and ultrasonic components which reflect or diffract at the end portion of a flaw in, for example, Yugoro Ishi ("New edition non-destructive-testing engineering," Sanpo Shuppan, 1993, P 242).

On the other hand, a technique of utilizing the properties where a surface wave distributes, installing each of probes for generation and reception at a position sandwiching a flaw, and estimating a flaw depth based on the fluctuation of a surface wave generating a flaw has been also disclosed in, for example, Japanese Unexamined patent application Publication No. HEI 10-213573.

According to the disclosed technology, as shown in FIG. 83, an oscillator 501 for generating a signal having a predetermined frequency f generates the signal, which is then converted into a surface wave by a generation ultrasonic probe 502 and generated to an object TP to be tested.

A surface wave SR propagates the surface of the object TP to be tested, and if a flaw C exists in the object TP, the surface wave SR interacts with the flaw C to become a generation wave ST, and is received at a reception ultrasonic probe 503. This reception signal is received by a receiver 504, processed by a data analyzing device 505, and then, the presence and depth of the flaw C are calculated.

It is to be noted that a probe to be employed for generation and reception is a contact-type probe utilizing piezoelectric effect. In this case, an ultrasonic propagation medium 506 is applied between the object TP to be tested and the generation and reception probes 502 and 503.

This technique is for utilizing that the penetration (flaw) depth of a surface wave varies depending on the frequency f, and estimating a flaw depth by the attenuation ratio for each frequency of the surface wave generated through a flaw of a material surface layer. Specifically, a waveform including several different frequencies $f_1$, $f_2$, and so on through $f_n$ is employed as a generation wave, the attenuation ratio $\alpha(f)$ for each frequency of a reception wave generated through a flaw of a material surface layer is obtained on the basis of the reception wave propagated a sound portion, and the depth of the flaw C is calculated according to the attenuation ratio percentage.

Thus, according to the described prior technology, not only the presence of a flaw but also the depth thereof can be obtained by calculating the attenuation ratio of the surface wave for each frequency.

Further, as for a technique for obtaining the depth of a flaw from the frequency components of a generation wave, a technique for identifying the propagation properties of the surface wave has been proposed, for example, as disclosed in Japanese Unexamined patent application Publication P 3735650.

This technique provides two reception ultrasonic probes, detects a surface wave SR entering a flaw at the reception probe near the generation probe, detects a surface wave ST generated through a flaw C at the reception probe far from the generation probe, and obtains the propagation properties at a flawed portion of the surface wave based on these two signals.

For example, with the power spectrum of a surface-wave signal entering a flaw as R(f) and the power spectrum of a surface-wave signal generated the flaw Injected(f), change in the frequency components by the flaw, i.e., a transfer function H(f) is obtained as H(f)=T(f)/R(f).

This identifies the depth of the flaw logically from the response time and cut-off frequency of the propagation function H(f), or with reference to the results of a calibration test which has been obtained beforehand.

Further, it has been proposed that the detection of a flaw, identification of the position thereof, and measurement of the flaw depth are performed simultaneously by employing multiple reception ultrasonic probes.

This technique has also disclosed that the same operations can be realized by employing multiple generation ultrasonic probes instead of employing multiple reception ultrasonic probes, and also disclosed that as for a generation and reception method of a surface wave, a laser ultrasonic method and an electromagnetic wave method are employed.

Further, another technique for obtaining the depth of the flaw from the frequency components of a generation wave has been provided in the prior art publication mentioned above.

That is, in the above prior art technology, when the length of the flaw C becoming smaller than the width of a surface wave beam generating the flaw portion, the amount of attenuation of the surface wave receives is influenced by both the depth and length of the flaw, (in the surface wave beam, a part thereof is attenuated by generating the flaw, and detected in a mixture of remaining components which do not transmit the flaw), so that it is difficult to detect them distinctively, which leads in accurate detection of the depth of the flaw.

However, as mentioned above, the power spectrum R(f) of the generation wave generating a sound portion and the power spectrum Tc(f, h) of various generation waves, which have a sufficient length as compared with the width of the surface wave beam, generated through a flaw having a depth h, have been beforehand obtained at a calibration test. In addition, a generation power spectrum T(f, h) generated through a flaw having an unknown length and depth is measured, which is represented, by using a coefficient K, as T(f, h)=K×Tc(f, h)+(1−k)×R(f).

Then, the parameter K regarding the flaw length and the flaw depth h are estimated with a regression calculation.

Still furthermore, another technique for obtaining the depth of a flaw from the frequency components of a generation wave has been disclosed in Japanese Unexamined patent application Publication No. 2001-4599.

This technique employs an ultrasonic wave including multiple frequency components, normalizes the amount of generation of an ultrasonic wave generating a test object, and detects the type and depth of the surface flaw from the frequency distribution pattern of the normalized amount of generation.

The technologies disclosed in the above patent publications are ones to measure the depth of a flaw by focusing attention on the attenuation of the frequency components of a surface wave generated through a flaw, which is effective in that the depth of a flaw can be correctly planned.

However, these technologies involve several problems such as follows. Noise generation is a first problem. With this noise problem, as shown in FIG. 84, when the horizontal axis is taken as a frequency f, and the vertical axis is taken as a power P, when a noise is applied to the true power spectrum shown in a dashed line in FIG. 84, this becomes a jagged parabola line such as shown with a solid line, and a comparatively great measurement error is generated as to the true power spectrum.

Particularly, the prior technologies mentioned above focus attention on the discrete and effective number of frequencies, employs a technique for estimating a flaw depth based on the attenuation ratio α(f) or the generation power T(f, h) in each frequency, and accordingly, influence of noise is great, a measurement error occurs, which has involved some uncertainty about measurement values.

Measurement precision is a second problem. That is, a flaw depth which can be measured depends on the band width of a probe or a transmitter/receiver, or the attenuation properties for each frequency of a material, and accordingly, measurement precision gets worse as to a relatively shallow flaw or a relatively deep flaw.

Such a problem will be described in more detail.

Generally, a surface wave has properties to be localized over a surface layer portion of one wavelength thereof. With a material, of which sound velocity of a surface wave is 2900 m/s, e.g., a stainless steel, the penetration (flaw) depth of the surface wave of each frequency forms a depth diagram markedly varying at frequency of 0.1 MHz through 100 MHz as shown in FIG. 85.

For example, the prior technologies mentioned above have a bandwidth up to 10 MHz and employ an ultrasonic wave having a peak at 6 MHz. Upon plotting this peak frequency 6 MHz in FIG. 85, the penetration depth thereof exhibits 0.5 mm. Accordingly, in the event of measuring a fine flaw depth of 0.5 mm or less, a frequency band becomes a frequency region higher than 6 MHz. Consequently, evaluation is performed with weaker signal power than at the time of evaluating a flaw depth of 0.5 mm or more. This means deterioration of the signal-to-noise ratio (SNR) of a signal to be evaluated, and consequently, for example, between a flaw depth of 0.3 mm or less to be evaluated principally with surface wave components of 10 MHz, and a flaw depth of 0.5 mm or less to be evaluated principally with surface wave components of 6 MHz cause a difference in measurement precision thereof. That is, the finer a flaw is, the poorer the estimation precision of the flaw depth becomes.

Such a problem could be avoided by employing an ultrasonic signal having broad and flat power spectrum distribution from a low frequency to a high frequency band as ultrasonic signal strength to be generated/received.

However, in order to realize the wideband properties using an ultrasonic probe which employs a normal piezoelectric device, a lot of cost needs to be spent. As for a high-frequency band, even if an ultrasonic signal having a wide and flat power spectrum distribution can be oscillated, and the propagation attenuation within a material differs for each frequency, so that the signal strength of a high-frequency region decreases at the time of receiving a signal, and the measurement precision of a fine flaw depth gets worse.

Furthermore, another method for obtaining the depth of a flaw from the frequency components of a generation wave is a method for detecting a surface flaw which is characterized by the technologies such that an ultrasonic wave including multiple frequency components is employed, the amount of generation of the ultrasonic wave generating a body to be inspected is obtained for each frequency, which is then normalized with the amount of generation of the ultrasonic wave generating a sound portion of the body to be inspected obtained for each frequency, and the type and depth of the surface flaw are detected from the frequency distribution pattern of the normalized amount of generation such as disclosed in, for example, Japanese Unexamined patent application Publication No. 2001-4600.

As for another ultrasonic flaw-detecting device, there is proposed a technique for determining the presence of a flaw based on change in attenuation or the generation time ratio of the amplitude of the generation ultrasonic waves of a sound portion having no flaw and flawed portion such, as disclosed in, for example, Japanese Unexamined patent application Publication No. 2000-241397.

However, these conventional techniques provide a problem of deviations occurring in each surface wave to be measured depending on surface state.

That is, when generating an ultrasonic wave to an object to be tested, in the case of a piezoelectric device, there will often case a case in which deviations regarding strength of being pressed to the object to be tested vary for each inspected portion, and the ultrasonic signal level varies.

Further, with the electromagnetic ultrasonic method, the ultrasonic signal level varies for each inspected portion due to the changing in the lift-off with respect to the object to be tested. This causes a problem particularly at the time of performing an in-service component such as the case in which the object to be tested includes a curvature, or by driving precision of the driving mechanism of a probe.

Furthermore, in the laser ultrasonic method, the deviations in surface states cause the deviations in the reception sensitivity and the ultrasonic signal level to be excited.

Generally, these deviations are caused by the deviations of the surface condition for each inspected portion, and the installation position errors of a measuring device, which cause flaw depth measuring error.

Furthermore, the conventional techniques provide a further problem of an error in estimation of a flaw depth by the deviations of the evaluation index values at a sound portion and the deviations of the evaluation index values at a flawed portion occurring when comparing the amount of generation of an ultrasonic wave between the sound portion and the flawed portion to perform determination and sizing of the presence of a flaw.

Still furthermore, many of the conventional techniques shown in the above prior art publications perform comparison with a sound portion at the time of estimating the presence and depth of a flaw, and estimate the presence and depth of a flaw based on the amount of change in amplitudes and frequencies. However, in a real measurement, deviations occur even in multiple data measured at a sound portion, and the deviations thereof are sometimes erroneously taken as the amount of change of a flawed portion.

Although these techniques have the assumption that a sound portion and a flawed portion could be measured with the same sensitivity, as described above, in the event of a piezoelectric device, the deviations regarding the strength to be pressed and the state of being pressed cause measurement error, and the lift-off for the electromagnetic ultrasonic method and the surface state for the laser ultrasonic method cause measurement error. Consequently, it becomes difficult to accurately compare the sound portion and the flawed portion.

A further problem of the conventional techniques resides in the case of accurately measuring the change in the depth of the flaw or the case of scattering, by the material itself, an ultrasonic wave strongly. There may cause a case that the change is not detected only by the amount of change of the generated surface wave. As a result, it sometimes becomes difficult to measure the depth of the flaw.

SUMMARY OF THE INVENTION

The present invention was conceived in consideration of the above circumstances encountered in the technologies mentioned above and a primary object of the present invention is to provide a laser such as laser-ultrasonics, maintenance apparatus wherein a great part of the device can be shared between nondestructive testing such as laser ultrasonic flaw detection and preventive maintenance such as stress improvement of the material surface using laser, and so forth.

Another object of the present invention is to provide a laser irradiation device related to the laser maintenance apparatus mentioned above, wherein the irradiation head can be easily inserted or removed while preventing noise interference and providing easy and accurate detecting of the crack and the depth thereof occurring in the axis direction and circumferential direction of the test object.

A further object of the present invention is to provide a laser ultrasonic detection (or reception) device, related to the laser maintenance apparatus mentioned above, which has a monitoring function of the device state appropriate for use at a site and an optimizing function of the device state, and which can perform flaw detection operations at a high degree of precision for a long period of time in a stable state.

A further object of the present invention is to provide a laser ultrasonic inspecting device related to the laser maintenance apparatus mentioned above, wherein data to be inputted into flaw-detecting means for detecting a flaw of a test object is decreased selectively, and also the storage capacity for recording the data and the data analysis time is reduced.

A still further object of the present invention is to provide an ultrasonic inspecting device and ultrasonic inspecting method related to the laser maintenance apparatus mentioned above which have traceability of the test data and test results.

A still further object of the present invention is to provide a surface testing or inspecting device and a surface testing or inspecting method, related to the laser maintenance apparatus mentioned above, so as to perform depth measurement with higher precision by correcting the irregularities of ultrasonic waves caused by the deviations of each object to be tested or inspected with the ultrasonic wave other than a surface wave.

The above and other objects can be achieved according to the present invention by providing, in one aspect, a laser maintenance apparatus comprising:

a laser system including a laser light source and an optical system and emitting a laser light;

a light transmitting device for transmitting the laser light emitted from the laser system; and a laser irradiation device for irradiating the laser light transmitted by the light transmitting device to an object portion, wherein the laser system includes an element for changing an irradiation condition of the laser light, and the irradiation condition of the laser light of the laser system is set to an irradiation condition enabling flaw detection and preventive maintenance.

In this aspect, the following preferred embodiments may be achieved.

The irradiation condition of the laser light of the laser system is of an oscillation energy of 30 mJ to 60 mJ.

The laser maintenance apparatus may further comprises:

a transporting/scanning mechanism for transporting the light transmitting device and the laser irradiation device to a portion near the object portion, and scanning over an arbitrary range at the object portion;

a control board for control/monitoring of scanning motion of the transporting/scanning mechanism; and a work carriage for suspending and moving the transporting/scanning mechanism one-dimensionally or two-dimensionally from an upper portion of a reactor vessel to the object portion so as to position the transporting/scanning mechanism.

In such embodiment, the transporting/scanning mechanism further comprises:

a polygonal main body casing opened on at least one side;

a seat for seating the transporting/scanning mechanism at the object portion; and a guide mechanism for guiding the light transmitting device and a cable for transmitting power/control signals for scanning operations, wherein an insertion tube for inserting the laser irradiation device disposed on a front end thereof to the object portion, a vertical driving mechanism and a rotational driving mechanism for causing vertical and rotation motion of the laser irradiation device via the insertion tube, a seating detecting device for detecting the seating of the transporting/scanning mechanism on the object portion, and a fixing mechanism for fixing the transporting/scanning mechanism to the object portion after the seating, are provided in the main body casing.

The rotational driving speed $V_R$ from the rotational driving mechanism and the vertical driving speed $V_A$ from the vertical driving mechanism are in a range determined by an expression of $$v_R(\text{deg/s}) \leq \frac{360(\text{deg}) \times 5(\text{mm})}{\pi \cdot ID(\text{mm})} \times f(\text{Hz})$$

$$v_A(\text{mm/s}) \leq \frac{5(\text{mm})}{\frac{360(\text{deg})}{v_R(\text{deg/s})}} = \frac{25(\text{mm}^2)}{\pi \cdot ID(\text{mm})} \times f(\text{Hz})$$

wherein ID represents the internal diameter of the object portion and f represents data obtaining intervals.

A laser light irradiated to the light transmitting device is split multiply, and the work carriage has carriage for handling the transporting/scanning mechanism for the split lights, and further comprising a plurality of flaw detection signal processing systems, one or more light transmitting devices, a laser irradiating device, transporting/scanning mechanisms, and control boards so as to perform parallel execution of testing, measuring, reforming, and processing of the object portion by multiple laser lights and combinations thereof.

The insertion tube provided for the transporting/scanning mechanism is of a hollow structure and formed of resin.

The transporting/scanning mechanism has overload insertion preventing member for preventing overload insertion of the inserting tube to be inserted to the object portion.

The overload insertion preventing member is disposed on the vertical driving mechanism so that the rotational driving mechanism is moved over an arbitrary range, and wherein a first vertical position measuring device for measuring the vertical position of the vertical driving mechanism, a second vertical position measuring device for measuring the vertical position of the rotational driving mechanism, a position deviation detecting device for detecting the difference in output values from both the vertical position measuring devices and an interlocking device for detecting an abnormality of the insertion action at a time when the output signals of the position deviation detecting device exceed a predetermined range to prevent overload insertion. The overload insertion preventing device is disposed on the vertical driving mechanism so that the rotational driving mechanism is moved over an arbitrary range, said vertical driving mechanism having a torque measuring device for monitoring torque, and an interlocking device for preventing overload insertion through a torque monitoring of the torque measuring device is disposed.

The light transmitting device may be composed of one or a plurality of optical fibers for generating laser light and an optical fiber protective tube for mechanically protecting the optical fibers, said laser maintenance apparatus further comprising: an optical fiber reel for adjusting a payout length of the optical fiber while maintaining at least more than smallest bending radius of the optical fibers and the optical fiber protective tube; a first optical fiber for generating laser ultrasonic flaw detection generation/detection laser light from the laser system to the upper portion of the transporting/scanning mechanism via the optical fiber reel; a second optical fiber for generating laser light from the upper portion of the transporting/scanning mechanism to the laser irradiation device via the guide mechanism; and an optical fiber connector, provided at connection portions of the first and second optical fibers with each other with a waterproof function for optically connecting the optical fibers to each other with a laser light reflection preventing device being provided to the connection portion of the first and second optical fibers.

The laser light reflection preventing device is disposed at the connection portion of the first and second optical fibers with a liquid having a refractive index of more than 1.0 being sealed at the connection portion. An optical fiber underwater connecting device is disposed in order to seal the liquid having a refractive index of more than 1.0 in the connection portion of the first and second optical fibers, said optical fiber underwater connecting device comprising first and second fixing bases for fixing a first optical fiber protective tube and a second optical fiber protective tube, respectively, a slide guide for sliding the first and second fixing bases in a connection direction while maintaining the center axes thereof, and a water tank for holding the connection portion of the first and second optical fibers in an underwater environment.

An optical fiber core diameter of at least one of the first and second optical fibers is 1.5 mm or more.

The optical fiber core diameter of the first optical fiber is 1.5 mm or more, and the second optical fiber has a tapered structure such that the optical fiber core diameter of the second optical fiber is greater than the optical fiber core diameter of the first optical fiber at the connection side and is smaller than the optical fiber core diameter of the first optical fiber at the laser irradiation device side.

The apparatus further comprises a clean water supply device for supplying clean water excluding optical reflecting/scattering matter and a clean water guide device for guiding the clean water discharged from the clean water supply device to the laser irradiation device. The clean water supply device includes a first water tube for pumping up environmental water, a pumping device for pumping up the reactor coolant by the first water tube and discharging outside, and a filter device for filtering the reactor coolant pumped up by the pumping device.

The laser maintenance apparatus may further comprise one or a plurality of monitoring device, such as TV cameras, for confirming an operating state of the maintenance apparatus or a state in a nuclear reactor.

The laser irradiation device may comprise:

a first optical element for irradiating detection laser light on a test object so as to detect an ultrasonic wave;

a second optical element for irradiating generation laser light on a test object so as to excite the ultrasonic wave; and an optical system container for containing the first optical element and the second optical element, wherein the reflection direction of the first optical element and the reflection direction of the second optical element are arranged at an angle along the circumferential direction of the test object.

In this preferred embodiment, the reflection direction of the second optical element which reflects the generation laser light and the reflecting direction of the first optical element which reflects the detection laser light are arranged at an angle in the range of 30 to 60 degrees along the circumferential direction of the optical system container.

The optical system container contains at least one or more light path altering elements. The light path altering element is composed of a lens and a wedge plate.

The optical system container has an intermediate portion expanded as a curved surface toward an exterior.

The optical system container has a flow path and is formed from an acoustic absorption material. The optical system container is applied with an acoustic absorption material.

The first optical element and the second optical element are arranged so that the generation laser light and the detection laser light irradiate at symmetrical positions with respect to the axial direction of the optical system container.

The first optical element is arranged at a top portion of the optical system container and the second optical element is arranged at a bottom portion of the optical system container with respect to the axial direction of the optical system container so as to prevent intersection of that the generation laser light and the detection laser light.

The laser irradiation device is rotated in a predetermined constant direction which is same as fastening direction thereof.

The laser irradiation device may comprise:

an optical fiber for transferring a generation laser light which generates an ultrasonic wave to a test object and a detection laser light which detects the ultrasonic wave to detect a flaw of the test object;

a first optical element for irradiating each of the generation laser light and the detection laser light, and the detection laser light is irradiated on the test object position while generating the generation laser light, and a reflective component of the detection laser light reflected from the test object portion is irradiated in the optical fiber;

a second optical element for irradiating the generation laser light which generates the first optical element on the test object;

an optical system container which is connected to one end of the optical fiber and contains the first optical element and the second optical element, wherein the reflection direction of the second optical element which reflects the generation laser light and the reflecting direction of the first optical element which reflects the detection laser light are arranged at an angle along a circumferential direction of the optical system container.

According to such laser maintenance apparatus of the characters mentioned above, it is not necessary to exchange the devices each time of test work or maintenance work, so that these works can be effectively and efficiently performed, resulting in the reduction in time of the working processing, leading to cost down.

According to the laser irradiation device of the present invention, crack can be easily and accurately detected, and the depth of the crack can be also easily inspected.

In another aspect of the present invention, there is also provided a laser ultrasonic detection device comprising:

a laser oscillating device including a seed laser oscillating element for oscillating seed laser light irradiated on a surface of an object to be measured from which an ultrasonic signal is detected and an optical amplifier for amplifying an oscillating light of the seed laser oscillating element in form of pulses;

an optical interference device for extracting an ultrasonic signal from a signal light of the laser light reflected and scattered from a measurement object surface;

a signal processing device for processing an output signal of the optical interference device; and a condition detecting device for detecting condition of the laser oscillating device.

In this aspect, the following preferred embodiments or examples may be provided.

The condition detecting device detects an oscillating condition of the seed laser oscillating device.

The condition detecting device detects the condition of the laser light oscillated in pulse from the optical amplifier.

The optical amplifier includes a coolant supplying device for supplying coolant to and cooling a pumping optical source which pumps an optical amplification medium contained in the optical amplifier, the condition detecting device executes at least one of an operation for detecting the condition of the coolant supplied from the coolant supplying device or an operation for controlling the condition of the coolant.

The laser ultrasonic detection device may further comprise:

an optical fiber for transferring the laser light irradiated on a measurement object from the laser oscillation device;

an image sensor for detecting an input end face of the optical fiber;

an image processing device for detecting an incident state of the laser light of the optical fiber from the detecting results from the image sensor; and a control drive device for controlling the incident state of the laser light of the optical fiber from the incident state results of the laser light which is detected by the image processing device, wherein the condition detecting device displays and records the incident state of the laser light which is detected by the image processing device.

The laser ultrasonic detection device may further comprise:

an optical fiber for transferring the laser light irradiated on an object to be measured from the laser oscillation device;

an end face reflecting detector for detecting a back-scattering and back-reflection light from the optical fiber; and a control drive device for controlling the incident state of the laser light to the optical fiber from the incident state results of the laser light which is detected by the end face reflecting detector, wherein the end face reflecting detector displays and records the incident state of the laser light which is detected by the detecting device.

The laser ultrasonic detection device may further comprise a pulse power source for driving the pumping optical source which pumps the optical amplification medium contained in the optical amplifier, wherein the condition detecting device executes at least one of an operation for detecting the oscillating condition of the pulse power source and an operation for controlling the oscillating condition.

The laser ultrasonic detection device may further comprise a data storing device for storing the output signal of the condition detecting device or a portion or all of the feature amounts, and a communication device for performing transferring of a readout of a portion or all of the signal accumulated in the data storing device, or for transferring the control signal.

In a further aspect, there is provided a laser ultrasonic detection device comprising:

a laser oscillating device including a seed laser oscillating device for oscillating seed laser light irradiated on a surface of an object to be measured from which an ultrasonic signal is detected and an optical amplifier for amplifying an oscillating light of the seed laser oscillating device in form pulse;

a Fabry-Perot interferometer having incident light amount detector for detecting the incident light amount and output light amount detector for detecting an output light amount and for extracting an ultrasonic signal from a signal light of the laser light reflected and scattered from a measurement object surface;

a signal processing device for processing an output signal of the optical interference device; and a condition detecting device for displaying and recording at least one of the output signal of the incident light amount detecting device and the output signal of the output light amount detecting device synchronous with the ultrasonic signal of the signal processing device.

In a further aspect, there is also provided a laser ultrasonic inspecting device comprising:

a surface-wave generating device which irradiates laser light to a test object so as to excite a surface wave;

a surface-wave detecting device for detecting a surface wave including a flaw wave generated at a flawed portion of the test object by irradiating the laser light to the test object at a position apart by a known distance with respect to the laser irradiating position of the surface-wave generating device and detecting the reflected light of the laser light; and a flaw-detecting device for recording a surface-wave detection signal from the surface-wave detection device for a predetermined period since the time of synchronizing with the output signal of the surface-wave generating device, and detecting the flawed portion based on the surface-wave detection signal.

In this aspect, the flaw-detecting device may include an element for detecting at least one of presence of the flawed portion, the position of the flawed portion and a depth thereof.

The laser ultrasonic inspecting device may further comprise a scanner for scanning over the surface of the test object in a state in which both laser light irradiation positions of the surface-wave generating device and the surface-wave detection device are retained with the predetermined interval, and giving the scanning position signal to the flaw-detecting device to identify a flawed position.

The laser ultrasonic inspecting device may further comprise: a shutter device for opening/closing the irradiation optical path to be irradiated to the test object from the surface-wave generating device; a clock for giving a synchronizing signal to the scanner, the shutter device, the surface-wave generating device, the surface-wave detection device, and the signal recording device, for synchronizing the operations thereof; and a delaying device for delaying the opening operation for opening the laser optical path, and the signal recording operation for a predetermined period with respect to the laser light oscillation of the surface-wave generating device.

The flaw-detecting device includes a display unit for displaying an input signal and a detection signal thereof.

The laser ultrasonic inspecting may further comprise a remote-monitoring device for remote-monitoring an input signal and a detection signal of the flaw-detecting device.

The laser ultrasonic inspecting device may further comprise a surveillance camera for imaging a surface inspection work of the test object.

In a further aspect of the present invention, there is also provided a laser ultrasonic inspecting system comprising:

the laser ultrasonic inspecting device including: a surface-wave generating device for irradiating laser light to a test object so as to excite a surface wave; a surface-wave detection device for detecting a surface wave including a flaw wave generated at a flawed portion of the test object by irradiating the laser light to the test object at a position apart by a known distance with respect to the laser irradiating position of the surface-wave generating device and detecting the reflected light of the laser light; a flaw-detecting device for recording a surface-wave detection signal from the surface-wave detection device for a predetermined period since the time of synchronizing with the output signal of the surface-wave generating device, and detecting the flawed portion based on the surface-wave detection signal; and a scanner for scanning over the surface of the test object in a state in which both laser light irradiation positions of the surface-wave generating device and the surface-wave detection device are retained with the predetermined interval, and giving the scanning position signal to the flaw-detecting device to identify a flawed position;

a container for accommodating the laser ultrasonic inspecting device; and a temperature controller for controlling a temperature in the container.

In this aspect, the container may include a see-through window for visually observing the scanner and the test object disposed outside thereof from the inside of the container.

The laser ultrasonic inspecting system may further comprise a sheet for covering an outer surface of the container.

The container may comprise an optical system container for accommodating an optical unit including the optical unit of the laser ultrasonic inspecting device in the container and an electric unit container for accommodating electric units other than the optical unit, in which the containers are combined by a connecting member in a state in which the electric unit container is stacked on the optical unit container.

The laser ultrasonic inspecting system may further comprise an air-pressure controller for adjusting the inside of the container to a positive pressure.

In a further aspect of the present invention, there is also provided an ultrasonic inspecting device comprising:

an ultrasonic flaw detection mechanism for performing ultrasonic flaw detection;

a control board for moving the ultrasonic flaw detection mechanism and controlling the movement thereof;

a data storing mechanism for creating a condition file in which data showing condition of the ultrasonic flaw detection is stored and for storing the ultrasonic data obtained from the ultrasonic flaw detection mechanism and the test data of a position data obtained from the control board into a data file;

a data analysis mechanism for analyzing the test data stored in the data storing mechanism and for creating and outputting a test report based on test results obtained from the data analysis; and a data generating mechanism for transferring the test data between the data storing mechanism and the data analysis mechanism.

In this aspect, an ultrasonic flaw detection mechanism utilizes a laser ultrasonic flaw detection method in which ultrasonic is generated by utilizing elastic distortion generated at a time of irradiating a pulse laser light onto a test object.

The data storing device stores information of an intensity of the laser irradiated to a test object surface and an intensity of the laser returning from the test object surface in addition to the ultrasonic data and position data.

The ultrasonic inspecting device may further comprise a remote control mechanism for remotely controlling an operation of the ultrasonic flaw detection device and the data storing mechanism.

The data storing mechanism is configured to create a log file which records the operation of the data storing mechanism or an occurring event.

An electronic signature indicating a tester is recorded in the test data stored by the data storing mechanism or test report data created by the data analysis mechanism.

A digital watermark is recorded for each ultrasonic test in the test data and the test report.

A tamper-proof mechanism is provided on the test data stored by the data storing mechanism or the test report data created by the data analysis mechanism.

In a further aspect, there is provided an ultrasonic inspecting method comprising the steps of:

preparing a condition file in which data showing a condition of an ultrasonic flaw detection is stored;

controlling a movement of a ultrasonic flaw detection mechanism for detecting an ultrasonic flaw;

storing a test data of the ultrasonic data obtained from the ultrasonic flaw detection mechanism in a data file; and analyzing the test data is analyzed and preparing a test report based on a test result obtained from the data analysis.

In this aspect, a log file is prepared for recording operations and an occurring event at a time of storing the test data.

An electronic signature indicating the tester is recorded in the test data or the test report data.

A specific digital watermark is recorded for each ultrasonic test in the test data and the test report.

A tamper-proof mechanism is provided on the test data or the test report data.

There may be also provided a surface inspecting method for inspecting a flaw of a test object using a surface wave and estimating a depth of the flaw of the test object from an attenuation ratio of a frequency of a generation wave, the surface inspecting method comprising the steps of:

calculating a power spectrum of generation wave generating the flaw of the test object;

integrating the power spectrum of the generation wave passing the flaw of the test object and calculating an integration value thereof;

collating the calculated integration value by converting the integration value into a flaw depth for calibration created beforehand and calculating the flaw depth of the test object; and displaying the calculated flaw depth of the test object.

There may be also provided a surface inspecting method for inspecting a flaw of a test object using a surface wave and estimating a depth of the flaw of the test object from an attenuation ratio of a frequency of a generation wave, said surface inspecting method comprising the steps of:

classifying the test object into a sound portion and a flawed portion at a time of estimating the depth of the flaw of the test object;

calculating a power spectrum of a generation light passing through the classified sound portion;

calculating weighting for each frequency component to be evaluated;

calculating the power spectrum of generation wave passing the classified flawed portion;

calculating weighting for each frequency component to be evaluated in the flawed portion;

calculating the amount of attenuation for each frequency component to be evaluated based on the weighting value for each frequency component in the classified sound portion;

collating the calculated amount of attenuation with a database for converting the amount of attenuation into the flaw depth for calibration created beforehand and calculating the flaw depth of the test object; and displaying the calculated flaw depth of the test object.

There may be further provided a surface inspecting method for inspecting a flaw of a test object using a surface wave and estimating a depth of the flaw of the test object from an attenuation ratio of a frequency of a generation wave, said surface inspecting method comprising the steps of:

calculating a power spectrum of generation wave passing the flaw of the test object;

calculating a product of a weighting function as to the power spectrum of the generation wave;

calculating an integration value of the weighting power spectrum in a frequency region to be evaluated;

collating the calculated integration value of the weighting power spectrum for converting the integration value of the weighting spectrum into the flaw depth for calibration created beforehand and calculating the flaw depth of the test object; and displaying the calculated flaw depth of the test object.

There may be further provided a surface inspecting method for inspecting a flaw of a test object using a surface wave and estimating a depth of the flaw of the test object from an attenuation ratio of a frequency of a generation wave, the surface inspecting method comprising the steps of:

classifying the flaw, at the time of estimating the depth of the flaw of the test object, into a calibration flaw depth calculating section, a real machine sound portion data information collecting section, and a real machine flaw depth calculating section;

calculating, in the classified calibration flaw depth calculating section, the power spectrum in a time region to be evaluated;

calculating a product of the power spectrum and a weighting function, calculating an integration value of the weighting power spectrum in a frequency region to be evaluated;

deriving a conversion function from the depth of the flaw;

calculating the power spectrum in the time region to be evaluated in the real machine sound data information collecting section;

calculating the product of the power spectrum and the weighting function;

calculating the integration value of the weighting power spectrum in the frequency region to be evaluated;

deriving a function for converting the integration value of the corrected weighting power spectrum into the flaw depth based on the sound specimen data in the calibration flaw depth calculating section;

calculating, in the classified real machine flaw depth calculating section, the power spectrum in a time region to be evaluated;

calculating the product of the power spectrum and the weighting function;

calculating the integration value of the weighting power spectrum in a frequency region to be evaluated;

collating the calculated integration value of the weighting power spectrum with the function for converting the integration value of the weighting power spectrum into the flaw depth, which is derived in the real machine sound portion data information collecting section to thereby calculate the flaw depth of the test object; and displaying the calculated flaw depth of the test object.

In these aspects, the weighting function is represented with the following expression of $W(f)=f^n$, in which f represents a frequency and n is an optional number excluding zero.

In the above connection, there may be also provided a surface inspecting device for inspecting a flaw of a test object using a surface wave and estimating a depth of the flaw of the test object from the attenuation ratio of a frequency of a generation wave, said surface inspecting device comprising:

a unit configured to calculate a power spectrum of generation wave generating the flaw of the test object;

a unit configured to integrate the power spectrum of the generation wave generating the flaw of the test object and calculating an integration value thereof;

a unit configured to collate the calculated integration value by converting the integration value into a flaw depth for calibration created beforehand and calculating the flaw depth of the test object; and a unit configured to display the calculated flaw depth of the test object.

There may be also provided a surface inspecting device for inspecting a flaw of a test object using a surface wave and estimating a depth of the flaw of the test object from an attenuation ratio of a frequency of a generation wave, said surface inspecting device comprising:

a unit configured to classify the flaw, at the time of estimating the depth of the flaw of the test object, into a calibration flaw depth calculating section, a real machine sound portion data information collecting section, and a real machine flaw depth calculating section;

a unit configured to calculate, in the classified calibration flaw depth calculating section, the power spectrum in a time region to be evaluated;

a unit configured to calculate a product of the power spectrum and a weighting function;

a unit configured to calculate an integration value of the weighting power spectrum in a frequency region to be evaluated;

a unit configured to derive a conversion function from the depth of the flaw;

a unit configured to calculate the power spectrum in the time region to be evaluated in the real machine sound data information collecting section;

a unit configured to calculate the product of the power spectrum and the weighting function;

a unit configured to calculate the integration value of the weighting power spectrum in the frequency region to be evaluated;

a unit configured to derive a function for converting the integration value of the corrected weighting power spectrum into the flaw depth based on the sound data in the calibration specimen flaw depth calculating section;

a unit configured to calculate, in the classified real machine flaw depth calculating section, the power spectrum in a time region to be evaluated;

a unit configured to calculate the product of the power spectrum and the weighting function;

a unit configured to calculate the integration value of the weighting power spectrum in a frequency region to be evaluated;

a unit configured to collate the calculated integration value of the weighting power spectrum with the function for converting the integration value of the weighting power spectrum into the flaw depth, which is derived in the real machine sound portion data information collecting section to thereby calculate the flaw depth of the test object; and a unit configured to display the calculated flaw depth of the test object.

There may be further provided a surface inspecting method comprising the steps of:

irradiating a laser light to a test object to be inspected so as to generate an ultrasonic wave;

irradiating the laser light at a position apart by a known distance from a position where the laser light is irradiated and receiving a reflection light thereof; and correcting a generation surface wave of the received ultrasonic wave by the ultrasonic wave other than the surface wave to thereby detect a flaw of the test object.

In the above aspect, a predetermined characterization of the generation surface wave is divided or integrated by the same characterization of the ultrasonic wave other than the surface wave included in an output signal to obtain an evaluation index value and obtain the depth of the flaw by applying the evaluation index value to a calibration curve in which a corresponding relation between the evaluation index value and the depth of the flaw is obtained preliminarily.

The ultrasonic wave other than the surface wave is at least one of a longitudinal wave and a bulk wave which are propagated over a surface layer of the test object to be inspected.

Both the characterizations of the surface wave and the ultrasonic wave other than the surface wave are the mean-square values of amplitude.

The characterizations of the surface wave and the ultrasonic wave other than the surface wave are integrated values of power spectra. The integration range of the power spectra is arbitrarily selected.

There may be also provided a surface inspecting device comprising:

an ultrasonic generating unit for irradiating a laser light to a test object to be inspected so as to generate an ultrasonic wave;

an ultrasonic receiving unit for irradiating the laser light to a position apart by a known distance from a position where the laser light from the ultrasonic generating device is irradiated and receiving an ultrasonic wave by receiving a reflection light thereof; and a correcting unit for inputting and recording the output signal from the ultrasonic receiving device so as to detect a flaw of the test object, wherein the correcting unit corrects a generation surface wave of the output signal with an ultrasonic wave other than a surface wave.

According to the laser ultrasonic reception device of the characters mentioned above, the state quantity of the device is appropriately monitored and detected, and even in the case wherein fluctuation occurs from external disturbances, the flaw detection operation can be made with a high precision over a long period of time in a more stable condition, so that the state quantity can be controlled to constantly be a proper value.

Furthermore, the flaw detecting device record a surface-wave signal for a predetermined period alone since the irradiation starting time of laser light for generation to the test object and detect a flaw. Therefore, the reduction of the recording time of this surface-wave signal can be reduced, and thus, the reduction of the storage capacity for recording the surface-wave signal and the reduction of the flaw analysis and detection time can be realized, and the flaw depth measurement precision can be improved, thus being advantageous.

The flaw depth measurement can be performed with high precision.

The nature and further characteristic features of the present invention will be made more clear from the following descriptions made with reference to the accompanying drawings.

DESCRIPTION OF THE PREFERRED EMBODIMENTS

Herein first, embodiments concerning to a laser maintenance apparatus according to the present invention will be described with reference to the accompanying drawings.

First Embodiment

Figure 1:
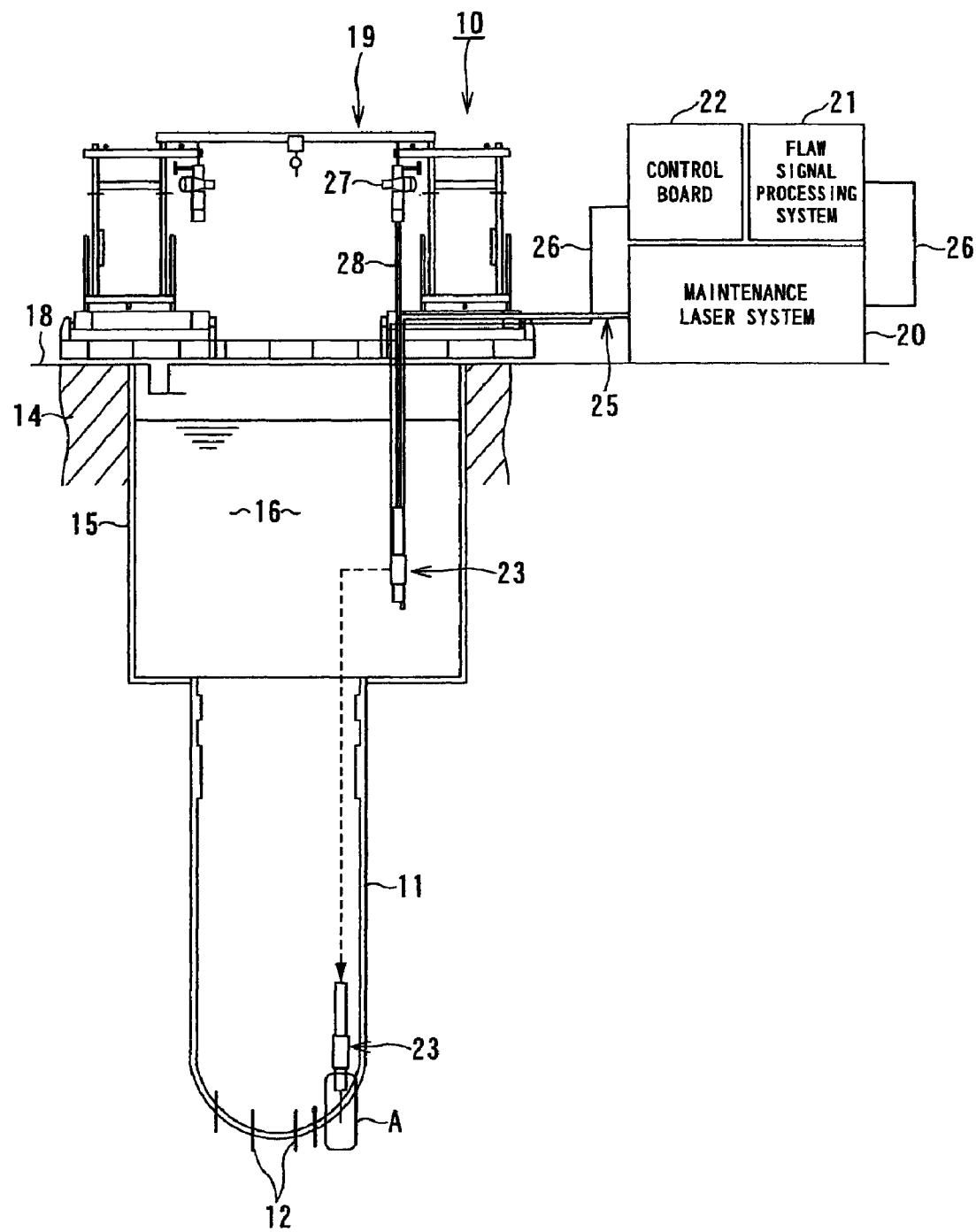
FIG. 1 is an overall configuration diagram illustrating a first embodiment of an ultrasonic maintenance apparatus according to the present invention.

FIG. 1 is an overall configuration diagram illustrating a first embodiment of the laser such as laser-ultrasonics maintenance apparatus according to the present invention, which will be called hereinafter laser maintenance apparatus.

This laser maintenance apparatus 10 is a device adapted to be able to serve for flaw detection testing for nuclear reactor tubular structures in boiling water reactors or pressurized water reactors such as bottom-mounted instrumentation tubes and for preventive maintenance such as stress improvement of the material surface.

FIG. 1 illustrates an example of applying the laser maintenance apparatus 10 for a nuclear reactor tubular structure to an in-core (reactor) instrument tube 12 of a reactor pressure vessel 11 of a boiling water nuclear reactor, as well as bottom-mounted instrumentation tubes of a reactor vessel for pressurized water reactors.

The reactor pressure vessel 11 is disposed in a reactor building 14, with a reactor well 15 formed above the reactor pressure vessel 11. Reactor coolant 16 is filled in the reactor well 15 and the reactor pressure vessel 11. An operation floor 18 is formed above the reactor well 15, and a work carriage 19 is provided on the operation floor 18 to be movable one-dimensionally or two-dimensionally.

A laser system 20 for maintenance or test/maintenance, making up a laser ultrasonic sensing system is provided on the operation floor 18 within the reactor building 14. The laser system 20 constitutes a laser source and optical system for testing, measuring, reforming, and processing the subject portion of the nuclear reactor tubular structure. On the operation floor 18, there is disposed an operation panel 23 for controlling, monitoring and scanning operations of a flaw detection signal processing system 21 and transporting/scanning mechanism 22 which perform processing of such as the flaw detection signals received by the laser system 20, displaying, analyzing and recording of these flaw detection signals. The maintenance laser system 20 has components necessary for generation and detection of ultrasonic signals according to laser ultrasonics, such as ultrasonic wave generation laser light source (Hereafter referred to as generation laser light source.), ultrasonic wave reception laser light source (Hereafter referred to as detection or reception laser light source.), ultrasonic detection (reception) interferometer, and the like.

Figure 2:
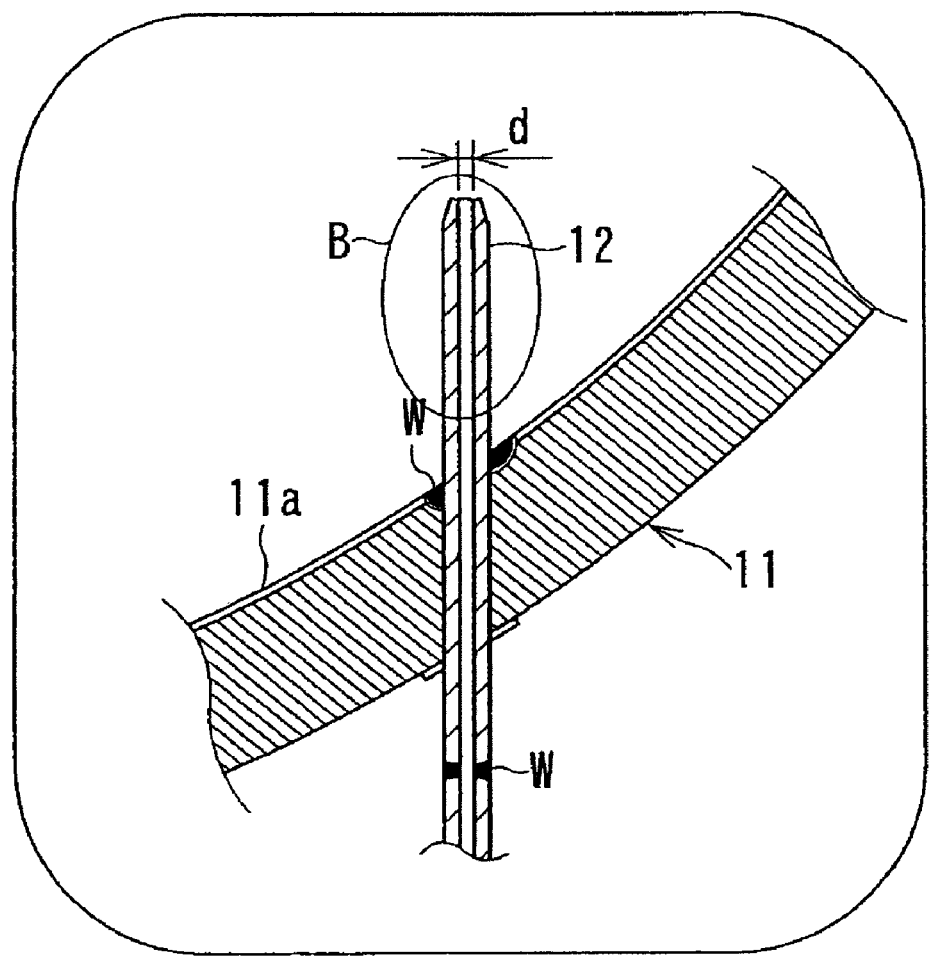
FIG. 2 is an enlarged cross-sectional view of portion A in FIG. 1.

Further, the reactor well 15 and the reactor pressure vessel 11 are filled with reactor coolant 16, and the bottom-mounted instrumentation tubes 12 are formed on the lower portion (lower mirror portion) of the reactor pressure vessel 11. The bottom-mounted instrumentation tubes 12 are for guiding neutron instrument tubes, not shown, and have a narrow inner diameter d such as approximately 9.5 mm, 15.2 mm or the like, for example. As shown in FIG. 2, all-around connection W is utilized for the fixture to the lower mirrors portion 11a of the reactor pressure vessel 11 and for connection of piping (tubes).

While the maintenance laser system 20 is connected to the transporting/scanning mechanism 23 by one or plural optical fibers 25 serving as light generating means, the transporting/scanning mechanism 23 is connected to the control board 22 by a power/signal electrical cable group 26. The maintenance laser system 20 and the flaw detection signal processing system 21 are also connected through the power/signal electrical cable group 26.

The transporting/scanning mechanism 23 connected to the maintenance laser system 20 by the optical fibers 25 is suspended so as to be raised and lowered by a suspending wire or cable 28 suspended from an elevator mechanism 27 of the work carriage 19 to be movable one-dimensionally or two-dimensional movement. The work carriage 19 may be a carriage dedicated to preventive maintenance such as internal flaw detection or material surface stress improvement of the bottom-mounted instrumentation tubes 12, or may be substituted with fuel exchanging facilities provided above the reactor pressure vessel (RPV) for replacing fuel.

A generation laser beam $L_1$ emitted from the maintenance laser system 20 is guided to the optical fiber 25, generated to the transporting/scanning mechanism 23 from the exit end thereof, and is used for the inner face flaw detection and preventive maintenance of the nuclear reactor tubular structures. As for the generation laser light source included in the maintenance laser system 20, the second-harmonic (wavelength 532 mm) of Q-switched Nd-YAG laser, for example, can be used. This laser light source can be used as it is as a laser peening light source also serving for the preventive maintenance by adjusting the oscillation energy and scanning conditions and the like. The laser light source can be used as both a flaw detection light source and a preventive maintenance light source by adjusting the oscillation energy and scanning conditions and the like. Specifically, the oscillation energy is set at 30 mJ for the flaw detection and at 60 mJ for the preventive maintenance.

Figure 3:
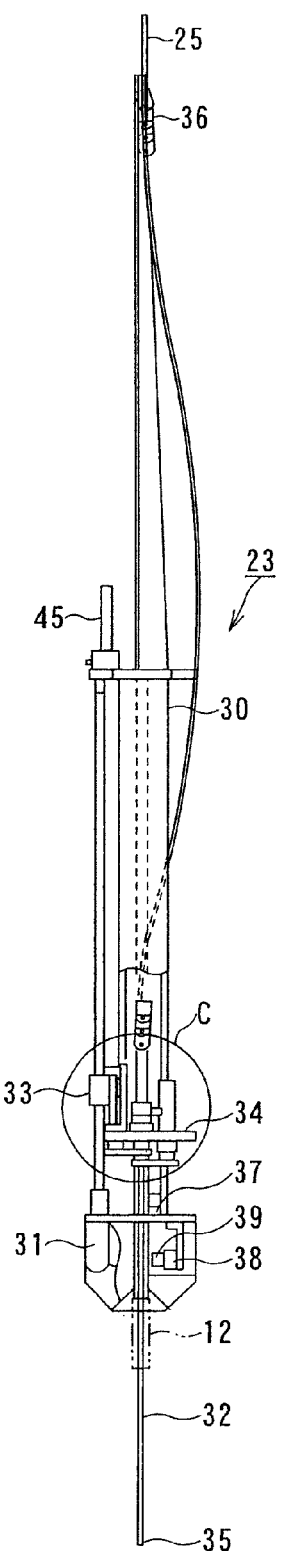
FIG. 3 is an explanatory diagram of a transporting/scanning mechanism provided to the maintenance apparatus for reactor tubular structures according to the present invention.

The transmission (generation) laser beam $L_1$ emitted at the maintenance laser system 20 is guided to the optical fiber 25 and generated to the transporting/scanning mechanism 23 from the fiber exit end thereof. Detailed structure of the transporting/scanning mechanism 23 is shown in FIG. 3.

The transporting/scanning mechanism 23 has, as the principal structures thereof, a main unit casing 30 having a long rectangular (polygonal) shape or a box-like shape with at least one side face opened, and a seat 31 provided to the lower portion of the main unit casing 30. An insertion tube 32 is provided in the main unit casing 30 and is provided to be vertically movable and also rotatable by a vertical movement driving mechanism 33 and a rotational driving mechanism 34.

Attached to the tip of the insertion tube 32 is a laser irradiation head 35 having the structure as disclosed in Japanese Unexamined patent application Publication No. 2005-40809, as laser irradiating means. One side of the main unit casing 30 is opened in a rectangular form, giving consideration to maintenance of the internally-disposed vertical movement driving mechanism 33, rotational driving mechanism 34, insertion tube 32 to be elevated and rotated, and laser irradiation head 35 as laser irradiation device.

Reactor observation means such as a TV camera or the like are provided to the transporting/scanning mechanism 23. Providing a reactor TV camera or the like allows the operations of objects within the reactor (internal objects) of the reactor pressure vessel 11 to be observed during actual operations.

The transporting/scanning mechanism 23 shown in FIG. 3 illustrates a state in which the insertion tube 32 and laser irradiation head 35 have been sufficiently inserted into the bottom-mounted instrumentation tube 12 due to the lowering action of the vertical movement driving mechanism 33. In the event that the insertion tube 32 and laser irradiation head 35 are raised to the highest portion, i.e., in the initial state, the insertion tube 32 and laser irradiation head 35 are held in a state completely extracted upwards from the highest point of the bottom-mounted instrumentation tube 12.

The insertion tube 32 is supported to be rotatable by the rotational driving mechanism 34, which is supported so as to be vertically moveable by the vertical movement driving mechanism 33, whereby the laser irradiation head 35 is positioned by rotating and moving vertically in the bottom-mounted instrumentation tube 12, with the laser irradiating head 35 being supported so as to be inserted or extracted into or from the bottom-mounted instrumentation tube 12. Various reactor tubular structures can be conceived besides the bottom-mounted instrumentation tubes.

The optical fiber 25 for generating the generation laser beam $L_1$ and detection laser beam $L_2$ used for laser ultrasonic flaw detection is guided into a cable tray 36 from the upper side of the transporting/scanning mechanism 23 as shown in FIG. 3. The insertion tube 32 has an internal diameter which is greater than the external diameter of the optical fiber 25. The optical fiber 25 passes through the insertion tube 32, and the tip of the optical fiber 25 is fixed to a suitable positional relation so as to be optically connected to the laser irradiation head 35 provided at the tip of the insertion tube 32.

Hereunder, the operations of the laser maintenance apparatus of this embodiment will be described.

The transporting/scanning mechanism 23 suspended from the work carriage 19 by the suspending wire 28 is seated on the bottom-mounted instrumentation tube 12 provided on the reactor bottom of the reactor pressure vessel 11 following the raising/lowering path indicated in FIG. 1 by the dotted arrow, through the operations of the elevator mechanism 27 provided to the work carriage 19 and operations of the suspending wire 28.

The fact that the transporting/scanning mechanism 23 has been seated on the bottom-mounted instrumentation tube 12 in a sure manner is detected by a seating sensor 37 serving as seating detecting means, and seating-completed signals are generated via the cable 26 to the control board 22. Upon confirming the seating-completed signals at the control board 22, a supporting mechanism (operation rod) 39 is pressed against the bottom-mounted instrumentation tube 12 by operations of a hydraulic cylinder 38 serving as a driving fixing mechanism, and the transporting/scanning mechanism 23 is fixed to the bottom-mounted instrumentation tube 12.

In the state that the transporting/scanning mechanism 23 is fixed to the bottom-mounted instrumentation tube 12, driving force and driving signals are generated by the control board 22 to the vertical movement driving mechanism 33 via the power/signal electrical cable group 26, and the insertion tube 32 and the laser irradiation head 35 at the tip thereof are inserted into the bottom-mounted instrumentation tube 12. When the laser irradiation head 35 is disposed at a predetermined vertical position by a vertical position sensor provided to the vertical movement driving mechanism 33, the generation laser beam $L_1$ and reception laser beam $L_2$ are emitted from the laser maintenance apparatus 10, and irradiated upon a subject portion on the inner wall of the bottom-mounted instrumentation tube 12 under appropriate irradiation conditions through the optical fiber 25 and laser irradiation head 35, and the flaw testing starts.

Upon the flaw testing starting, the driving force and driving signals are generated again by the control board 22 to the vertical movement driving mechanism 33 and the rotational driving mechanism 34 shown in FIG. 3, so that the laser irradiation head 35 performs helical scanning, axial direction scanning, or rotational scanning, at a predetermined position, thereby testing the subject portion of the bottom-mounted instrumentation tube 12.

Following the flaw detection scanning of the predetermined scanning range on the inner face of the bottom-mounted instrumentation tube 12, the laser irradiation head 35 is raised by the vertical movement driving mechanism 33 to a predetermined extraction position, and is moved to the next bottom-mounted instrumentation tube 12, or storage work of the transporting/scanning mechanism 23 is performed according to reverse operation procedures from starting work.

By operating the transporting/scanning mechanism 23 under the control of the scanning panel 22, desired nondestructive testing can be easily realized at the inner face of the bottom-mounted instrumentation tube 12. In addition, in a case, for example, in which, at completion of flaw detection by nondestructive testing, the results of the flaw detection do not detect a crack in the inner face of the bottom-mounted instrumentation tube 12 or the like, the operations can be transitioned to the preventive maintenance work using laser such as measuring, reforming, working stress improvement, and so forth, simply by changing the irradiation conditions of the generation laser beam $L_1$ or simply by changing or adding a part of one of the above-described components.

FIG. 4 illustrates a first modification of the first embodiment of the laser maintenance apparatus according to the present invention.

The overall configuration of the laser maintenance apparatus 10 is no different from the laser maintenance apparatus of the first embodiment except for the insertion tube, and accordingly, the same configurations will be denoted with the same reference numerals, and illustration in the drawings and description thereof will be omitted.

The laser maintenance apparatus 10 of the first modification uses an insertion tube 32a formed of a resin such as polycarbonate or the like. The feature of this laser maintenance apparatus 10 resides in that the insertion tube 32a is formed of resin.

Figure 4C:
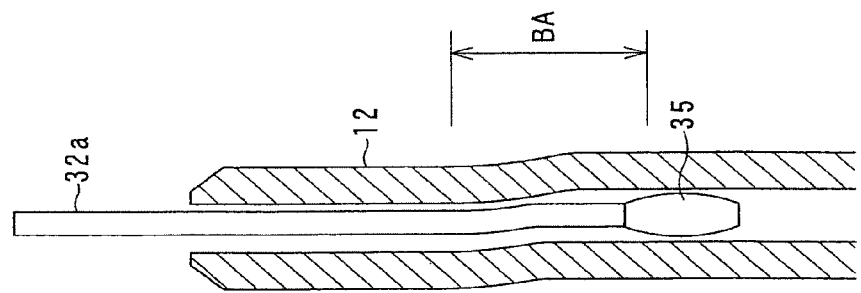
FIGS. 4A, 4B, and 4C are operation explanatory diagrams illustrating a first modification of the first embodiment, enlarging portion B in FIG. 2.
Figure 4B:
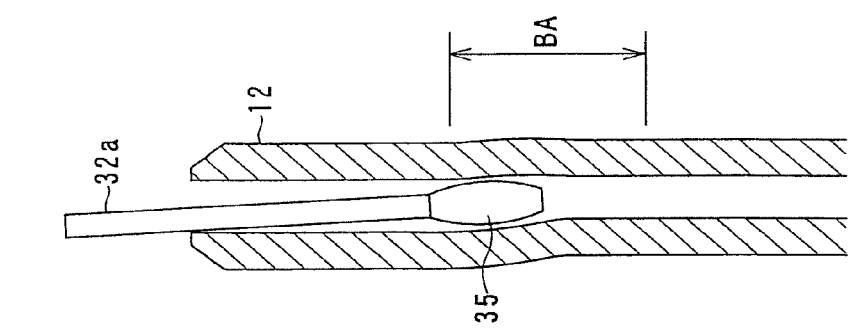
Figure 4A:
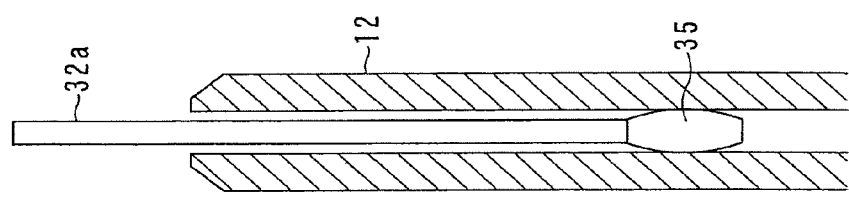

The bottom-mounted instrumentation tube 12 which is a reactor tubular structure is fixed by welding to the lower mirror portion 11a (see FIG. 2) of the reactor pressure vessel 11, as shown in FIG. 4A. There is the possibility that the inner diameter of the long bottom-mounted instrumentation tube 12 may be bent into a dogleg shape or into an S shape as shown in FIGS. 4B and 4C, due to heat inputted at the time of welding. While the bending region BA of the bottom-mounted instrumentation tube 12 is not problematic as far as functions and strength of the bottom-mounted instrumentation tube 12 is concerned, the following problem will occur in consideration of the insertion of the insertion tube 32a along the inner face of the bottom-mounted instrumentation tube 12. That is, in the event that the bottom-mounted instrumentation tube 12 is of a standard straight-pipe shape (FIG. 4A), the insertion tube 32 can be inserted and (or) extracted even if it is formed of metal.

However, in the use of the insertion tube 32 formed of metal in a state of the bottom-mounted instrumentation tube 12 being bent, when the laser irradiation head 35 reaches near the bent portion of the bottom-mounted instrumentation tube (pipe) 12, the insertion tube 32a and the bottom-mounted instrumentation tube 12 interfere each other, as schematically illustrated in FIG. 4B, making it difficult to insert the tube or extract it. Now, in the case that the insertion tube 32a is formed of resin such as polycarbonate or the like, the bent portions can be handled flexibly while maintaining supporting strength, and accordingly, can be easily inserted/extracted to and from the bottom-mounted instrumentation tube 12 even if the tube is bent.

Figure 5:
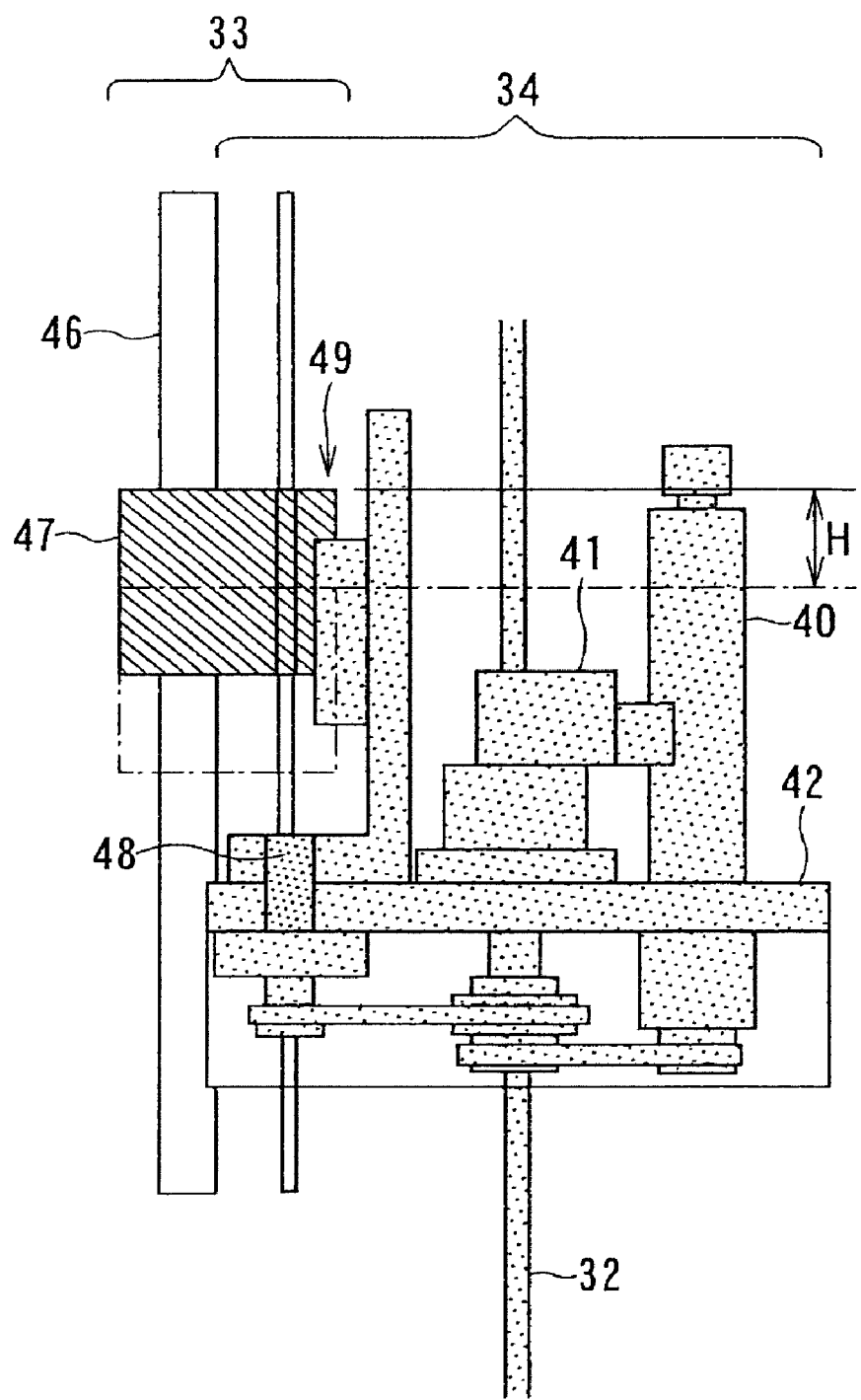
FIG. 5 is an enlarged view of portion C in FIG. 3, illustrating a transporting/scanning mechanism of a second modification of the first embodiment of the maintenance apparatus.
Figure 6:
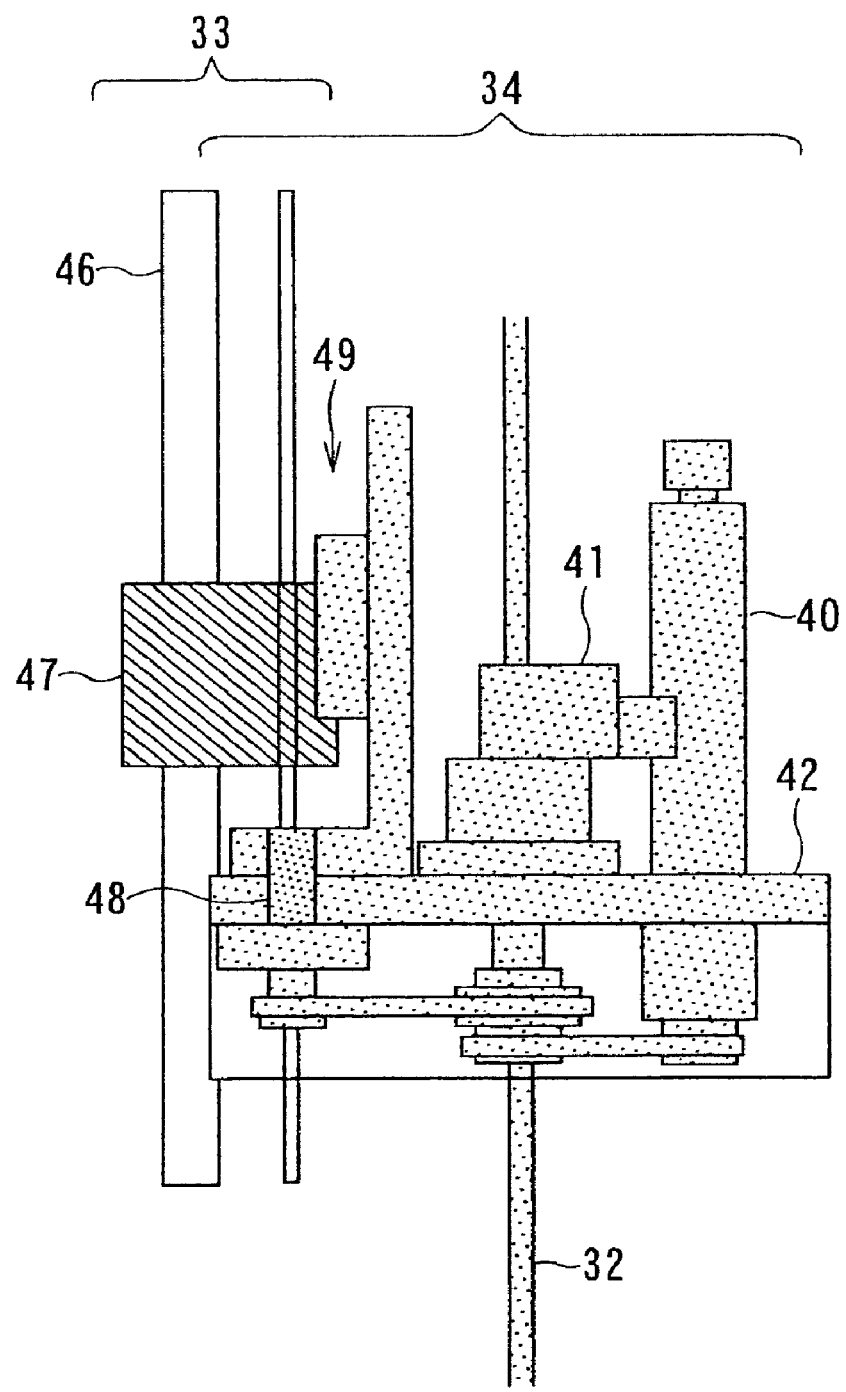
FIG. 6 is an enlarged view of portion C in FIG. 3, as with FIG. 5, and is an explanatory diagram of overload prevention interlocking functionality for the maintenance apparatus.

FIG. 5 and FIG. 6 are explanatory diagrams illustrating a second modification of the first embodiment of the laser maintenance apparatus according to the present invention.

The illustrated laser maintenance apparatus 10 of this second modification has an overload prevention interlocking function, and the overall configuration of the maintenance apparatus is no difference from the laser maintenance apparatus 10 shown in FIG. 1 through FIG. 3, so that the same configurations will be denoted with the same reference numerals, and illustration in the drawings and description thereof will be omitted.

The laser maintenance apparatus 10 shown in FIG. 5 and FIG. 6 has an interlocking function for preventing the insertion tube 32 from being inserted into the bottom-mounted instrumentation tube 12 under excessive load. That is, the transporting/scanning mechanism 23 of the laser maintenance apparatus 10 has overload insertion preventing means 49 for preventing overload insertion of the insertion tube 32 and the laser irradiation head 35.

On the other hand, the bottom-mounted instrumentation tube 12 which is a reactor tubular structure may have curved portions or bent portions such as shown in FIGS. 4B and C.

Even in a case that there are curved portions or bent portions in the bottom-mounted instrumentation tube 12, the employment of a resin tube for the insertion tube 32 sufficiently ensure the insertion ability to the bent portion BA.

However, in the case that the bottom-mounted instrumentation tube 12 is extremely bent, the insertion of the insertion tube 32 may become difficult, or even in the case of employing the resin insertion tube 32, the insertion will also become difficult.

In the case that it is difficult to insert the insertion tube 32 into the bottom-mounted instrumentation tube 12, it becomes also difficult to insert the insertion tube 32 and laser irradiation head 35 beyond a certain point only by the normal handling operations of the insertion tube 32. In spite of the difficulty of the insertion beyond a certain point, the device side of the vertical movement driving mechanism 33 applies an insertion load so that the insertion tube 32 and the laser irradiation head 35 will be inserted to the predetermined position. Consequently, this operation may lead to the insertion tube 32 and the laser irradiation head 35 being rammed into the bottom-mounted instrumentation tube 12, or ultimately damaging the vertical movement driving mechanism 33.

The laser maintenance apparatus 10 according to the second modification has overload insertion preventing means 49 having a overload prevention interlocking function, thereby preventing ramming of the insertion tube 32 and the laser irradiation head 35 into the bent portion, and the damage of the transporting/scanning mechanism 23 such as the vertical movement driving mechanism 33 and the like.

FIG. 5 and FIG. 6 illustrate an enlarged view of the C portion in FIG. 3, showing a part of the vertical movement driving mechanism 33 and rotational driving mechanism 34 provided for the transporting/scanning mechanism 23.

The rotational driving mechanism 34 has as the primary components thereof a rotational driving motor 40, an insertion tube guide mechanism 41, and a rotational driving base 42. The rotational driving mechanism 34 is of a configuration hanging from the vertical movement driving mechanism 33 by its own weight. The vertical movement driving mechanism 33 has as the primary components thereof a vertical movement driving motor 45, and a lead screw 46 serving as a screw shaft and nut 47.

The employment of a hanging structure in which the rotational driving mechanism 34 hangs from the vertical movement driving mechanism 33 enables the rotational driving mechanism 34 to move upwards from the initial position in a certain range H, with regard to the vertical movement driving mechanism 33.

With the rotational driving mechanism 34, when the lead screw 46 is rotated by the vertical movement driving motor 45, nut 47 is vertically moved, and the entire rotational driving mechanism 34 follows the vertical movement of the nut 46 so as to be also vertically moved. In the normal case, by coinciding the vertical movement actions with the rotational actions of the rotational driving mechanism 34, the laser irradiation head 35 can be set to an optional vertical position and optional angle in the bottom-mounted instrumentation tube 12, and the continuous vertical/rotational driving, including the helical action, over an optional range can be realized.

In the event that the insertion of the laser irradiation head 35 attached to the tip of the insertion tube 32 beyond a certain point becomes difficult due to some reason during the downward insertion operation of the insertion tube 32 into the bottom-mounted instrumentation tube 12, the nut 47 continues the downward moving toward the set value as indicated by the broken line in FIG. 5, but the rotational driving mechanism 34 is not pressed inside under an overload state, as shown in FIG. 6, due to the hanging structure 49, and the rotational driving mechanism 34 stops at the position.

To the vertical movement driving motor 45 of the vertical movement driving mechanism 33, there is provided a first position detecting sensor, not shown, serving as first vertical position measuring means for measuring the vertical position of the vertical movement driving mechanism 33, and also, to the rotational driving base 42 of the rotational driving mechanism 34, there is provided a second position detecting sensor 48 serving as second vertical position measuring means for measuring the vertical position of the rotational driving mechanism 34 so that the second position detecting sensor 48 measures and detects the actual elevation, i.e. vertical movement, position of the rotational driving mechanism 34.

This arrangement provides an interlocking function such that the output values of the first and second position detecting sensors 48 are constantly monitored at the control board 22 (FIG. 1), and in the case that the difference between the output value of the first position detecting sensor and the output value of the second position detecting sensor 48 exceeds the set value H, the control board 22 indicates that it is impossible to further insert the insertion tube 32, and the vertical driving is stopped. By locating the position detecting sensor 48 to the vertical movement driving mechanism 33 and the rotational driving mechanism 34 and always monitoring the vertical position or relative position of the vertical movement driving mechanism 33 and the rotational driving mechanism 34, the ramming of the insertion tube 32 and the laser irradiation head 35 into the bent portion BA of the bottom-mounted instrumentation tube 12 can be surely prevented, and damage of the transporting/scanning mechanism 23 can be also prevented beforehand.

Further, the overload insertion preventing means may have torque measuring functions given to the vertical movement driving motor 45 to thereby prevent insertion under overload by monitoring the torque.

Second Embodiment

Figure 7:
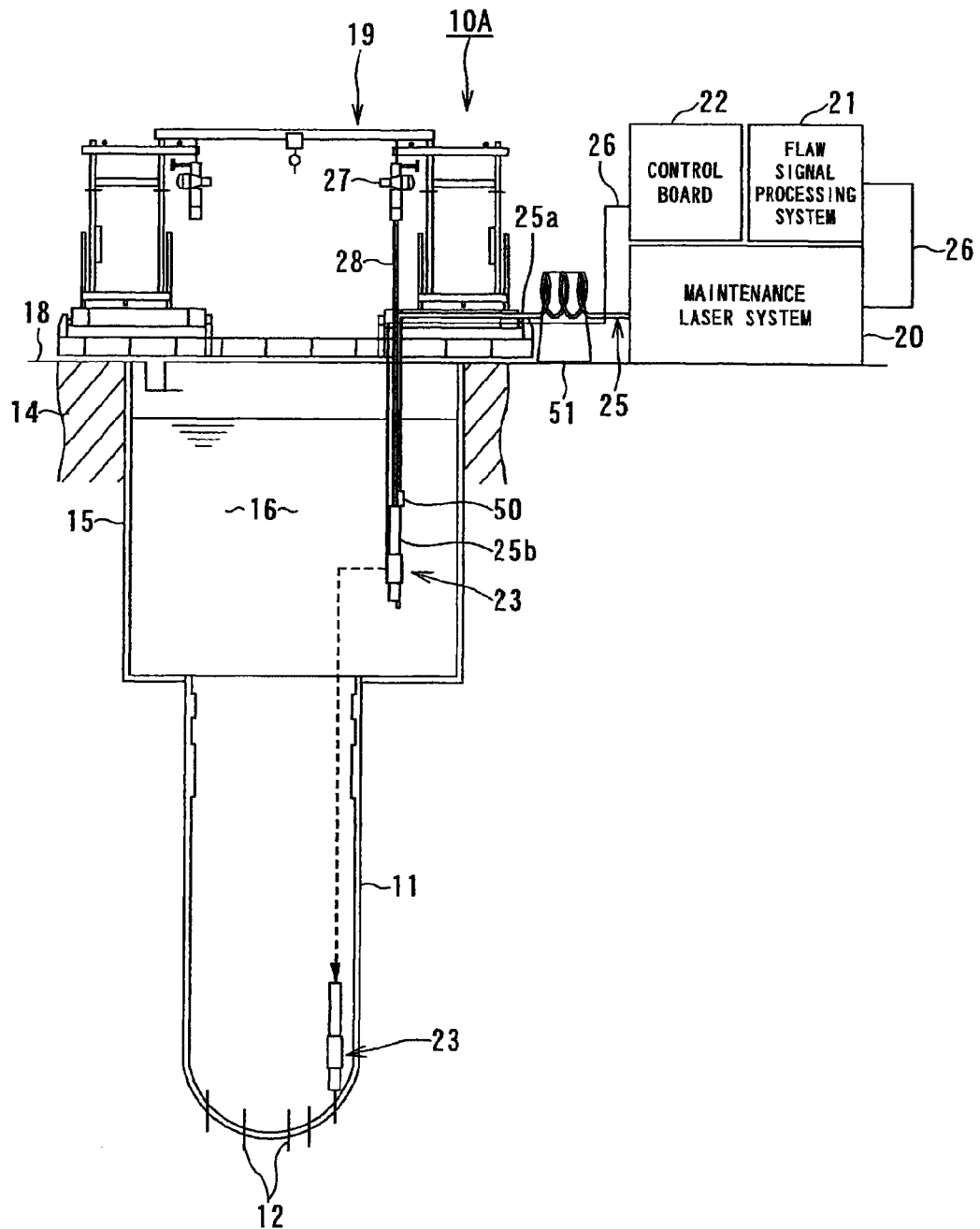
FIG. 7 is an overall configuration diagram illustrating a second embodiment of the laser maintenance apparatus according to the present invention.

FIG. 7 is an overall configuration diagram illustrating a second embodiment of the laser maintenance apparatus according to the present invention.

The laser maintenance apparatus 10A illustrated in this embodiment is specifically characterized by the handling of the one or plural optical fibers 25 for delivering the generation laser beam $L_1$ and detection laser beam $L_2$ has been improved, and hence, the same components as those of the laser maintenance apparatus 10 of the first embodiment will be denoted with the same reference numerals, and the illustration in the drawings and description thereof will be omitted herein.

With the laser maintenance apparatus 10A shown in FIG. 7, only in an optical perspective, the optical fiber 25 is preferably a single uninterrupted optical fiber used from the input end connected to the laser system 20 to the output end in the insertion tube 32 near the laser irradiation head 35 (see FIG. 3). In a case when the optical fiber 25 is separated, part of the laser beam energy is reflected and scattered at the connecting portion, so that the laser beam energy which can be actually delivered is reduced, and further, the laser beam energy reflected and scattered at the connecting portion may cause damage to the optical fiber or other optical elements.

However, since the bottom-mounted instrumentation tubes 12 are situated about 20 meters below the level of the operation floor 18, the entire length of the optical fiber 25 is at least 20 meters or more, providing a problem in handling thereof.

With the laser maintenance apparatus 10A for reactor tubular structures shown in FIG. 7, a waterproof optical fiber connector 50 is introduced to the optical fiber 25 connecting the laser system 20 and the transporting/scanning mechanism 23 so as to provide a structure in which an optical fiber 25a of a length la at the system 20 side and an optical fiber 25b of a length lb at the laser irradiation head 35 (see FIG. 3) side are dividable. Enabling the optical fiber 25 for delivering the generation laser beam $L_1$ and detection laser beam $L_2$ to be divided improves the handling of the optical fiber 25.

Although the ratio in length of the optical fibers 25a and 25b making up the optical fiber 25 is optional, by taking into consideration of the handling of the transporting/scanning mechanism 23, it becomes possible to make 1a>1b and 1a+1b≧20 m for the fiber length 1a of the optical fiber 25a and the fiber length 1b of the optical fiber 25b with the payout length of the optical fiber being adjustable at the optical fiber 25a with an optical fiber reel 51.

Connecting the optical fiber 25 with the waterproof optical fiber connector 50 causes the reflection/scattering of the laser beam at the connector portion. In order to solve the reflection/scattering problem, the connecting surface of the optical fiber 25a and the optical fiber 25b is provided with anti-reflection means so as to have the anti-reflection function. As for the anti-reflection means, it is preferable and optimal to provide a method of providing an optical anti-reflection film tuned to the laser wavelengths of each of the generation laser beam $L_1$ and detection laser beam $L_2$.

As a more simple anti-reflection measure for the optical fiber 25, the connector component at the optical fiber 25b side may be of a sealed type as to the optical fiber protective tube (waterproof as to external water environment), and the connector component at the optical fiber 25a side may be of a non-sealed type as to the optical fiber protective tube (waterproof as to external water environment), by filling water at the joint, as reflection prevention means.

Figure 8B:
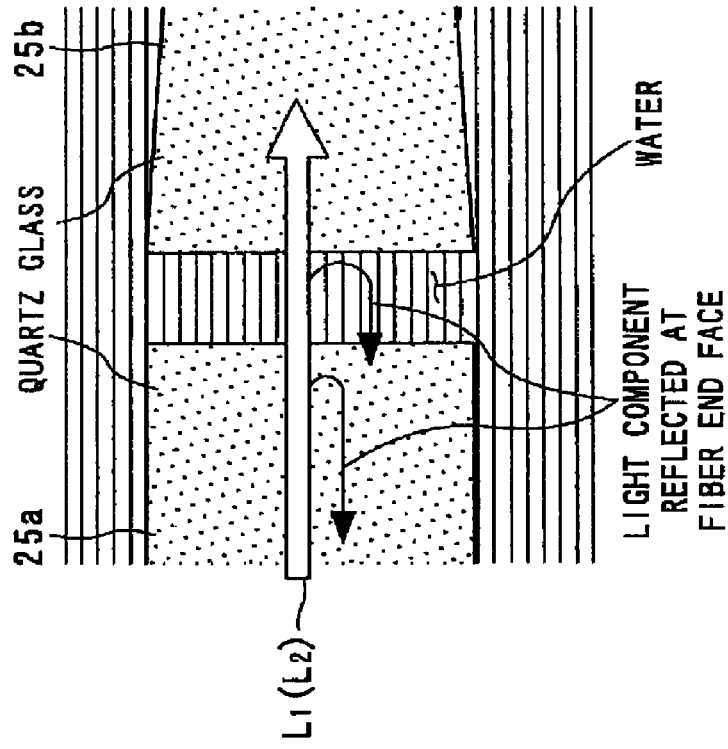
FIGS. 8A and 8B are operational explanatory diagrams of reflection-prevention functions indicating reflection properties of the optical fiber provided to the maintenance apparatus for reactor tubular structures according to the present invention.
Figure 8A:
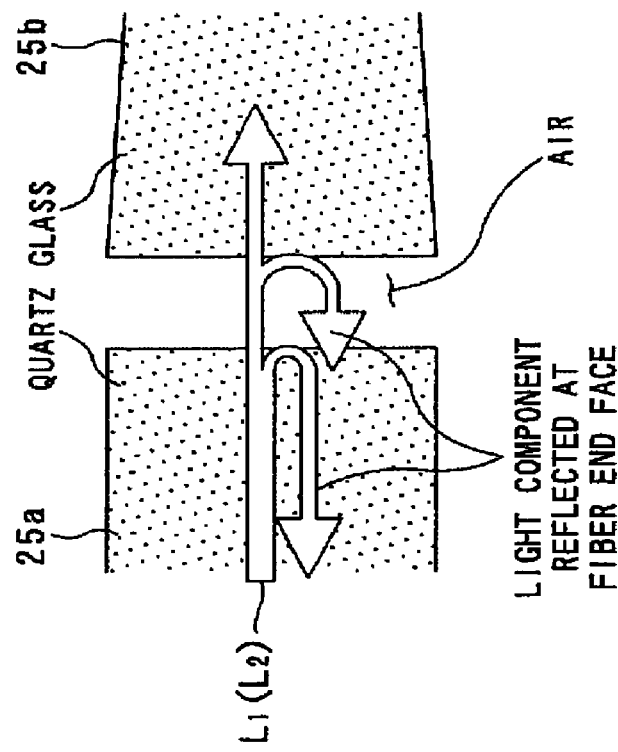

Further, it may be sufficient to simply connect a sealed connector component at the optical fiber 25b side and an unsealed connector component at the optical fiber 25a side underwater. The function for preventing the reflection/scattering of laser light at the connector portion by injecting water into the seam will be described hereunder with reference to FIG. 8.

Reflection of the light of a laser beam (generation laser beam $L_1$ and/or detection laser beam $L_2$) occurs on such a case that there is difference in the refractive index of two mediums through which the laser beam is propagated, and it is known that the greater the difference in refractive index is, the greater the reflection is. Providing that the material of the fiber core of the optical fibers 25a and 25b is quartz glass, the refractive index is approximately 1.46, and in the event that the ambient atmosphere is air having refractive index of 1.00, the reflectivity R of perpendicular incident light is

[Expression 1]

$$R = \left(\frac{1.46 - 1.00}{1.46 + 1.00}\right)^2 = 3.5\% \tag{1}$$

On the other hand, by replacing a portion around the seam between the optical fibers 25a and 25b with a water atmosphere means, the reflectivity is approximately 0.2% from the same calculation because of the refractive index of water of 1.33, and accordingly, the light component reflecting at the fiber end faces can be reduced to 1/10 or lower. Further, an underwater connecting jig 55 such as shown in FIG. 9 and FIG. 10 is used for connecting the optical fibers 25a and 25b under the water.

Figure 9:
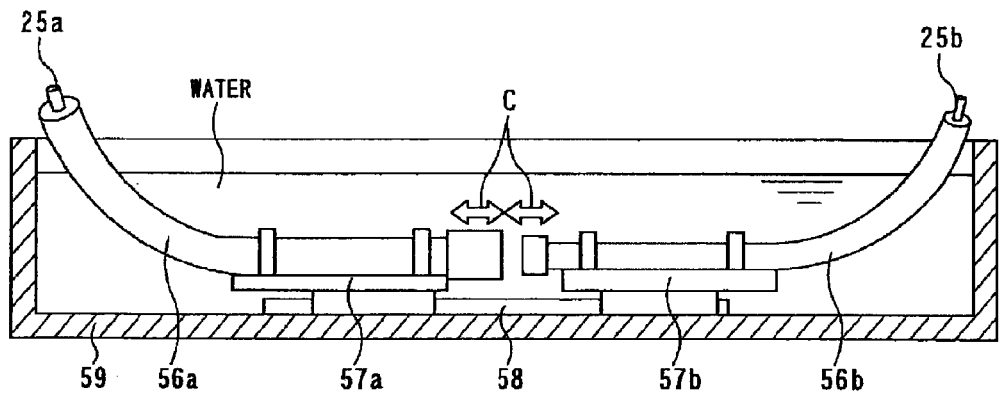
FIG. 9 is a side view illustrating a configuration example of an underwater connection jig for the laser maintenance apparatus according to the present invention.
Figure 10:
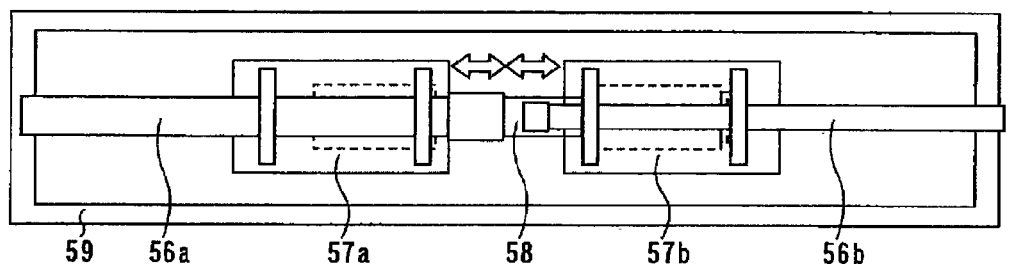
FIG. 10 is a top plan view illustrating of the underwater connection jig shown in FIG. 9.
Figure 11:
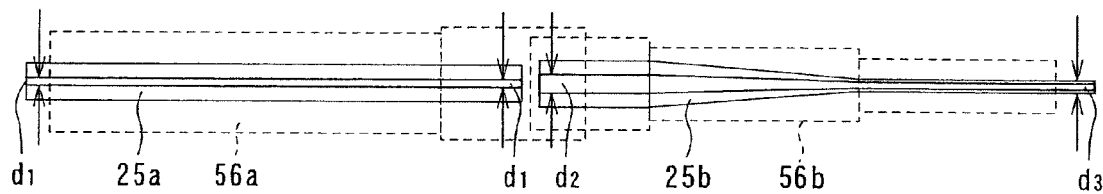
FIG. 11 is an explanatory diagram of optical fiber of the laser maintenance apparatus according to the present invention.

FIG. 9 is a side view of the underwater connecting jig 55, and FIG. 10 is a plan view (top view) of the underwater connecting jig 55. The underwater connecting jig 55 is composed of fixing bases 57a and 57b for fixing optical fiber protective tubes 56a and 56b, through which the optical fibers 25a or 25b are respectively inserted, a slide guide 58 for sliding the fixing bases 57a and 57b in the direction of the arrow C while maintaining the center axes thereof, and a water tank 59 for keeping them in a water environment, thereby enabling the two optical fibers 25a and 25b to be effectively connected under the water.

Comparing the generation laser beam $L_1$ and detection laser beam $L_2$ generated through the optical fibers 25a and 25b, the generation laser beam $L_1$ has greater laser energy. If the laser ultrasonic flaw detection is only considered, a generation laser beam $L_1$ with a relatively low energy will be sufficiently utilized.

The laser maintenance apparatus 10A according to the present embodiment assumes an apparatus which can be also used for preventive maintenance laser technology in addition to the flaw detection, so that device specifications which enable the using of the high laser energy will be needed. According to the prior technology, it can be found that the use of an optical fiber having a core diameter of 1.5 mm or greater is preferably for delivering laser beams for the laser peening, for example.

With the second embodiment as well, the core diameter d1 of the optical fiber 25 is 1.5 mm or greater, from the viewpoint of the nondestructive testing and the sharing of the device in the preventive maintenance. The connector-side core diameter d2 of the optical fiber 25b connected to the optical fiber 25a is preferably such that core diameter d2≧core diameter d1 wherein the connector-side core diameter of the optical fiber 25 is d1, for generation efficiency. Further, a tapered optical fiber 25b, in which the core diameter is smoothly reduced from the input side to the output side, may be used for one of the optical fibers 25a or 25b.

Further, since the optical fibers 25a or 25b may be broken due to bending relatively greater in comparison with the case of the electric cables or the like, the fibers are inserted into optical fiber protecting tubes 56a and 56b, respectively, and used. The optical fiber protecting tubes 56a and 56b guarantee a smallest bending radius, and additionally, a cable tray 13 has a structure capable of mechanically bending at the smallest bending radius, thereby further facilitating handling of the optical fiber 25.

Figure 12:
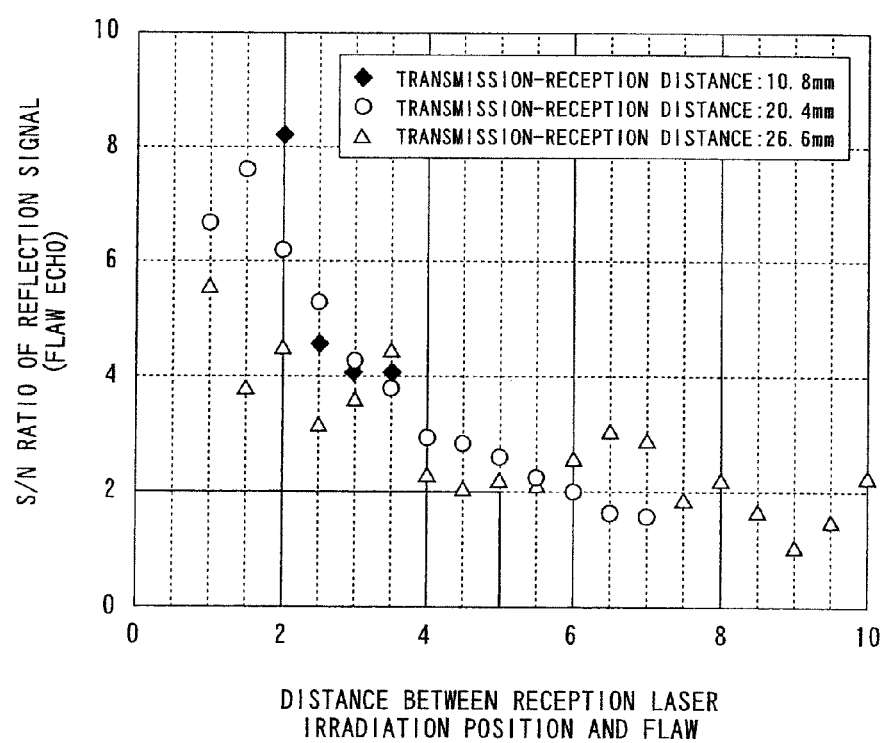
FIG. 12 is an explanatory diagram of the range of laser ultrasonic inspecting illustrating a modification of the second embodiment of the laser maintenance apparatus according to the present invention.
Figure 13:
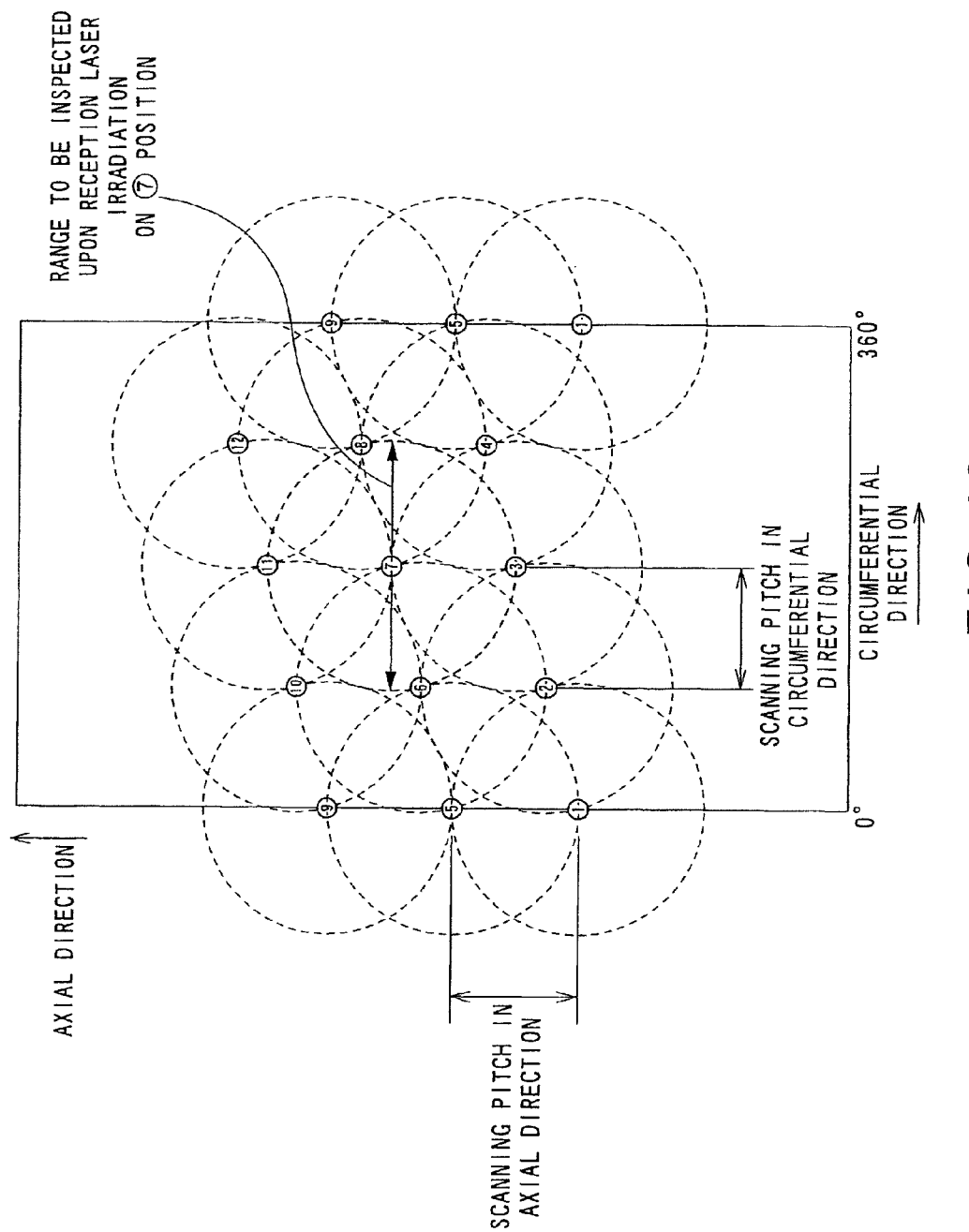
FIG. 13 is an explanatory diagram of the range of laser ultrasonic inspecting illustrating a modification of the second embodiment of the laser maintenance apparatus according to the present invention.

FIG. 12 and FIG. 13 are explanatory diagram illustrating a modification of the second embodiment of the laser maintenance apparatus according to the present invention.

The laser maintenance apparatus 10A illustrated in this modification is a laser maintenance apparatus aiming to obtain test results with high reliability by appropriately setting the operation range of the vertical movement driving mechanism 33 and the rotational driving mechanism 34 in the case of performing laser ultrasonic nondestructive testing of the inner face of a bottom-mounted instrumentation tube 12, which is a reactor tubular structure, provided within a reactor pressure vessel 11.

Detection of defects in laser ultrasonic nondestructive testing uses surface waves propagating concentrically with the irradiation position of the generation laser light $L_1$ as the sound source thereof, and detects reflection signals of the surface waves reflected by the surface opening defects with a detection laser light $L_2$.

According to the experiment data illustrated in FIG. 12 on a test piece simulating the bottom-mounted instrumentation tube 12 with an inner diameter of 9.5 mm for example disposed underwater in a reactor pressure vessel or reactor vessel 11, it has been found that a range approximately 5 mm in radius from the irradiation position of the detection laser light is a region where reflecting signals can be detected with a good signal-to-noise (SN) ratio.

On the other hand, from the viewpoint of the sure detection of the defects on the bottom-mounted instrumentation tube 12, the same position is preferably tested several times (at least two times) in an overlapped manner. In consideration of a case in which the irradiation position of the detection laser light $L_2$ is scanned in the radius direction and axial direction two-dimensionally on the inner surface of the bottom-mounted instrumentation tube 12.

FIG. 13 is an inner surface opened diagram (i.e., the testing surface) of the bottom-mounted instrumentation tube 12, with the symbols 1 through 12 shown with circle marks are irradiation positions of the reception laser light $L_2$ in a certain region, and the dotted lines represent regions in which the reflection signals can be detected with a good SN ratio (i.e., a circuit with a radius of 5 mm entered on the irradiation position). With the scanning pitch of the detection laser light $L_2$ in the circumferential direction and axial direction at 5 mm or less, it can be understood that test data is obtainable at least two or more times regarding an arbitrary point on the testing surface.

Now, providing that the inner diameter of the bottom-mounted instrumentation tube 12 is ID, the circumferential length thereof is πID, and accordingly, with the test data obtaining interval as f (Hz), the scanning speed $V_R$ in the circumferential direction is

[Expression 2]

$$v_R(\text{deg/s}) \leq \frac{360(\text{deg}) \times 5(\text{mm})}{\pi \cdot ID(\text{mm})} \times f(\text{Hz}) \quad (2)$$

Further, since it is sufficient that movement amount in the axial direction following one full circle be 5 mm or less, the scanning speed $V_A$ in the axial direction is

[Expression 3]

$$v_A(\text{mm/s}) \leq \underbrace{\frac{5(\text{mm})}{360(\text{deg})}}_{v_R(\text{deg/s})} = \frac{25(\text{mm}^2)}{\pi \cdot ID(\text{mm})} \times f(\text{Hz}) \quad (3)$$

Setting the scanning speed within the range of the scanning speeds $V_R$ and $V_A$, and taking into consideration the overlapping rate of data obtaining, the amount of time necessary for testing, operation limitations of the scanning mechanism, and the like, the highly-reliable test results, in which data is obtained multiple times from the same position, can be obtained.

Third Embodiment

Figure 14:
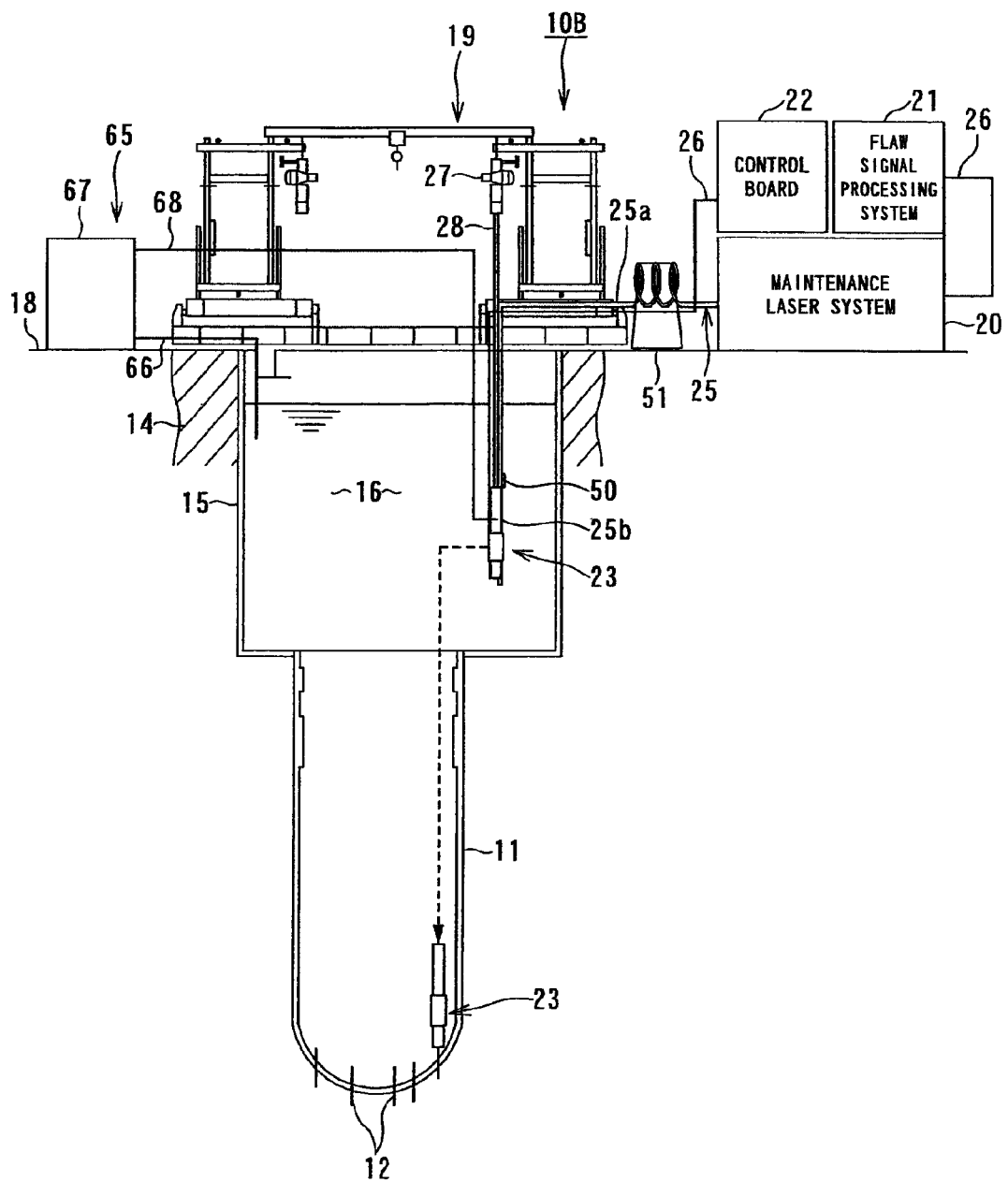
FIG. 14 is an overall configuration diagram illustrating a third embodiment of the laser maintenance apparatus according to the present invention.

FIG. 14 is an overall configuration diagram illustrating a third embodiment of the laser maintenance apparatus according to the present invention.

The laser maintenance apparatus 10B for reactor tubular structures illustrated in this embodiment is a laser maintenance apparatus of which the object is to improve reliability of data obtaining in the case of performing laser ultrasonic nondestructive testing on the inner surface of an bottom-mounted instrumentation tube 12, and accordingly, the components which are the same as with the laser maintenance apparatus 10 according to the first embodiment will be denoted with the same reference numerals, and description thereof will be omitted herein.

With the laser maintenance apparatus 10B shown in FIG. 14, the generation laser beam $L_1$ and detection laser beam $L_2$ necessary for the laser ultrasonic flaw detection are generated through the optical fiber 25, and are ultimately irradiated on the inner surface of the bottom-mounted instrumentation tube 12 by being propagated through the underwater atmosphere from the laser ultrasonic irradiation head 35 of the insertion tube 32. While the reactor coolant 16 is clean pure water, in the case that some kinds of inclusion is floating in the optical path, in a worst-case scenario, one of both of the generation laser beam $L_1$ and detection laser beam $L_2$ may be reflected and/or scattered by the floating matter before being irradiated on the inner surface of the bottom-mounted instrumentation tube 12, and test data cannot be obtained.

The maintenance apparatus 10B according to the third embodiment has a circulatory cleaning device 65 serving as clean water supplying means for forcibly circulating reactor coolant. This circulatory cleaning device 65 has a first water tube 66 for pumping up the reactor coolant 16, a pump system 67 with a filter for removing inclusions and discharging to a pump output side, and a second water tube 68 connected to the output of the pump system 67 with a filer and also connected to the insertion tube 32 of the transporting/scanning mechanism 23 via the cable tray.

The clean water discharged form the second water tube 68 passes between the insertion tube 32 and the optical fiber 25, and ultimately is discharged from the laser irradiation opening of the laser ultrasonic irradiation head 35.

By the provision of the circulatory cleansing device 65 for reactor coolant, the water in the underwater atmosphere optical paths for the generation laser beam $L_1$ and detection laser beam $L_2$ is replaced with clean water to thereby ensure the integrity of the optical paths of the laser beams.

With this laser maintenance apparatus 10B, test data can be normally obtained in the case that there is some kinds of floating particles or materials in the water atmosphere on the inner surface of the bottom-mounted instrumentation tube 12. Now, assuming the using of the reactor coolant 16 as the clean water, the clean water can be supplied from a clean water tank or the like disposed separately, as a matter of course. In this case, increase in the reactor coolant level must be kept in mind.

Figure 15:
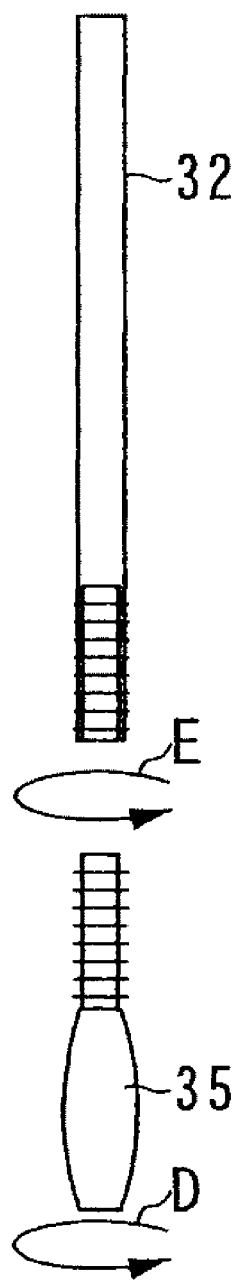
FIG. 15 illustrates a modification of the third embodiment of the laser maintenance apparatus according to the present invention, and is a conceptual diagram illustrating an attachment example of the laser irradiation head.

FIG. 15 illustrates a modification of a third embodiment of the laser maintenance apparatus according to the third embodiment.

The laser maintenance apparatus 10B illustrated in this modification is a laser maintenance apparatus with high structural reliability, in which loss of the reactor insertion parts and the like does not occur.

The insertion tube 32 and the laser ultrasonic irradiation head 35 shown in FIG. 15 are inserted into the inner face of the bottom-mounted instrumentation tube 12.

This laser maintenance apparatus 10B serves as a laser nondestructive test device for the bottom-mounted instrumentation tube 12, and a great part of the apparatus also serves as a flaw detection device and a preventive maintenance device using laser. With an arrangement wherein the maintenance apparatus 10B is to be combined with other laser preventive maintenance technology, it is easy to consider the sharing of the insertion tube 32, but the laser ultrasonic irradiation head 35 is preferably to be exchangeable from the viewpoint of differences in irradiation conditions between the laser-ultrasonics and the laser preventive maintenance and so on.

A simple and easy way to arrange for the laser ultrasonic irradiation head 35 to be detachably mounted to the insertion tube 32 is to screw the laser ultrasonic irradiation head 35 to the insertion tube 32. In this case, there is the concern that the screwed portion might loosen due to rotation movements at the inner surface of the bottom-mounted instrumentation tube 12, and the laser ultrasonic irradiation head 35 is left in the bottom-mounted instrumentation tube 12.

With the modification of the laser maintenance apparatus 10B shown in FIG. 15, the rotational direction D of the laser ultrasonic irradiation head 35 in the bottom-mounted instrumentation tube 12 is fixed to one-way use, and the screwing direction of the laser ultrasonic irradiation head 35 as to the insertion tube 32 is matched with the tightening direction E by the rotational movement. Thus, the laser ultrasonic irradiation head 35 can be exchanged in accordance with the use thereof, and also the transporting/scanning mechanism 23 of the maintenance apparatus 10B, in which there is no danger of the laser ultrasonic irradiation head 35 coming loose, can be realized.

Fourth Embodiment

Figure 16:
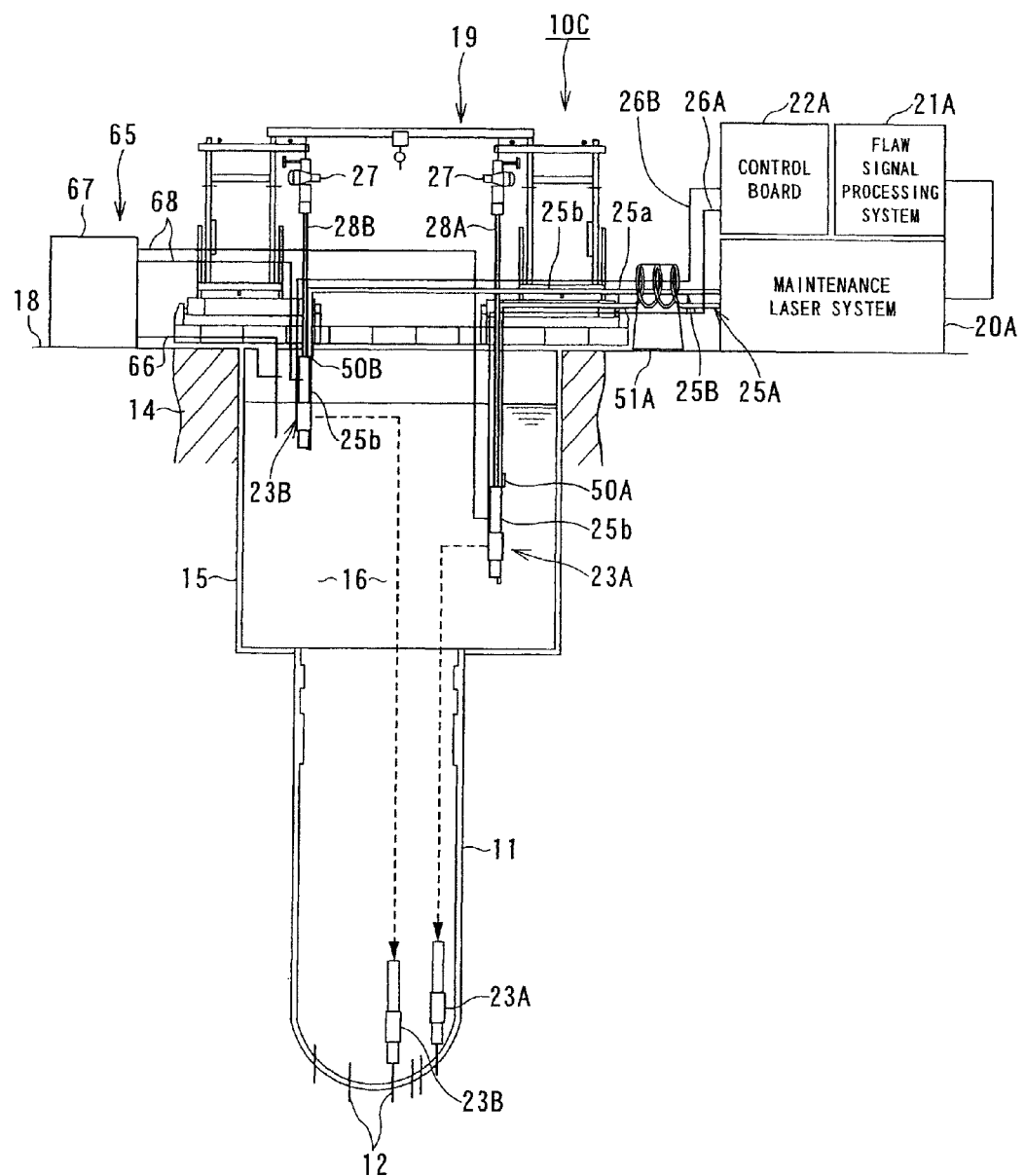
FIG. 16 is an overall configuration diagram illustrating a fourth embodiment of the laser maintenance apparatus according to the present invention.

FIG. 16 is an overall configuration diagram illustrating a fourth embodiment of the laser maintenance apparatus according to the present invention.

The laser maintenance apparatus 10C for reactor tubular structures illustrated in this embodiment is a laser maintenance apparatus for efficiently realizing laser ultrasonic nondestructive testing and laser preventing maintenance of the inner surface of an bottom-mounted instrumentation tube 12. Components which are the same as those of the laser maintenance apparatus 10 (10A, 10B) according to the first through third embodiments will be denoted with the same reference numerals, and description thereof will be omitted herein.

The operations of the laser maintenance apparatus 10C shown in FIG. 16 are the same as those of the laser maintenance apparatus 10 (10A, 10B) according to the first through third embodiments.

The laser maintenance apparatus 10C for reactor tubular structures has a flaw detection signal processing system 21A including a plurality of systems, a plurality of transporting/scanning mechanisms 23A and 23B, an control board 22A including a plurality of systems for operating and monitoring each of the transporting/scanning mechanisms 23A and 23B, a maintenance laser system 20A capable of optically splitting the emitted generation laser beam $L_1$ and detection laser beam $L_2$ and outputting the output light form multiple systems, one or more optical fibers 25A and 25B for generating the output light from the laser system 20A to each of the transporting/scanning mechanisms 23A and 23B, and wires (cables) 28A and 28B for suspending the transporting/scanning mechanisms 23A and 23B from the work carriage 19.

According to the configuration of the laser maintenance apparatus 10C as shown in FIG. 16, a plurality of the devices in the reactor proceed the works in parallel by using a single maintenance laser system 20A and a single work carriage 19. With this laser maintenance apparatus 10C, all of the transporting/scanning mechanisms 23A and 23B can be used for the laser ultrasonic nondestructive testing, but the feature of the laser maintenance apparatus 10C for reactor tubular structures has an ability to achieve both laser flaw detection technology and laser maintenance technology, and therefore, a portion or all the maintenance apparatus 10C may be used for both the laser ultrasonic nondestructive testing and laser preventive maintenance.

Fifth Embodiment

Figure 17:
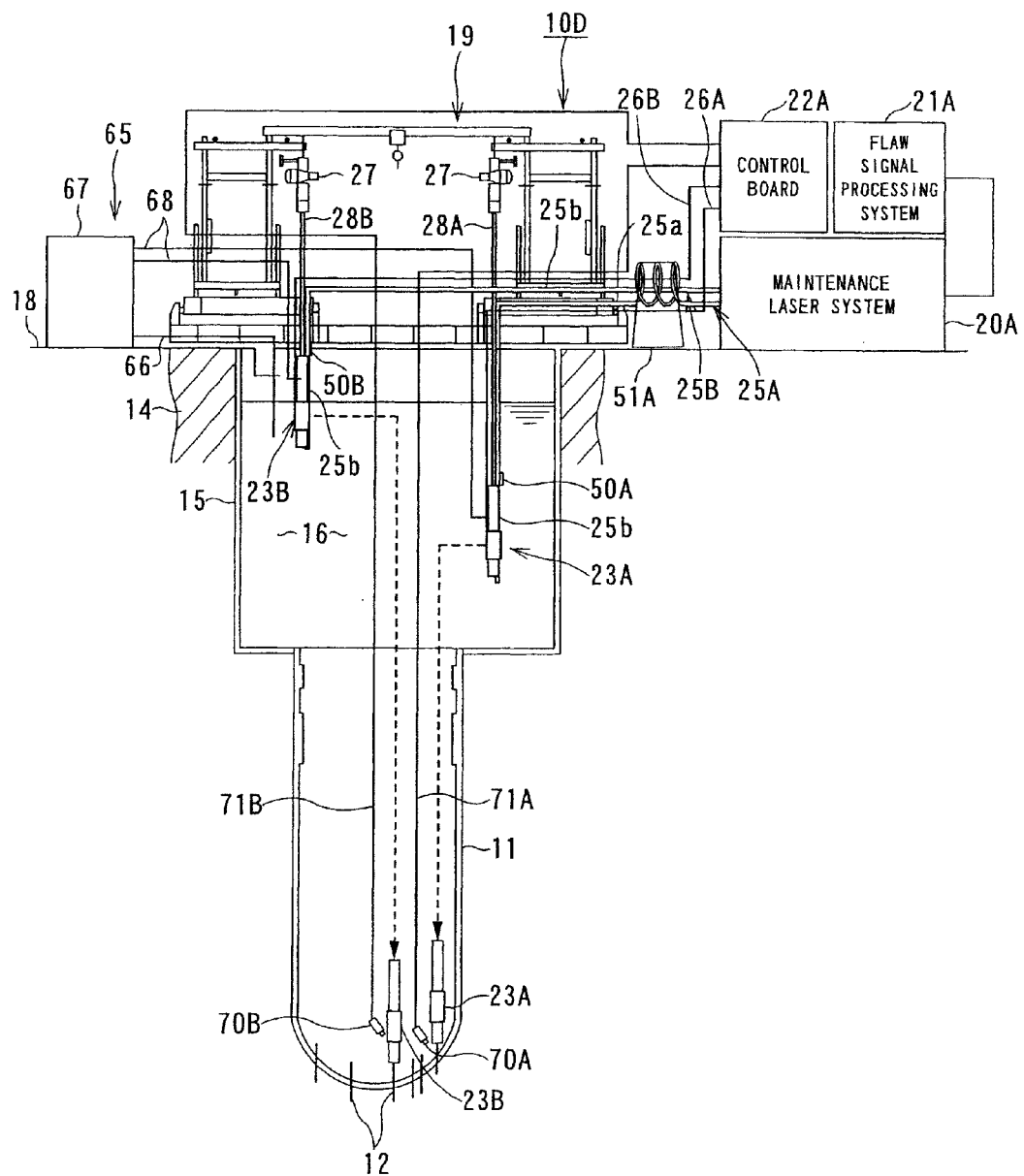
FIG. 17 is an overall configuration diagram illustrating a fifth embodiment of the laser maintenance apparatus according to the present invention.

FIG. 17 is an overall configuration diagram illustrating a fifth embodiment of the laser maintenance apparatus according to the present invention.

The laser maintenance apparatus 10D illustrated in this embodiment is a laser maintenance apparatus for more efficiently realizing the laser ultrasonic nondestructive testing and the laser preventing maintenance of the inner surface of an bottom-mounted instrumentation tube 12. Components which are the same as with the laser maintenance apparatus 10C according to the fourth embodiment will be denoted with the same reference numerals, and description thereof will be omitted herein.

The laser maintenance apparatus 10D shown in FIG. 17 has reactor TV cameras 70A and 70B serving as observation means for observing the operating state of the laser maintenance apparatus 10D provided in the reactor pressure vessel 11, the reactor TV cameras 70A and 70B confirming the state in the reactor around the bottom-mounted instrumentation tubes 12, seating of the transporting/scanning mechanism 23A or 23B on the bottom-mounted instrumentation tubes 12, operating state of the vertical movement driving mechanism 33, the rotational driving mechanism 34, the insertion tube 32, and the laser irradiation head 35 (see FIG. 3), which are disposed inside the transporting/scanning mechanism 23A or 23B.

With the laser maintenance apparatus 10D according to the fifth embodiment, reactor TV cameras 70A and 70B are provided as observation means, the output images of the reactor TV cameras 70A and 70B are sent to the control board 22A via image cables 71A and 71B, and observation is enabled at display means, not shown, near the control board 22A, whereby even in the case of troubles around the transporting/scanning mechanisms 23A and 23B of the laser maintenance apparatus 10D or on the laser maintenance apparatus 10D, the trouble can be speedily detected, thus realizing more efficient laser ultrasonic nondestructive testing and laser preventing maintenance of the inner surface of the bottom-mounted instrumentation tube 12.

Embodiments of the laser irradiation head 35 as laser irradiation device for the laser maintenance apparatus according to the present invention of the structure mentioned above will be further described hereunder with reference to the drawings or diagrams attached.

Figure 18:
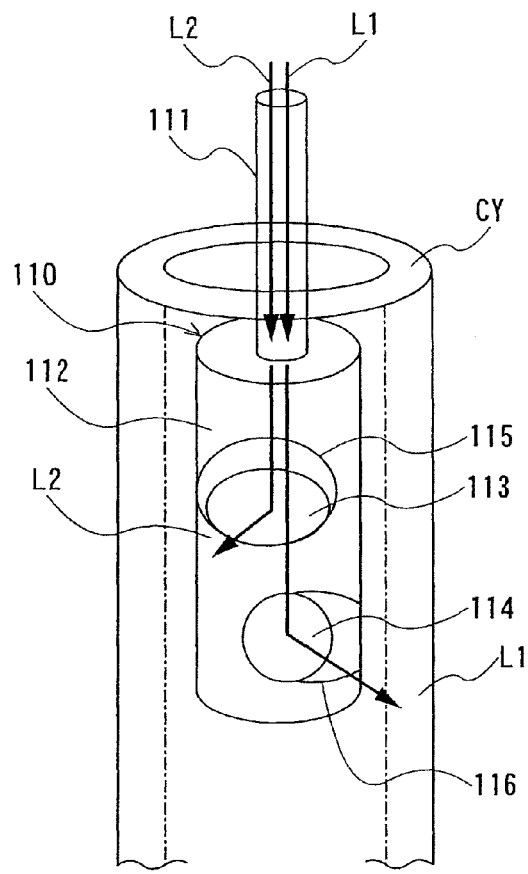
FIG. 18 is a schematic diagram illustrating a first embodiment of an irradiation head to be used in a laser irradiation device relating to the present invention.

FIG. 18 is a schematic diagram illustrating an irradiation head corresponding to the laser irradiation head 35 in FIG. 3, for example, to be used in a first embodiment of a laser irradiation device relating to the present invention.

The laser irradiation device relating to the present invention is applicable for use in testing a crack or the like, and an example is given of a inner surface of a cylinder portion CY of a narrow tube or the like which is contained in a nuclear reactor.

The irradiation head 110 which is inserted into the cylinder portion CY provides an optical fiber 111 and an optical system container 112.

Further, with the optical system container 112, along the axis direction of the cylinder portion CY, and at a distance from each other, a first optical element 113 constituting a dichroic mirror and a second optical element 114 constituting a mirror are provided in the order toward the direction in which the laser light advances.

The first optical element 113 and the second optical element 114 are arranged in a position so that the irradiation positions of the laser light are shifted apart from each other along the circumferential direction of the optical system container 112. It is desirable for the angle θ of the positions for these elements to be shifted apart to be set within the range of 30°≦θ≦60 degrees.

With an irradiation head 110 having such a configuration, in the generation laser light L1 and the detection laser light L2 which are generated from the optical fiber 111, the detection laser light L2 is reflected by the first optical element 113, and irradiates the cylinder portion CY via the first outlet window 115.

Furthermore, the generation laser light L1 transits the first optical element 113, is reflected by the second optical element 114, and irradiates the cylinder portion CY via the second outlet window 116.

With the first optical element 113 which constitutes a dichroic mirror, only the detection laser light L2 is reflected, and the generation laser light L1 is allowed to transit. The first optical element 113 also has a curved surface, in which when the reflected detection laser light L2 is returned from the cylinder portion CY of the test object, the returned detection laser light L2 can be irradiated into the optical fiber 111 on the same path as the outward path, i.e. return path.

Furthermore, the second optical element 114 constituting a mirror also has a curved surface for focusing, and then irradiating, the generation laser light L1 on the cylinder portion CY.

Figure 19:
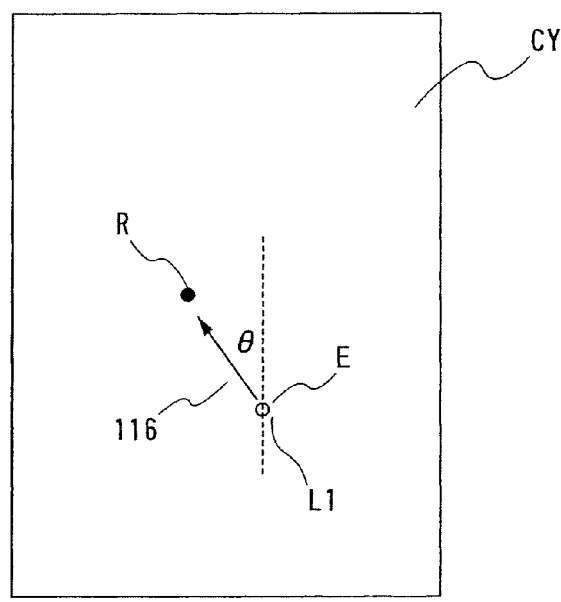
FIG. 19 is a diagram showing the behavior of generating ultrasound with the first embodiment as shown in FIG. 18.

On the other hand, the generation laser light L1 which irradiates the cylinder portion CY is focused on the sending (generating) point E, as shown in FIG. 19, and generate ultrasonic waves here, and a direct surface wave 116 is generated to the receiving point R.

This receiving point R is the irradiation position of the detection laser light L2 which has been shifted toward the axis direction of the cylinder portion CY, and faces the circumferential direction only by an angle θ from the generation laser light L1 shown in FIG. 18.

FIG. 20 through FIG. 23 are diagrams showing the behavior of the ultrasonic waves generated by the generation laser light L1 which is excited in the cylinder portion CY, in a case of detecting cracks and measuring the depth of the crack in the cylinder portion CY.

Figure 20:
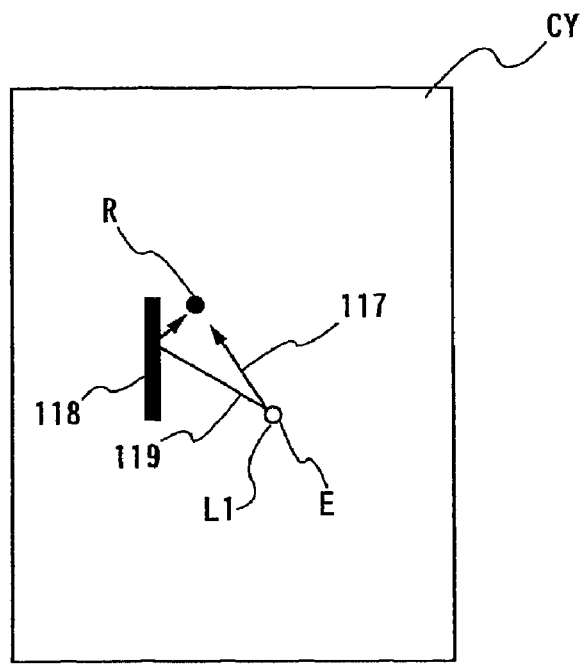
FIG. 20 is a diagram showing the behavior of generating ultrasound with the first embodiment as shown in FIG. 18, in the case that a crack has occurred along the axis direction of the cylindrical portion.
Figure 22:
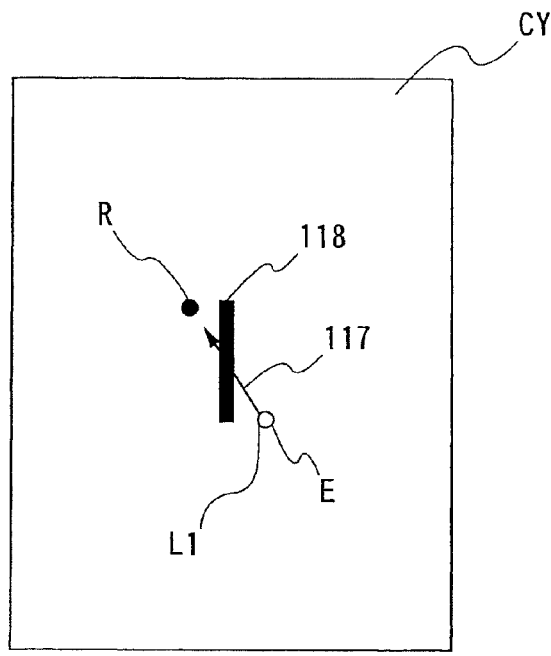
FIG. 22 is a diagram showing the behavior of generating ultrasound with the first embodiment as shown in FIG. 18, in the case that a crack has occurred along the axis direction of the cylindrical portion, and the depth of such crack is to be measured.

In these figures, FIG. 20 and FIG. 22 are enlarged plan views of the cylinder portion CY which is a test object, in which a crack 118 is generated along the axial direction of the cylinder portion CY.

Figure 21:
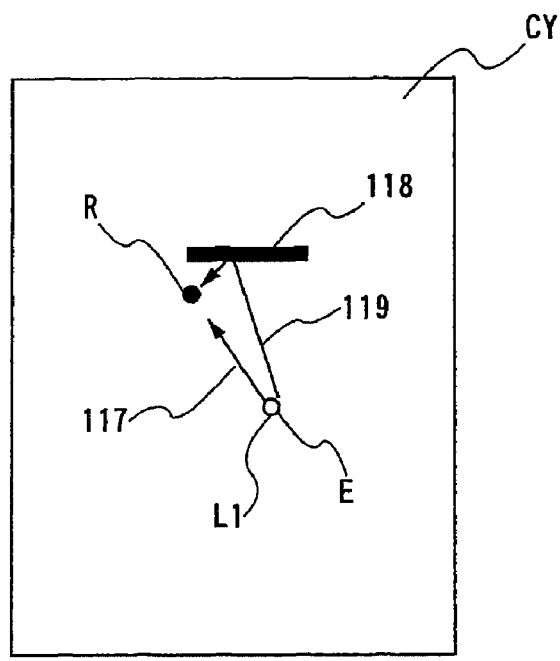
FIG. 21 is a diagram showing the behavior of generating ultrasound with the first embodiment as shown in FIG. 18, in the case that a crack has occurred along the transverse direction as to the axis direction of the cylindrical portion.
Figure 23:
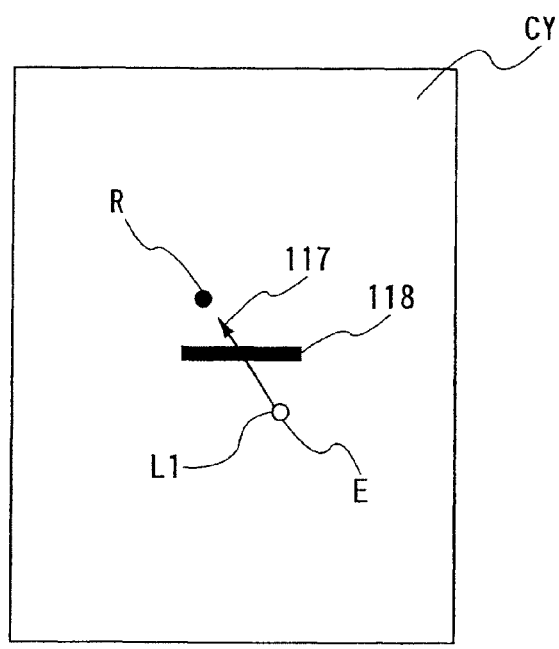
FIG. 23 is a diagram showing the behavior of generating ultrasound with the first embodiment as shown in FIG. 18, in the case that a crack has occurred along the transverse direction as to the axis direction of the cylindrical portion, and the depth of such crack is to be measured.

FIG. 21 and FIG. 23 are enlarged plan views of the cylinder portion CY which is a test object, in which a crack 118 is generated along the transverse direction to the axial direction of the cylinder portion CY.

As shown in FIG. 20, when the crack 118 is generated along the axial direction of the cylinder portion CY, the generation laser light L1 irradiates at the generating point E and generates ultrasonic waves, which are detected as direct surface waves 117 and reflection waves 119 at the receiving (detecting) point R.

Furthermore, as shown in FIG. 21, when the crack 118 is generated along the transverse direction to the axial direction of the cylinder portion CY, the generation laser light L1 irradiates the transmitting point E and generates ultrasonic waves, which are detected as direct surface waves 117 and reflection waves 119 as mentioned above at the receiving point R.

In FIG. 22 and FIG. 23, the transmitting point E and the receiving point R are arranged as shown in FIGS. 22 and 23, and because both the points E and R are in positions sandwiching the crack 118, the depth of the crack 118 can be measured.

Thus, according to this embodiment of the present invention, the reflecting position of the detection laser light of the first optical element 113 and the reflecting position of the generation laser light of the second optical element 114 are arranged in positions which are shifted by the angle θ along the circumferential direction of the optical system container 112. Therefore, the position and depth of the crack 118 generated in the axial direction and the circumferential direction of the inner surface of the cylindrical portion CY can be easily and accurately measured.

Furthermore, the crack is tested with a surface wave which is generated in the angle θ direction, and therefore, the generating distance becomes shorter and noise interference can be prevented.

Figure 24:
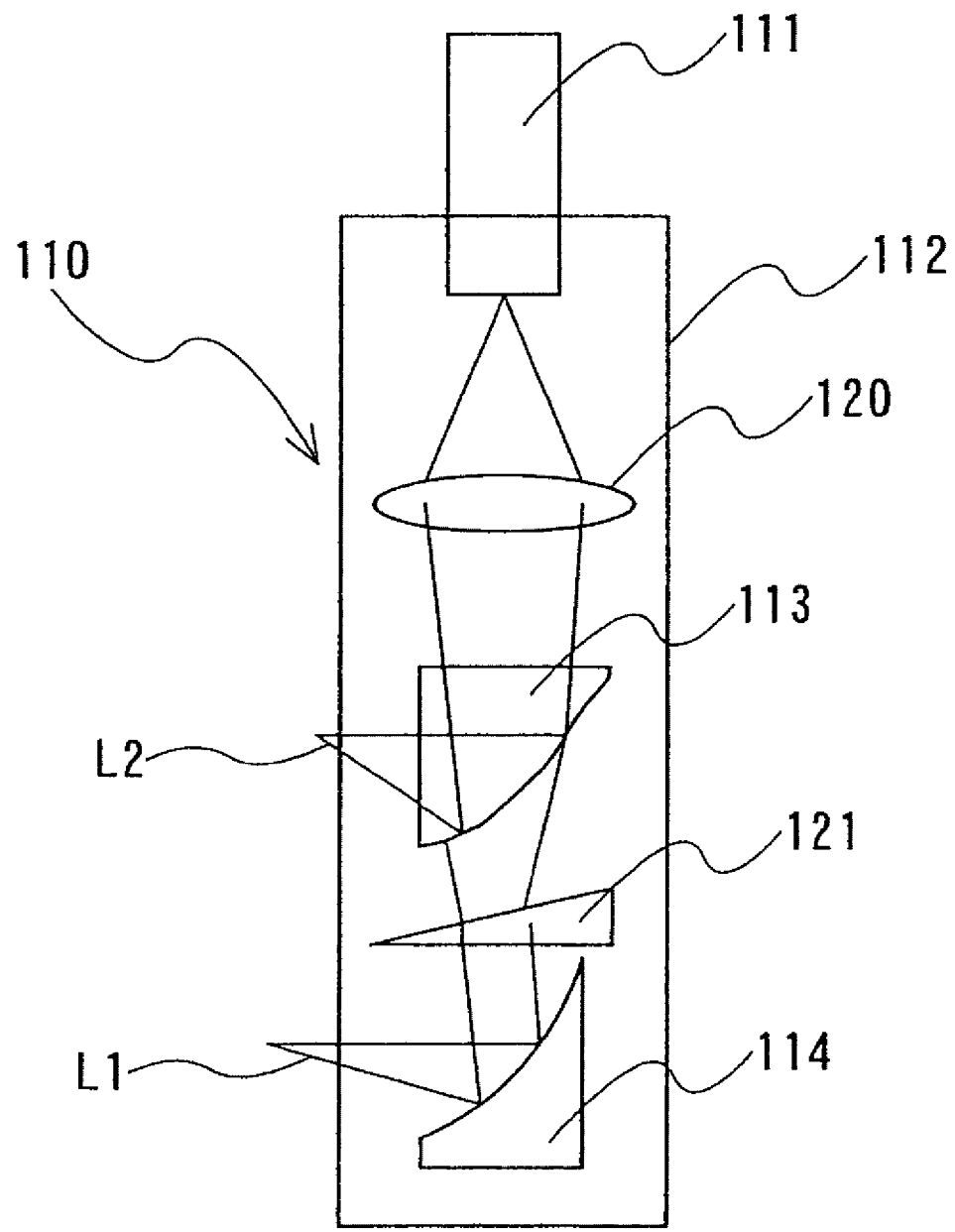
FIG. 24 is a schematic diagram illustrating a second embodiment of an irradiation head to be used in a laser irradiation device relating to the present invention.

FIG. 24 is a schematic diagram illustrating a second embodiment of an irradiation head to be used in a laser irradiation device relating to the present invention.

The components which are the same as those of the first embodiments have the same reference numerals, and redundant descriptions will be hence omitted herein.

The laser irradiation device relating to the present embodiment is added with a focusing lens 120 and a wedge plate 121 as a light path altering element in the optical system container 112 of the irradiation head 110.

The generation laser L1 and the detection laser L2 which are generated in the optical fiber 111 is discharged from the optical fiber 111 with a specified divergence (NA: numerical aperture number).

Thus, in the case of injecting the laser light into the optical element directly from the optical fiber 111, the reflective surface of the first optical element 113 and the second optical element 114 must be made larger.

When the generation laser light L1 passes through the first optical element 113 and is injected into the second optical element 114, the light path may be shifted when passing through the first optical element 113.

The present embodiment has focused on such points, and by providing a focusing lens 120 between the optical fiber 111 and the first optical element 113, making small the reflective surface of the first optical element 113 and the second optical element 114, providing a wedge plate 121 between the first optical element 113 and the second optical element 114, and correcting the shifted the light path, the entire irradiation head 110 can be made compact, and a crack in a cylinder can be accurately detected with the correct light path.

Figure 25:
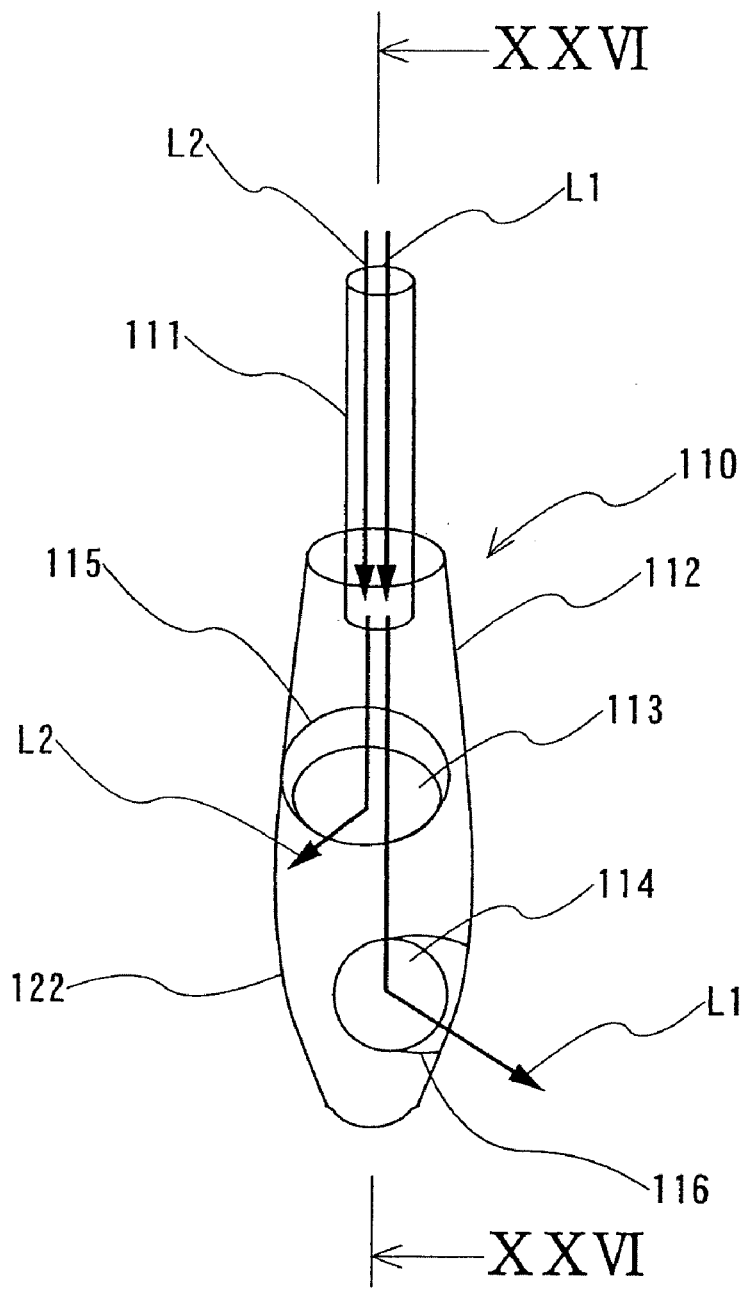
FIG. 25 is a schematic diagram illustrating a third embodiment of an irradiation head to be used in a laser irradiation device relating to the present invention.
Figure 26:
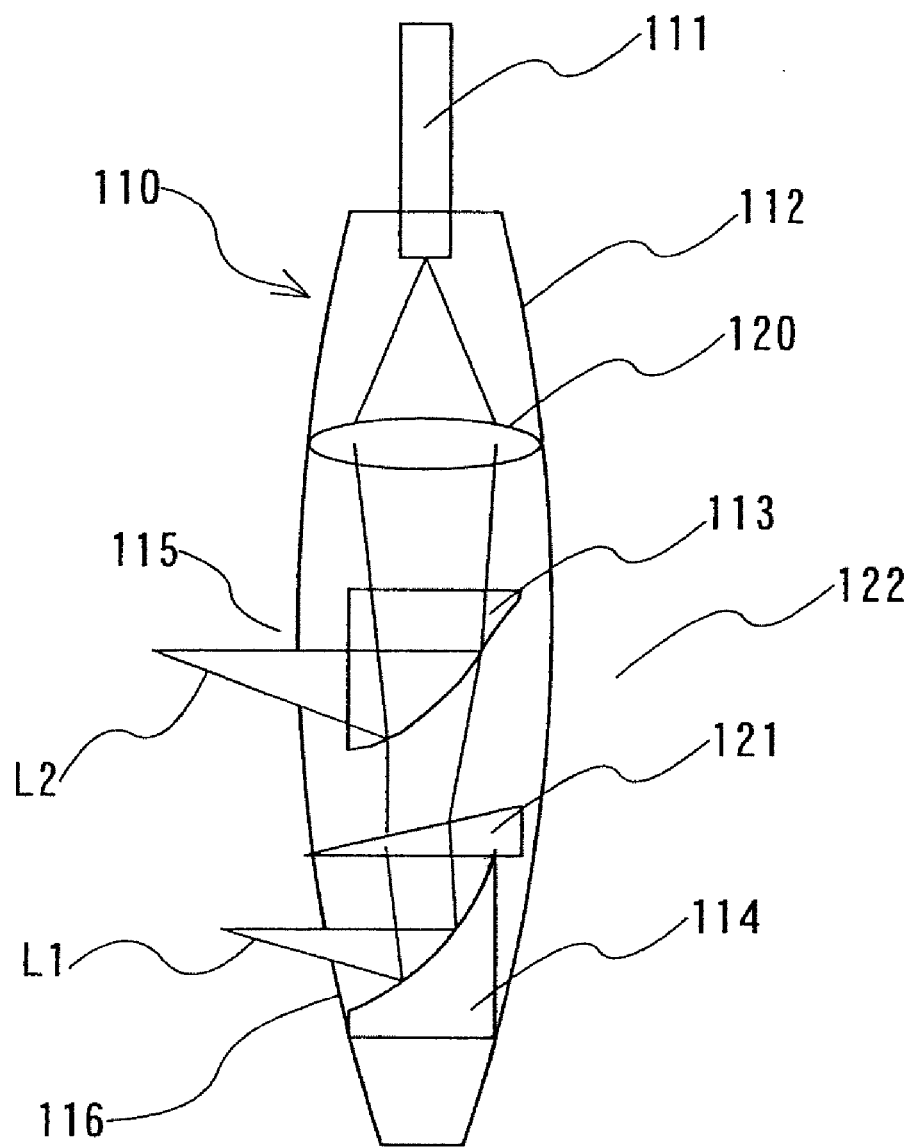
FIG. 26 is a cross-sectional view of FIG. 25 in a cross-section from the view direction of XXVI-XXVI.

FIG. 25 and FIG. 26 are schematic diagrams illustrating a third embodiment of an irradiation head to be used in a laser irradiation device relating to the present invention, in which the components which are the same as those of the first and second embodiments will have the same reference numerals, and redundant descriptions will be omitted herein.

The laser irradiation device relating to the present embodiment has the optical system container 112 of the irradiation head 110 formed in a spindle shape, providing a convexity curved surface 122 so as to direct the middle position to the outer side.

In the case of the optical system container 112 being a cylindrical shape, when the test object position has minute curves or contractions, the irradiation head 110 cannot move well.

This embodiment was conceived in consideration of such points, and the optical system container 112 of the irradiation head 120 is hence formed in a spindle shape to easily move the irradiation head 110.

Accordingly, with the present embodiment, inserting or removing the irradiation head 110 from the cylinder portion CY can be performed easily, and working efficiency can be further improved.

Figure 27:
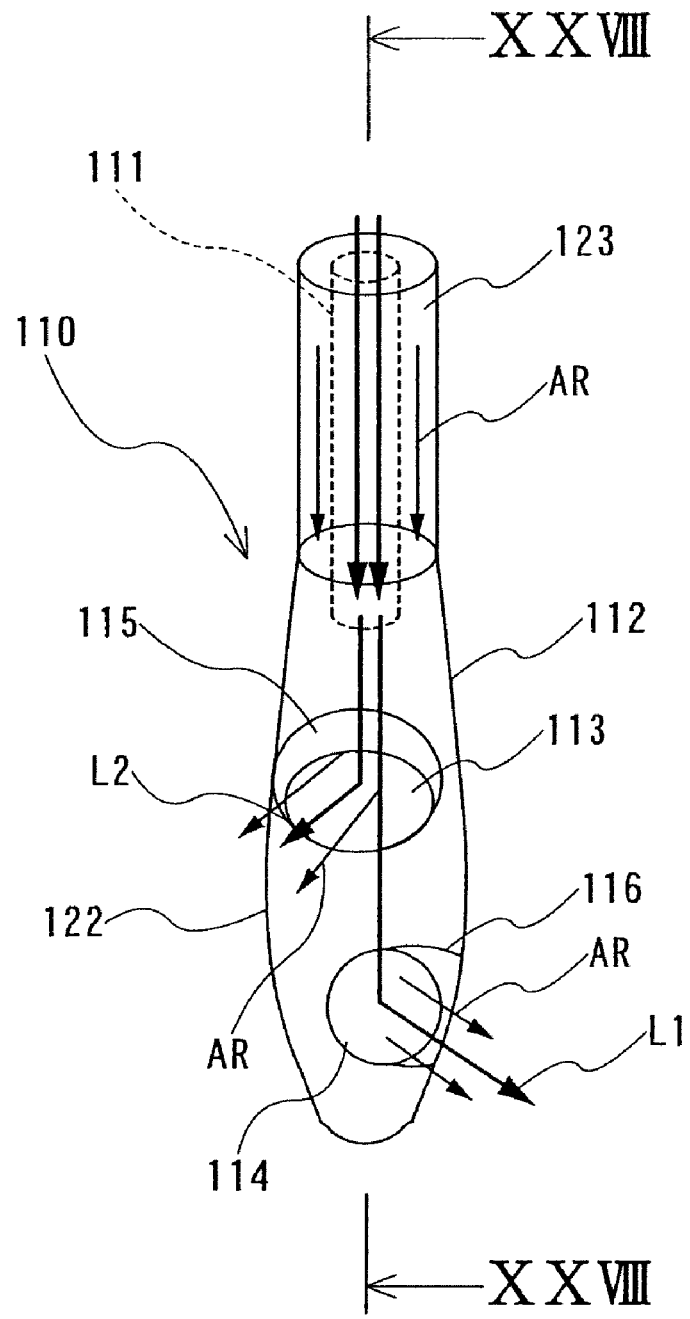
FIG. 27 is a schematic diagram illustrating a fourth embodiment of an irradiation head to be used in a laser irradiation device relating to the present invention.
Figure 28:
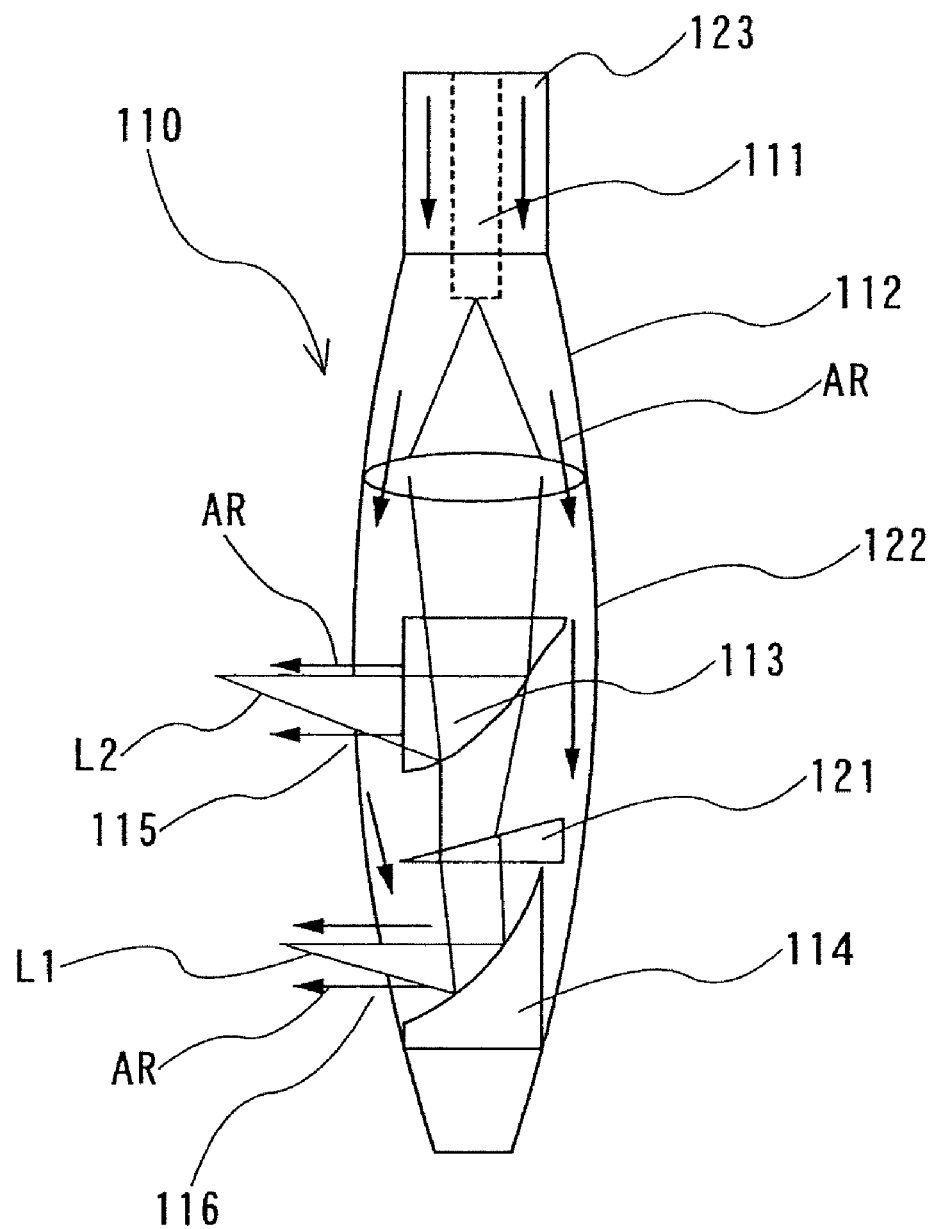
FIG. 28 is a cross-sectional view of FIG. 27 in a cross-section from the view direction of XXVIII-XXVIII.

FIG. 27 and FIG. 28 are schematic diagrams illustrating a fourth embodiment of an irradiation head to be used in a laser irradiation device relating to the present invention, in which the components which are the same as those of the first, second, and third embodiments have the same reference numerals, and redundant descriptions will be omitted herein.

The laser irradiation device relating to the present embodiment provides the optical system container 112 of the irradiation head 110 with a flow path 123, and the water flows along this flow path 123 in the direction of the arrow AR.

The generation laser light L1 has a relatively high energy, and accordingly, when the cylinder portion CY is irradiated, dust and dross are generated from the surface, which may give adverse effects such as causing of a disturbance to the light path of the laser light.

The present embodiment was conceived in consideration of such points, and accordingly, a flow path 123 is provided in the optical system container 112 concentric with the optical fiber 111, and the water flows along this flow path 123 in the direction of the arrow AR so as to remove the foreign particles such as dust from the optical system container 112 and flush them out of the first outlet window 115 and the second outlet window 116.

Thus, the present embodiment provides a flow path 123 on the optical system container 112, the water flows in this flow path 123, and foreign particles such as dust are removed. Therefore, a light path can be maintained in a stable state without giving disturbance to the light path of the laser light.

Figure 29:
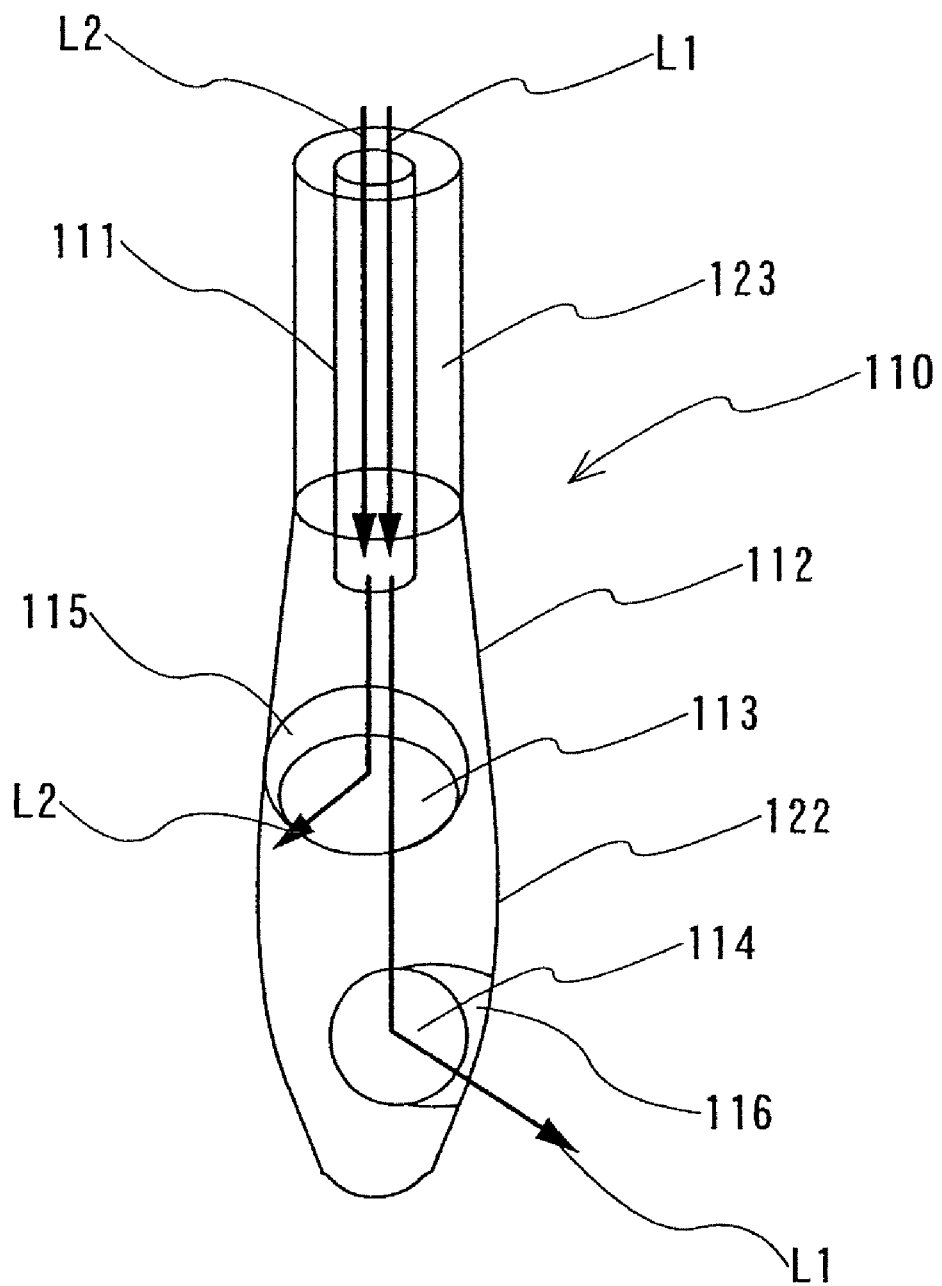
FIG. 29 is a schematic diagram illustrating a fifth embodiment of an irradiation head to be used in a laser irradiation device relating to the present invention.

FIG. 29 is a schematic diagram illustrating a fifth embodiment of an irradiation head to be used in a laser irradiation device relating to the present invention, in which the components which are the same as those of the first through fourth embodiments have the same reference numerals, and redundant descriptions will be omitted herein.

In the laser irradiation device relating to the present embodiment, the optical system container 112 of the irradiation head 110 is formed from an acoustic absorption material 124.

In the case of using the irradiation head 110 in an ultrasonic conductive environment such as water, sound wave oscillation in water can be generated by the irradiation to the test object positions of the generation laser light L1 and the detection laser light L2. This sound wave oscillation is an adverse effect causing disturbance to the testing as noise.

The present embodiment was conceived in consideration of such points, and the optical system container 112 is manufactured with an acoustic absorption material 124. The sound waves vibrations generated in the case of irradiation of the laser light onto the cylinder portion CY are absorbed.

Thus, according to configuration of the present embodiment, the optical system container 112 is manufactured with an acoustic absorption material 124, and the sound wave vibrations are absorbed, so that the laser light can be irradiated on the cylinder portion CY in a stable state, and a crack on the cylinder portion CY can be accurately detected.

It should be noted that with the present embodiment, the optical system container 112 has been fabricated with an acoustic absorption material 124, but it should be not limited to this example, and the acoustic absorption material 124 may be coated onto the optical system container 112.

Figure 30:
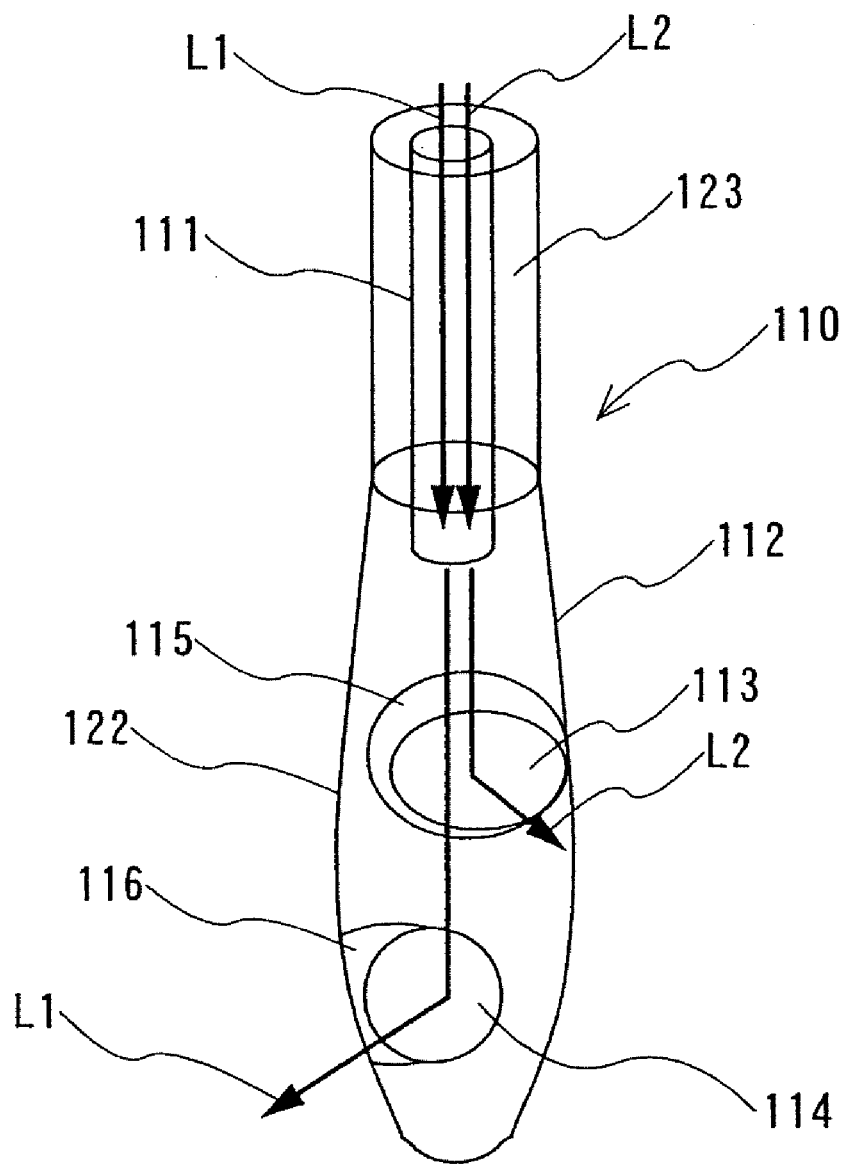
FIG. 30 is a schematic diagram illustrating a sixth embodiment of an irradiation head to be used in a laser irradiation device relating to the present invention.

FIG. 30 is a schematic diagram illustrating a sixth embodiment of an irradiation head to be used in a laser irradiation device relating to the present invention, in which the components which are the same as those of the first through fourth embodiments have the same reference numerals, and redundant descriptions will be omitted herein.

The laser irradiation device relating to the present embodiment changes in the reflective position of the first optical element 113 and the reflective position of the second optical element 114 so that the irradiation position of the detection laser light L2 which is irradiated through the first optical element 113 to the cylindrical portion CY, and the irradiation position of the generation laser light L1 which is irradiated through the second optical element 114 to the cylindrical portion CY face each other so as to be laterally symmetric with respect to the axial direction of the optical system container 112.

In the case of causing a crack in position in parallel with the paths connecting the irradiation position of the generation laser light L1 and the irradiation position of the detection laser light L2, it is possible to detect the crack, but is difficult to measure the depth of the crack.

The present embodiment was conceived in consideration of such points, in which the reflecting position of the first optical element 113 and the reflecting position of the second optical element 114 are arranged so as to be in the lateral symmetric positions with respect to the axial direction of the optical system container 112.

Accordingly, with the configuration of the present embodiment, the reflecting position of the first optical element 113 and the reflecting position of the second optical element 114 are arranged to be in the lateral symmetric positions with respect to the axial direction of the optical system container 112, and therefore, the depth of a crack occurring on the cylindrical portion CY can be accurately measured.

Figure 31:
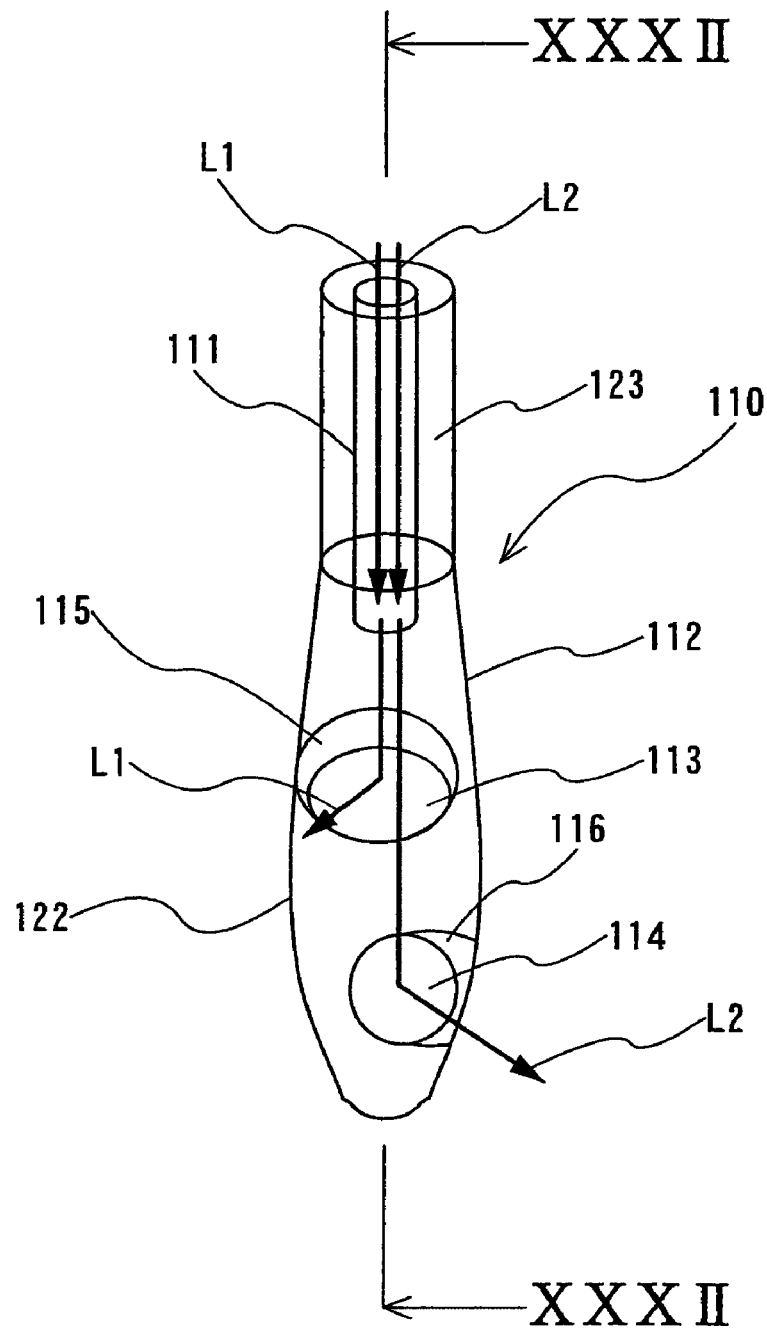
FIG. 31 is a schematic diagram illustrating a seventh embodiment of an irradiation head to be used in a laser irradiation device relating to the present invention.
Figure 32:
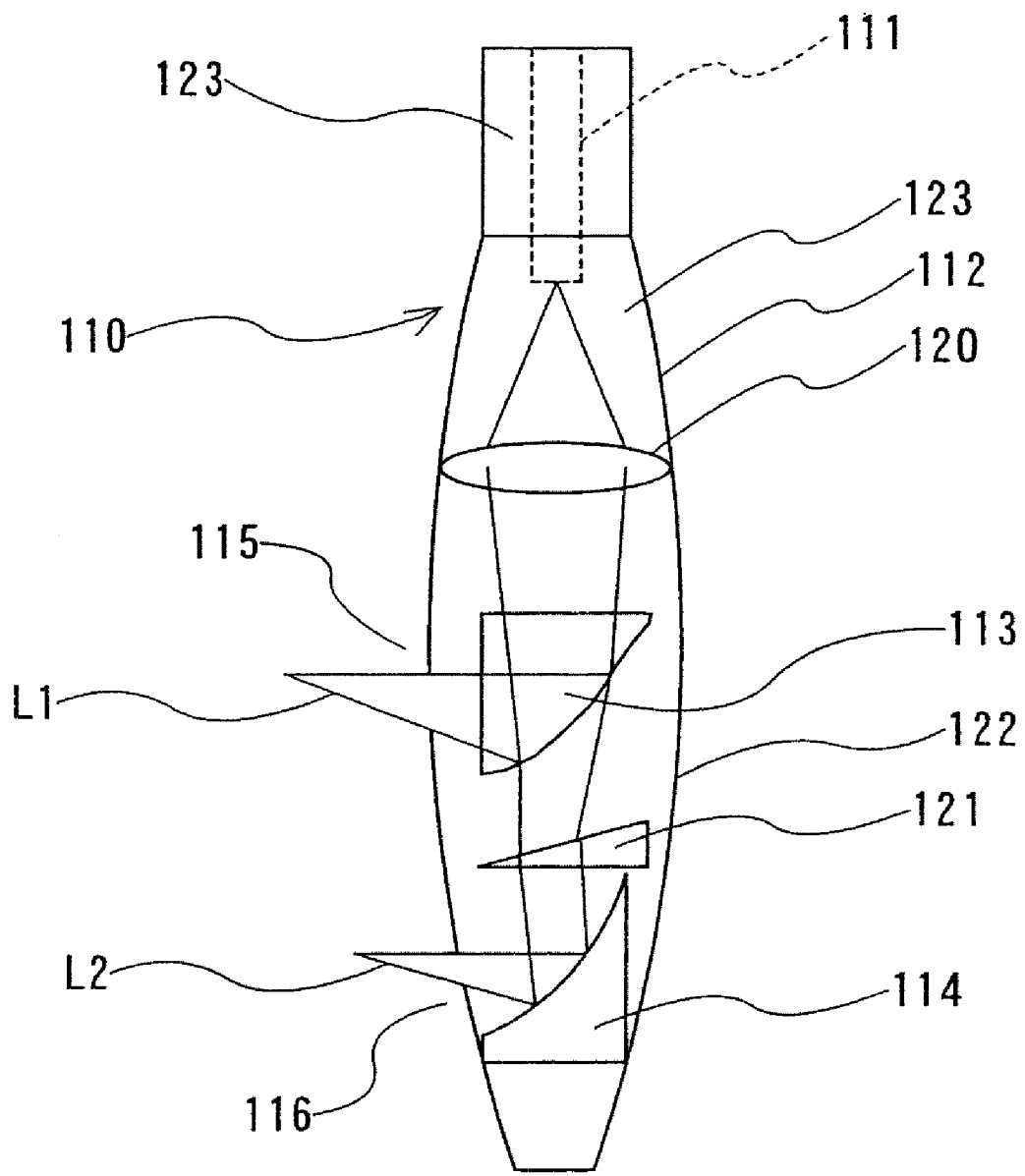
FIG. 32 is a cross-sectional view of FIG. 31 in a cross-section from the view direction of XXXII-XXXII.

FIG. 31 and FIG. 32 are schematic diagrams illustrating a seventh embodiment of an irradiation head to be used in a laser irradiation device relating to the present invention, in which the components which are the same as those of the first and fourth embodiments have the same reference numerals, and redundant descriptions will be omitted herein.

In the laser irradiation device relating to the present embodiment, first optical element 113 is arranged at the top portion of the optical system container 112 and the second optical element 114 is arranged at the bottom portion of the optical system container 112, so that the generation laser light L1 and the detection laser light L2 do not intersect in the axial direction of the optical system container 112 so as to be irradiated on the positions of the top portion and the bottom portion, respectively.

In this case, the first optical element 113 is coated so as to reflect the generation laser light L1 and transmit the detection laser light L2. The second optical element 114 is also coated so as to reflect the detection laser light L2.

Moreover, the second optical element 114 is configured to have a mirror shape having a curved surface, in which when the reflected detection laser light L2, reflective components of the detection laser light L2 reflected from the cylinder portion CY which is the test object are injected into the optical fiber 111 on the same path.

The generation laser light L1 and the detection laser light L2 are using different wavelengths, but manufacturing is easier in the case that the wavelength of the detection laser light L2 is longer than the wavelength of the generation laser light L1, and the coating layer of the reflective surface of the first optical element 113 reflects the short wavelength and the long wavelength passes through.

Accordingly, with the configuration of the present embodiment, the first optical element 113 is positioned on the top portion of the optical system container 112, and the second optical element 114 is positioned on the bottom portion of the optical system container 112. Thus, the generation laser light L1 and the detection laser light L2 do not intersect to each other and the laser lights L1 and L2 can be generated in a stable state.

Furthermore, with the configuration of the present embodiment, the first optical element 113 is coated so as to reflect the generation laser light L1 and transmit the detection laser light L2, and accordingly, in the case of reflecting the short wavelength and generating the long wavelength, the first optical element 113 can be easily manufactured.

Further, concerning the laser maintenance apparatus of the present invention mentioned above, preferred embodiments of a laser ultrasonic detection device will be described hereunder with reference to the accompanying drawings. The laser ultrasonic detection device in the present embodiment may concern the laser detection described in connection with the maintenance system 20 in FIG. 1, and more specifically, surface-wave detection device 213, which will be referred to hereinlater.

First Embodiment

Figure 54:
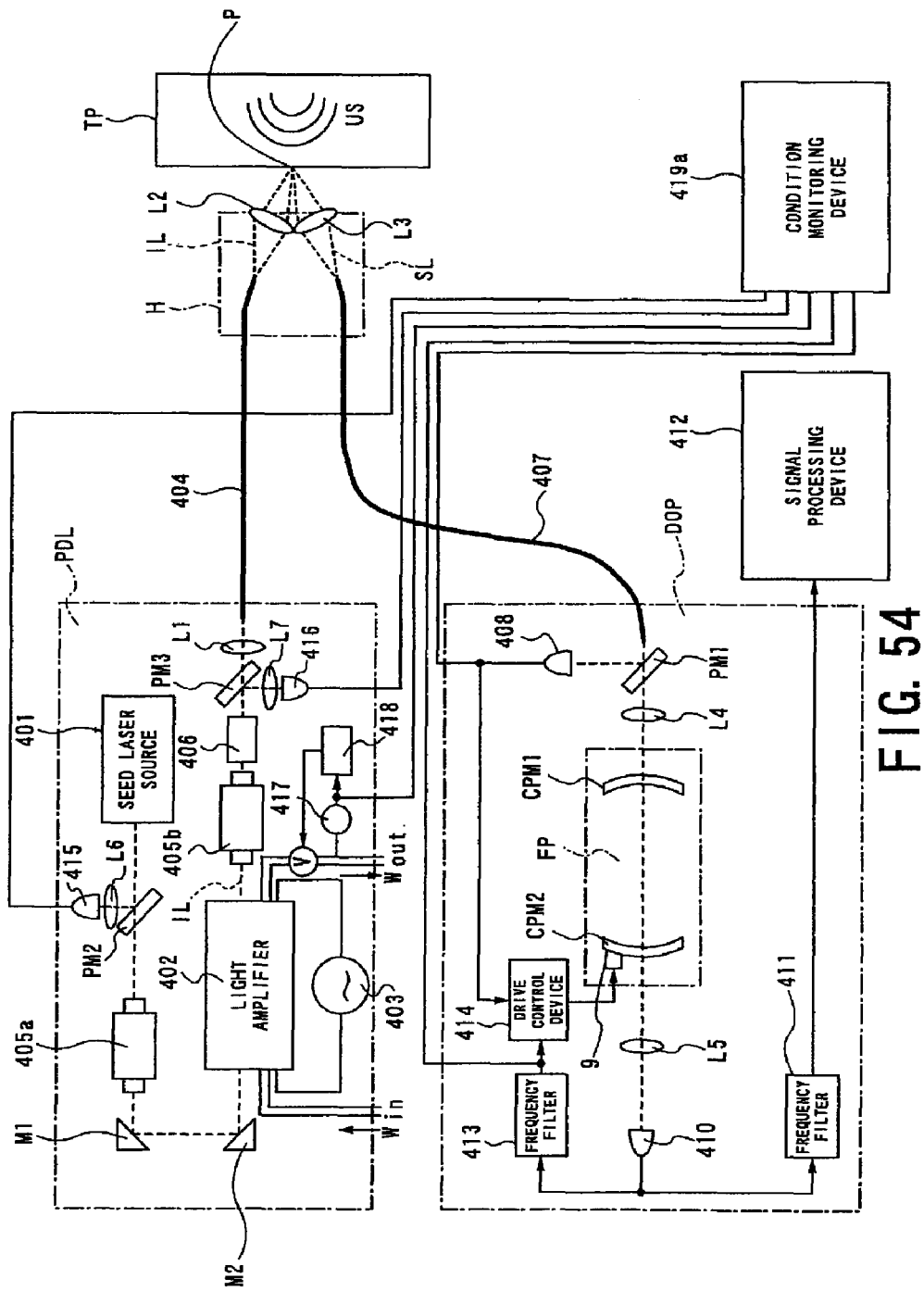
FIG. 54 is a block diagram illustrating a first embodiment of a laser ultrasonic reception device relating to the present invention.
Figure 80:
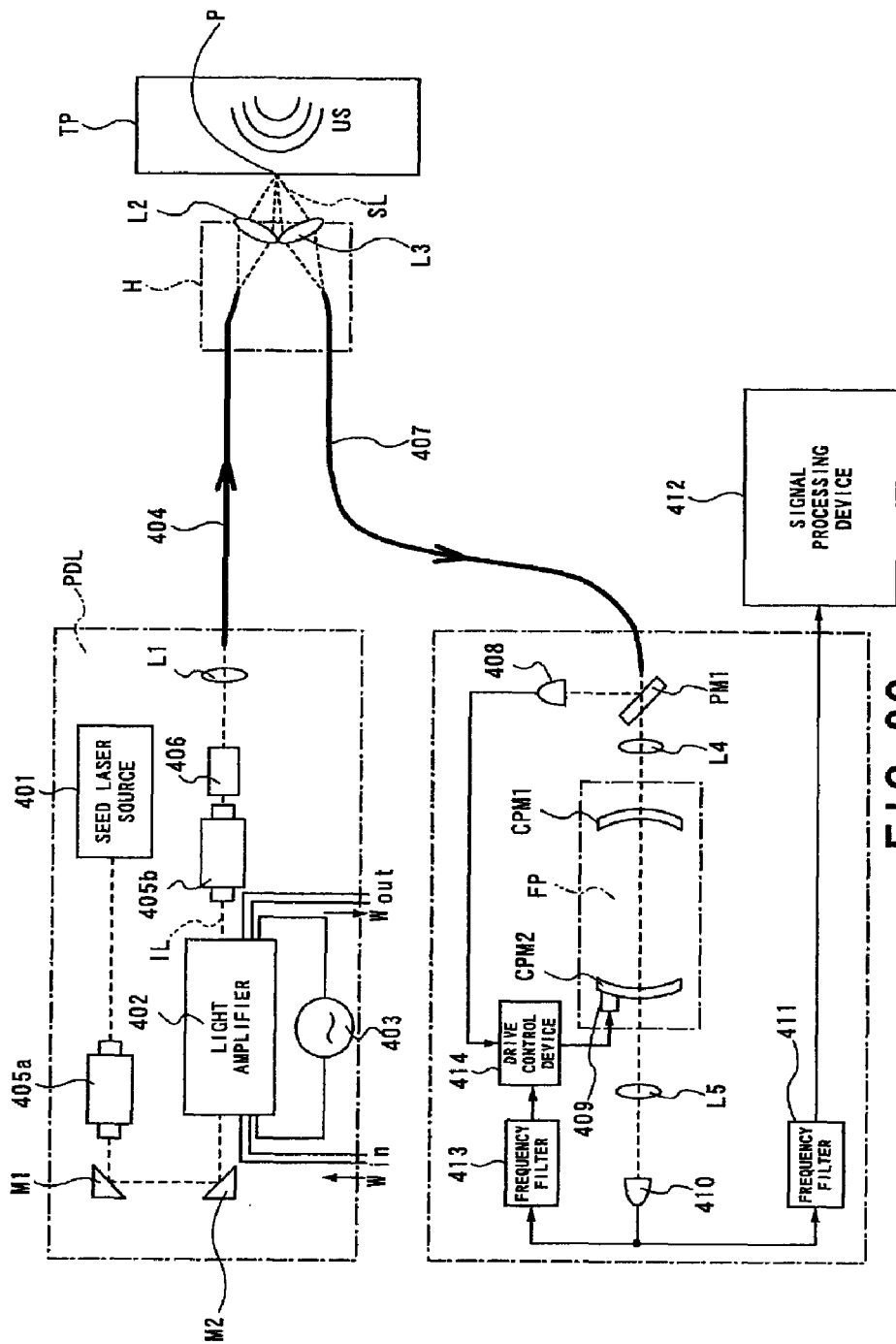
FIG. 80 is a block diagram illustrating a configuration of a conventional laser ultrasonic detection device.
Figure 81:
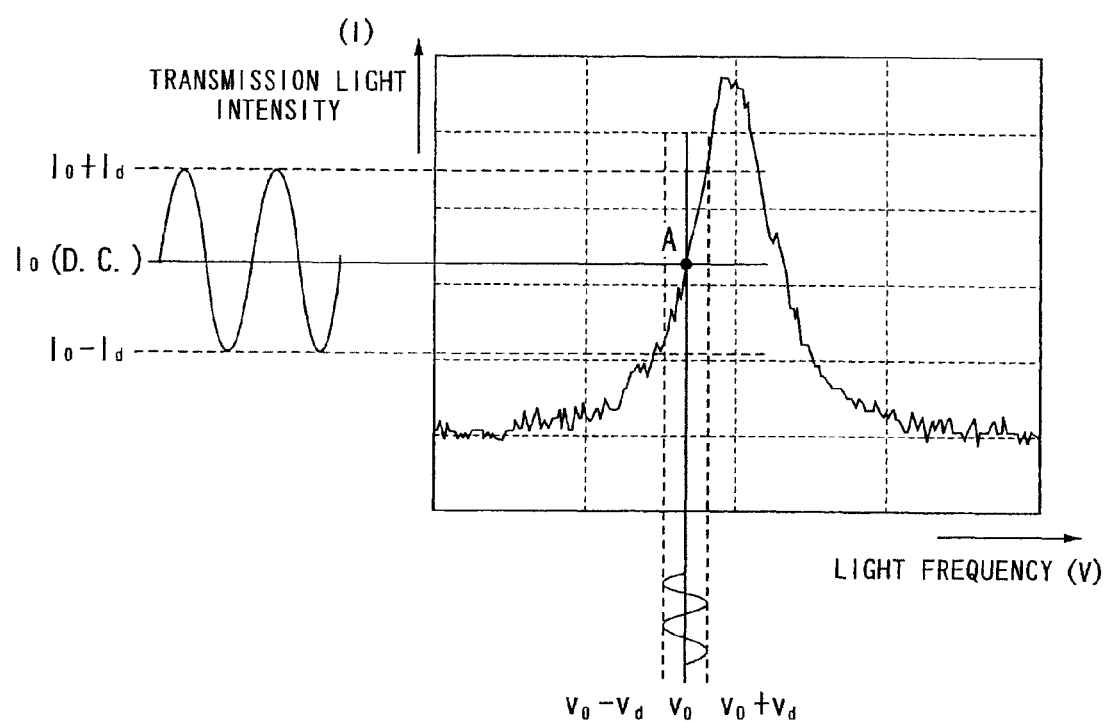
FIG. 81 is a diagram describing the operation of a Fabry-Perot interferometer.
Figure 82:
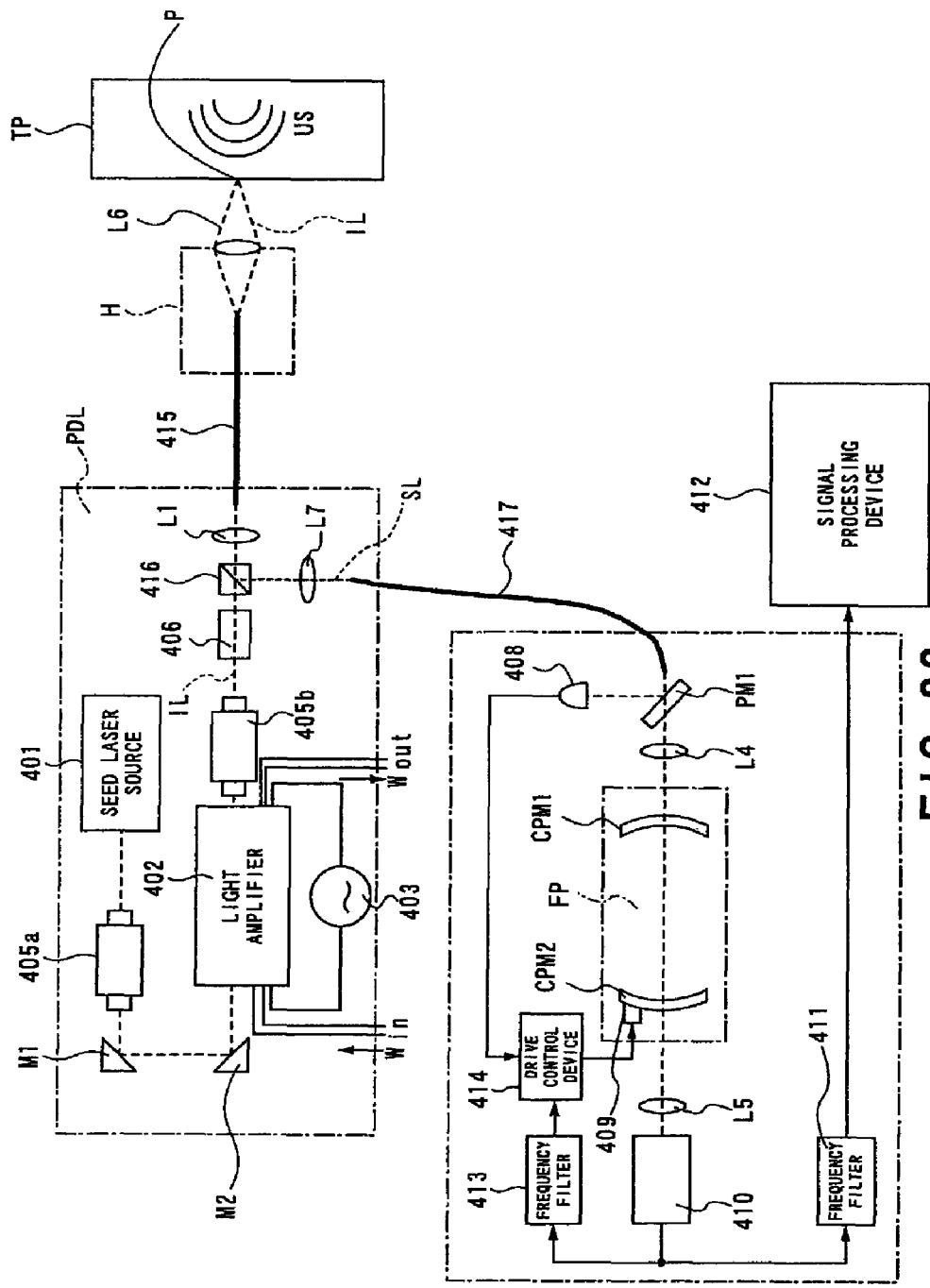
FIG. 82 is a block diagram illustrating another configuration of a conventional laser ultrasonic detection device.
Figure 83:
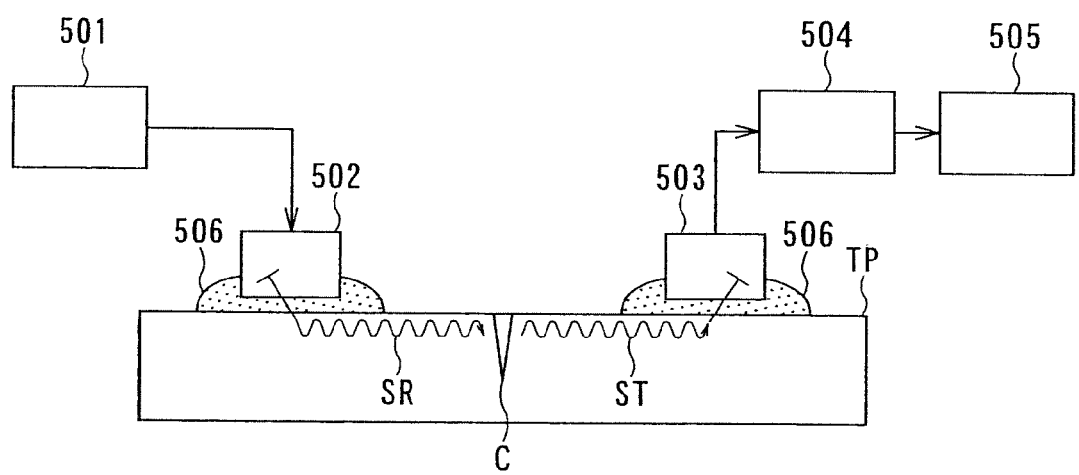
FIG. 83 is a conceptual diagram illustrating a conventional surface testing device.
Figure 84:
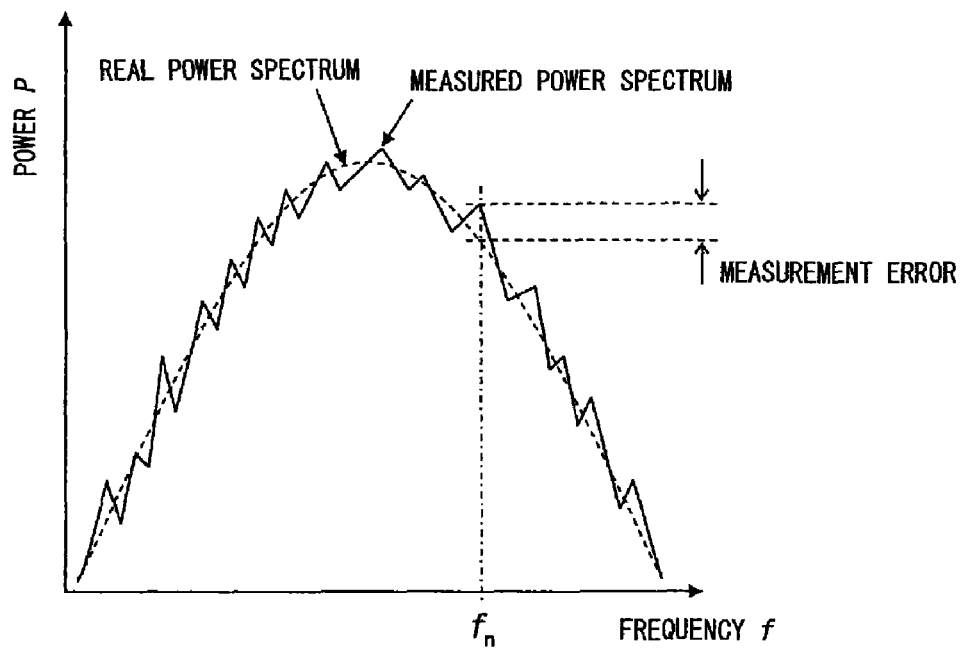
FIG. 84 is a power spectrum comparison diagram for comparing the power spectrum distribution of an ideal surface wave and the power spectrum distribution to be actually measured.
Figure 85:
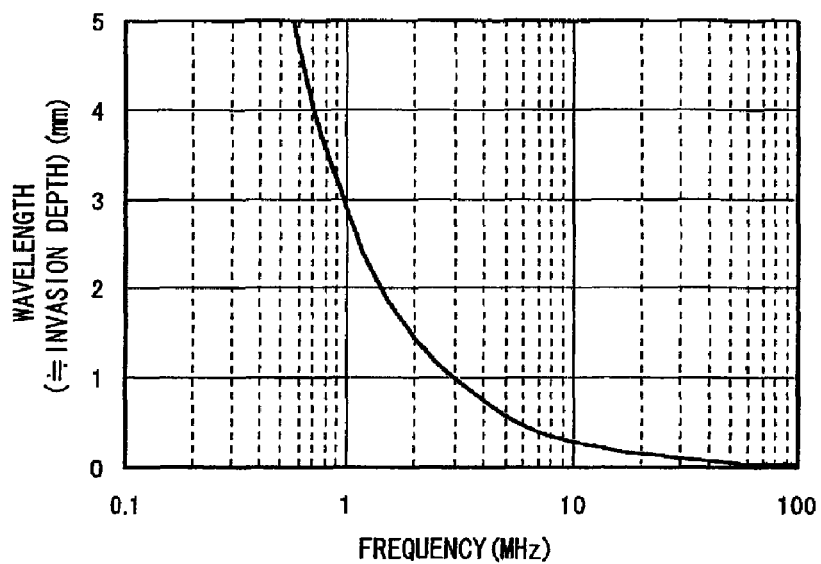
FIG. 85 is a penetration depth diagram illustrating the relation between a frequency and a flow depth of a test object.

FIG. 54 is a block diagram illustrating a first embodiment of a laser ultrasonic detection device relating to the present invention. Components which are the same elements as the components in the conventional laser ultrasonic detection device of FIG. 80 are denoted with the same reference numerals. In FIG. 54, a symbol TP indicates am object to be measured, a symbol US indicates an ultrasonic signal, and a symbol H indicates an irradiation head of a detection laser light.

The laser light oscillated from the seed laser 401 in a receiving pulse laser light source PDL is pulse-amplified with a light amplifier 402 and is injected into an optical fiber 404 via a coupling lens L1. The output light IL of the optical fiber 404 is irradiated onto the irradiating point P on the measurement object TP with lens or any appropriate optical system L2 in the irradiating head H. The output light IL of the optical fiber 404 which is irradiated to the surface of the object TP to be measured is frequency-modulated from the surface vibrations originated from the ultrasonic signal US, and is reflected and scattered on the surface and collected with a leans of any appropriate optical system L3. The collected scattered light SL is guided to a detecting interferometer DOP via an optical fiber 407.

A portion of the scattered light SL is reflected with the partial reflective mirror PM1 and is detected with the photo detector 408. The light components transiting the partial reflective mirror PM1 is injected into the Fabry-Perot resonator FP wherein the resonator is controlled by the piezoelectric element 409, and the transiting light is inputted into the photo detector 410 by the lens L5 and is converted to an electric signal which includes the ultrasonic signal US. The electric signal is used as a drive signal of the piezoelectric element 409 which controls the separation of the resonator of the Fabry-Perot interferometer FP via a frequency filter 413 and drive control device 414. On the other hand, an ultrasonic signal is extracted from the electric signal via a frequency filter 411 and is appropriately signal-converted, signal-processed, displayed and recorded with the signal processing device 412.

A first feature of the present embodiment resides in that there is a partial reflective mirror PM2 which reflects a portion (often 10% or less) of the output light of the seed laser light source 401, and a light detector 415 for measuring this, and the output signal of the light detector 415 is appropriately converted, processed, displayed with real time values or displayed with trends, and recorded with a condition monitoring device 419a, and also in the case that the signal exceeds the specified values, a warning to that effect, or a shutdown signal to the device, is output. The output signal of the light detector 415 is light power (light energy), light frequency (wavelength), and so forth.

With the above-described configuration, there can be monitored a temporal change or abnormality of the seed laser light source 401, or oscillating abnormalities or output decrease of the seed laser light by mixing any edge face reflections from the position shifting of an optical element into the seed laser light source 401, and also in the case of an abnormality to a device, feedback can be provided appropriately and quickly to the device operation.

A second feature of the present embodiment resides in that there is a partial reflective mirror PM3 which reflects a portion (often 10% or less) of the detection laser light IL which is amplified in pulse form with the optical amplifier 402 and adjusted to the appropriate power with the optical attenuator 406, and a light detector 416 for measuring this, and the output signal of the light detector 416 is appropriately converted, processed, displayed with real time values or displayed with trends, and recorded with a condition monitoring device 419a, and also in the case that the output signal exceeds the specified values, a warning to that effect, or a shutdown signal to the device, is outputted.

The output signal of the light detector 416 is time waveforms of pulsing light, light power (light energy), light frequency (wavelength), pulse width, repetition rate, and so forth.

With the above-described configuration, there can be monitored a temporal change or abnormality of the optical amplifier 402, temporal deterioration of a flash lamp, or waveform distortion or output decrease of the detection pulse laser light by mixing edge face reflections from the position shifting of an optical element into the optical amplifier. Furthermore, in the case of an abnormality to a device, feedback can be provided appropriately and quickly to the device operation.

A third feature of the present embodiment resides in that there is an optical amplifier 402 for amplifying the detection laser light in pulse form, having a coolant measuring device 417 for measuring the condition of the coolant system W for cooling the optical amplifier. The output signal of the coolant measuring device 417 is appropriately converted, processed, displayed with real time values or displayed with trends, and recorded with a condition monitoring device 419a. In the case that the signal exceeds the specified values, a warning to that effect, or a shutdown signal to the device, is outputted. The output signal of the coolant measuring device 417 corresponds to the flow rate and temperature of the coolant.

With the above-described configuration, there can be monitored an output decrease of the detection pulse laser light from abnormalities such as coolant flow rate or temperature, or operations under abnormally high temperature conditions which can lead to deterioration or failure of a device. Furthermore, by adjusting the operation or level of opening of the valve V for adjusting the coolant with an output signal from the coolant measuring device 417 and the valve control drive device 418, in the case of an abnormality to the coolant system, the feedback can be provided appropriately and quickly to the device operation.

A fourth feature of the present embodiment resides in that two output signals of the light detector 408 and frequency filter 413 are appropriately converted, processed, displayed with real time values or displayed with trends, and recorded with a condition monitoring device 419a, and also in the case that the signal exceeds the specified values, a warning to that effect, or a shutdown signal to the device, is outputted.

The ratio of the two output signals of the light detector 408 and frequency filter 413 are a fixed value if the device is in normal operation, but if the resonator separation control becomes unstable for any reason, the output value of the frequency filter 413 fluctuates, and the ratio of the two output signals changes. Therefore, by constantly monitoring the ratio of the two signals, the stability of the resonator control of the Fabry-Perot interferometer with environmental temperature changes or environmental vibrations can be monitored. Furthermore, in the case of control instability, the feedback can be provided appropriately and quickly for device operation control.

Further, by displaying and recording at least one output signal shown in the present embodiment and the ultrasonic signal which has been converted or processed with the signal processing device 412 with the same timing with the condition monitoring device 419a, there can be understood the device condition of the device measuring the individual waveforms of the ultrasonic signals continuously acquired.

Second Embodiment

Figure 55:
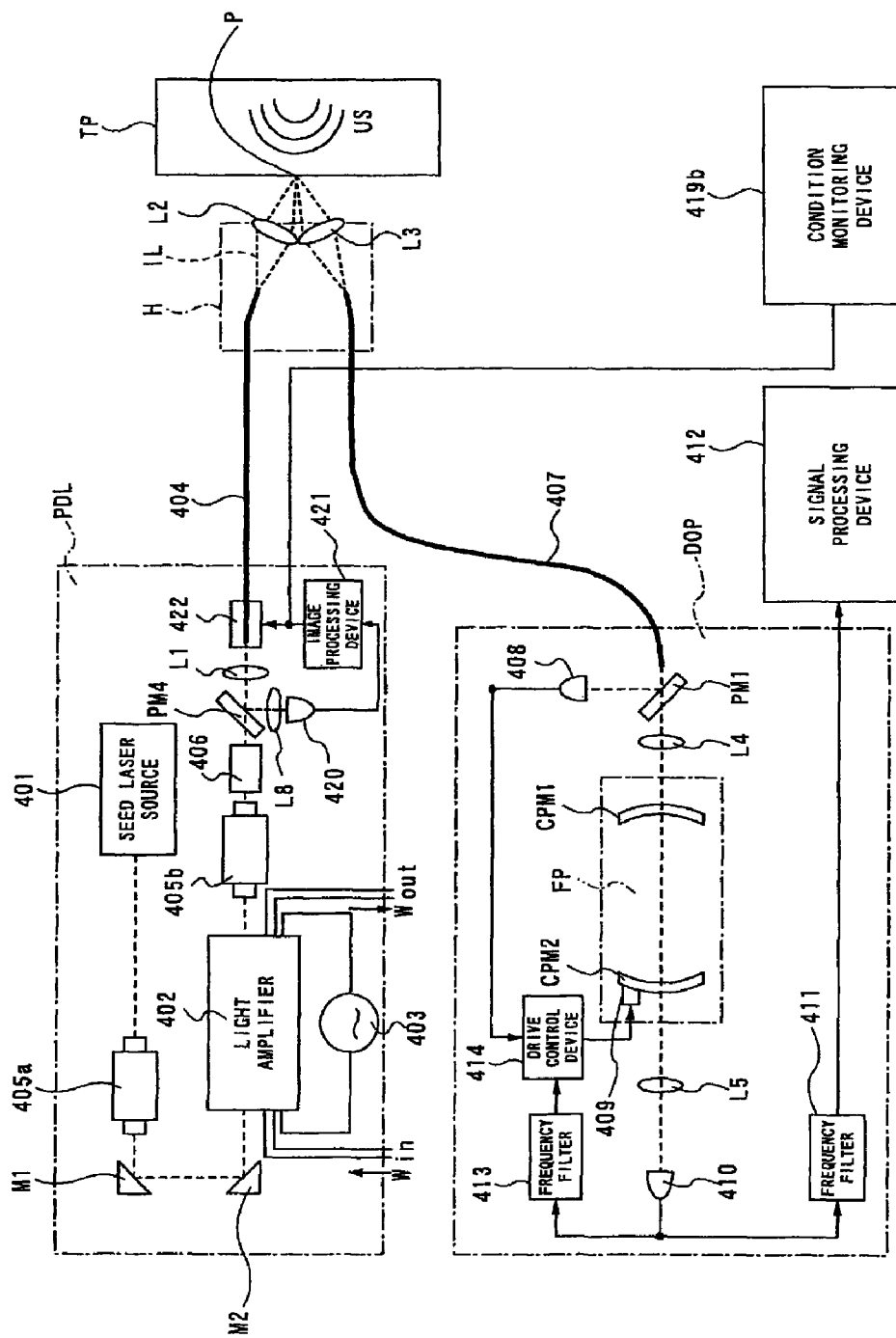
FIG. 55 is a block diagram illustrating a second embodiment of the laser ultrasonic reception device relating to the present invention.

Next, a second embodiment of the laser ultrasonic detection device relating to the present invention will be described with reference to FIG. 55, in which components which are the same as those of the first embodiment are denoted with the same reference numerals, and redundant description will be omitted herein.

The present embodiment comprises an imaging optical system L8 for observing an input end face of an optical fiber 404 wherein the detection laser light IL is to be injected, a CCD camera 420, an image processing device 421 for detecting the incident position of the detection laser light IL from the image information obtained with the CCD camera 420 into the optical fiber 404 and for generating a control signal for controlling the correct position of the incident position in the core of the optical fiber 404 end face from the results thereof, and a moving mechanism 422 for moving the end face position of the optical fiber 404 into the above-described correct position.

Figure 56:
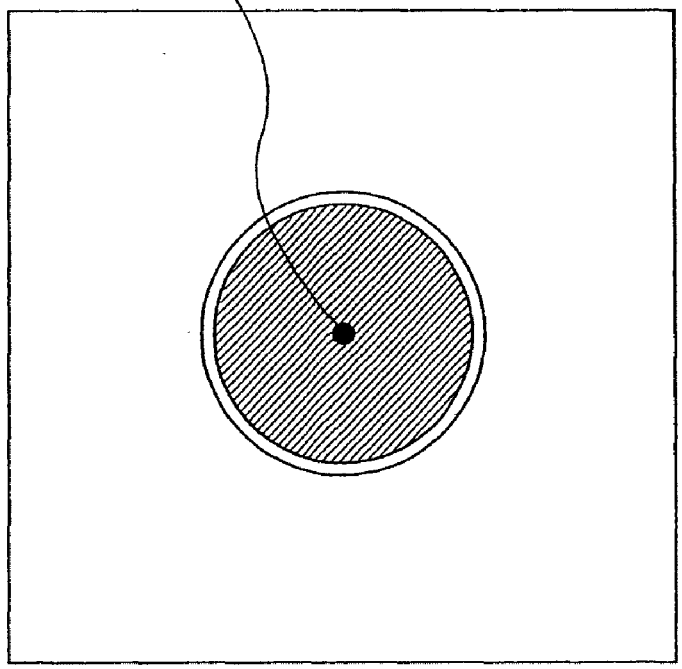
FIG. 56 is a view illustrating an incident state of a reception laser light to an optical fiber.
Figure 56:
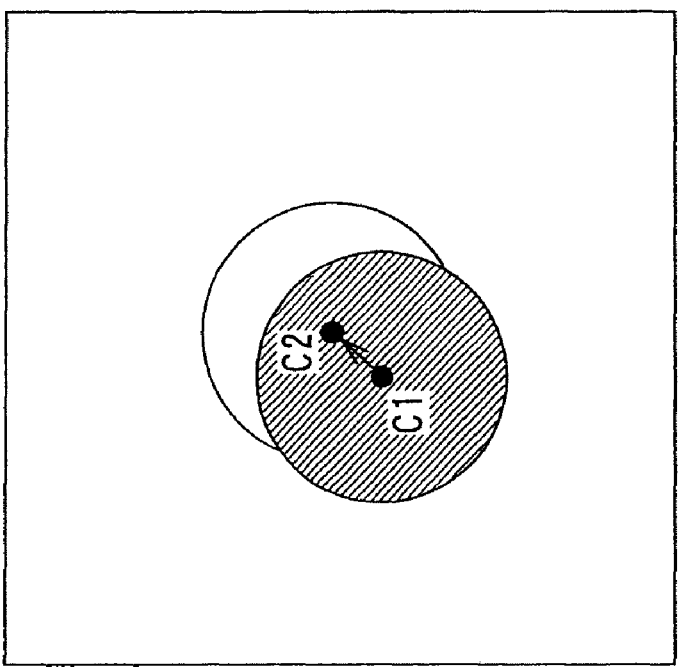

When the input end face of the optical fiber 404 is observed in a two-dimensional image, for example, as shown in FIG. 56, the input end face of the optical fiber 404 (center: C2) and the incident position of the detection laser light IL (center: C1) can be observed simultaneously. Here, the shifting amount thereof (C1-C2) is measured quantitatively with the image processing device 421 shown on the left side in FIG. 56, and by correcting this shifting amount to superimpose both centers (C1, C2) with the moving mechanism 422 as shown on the right side in FIG. 56, a constant optical fiber coupling efficiency can be obtained.

For the movement mechanism 422, a movement mechanism having freedom in two horizontal and vertical axes, or a movement mechanism having freedom in a rotating direction, can be used. It should be noted that instead of an end face position of the optical fiber 404 as described above, the incident position of the detection laser light IL as to the fixed optical fiber 404 end face can be controlled by using an optical system, not shown.

With the above-described configuration, the increased optical fiber coupling loss due to the position shifting of the optical element from temperature changes or vibrations of the environment where the device is installed can be observed, and in the case of the position shifting exceeding the predetermined allowable range, the position thereof can be appropriately and quickly reset.

The position correcting signal can be appropriately converted, processed, displayed with real time values or displayed with trends, and recorded with a condition monitoring device 419b, and also in the case that the signal exceeds the specified values, a warning to that effect, or a shutdown signal to the device, is outputted.

Third Embodiment

Figure 57:
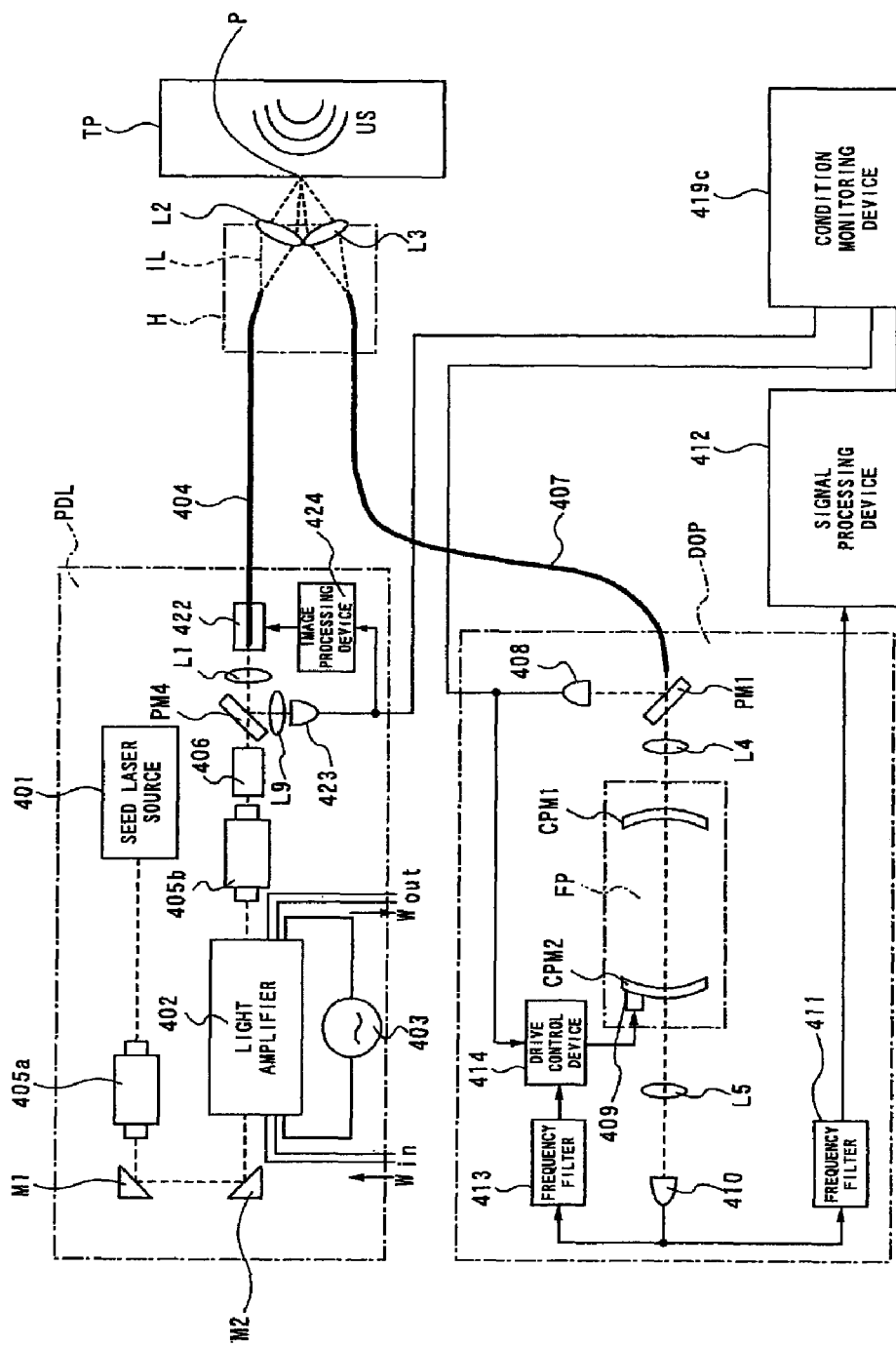
FIG. 57 is a block diagram illustrating a third embodiment of a laser ultrasonic reception device relating to the present invention.

Next, a third embodiment of the laser ultrasonic detection device relating to the present invention will be described with reference to FIG. 57, in which components which are the same as those of the first and second embodiments are denoted with the same reference numerals, and redundant description will be omitted herein.

This embodiment comprises: a light detector 423 for measuring the light amount back-reflection and back-scattering toward the direction of the optical amplifier 402 (hereafter called the "end face reflecting light amount") from the optical fiber 404 into which the detection laser light IL is injected; the image processing device 421 for generating a control signal for controlling the incident position of the detection laser light IL in an appropriate position within the core of the optical fiber 404 end face so as to maintain the output signal as a fixed value; and a moving mechanism 422 for moving the end face position of the optical fiber 404 into the above-described appropriate position. For the movement mechanism 422, a movement mechanism having freedom in two horizontal and vertical axes, or a movement mechanism having freedom in a rotating direction may be used During the generation of the detection laser light IL from the optical fiber 404 to the irradiating head H, a portion of the laser light (for example, if the material of the optical fiber is quartz glass, and the installation environment is in the air, then 3 to 5% of light amount) is back-scattered and back-reflected from the input end face and output end face of the optical fiber 404 and the end face of the leans or any appropriate optical system L2. The scattering and reflecting amount is constantly a fixed value if the state of the device is stable. Herein, by correcting the coupling of the optical fiber 404 with the moving mechanism 422 so that the end face reflecting light amount is maintained as a fixed value by the image processing device 421, a constantly fixed optical fiber coupling efficiency can be obtained. Moreover, the incident position of the detection laser light IL as to the end face of the fixed optical fiber 404 can also be controlled and driven using an optical system not shown, rather than the end face position of the optical fiber 404.

With the above-described configuration, increased optical fiber coupling loss due to the position shifting of the optical element from temperature changes or vibrations of the device installation environment can be monitored, and in addition, the case of the position shifting exceeding the predetermined allowable range, the position thereof can be appropriately and quickly reset. Furthermore, in the case that the output signal of the light detector 423 does not return to the normal value even with the operation of the moving mechanism 422, the generating path of the detection laser light IL (optical fiber 404 and object lens L2 in FIG. 57) can be estimated to have some type of abnormality.

The signal of the light detector 423 can be appropriately converted, processed, displayed with real time values or displayed with trends, and recorded with a condition monitoring device 419c, and also in the case that the signal exceeds the specified values, a warning to that effect or a shutdown signal to the device is outputted. By monitoring and recording this signal and the output signal of the light detector 408 which indicates the output of the scattered light SL which is injected into the receiving interferometer, the integrity of the optical fiber 404 or 407 or the irradiating head H can be estimated.

Fourth Embodiment

Figure 58:
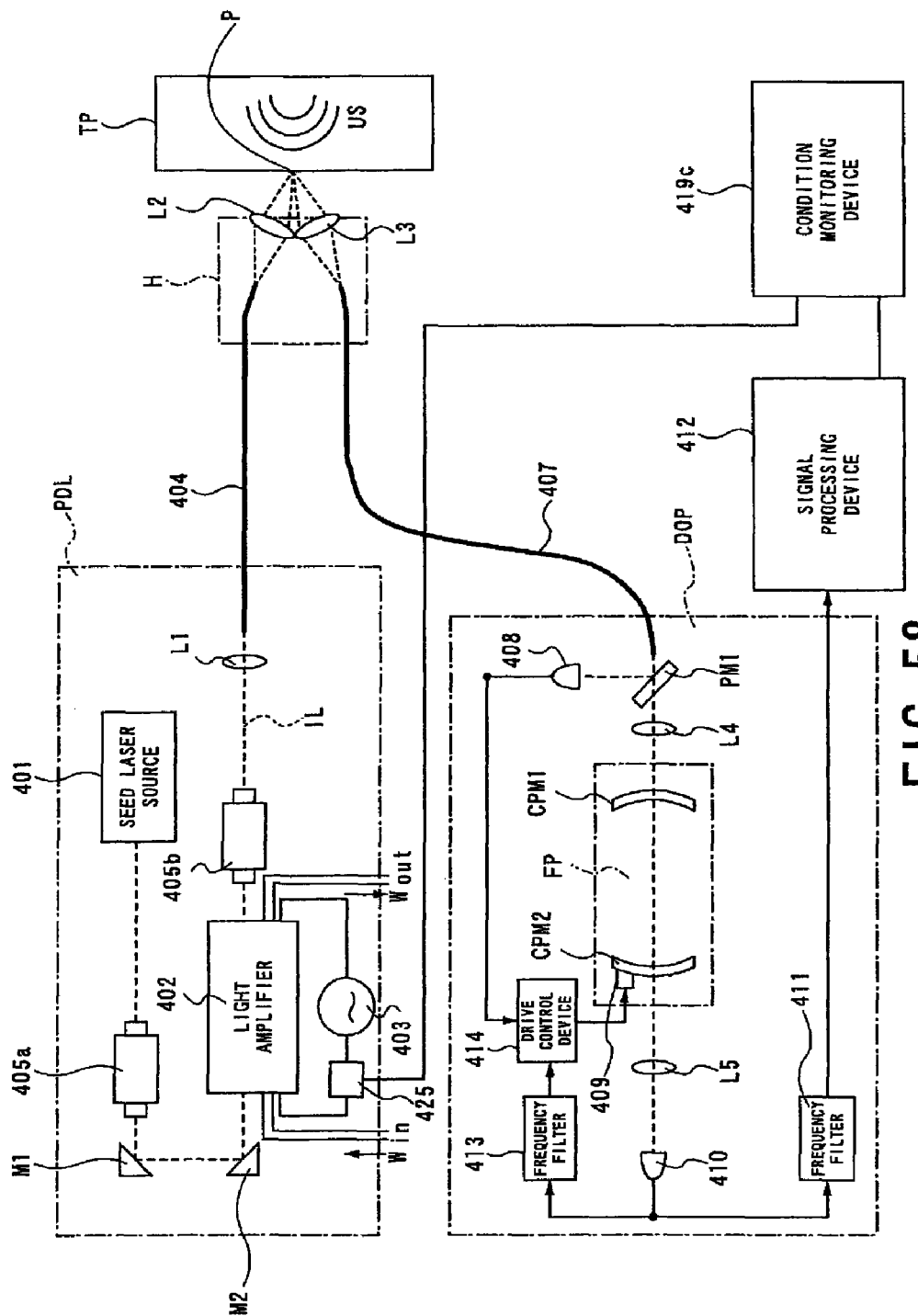
FIG. 58 is a block diagram illustrating a fourth embodiment of a laser ultrasonic reception device relating to the present invention.

Next, a fourth embodiment of the laser ultrasonic detection device relating to the present invention will be described with reference to FIG. 58, in which components which are the same as those of the first through third embodiments are denoted with the same reference numerals, and redundant description will be omitted herein.

This embodiment includes a power source monitoring control device 425 for measuring and controlling the oscillating state of the power source 403 of the optical amplifier 402 which amplifies the laser light (pulse) oscillating from the seed laser light source 401. The output signal of the power source monitoring control device 425 can be appropriately converted, processed, displayed with real time values or displayed with trends, and recorded with a condition monitoring device 419d, and also in the case that the signal exceeds the specified values, a warning to that effect or a shutdown signal to the device is outputted. The output signal of the power source monitoring control device 425 is a reception rate of the pulse power source, peak voltage, integrated oscillating pulse count or the like.

With the above-described configuration, temporal deterioration of the flash lamp for exciting can be monitored, and in the case of limiting the oscillating output by decreasing the output of the detection laser light IL, the power source 403 can be decreased and thus limit the oscillating output without relying on the optical attenuator 406 as shown in FIG. 54, and the life of the power source 403 and the flash lamp can be extended.

Fifth Embodiment

Figure 59:
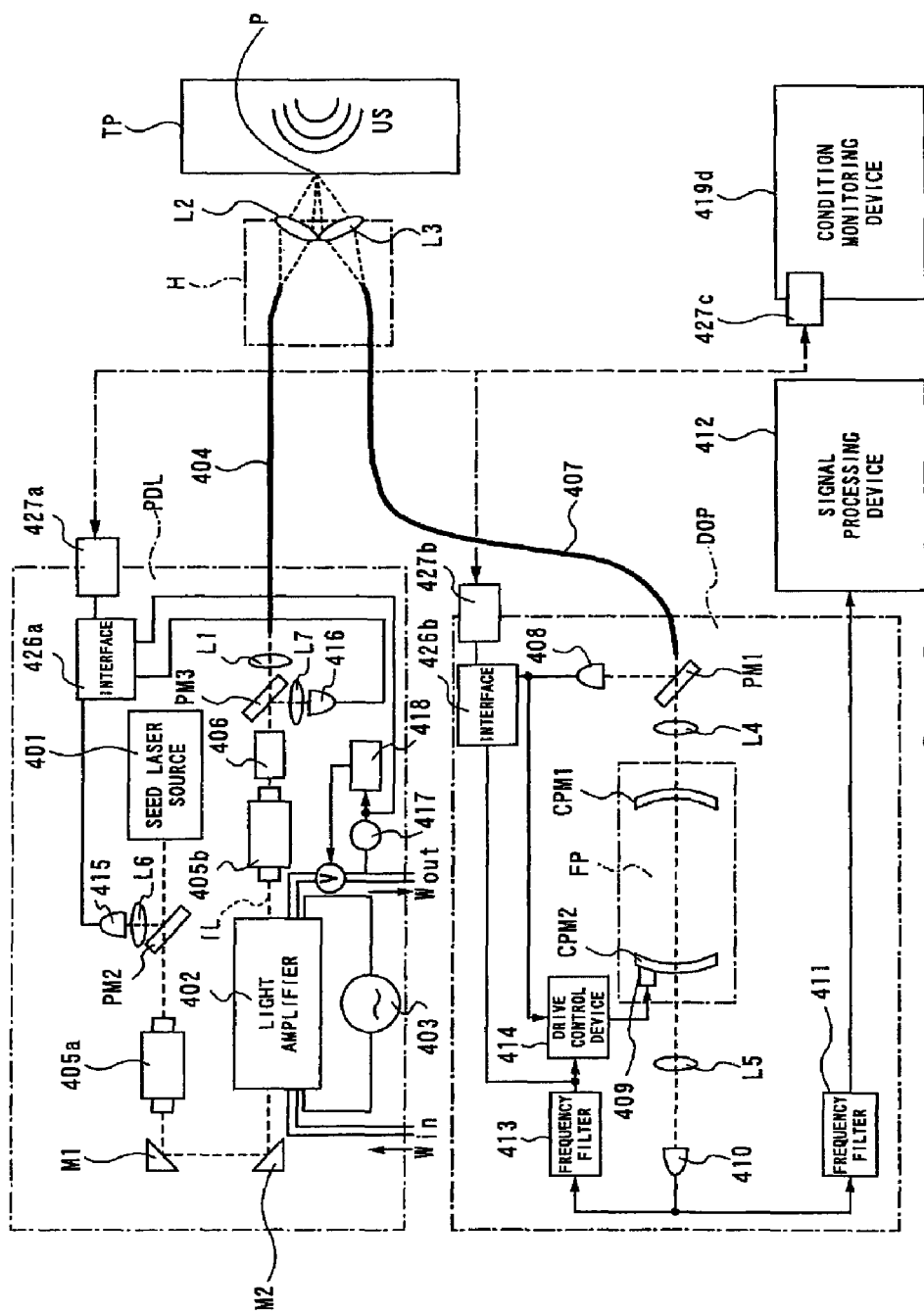
FIG. 59 is a block diagram illustrating a fifth embodiment of a laser ultrasonic reception device relating to the present invention.

Next, a fifth embodiment of the laser ultrasonic detection device relating to the present invention will be described with reference to FIG. 59, in which components which are the same as those of the first through fourth embodiments are denoted with the same reference numerals, and redundant description will be omitted herein.

This embodiment comprises a data recording device 426a, 426b which records a portion or all of an output signal or feature amount representing the monitoring and control functionalities described in the first to fourth embodiments mentioned above in at least one of a detection pulse laser light source PDL or a detection interferometer DOP. The data can be appropriately read, converted, processed, displayed with real time values or displayed with trends, and recorded using interfaces 427a and 427b with a condition monitoring device 419e. Further, in the case that the signal exceeds the specified values, a warning to that effect or a shutdown signal to the device is outputted. The interfaces 427a and 427b can be any combination of a wired or wireless analog or digital format. The control signal can be transferred from the condition monitoring device 419e to the detection pulse laser light source PDL and the receiving interferometer DOP, and the operation of the drive mechanism 422, the degree of opening of the valve V, and the oscillating condition from the power source monitoring control device 425 can be controlled remotely.

Hereinafter, embodiments of a laser ultrasonic inspecting device relating to the laser maintenance apparatus of the present invention will be described hereunder with reference to the accompanying drawings. The following embodiments will concern the details of the laser system 20, the flaw detection signal processing system 21 and the control board 22 of FIG. 1. Further, it is to be noted that, in the drawings, the same and equivalent portions are denoted with the same reference numerals.

First Embodiment

Figure 33:
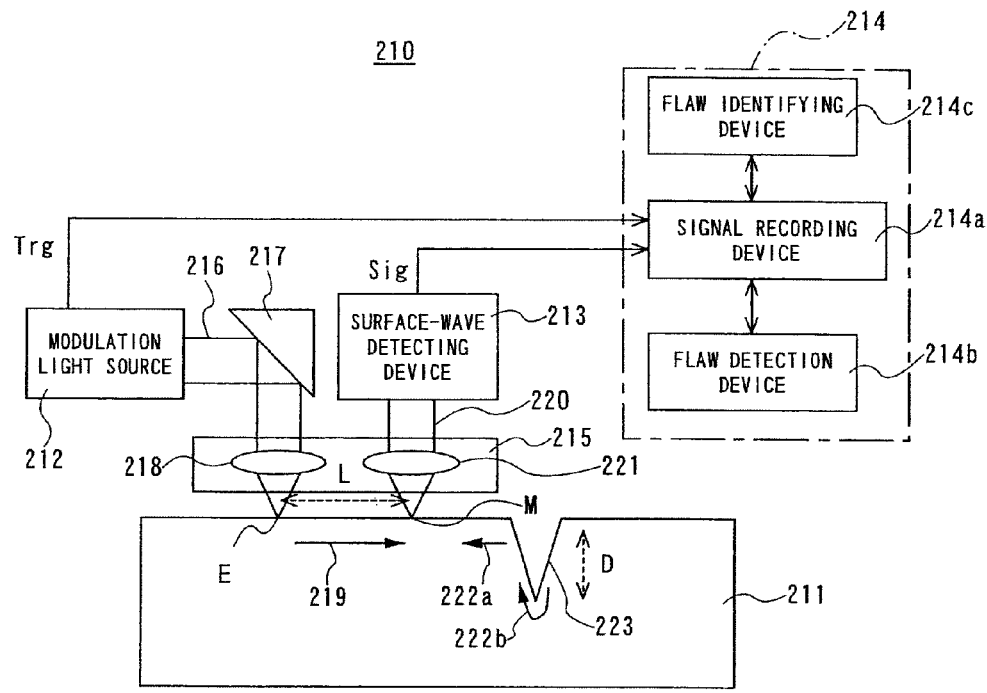
FIG. 33 is a functional block diagram of a first embodiment of a surface inspecting device according to the present invention.

FIG. 33 is a block diagram illustrating a first embodiment of a laser ultrasonic inspecting device 210 related to the laser maintenance apparatus of the present invention.

This laser ultrasonic inspecting device 210 comprises a modulation light source 212 serving as one example of surface-wave generating means which excite an ultrasonic surface wave by irradiating the laser light to a test object 211, a surface-wave detecting device 213 serving as one example of surface-wave detection means, a flaw detection device 214 serving as one example of flaw-detecting means, and a scanner 215.

The modulation light source 212 is for oscillating a pulse laser light 216 having a predetermined frequency modulated in a pulse shape with a trigger pulse Trg, and includes an optical system for irradiation which guides the light for irradiating this pulse laser light 216 to a predetermined position E on the surface of the test object 211, and a lens system 218 for focusing the light.

That is, the modulation light source 212 is configured as surface-wave generating means for exciting an ultrasonic surface wave 219 by irradiating the laser light 216 to the surface of the test object 211.

The surface-wave detecting device 213 irradiates a laser light 220 via an optical system 221 to a detection point M on the surface of the test object separated by a predetermined distance L from an irradiation position E of the laser light 216, and on the other hand, receives the reflected light reflected at this detection point M and detects the surface wave 219 based on the variation (deflection) of the direction of movement of laser light, the phase difference of the reflected light, the amount of frequency transition, and so on.

Furthermore, the surface-wave detecting device 213 detects flawed (flaw) waves 222a and 222b as well as the surface wave 219. When the surface wave 219 reaches a flaw portion 223 of a surface opening, the flawed waves 222a and 222b are generated at the edge portions of the opening portion and the bottom portion of this flaw portion 223, respectively, and when detected by the surface-wave detecting device 213 at the detection point M, these waves are included in a surface-wave detection signal sig to be outputted as an output signal.

The scanner 215 is for scanning the surface of the test object 211 in the X-Y direction in a state that the irradiation point E at which the laser light 216 is irradiated through the modulation light source 212 is disposed with a known predetermined distance L as to the detection point M.

The flaw detection device 214 comprises a signal recording device 214a, a flaw detecting device 214b, and a flaw identifying device 214c, and is configured so as to operate in synchronism with the trigger pulse Trg from the modulation light source 212. This is for receiving and recording at least one of the surface detection signal and the flaw detection signal detected by the surface-wave detecting device 213 as an output signal sig.

The flaw detecting device 214b receives the output signal sig from the surface-wave detecting device 213 via the signal recording device 214a, and when detecting that the flawed waves 222a and 222b are included in this output signal sig, the flaw detecting device 214b detects that the flawed portion 223 exists.

The flaw identifying device 214c receives the output signal sig from the surface-wave detecting device 213 via the signal recording device 214a, and when detecting that the flawed waves 222a and 222b are included in this output signal sig, the flaw identifying device 214c identifies the position and depth of the flawed portion 223.

That is, since the distance L from the generation point E to the detection point M is known, the flaw detection device 214 calculates unknown sound velocity Vs of the surface wave 219 based on Vs=L/T1 using a point in time T1 until the surface wave detecting device 213 receives the surface wave with an oscillating point in time To of the surface wave 219 shown in the trigger signal Trg serving as a reference.

Furthermore, since the time difference Td when the flawed waves 222a and 222b reach the detection point M is the time when the surface wave 219 is propagated in the depth direction of the flawed portion 223, the flaw detection device 214 obtains the depth D of the flawed portion 223 from an expression of D=L·Td/T1. That is, the flaw detection device 214 obtains the depth D without knowing the sound velocity Vs of the surface wave 219 beforehand.

Further, the unknown flawed portion can be obtained by employing the propagation time T3 of the flawed waves 222a and 222b, and obtaining the distance Ld from the generation point E to the position where the flawed portion 223 exists from the relation Ld=L·T3/T1.

Next, the operations of the laser ultrasonic inspecting device 210 of this embodiment will be described.

The laser light 216 modulated in a pulse shape is oscillated at the modulation light source 212 with the trigger pulse Trg, guided by the irradiation optical system 217, and focused by the lens system 218, which is then irradiated to the generation point E on the surface of the test object 211.

The ultrasonic surface wave 219 is then excited at the generation point E and is propagated over the surface of the test object 211, reaching the detection point M.

The laser light 220 oscillated from the surface-wave detecting device 213 is irradiated at this detection point M via the irradiation optical system 221. On the other hand, the reflected light thereof is received by the surface-wave detecting device 213, and at this time, the surface wave 219 is detected.

Further, the surface wave 219 passes and is propagated through the detection point M, which then reaches the flawed portion 223. The flawed waves 222a and 222b are generated at the edge portions of the opening portion and the bottom portion of the flawed portion 223.

These flawed waves 222a and 222b reach the detection point M again, and are detected by the surface-wave detecting device 213 and given to the signal recording device 214a of the flaw detection device 214 as an output signal sig.

The trigger signal Trg from the modulation light source 212 is inputted to the signal recording device 214a. The detection signals sig are recorded, respectively, only for a predetermined period from the time of synchronizing with the respective oscillations of the generation laser light of this modulation light source 212, and on the other hand, the detection signals sig are provided to the flaw-detecting device 214b and the flaw-identifying device 214c, respectively.

Accordingly, the flaw detecting device 214b detects the presence of the flawed portion 223 and provides the result to the signal recording device 214a for recording. Further, the flaw identifying device 214c includes a velocity correction function and detects the accurate sound velocity and the position and depth D of the flawed portion 223 on the route from the time difference of the surface-wave signals and flawed wave signals, and the detected results are given to the signal recording device 214a to be recorded therein.

Consequently, according to this laser ultrasonic inspecting device 210, the oscillation of the laser light for generation in a pulse shape of the modulation light source 212 is synchronized with the capture timing of the detection signal sig by the signal recording device 214a, so that the detection (output) signal sig from the surface-wave detecting device 213 should be recorded only for a predetermined period at the time of each oscillation of the laser light 216, thereby reducing the amount of recording of this detection signal sig.

For the reason mentioned above, in addition to the reduction in the recording capacity of the recording medium of the signal recording device 214a which records the detection signal sig, reduction in the detection and analysis time of the flawed portion 223 by the flaw detecting device 214b and the flaw identifying device 214c for detecting the presence, position and depth of the flawed portion 223 from this detection signal sig can be realized.

Furthermore, reduction in the amount of recording data of the surface wave and flawed wave by the signal recording device 214a can be realized, so that the flawed portion detection precision can be accordingly improved by increasing the amount of recording of these data.

Second Embodiment

Figure 34:
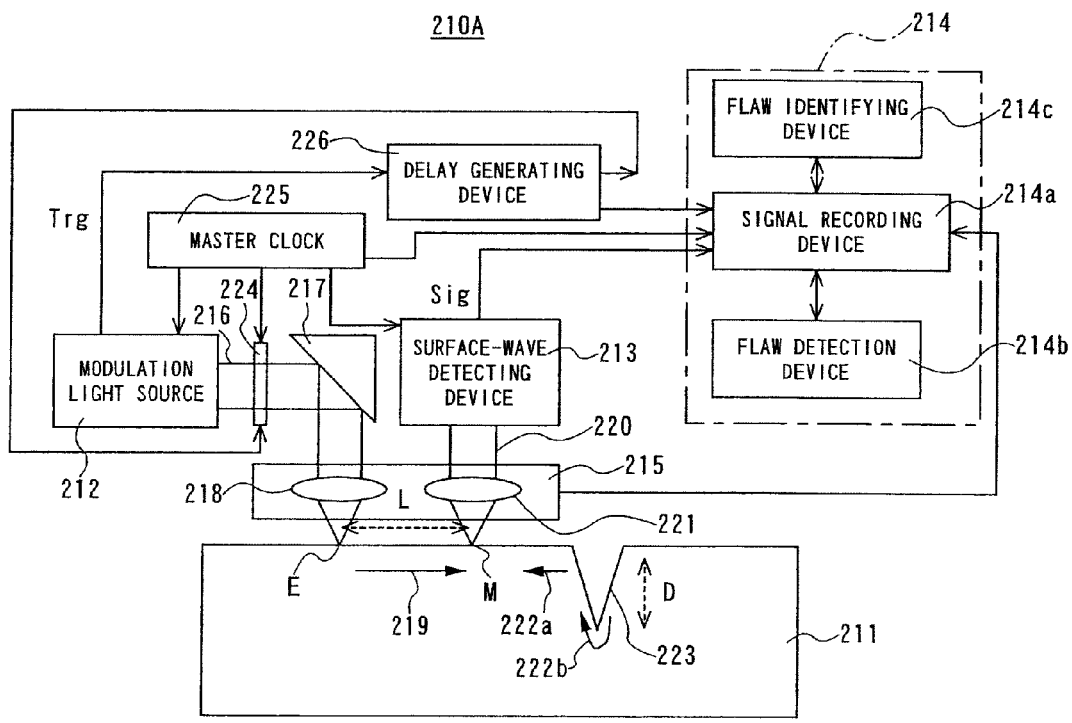
FIG. 34 is a functional block diagram of a second embodiment of a surface inspecting device according the present invention.
Figure 35:
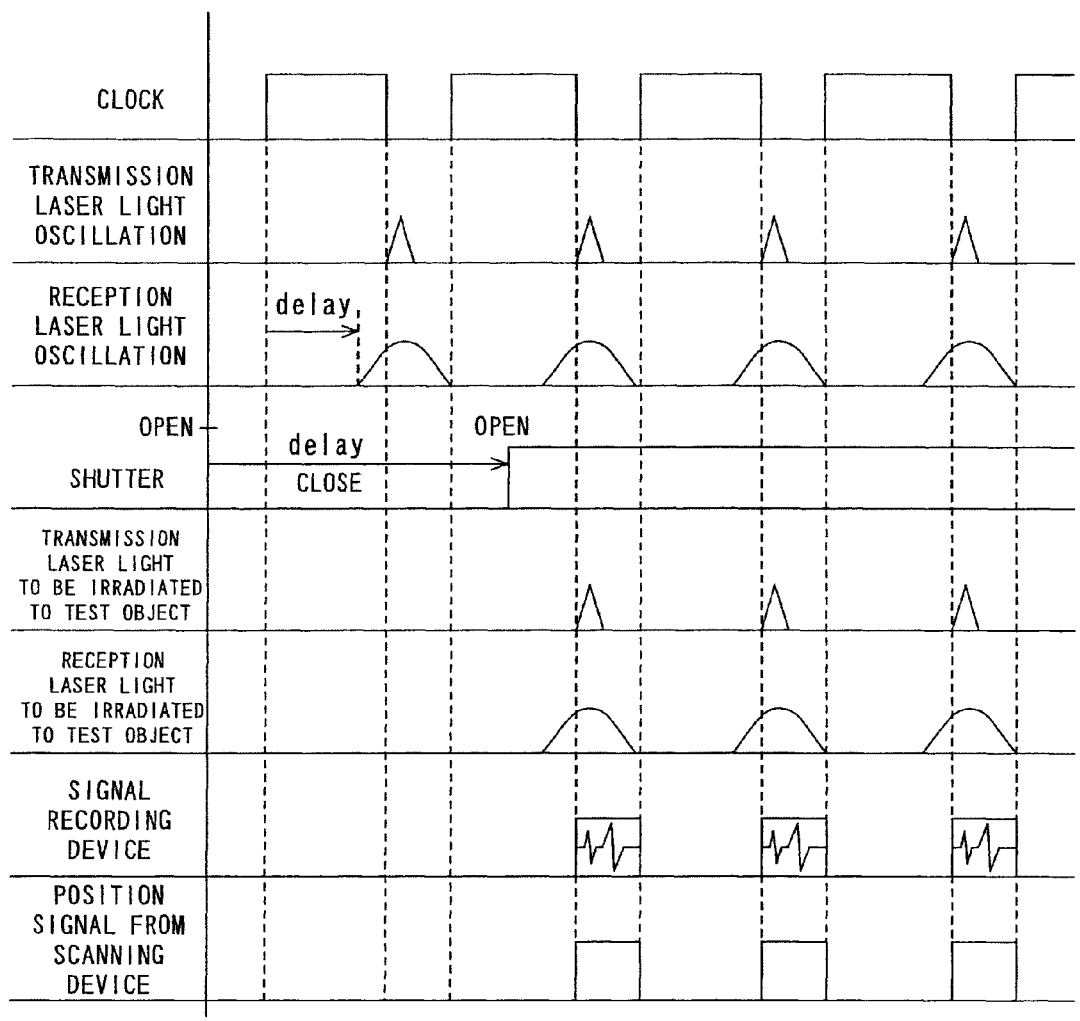
FIG. 35 is a timing chart of the surface inspecting device according to the second embodiment of the present invention.

FIG. 34 is a block diagram illustrating a second embodiment of the laser ultrasonic inspecting device 210A related to the laser maintenance apparatus according to the present invention, and FIG. 35 is a timing chart of the operations of the essential portions of this laser ultrasonic inspecting device 210A.

This laser ultrasonic inspecting device 210A is provided with a shutter device 224, a master clock 225, and a delay generating device 226.

The shutter device 224 is for performing ON/OFF control of irradiation of the laser light 216 to the test object 211 by inserting the shutter device 224 on the way of the laser light irradiation optical path in which the laser light 216 for generation from the modulation light source 212 is irradiated at the generation point E of the surface of the test object 211, and this laser light irradiation optical path is then opened or closed.

The master clock 225 is for providing a clock signal (synchronizing signal) to each of the modulation light source 212, the shutter device 224, the surface-wave detecting device 213, and the flaw detection device 214 to synchronize the operations of these devices.

As shown in FIG. 35, the delay generating device 225 is for delaying the opening operation of the shutter of the shutter device 224 for a predetermined period with respect to the clock signal and for opening the shutter after the output of generation laser light 216 outputted from the modulation light source 212 has been stabilized.

Accordingly, as shown in FIG. 35, according to this laser ultrasonic inspecting device 210A, even if the oscillation of the laser light 216 for generation of the modulation light source 212 starts, the laser light irradiation optical path is closed by the shutter device 224 until a predetermined delay period is elapsed from the starting of the oscillation thereof, so that the laser light 216 for generation is not irradiated to the test object 211 and waited.

Subsequently, after the delay period has elapsed, the oscillation of the laser light 216 for generation of the modulation light source 212 is stabilized, so that the shutter device 224 opens the laser light irradiation optical path. Thus, the laser light 216 for generation is irradiated to the generation point E of the test object 211.

The laser light 220 for detection which oscillates in synchronism with the oscillation of the laser light 216 for generation to this generation point E is irradiated to the detection point M. Further, the capturing of the data such as the surface-wave signal and flawed wave signal by the signal recording device 214a is started in synchronism with the irradiation to the detection point M of this laser light 220 and is recorded for a predetermined period. At this time of data recording, as shown in FIG. 35, the scanning position signal of the scanner 215 is provided to the signal recording device 214a so as to be recorded.

That is, the signal recording device 214a starts the recording of data at almost the same time as the shutter of the shutter device 224 is opened. A part of the signal is not stabilized immediately following the starting of the clock signal generation, so that the capturing of the data is performed after the numeric value has been stabilized by the delay for a very short period. As for recording of data, sensor information employed for inspection, laser irradiation position information, a laser condition signal, an ultrasonic signal, a condition signal generated from another apparatus, and the other necessary detailed data are converted from analog values to digital values (AD conversion), or obtained through a network such as LAN so as to be stored. A general-purpose PCI board can be applied to an AD converting device, and a device employing a PXI module may be applied to a high-speed AD converting device.

Consequently, according to this laser ultrasonic inspecting device 210A, the laser light for generation is irradiated to the test object 11 after the oscillation thereof has been stabilized, thereby improving the detection precision of the flawed portion 223 by the flaw detection device 214. Further, since this flaw detection device 214 is provided with the scanning position signal from the scanner 215, further improvement of the flawed position detection precision by this flaw detection device 214 can be achieved.

Furthermore, the data of, for example, the surface wave and flawed wave signals of the signal recording device 214a are recorded only for a predetermined period in synchronism with the irradiation of the laser light 216 for generation to the test object 211, and is not recorded during a period in which the laser light 216 for generation is not irradiated to the test object 211, thus reducing the amount of recording thereof. Therefore, the capacity of the memory medium to be recorded with the above data and recording time can be reduced.

Further, by increasing the necessary amount of recoding data and recording time for just the amount of reduction of recording data, it becomes possible to improve the signal recording precision and flaw detection precision to be realized.

Third Embodiment

Figure 36:
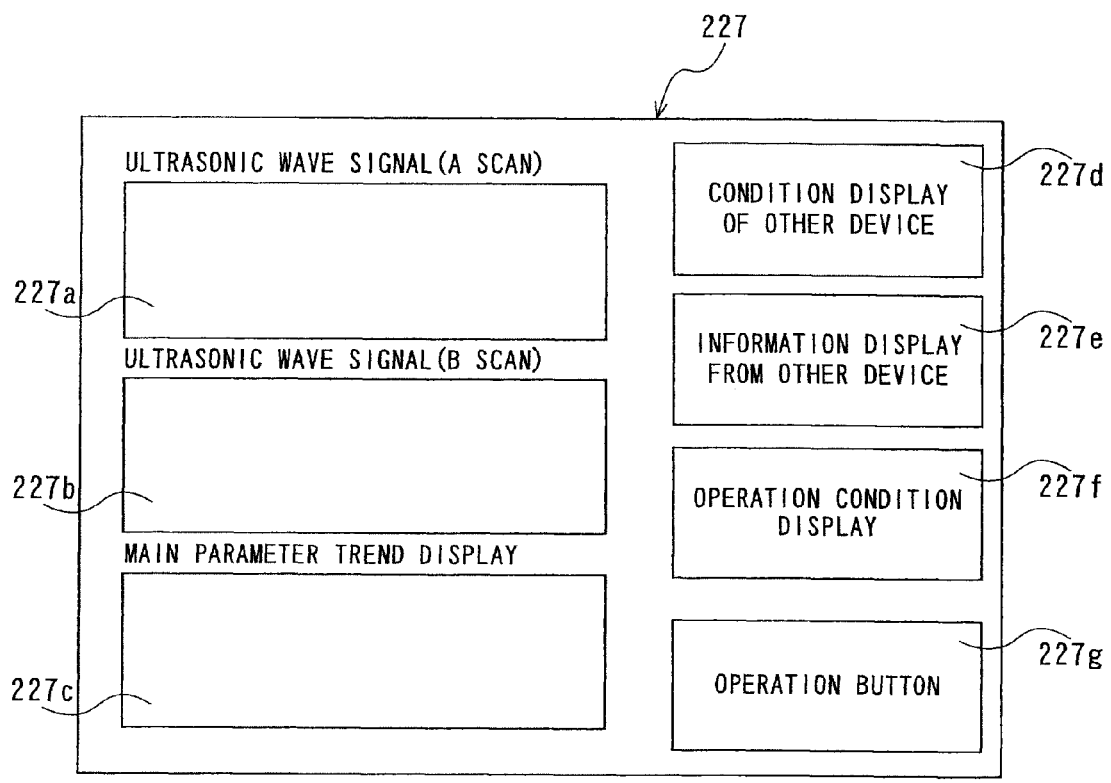
FIG. 36 is a front view of a display screen of a third embodiment of a surface inspecting device according to the present invention.

FIG. 36 is a schematic view of an enlarged view showing an essential portion of a display screen 227 of a signal recording device 214a according to a third embodiment of the present invention. This display screen 227 is configured to have a multi-window, for example. On the left-half side in FIG. 36, a time waveform display window 227a, trend display window 227b, and principal-parameters display window 227c are disposed, and on the right-half side, a condition display window 227d, another apparatus information display window 227e, a running state display window 227f, and an operating button display window 227g for controlling the driving of the scanner 215 are displayed.

The time waveform display window 227a is a small window for sequentially displaying the time waveform of each detection signal of the surface wave 219, and the flawed waves 222a and 222b to be inputted to the signal recording device 214a from the surface wave detecting device 213 only for a predetermined period for each irradiation to the test object 211 of the laser light 216 for generation in a pulse state.

The trend display window 227b is a small window for arraying the predetermined number of the surface wave 219 and the flawed waves 222a and 222b inputted to the signal recording device 214a in a time sequence to be displayed for a predetermined period, and also for displaying the trends of these surface wave 219 and flawed waves 222a and 222b.

The principal-parameters display window 227c is a window for displaying the trends of the principal parameters such as the waveforms showing the respective extensions of the laser light 216 for generation in a pulse shape and the laser light 220 for detection, irradiation to the test object 211 of the laser light 220 for detection, and the shift of timing of the opening operation of the shutter device 224.

The condition display window 227d is a small window for displaying the current states of, for example, the abnormal presence of another apparatus such as the modulation light source 212, surface-wave detecting device 213, flaw-detecting device 214b, flaw-identifying device 214c, scanner 215, shutter device 224, master block 225, or delay generating device 226.

Another apparatus information display window 227e is a small window for displaying the current X-Y position (scanning position) of the scanner 215, or information such as operation velocity from another apparatus.

The running state display window 227f is a window for displaying the running state of another apparatus such as regarding whether or not the scanner 215 is running.

The operating button display window 227g is a small window for displaying an operating button such as an ON/OFF button for operating the running of the scanner 215, and a display button for setting the scanning velocity or scanning range.

Consequently, according to the present embodiment, the running of the scanner 215 can be controlled while confirming each of the time waveforms, the trends of the surface wave 219 and flawed waves 222a and 222b, the trends of the other principal parameters, and the current state and running state such as the abnormal presence of another apparatus by viewing the display screen 227 of the signal recording device 214a.

Fourth Embodiment

Figure 37:
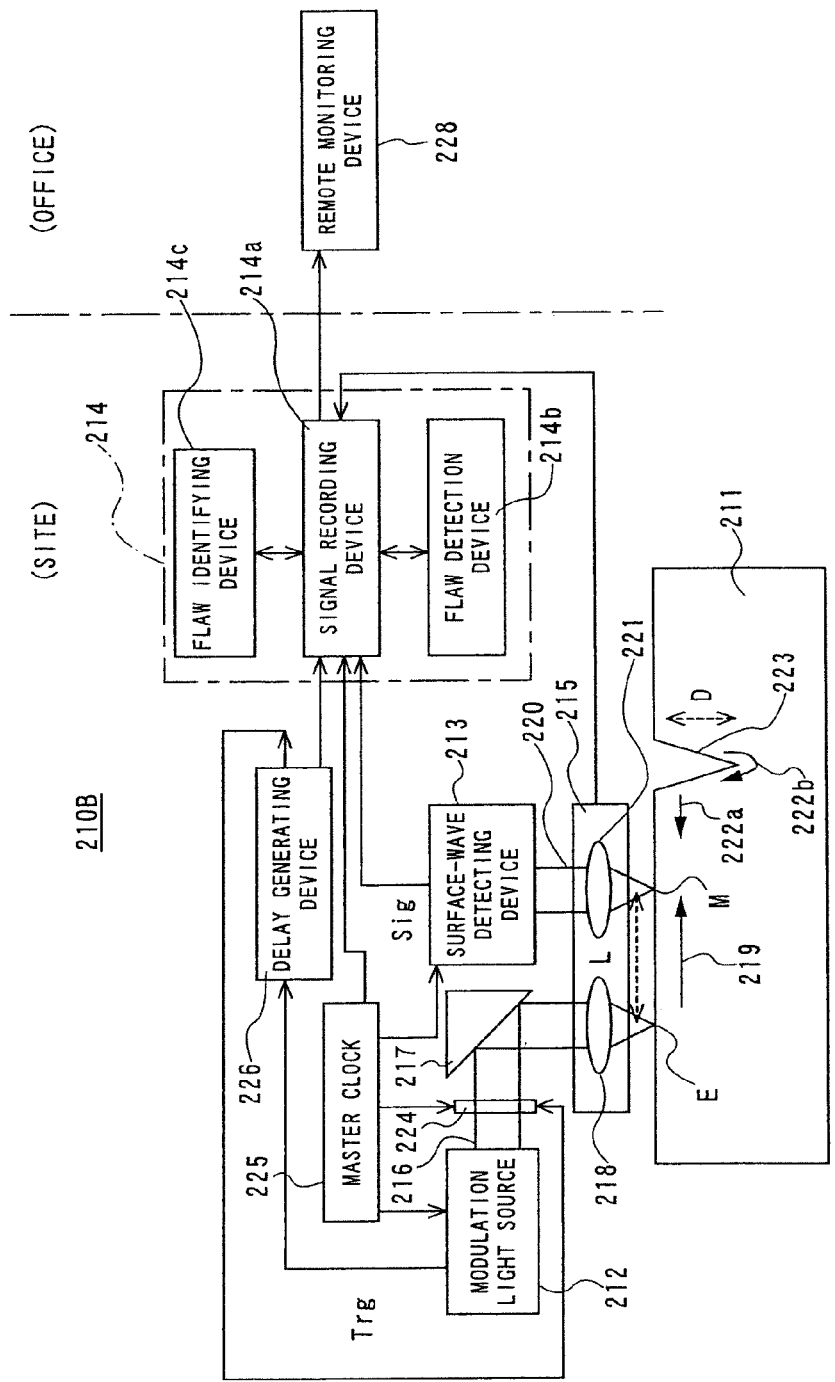
FIG. 37 is a functional block diagram of a fourth embodiment of a surface inspecting device according to the present invention.

FIG. 37 is a block diagram illustrating the entire configuration of a fourth embodiment of the laser ultrasonic inspecting device 210B of the present invention. In this laser ultrasonic inspecting device 210B, a remote monitoring device 228 for remote-monitoring the laser ultrasonic inspecting device 210A is provided to the flaw detection device 214 of the laser ultrasonic inspecting device 210A according to the second embodiment shown in FIG. 34.

That is, as shown in FIG. 37, in the event that the main device 210A other than the remote-monitoring device 228 is disposed at a site where it is difficult to access without any problem such as a radiation controlled area, the remote-monitoring device 228 is disposed at a place such as an office separated from the site. In the case of a short distance, a LAN cable can be conceived as communication means between the site and the office, but in the case of a middle or long distance, a wireless LAN or an ordinary public line may be employed for monitoring the real time state.

The remote-monitoring device 228 is configured similarly to the flaw detection device 214 of the field installation and includes the display screen 227 shown in FIG. 36.

Consequently, according to this laser ultrasonic inspecting device 210B, even in the office apart from the site, the running state of this laser ultrasonic inspecting device 210B can be monitored by the remote-monitoring device 228, and in addition, the running of the scanner 215 or the like can be also remote-monitored. Accordingly, even in a case that particular skills or experiences are required for a surveillance technique, a plurality of site fields can be handled only by one person to grasp the inspection state.

Fifth Embodiment

Figure 38:
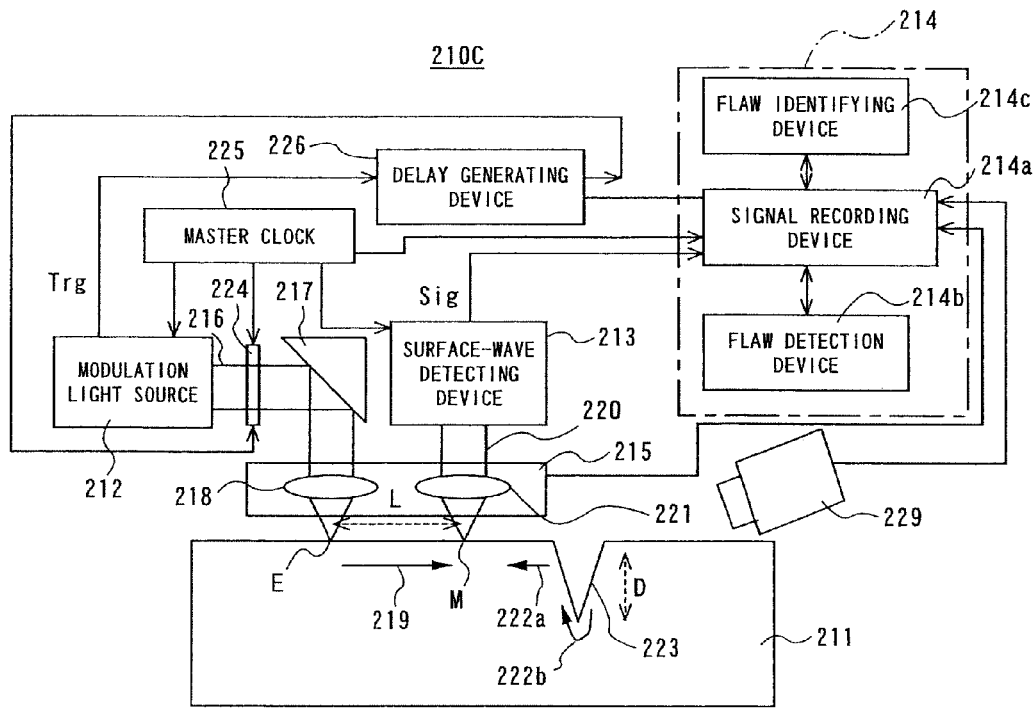
FIG. 38 is a functional block diagram of a fifth embodiment of a surface inspecting device according to the present invention.

FIG. 38 is a block diagram illustrating the entire configuration of a fifth embodiment of a laser ultrasonic inspecting device 210C of the present invention. In this laser ultrasonic inspecting device 210C, a surveillance camera 229 is provided to the laser ultrasonic inspecting device 210A according to the second embodiment shown in FIG. 34.

The surveillance camera 229 is principally for imaging the test object 211, the scan surface to be scanned over the surface thereof and a surface inspecting working, recording the imaged signal to the signal recording device 214a, and displaying the recorded signal on a display screen. The image-captured (imaged) signal may be generated to the remote-monitoring device 228 shown in FIG. 37 via the signal recording device 214a so that the captured image is displayed on the display screen.

That is, generally, as for the procedures of the surface inspection of the test object 211, visual inspection prior to implementation and visual inspection following implementation can be assumed. Further, it can be conceived for a surveyor to confirm the inspecting position and state on an image during the inspection of the state.

For this reason, the surface inspecting process is photographed by the surveillance camera 229. Further, the lights differ in their amounts between the time during the inspection and the time before and after this inspection, so that in the case of imaging with one surveillance camera 229, a camera (log camera) will be employed in which the quantity-of-light pair sensitivity has the relation of a logarithm. Otherwise, in the case of employing only one normal surveillance camera 229, there may be provided an electric configuration capable of adjusting the amount of exposure, or a mechanism for mechanically operating a dimmer filter to perform photographing. Even at the time of photographing with a plurality of surveillance cameras 229, the providing of the same configuration or mechanism will enable cost reduction to be realized.

Consequently, according to this laser ultrasonic inspecting device 210C, the inspecting states before and after the surface inspection of the test object 211 can be visually checked by a surveyor through visual inspection of the imaging screen of the surveillance camera 229.

Sixth Embodiment

Figure 39:
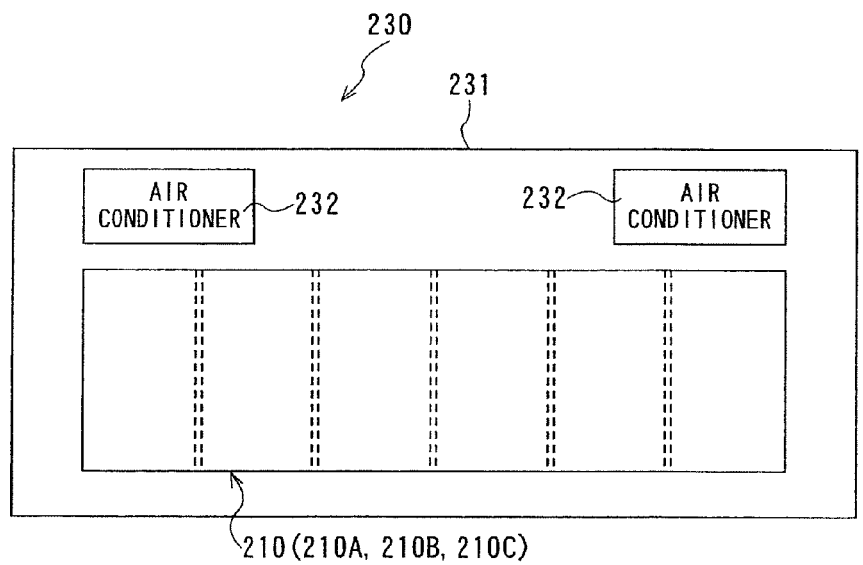
FIG. 39 is an explanatory diagram of a sixth embodiment of a surface inspecting device according to the present invention.

FIG. 39 is a schematic diagram illustrating the configuration according to a sixth embodiment of a laser ultrasonic inspecting system 230 of the present invention. In this laser ultrasonic inspecting system 230, either one of the above laser ultrasonic inspecting devices 210, 210A, 210B, and 210C is disposed in a container 231, and one or more air conditioners 232 serving as one example of a temperature controller are also disposed in this container 231.

According to this laser ultrasonic inspecting system 230, the temperature and humidity in the container 231 can be controlled in the temperature and humidity suitable for either one of the laser ultrasonic inspecting devices 210, 210A through 210C by the air conditioners 232 and 232, and therefore, particularly even in an environment of high heat and high humidity such as in the summertime, the laser ultrasonic inspecting devices 210, and 210A through 210C can be normally operated, thus ensuring the precision and quality of the surface inspection.

Seventh Embodiment

Figure 40:
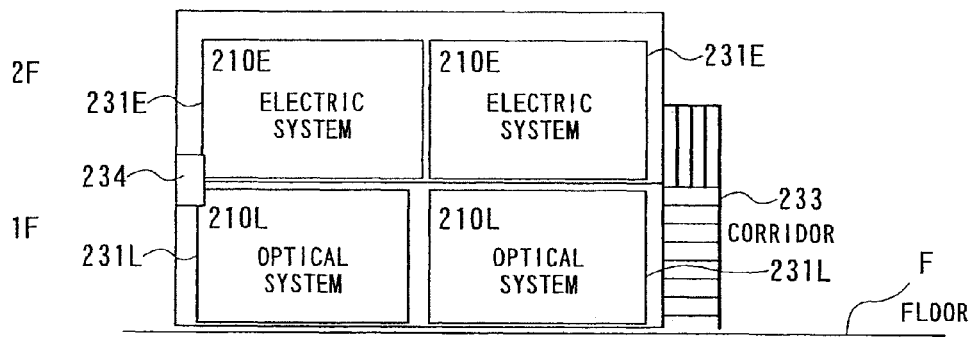
FIG. 40 is a schematic view of a seventh embodiment of a surface inspecting system according to the present invention.

FIG. 40 is a schematic diagram illustrating the configuration of a seventh embodiment of a laser ultrasonic inspecting system 230A according to the present invention. In this laser ultrasonic inspecting system 230A, either one or more, two, for example, of the laser ultrasonic inspecting devices 210, 210A, 210B, and 210C are classified into an optical system 210L including an optical system such as a laser light-resource, and an electric system 210E including the other control systems other than the optical system, which are accommodated within containers 231L and 231E, respectively. The electric system containers 231E are stacked on the respective optical system containers 231L and erected in two layers on the floor F.

The optical system mentioned herein may include the modulation light source 212, a surface-wave detecting device 213, a scanner 215, an irradiation optical system 217, a lens system 218, and a shutter device 224. The electric system mentioned herein may include the flaw detection device 214, a master clock 225 and a delay generating device 226.

Further, the laser ultrasonic inspecting system 230A comprises an external stairs 233 for accessing the electric container 231E of the second floor (2F) from a floor F of the first floor (1F), and a connector 234 serving as one example of a combining device for vertically combining the optical container 231L and the electric container 231E.

Further, the laser ultrasonic inspecting system 230A connects these optical system container 231L and electric system container 231E to a building or the other stabled portion by means of wire or the like. A connector box for connecting the respective floors may be provided to a part of these containers 231E and 231L, thereby enabling a signal cable to be exchanged without destroying boundary lines.

According to this laser ultrasonic inspecting system 230A, a plurality of containers 231E and 231L are piled up in two stages, thereby enabling the installation space at the inspecting field to be saved. Further, the optical system 210L, which is readily affected by the vibrations of any one of the laser ultrasonic inspecting devices 210, and 210A through 210C, is provided on the first floor (1F) at which the vibration is small, thus improving the reliability of the optical system 210L.

Eighth Embodiment

Figure 41:
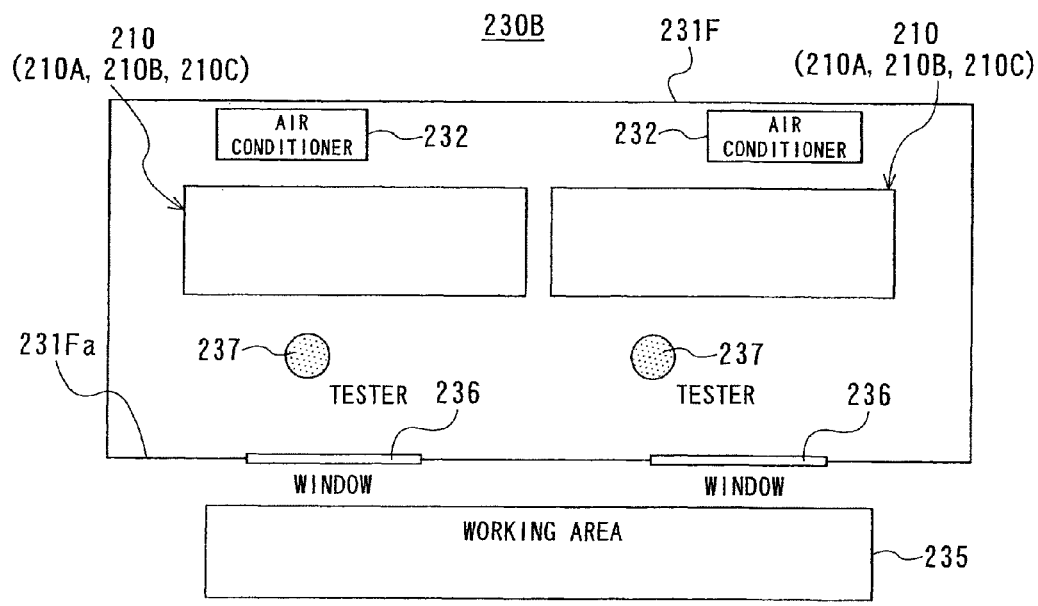
FIG. 41 is a schematic view of an eighth embodiment of a surface inspecting system according to the present invention.

FIG. 41 is a plane schematic diagram illustrating the configuration of an eighth embodiment of a laser ultrasonic inspecting system 230B of the present invention. In this laser ultrasonic inspecting system 230B, either one or more of the laser ultrasonic inspecting devices 210, and 210A through 210C, for example, two, main unit devices excluding the respective scanners 215 are accommodated each in a large-sized container 231F, and see-through windows 236 and 236 are formed on the side wall 231Fa of the container 231F on the work area (235) side outside the container 231F in which the scanner 215 and the test object 211 are installed.

The respective see-through windows 236 are formed with a size in which the inspecting working at the work area 235 can be visually observed, and formed of a transparent material such as a transparent synthetic resin or glass. These transparent materials are bonded with a scattering prevention film in the case of being destroyed, and the boundary from the outside can be secured by laminating a plurality of films.

According to this laser ultrasonic inspecting system 230B, since a surveyor 237 can view a work area 235 through a see-through window 236, an inspecting work can be done from the inside of the container 231F.

Ninth Embodiment

Figure 42:
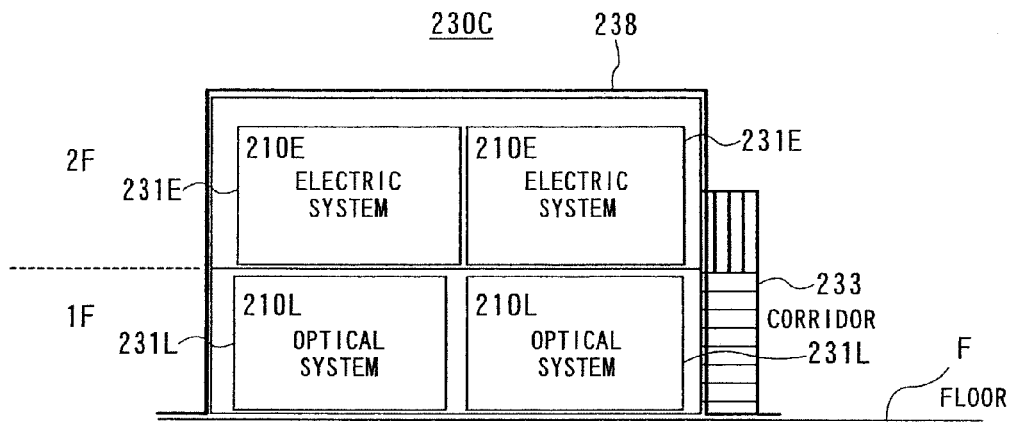
FIG. 42 is a schematic view of a ninth embodiment of a surface inspecting system according to the present invention.

FIG. 42 is a schematic view illustrating the configuration of a ninth embodiment of a laser ultrasonic inspecting system 230C according to the present invention. In this laser ultrasonic inspecting system 230C, the outer surfaces of the containers 231E and 231L of the laser ultrasonic inspecting system 230A shown in FIG. 40 are entirely covered with a cover 238 such as a vinyl sheet.

Generally, since the optical system 210L such as of the laser ultrasonic inspecting devices 210, and 210A through 210C has a high probability to malfunction due to dust or the like, the outer surfaces of the containers 231E and 231L accommodating the laser ultrasonic inspecting devices 210, and 210A through 210C are covered with the cover 238 to thereby reduce the dust or prevent the dust from flowing within the optical container 31. Thus, the precision regarding both the optical system 10L and the electric system 210E can be improved.

Tenth Embodiment

Figure 43:
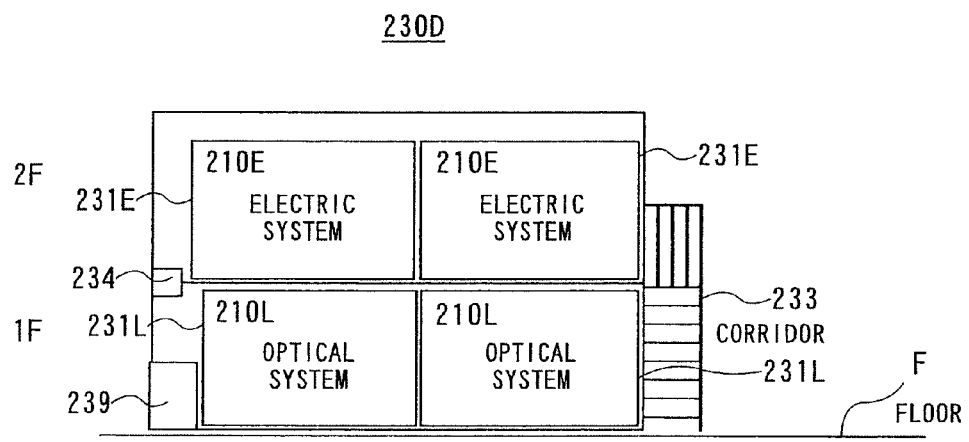
FIG. 43 is a schematic view of a tenth embodiment of a surface inspecting system according to the present invention.

FIG. 43 is a schematic view illustrating the configuration of a tenth embodiment of a laser ultrasonic inspecting system 230D according to the present invention. In this laser ultrasonic inspecting system 230D, an air-pressure controller 239 is provided in the laser ultrasonic inspecting system 230A shown in FIG. 40 for controlling the air pressure in the electric system container 231E and the optical system container 231L so as to provide a positive pressure higher than the ambient air pressure.

According to this laser ultrasonic inspecting system 230D, the insides of the electric system and optical system containers 231E and 231L are controlled by the air-pressure controller 239 so as to provide a positive pressure higher than ambient air pressure, and therefore, even in the case that the door is opened or closed at the time of entering or leaving the containers 231E and 231L, and the air flows from the inside of the containers 231E and 231L into the ambient air. Thus, the dust can be prevented from infiltrating.

In addition, in the case that the containers 231E and 231L are installed in the radiation controlled area, the inflow of radiation substances to the containers 231E and 231L can be prevented, realizing the reduction in the exposure of the radiation.

Embodiments of an ultrasonic inspecting device relating to the laser maintenance apparatus of the present invention will be described hereunder with reference to the accompanying drawings.

Figure 44:
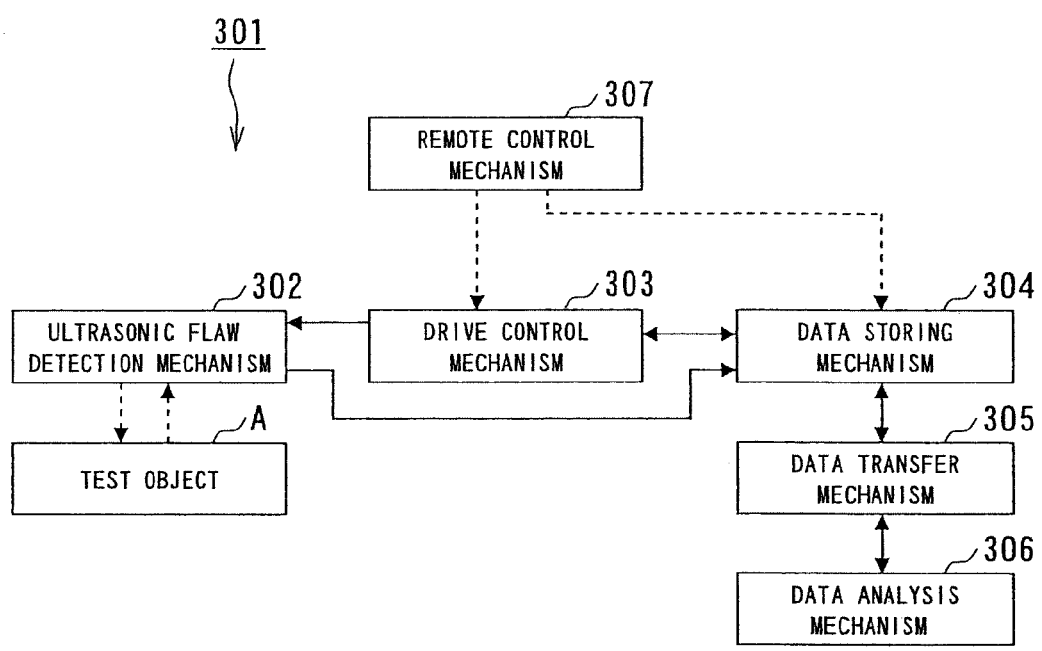
FIG. 44 is a configuration diagram illustrating a first embodiment of an ultrasonic inspecting device relating to the present invention.

FIG. 44 is a configuration diagram illustrating a further embodiment of an ultrasonic inspecting device relating to the laser maintenance apparatus of the present invention.

As illustrated in FIG. 44, the ultrasonic inspecting device 301 comprises an ultrasonic flaw detection mechanism 302 which has an ultrasonic transducer, not shown, for performing ultrasonic flaw detection of a test object A, a drive control mechanism 303 for the purpose of scanning the ultrasonic flaw detection mechanism 302 and controlling the driving, a data storing mechanism 304 for storing the test data such as ultrasonic data or position data or the like acquired from the ultrasonic flaw detection mechanism 302, and for storing various data such as flaw detection location information or scanning speed, or flaw detection condition signals which is generated from the drive control mechanism 303, a data generating mechanism 305 for generating the test data stored by the data storing mechanism 304, a data analysis mechanism 306 for analyzing the test data generated from the data generating mechanism 305, and a remote operating mechanism 307 for remotely operating the drive control mechanism 303 or the data storing mechanism 304.

The ultrasonic flaw detection mechanism 302 performs flaw detection at the interior and surface of the test object A using ultrasonic waves. With the ultrasonic flaw detection mechanism 302, ultrasonic waves can be generated using piezoelectric elements, for example, or ultrasonic waves can be generated by utilizing an ultrasonic focus flaw detection method or phased-array method which uses piezoelectric elements as a base.

Furthermore, for the ultrasonic flaw detection mechanism 302, a method using electromagnetic ultrasonics or a laser ultrasonic method for generating ultrasonic waves may be utilized. Herein, a laser ultrasonic method refers to a method which generates ultrasonic waves by using the distortion of an elastic region generated in a case that a pulse laser light is irradiated onto a material, and by using the interference effects of the laser light for detection which is irradiated onto another point of the material, the ultrasonic waves can be detected as a vibration signal. Thus, the generated ultrasonic wave is used for various crack testing or material characterization similar to the case of the ultrasonic waves generated by a normal contact element.

The drive control mechanism 303 performs movement of the ultrasonic flaw detection mechanism 302 or control of the movement. The drive control mechanism 303 has a program and a scan mechanism for scanning a test range specified with respect to the test portions of the test object A according to predetermined test guidelines with one or plural dimensions.

In the case of the ultrasonic inspecting with the drive control mechanism 303, the test ranges or test speeds to the test portions of the test object A should be set in advance, and the drive conditions are hence set by selecting the test portions of the test object A.

Further, the drive control mechanism 303 transmits the test data to the data storing mechanism 304 according to a communication protocol such as a LAN or DIO, RS-232C, USB, or IEEE 1394, for example, with a communication means, not shown, which is connected to the data storing mechanism 304.

The data storing mechanism 304 stores test data such as the ultrasonic data received from the ultrasonic flaw detection device 302 or the location data received from the drive control mechanism 303, and creates a condition file which records the test conditions and a data file which records the test data.

The data transferring mechanism 305 is a communication mechanism which connects the data storing mechanism 304 and the data analysis mechanism 306, and for example, has a data communication function using a wired LAN or wireless LAN, PHS, or mobile telephone, or communication function using a telephone circuit such as ISDN or DSL, or the like.

The data transferring mechanism 305 may be a storage device such as USB memory or an HDD, or may be a storage media such as an MO, a CD, a DVD, or the like.

The data analysis mechanism 306 performs data analysis to the test data that is stored with the data storing mechanism 304 and generated from the data transferring mechanism 305.

After the data file to be analyzed is selected, the data analysis mechanism 306 starts data analysis by executing an analysis program in which a predetermined analysis method is programmed for each test portion, and when the data analysis is completed, the analyzed result is displayed.

When the parameters for a digital filter, (i.e. a filter which removes or deletes specified elements from the signal) are adjusted and the analysis parameters are determined, for example, the analysis program automatically derives the analysis results.

The remote operating mechanism 307 is connected to the drive control device 303 or the data storing mechanism 304 with a communication means, not shown, and remotely operates the drive control device 303 or the data storing mechanism 304 according to a communication protocol such as a LAN or DIO, RS-232C, USB, or IEEE 1394, for example.

The procedures for storing the test data in the data storing mechanism 304 will be described hereunder in accordance with the flowchart shown in FIG. 45 with the ultrasonic inspecting device 301 according to this first embodiment of the ultrasonic inspecting device according to the present invention.

The data storing mechanism 304 awaits until a process start preparation signal, which indicates that preparation for starting the ultrasonic test is completed, is received from the drive control mechanism 303, and when the process start preparation signal is received (S101), a data folder is created (S102) for storing a string of data of the test data and so on.

Herein, the folder name for the created data folder can be set arbitrarily, such as the test object and date, or the test object portions and date.

Further, the data storing mechanism 304 creates a condition file for storing the test conditions in the case of the ultrasonic inspecting after the data folder is created (S103). The test date and time, test portions and the like should determine the file name for the created condition file and should include combinations of "test object portion", "test date and time", "flaw detection method used", "number of flaw detections", "tester name", "corresponding correction record", "flaw detection range", "speed", "flaw detection pitch", "name of device used", "name of procedure used", etc.

For example, if the test object portion is instrument tube No. 5 of a in-core (reactor) instrument tube (BMI), a laser ultrasonic method (LUT) is used, and process preparation signal is received at 14:30 and 25 seconds on Feb. 15, 2005, the condition file can be named "condition_BMI_05_LUT_20050215_143025_1 [extension]".

The data storing mechanism 304 records information relating to the "test object portions" which is set with the drive control mechanism 303, or the initial process information such as "flaw detection range", "flaw detection method used", "initialization position", "drive speed", "PC name of drive control mechanism" and the like into the created condition file, using an appropriate data format such as CSV (Comma Separated Values), XML (extensible Markup Language), text format, and the like (S104).

When the drive control mechanism 303 sends the processing start signal for starting the flaw detection, the data storing mechanism 304 receives this processing start signal (S105), and creates a data file with the conditions used in the condition file (S106). For example, this is "BMI_05_LUT_20050215_143025_1 [extension]" in the above example. The data format for the data file is CSV, XML, text and the like and is set appropriately.

When a data file is created, the data storing mechanism 304 stores the test data obtained with the ultrasonic flaw detection mechanism 302 and the position data obtained with the drive control mechanism 303 in the data file for each ultrasonic data capturing cycle (S107).

Further, it is to be noted that in the case of using a laser ultrasonic method with the ultrasonic flaw detection mechanism 302, the energy amount of the received detection laser light, which is irradiated onto the surface of the test object A, or the amount of light which is reflected from the surface thereof and returned may be calculated and additionally stored in the data file.

When the ultrasonic test or inspection of the predetermined flaw detection range is completed, the drive control mechanism 303 sends a process end signal indicating that the ultrasonic test is completed (S108), and also the data storing mechanism 304 receives the process end signal and writes the information such as "data file name", or the process end information such as "flaw detection end position", "number of storing data points" and the like into the above-described condition data file (S109), and the process of the flaw detection portions is thus ended.

Next, the procedure for the data analysis mechanism 306 to perform data analysis with the ultrasonic inspecting device 301 will be described in accordance with the flowchart shown in FIG. 46.

Figure 47:
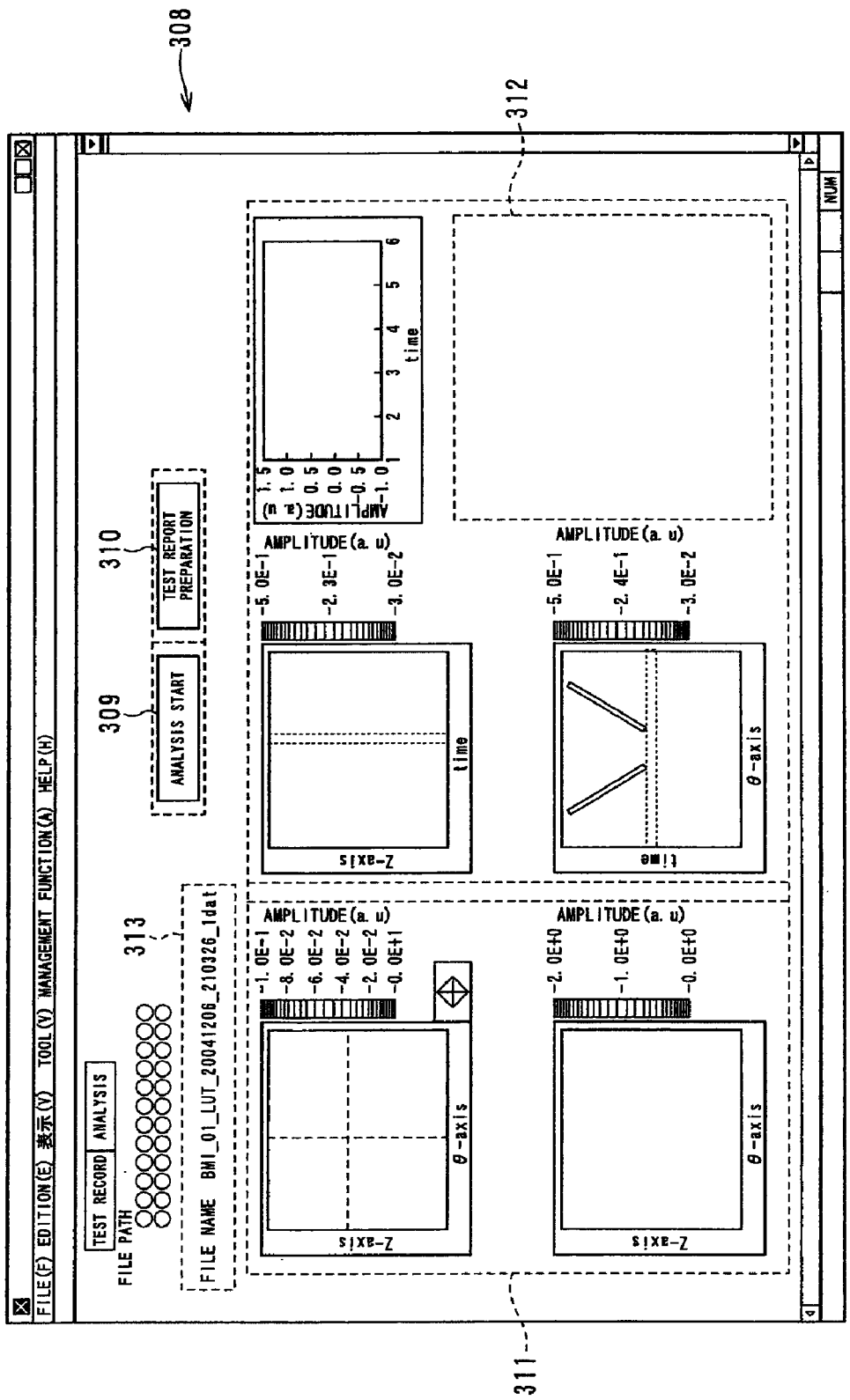
FIG. 47 is a diagram illustrating an analysis screen display example.

An analysis screen 308 for reference for the tester in the case of data analysis is shown in FIG. 47. The analysis screen 308 has an analysis start button 309 which is a trigger for executing processing of the analysis program into which a predetermined analysis method is programmed for each testing position, a test report creating button 310 which is a trigger for the process to create the test report, an analysis results display portion 311 on which the analysis result information is displayed, a defect existence display portion 312 which displays information as to whether or not defects exist, and a data file name display portion 313 on which the file name of the data file is displayed as needed.

First, the data analysis mechanism 306 prompts the tester to select a data file (S201) and also prompts the tester to depress the analysis start button 309. When the data analysis mechanism 306 recognizes that the analysis start button 309 has been depressed (S202), the analysis program is executed and analysis of the analysis data is performed (S203).

Herein, the analysis program have a parameter adjusting mechanism or the like for a digital filter, for example, but after such adjusting mechanisms have determined the analysis parameters, the parameters should be fixed, and the entire analysis result can be obtained without further inputting.

Furthermore, in the case of performing the data storing with an automated device, the data amount is often vastly increased and it requires increased analysis time. Thus, as needed, the data analysis mechanism 306 displays a progress bar which indicates the progress of the analysis (S204). However, in the case of a short analysis time, when analysis processing function is decreased by displaying a progress bar, the progress bar does not need to be displayed.

When the data analysis is ended (S205), the data analysis mechanism 306 displays the analysis results on the analysis result display portion 311 (S206). As for content to be displayed here, an A-scan which shows the ultrasonic waveform with time and amplitude, a B-scan which shows the ultrasonic waveform with time, position and intensity, and a C-scan which shows the ultrasonic waveform with a two-dimensional position and intensity, can be displayed. The numbers to be displayed are set as needed. Among the items to be included in the test report which is specified in "JIS Z 3060", the appropriate information can be selected and displayed.

Furthermore, the data analysis mechanism 306 displays defect indications on the defect existence display portion 312.

Figure 48:
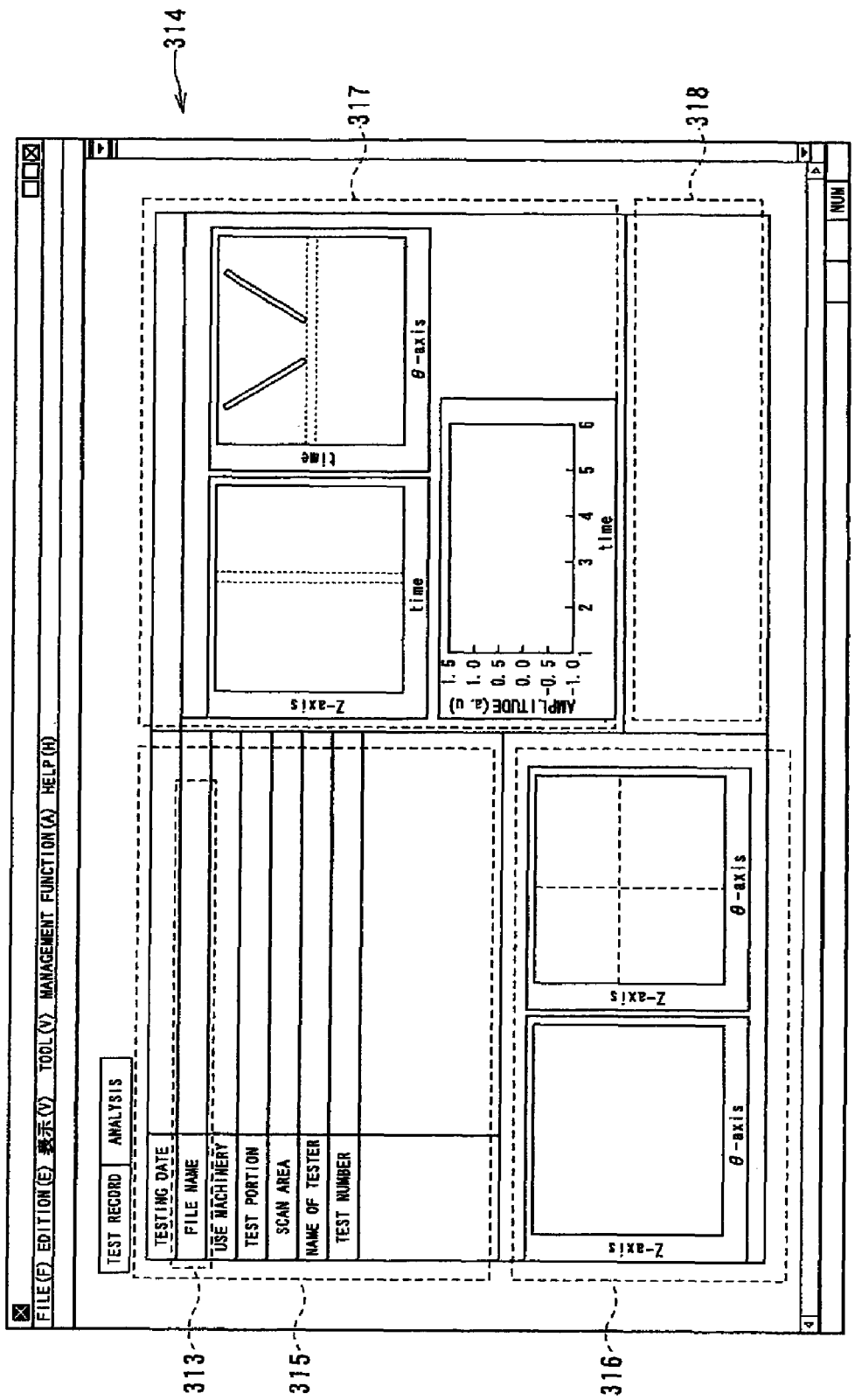
FIG. 48 is a diagram illustrating a testing report screen display example.

When the tester depresses the test report creating button 310 on the analysis display screen 308 (S207), as shown in FIG. 48, a test report screen 314 is created and displayed (S208) on which the items to be included in the test report specified in "JIS Z 3060" and the necessary item chart 312 of the test guidelines with the testing portions and the analysis results are attached.

FIG. 48 shows am example of the test report screen 314 for the tester to create the test report. The test report screen 314 has a necessary item display portion 315 on which items necessary for the test guidelines are displayed, a test result display portion 316 on which the test results are displayed, an analysis result display portion 317 on which the analysis results are displayed, and a reference display portion 318 on which the tester writes his comments if needed.

With the test result display portion 316 or the analysis result display portion 317, moving image data can also be displayed. For example, moving image data is comprised of a plurality of C-scans and it can display the test data three-dimensionally. The C-scan displays the flaw detection range x, y two-dimensionally, with the two-dimensional mapping intensity as the amplitude of the obtained ultrasonic waveform, and the image is animated with the x, y two-dimensional mapping as to the time axis of the ultrasonic data.

Furthermore, rather than the C-scan data, the image may be animated as to various testing data. For example, an appropriate two-dimensional axis may be selected as to the information obtained with a format called two-dimensional mapping+time, with the remaining dimension being animated, or animation can be achieved by having an appropriate one dimension as the time axis as to a two-dimensional data called one-dimensional data+time.

With a conventionally used analysis screen 308 for ultrasonic tests, information is often displayed for the items to be included in the test report specified by "JIS Z 3060" such as testing date and time or testing location. However, there is no guarantee that the test data being analyzed is the data actually desired to be analyzed. For example, when a large amount of data is being analyzed, the possibility of data becoming mixed up is undeniable, but according to the present invention, this problem could be solved.

With the first embodiment, the test location can be specified with the file name of the data file, and therefore, by constantly displaying the file name, determination can be easily made as to which test data is being analyzed.

According to this embodiment, by listing the file name of the data file in the test report, the test data when the various test reports are created can be made clear afterwards, and thus, the test data and test results can be traced.

Furthermore, according to this embodiment, the ultrasonic inspecting device 301 performs processing from the data storing to the data analysis, and greatly reduces the process in which humans are involved, and thus the workload of the people is greatly reduced, and also human error can be reduced.

Further, according to this embodiment, the testing can be performed without the tester going to the test site. In other words, in a case of a nuclear power plant, if the test object portions are within a radiation-controlled area, time restrictions may exist for the tester to be within this area. Thus, particularly, in cases in which many test objects remain to be tested but the entry time to be in the area is limited, the tester cannot spend the enough time needed for the testing.

Thus, according to this embodiment, the entry time for the tester is not restricted, and the tester can perform the testing in the office or another appropriate location, and therefore, any human error can be reduced.

First Example

Next, a first example of the ultrasonic inspecting device 301 according to this embodiment will be described in accordance with the flowchart in FIG. 49.

Figure 45:
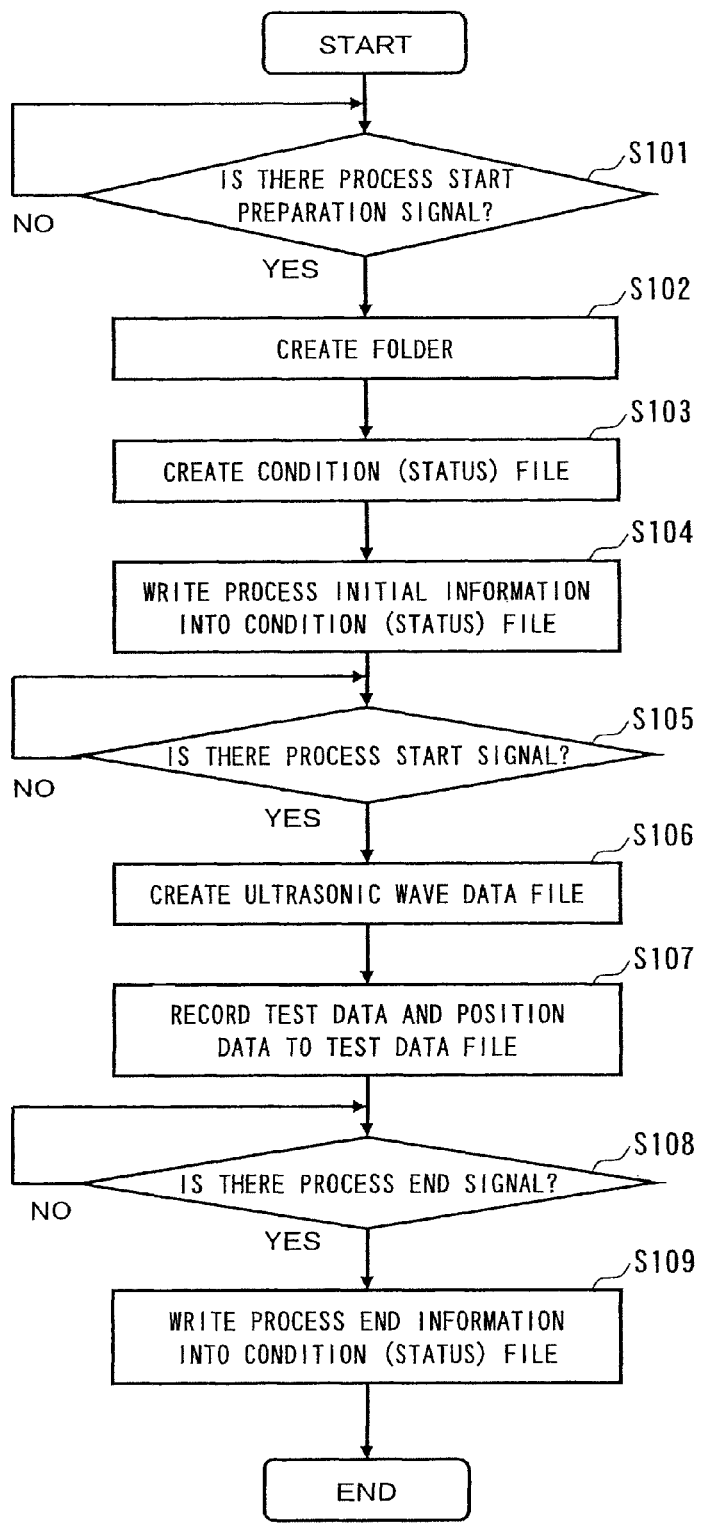
FIG. 45 is a flowchart showing a data storing sequence.
Figure 49:
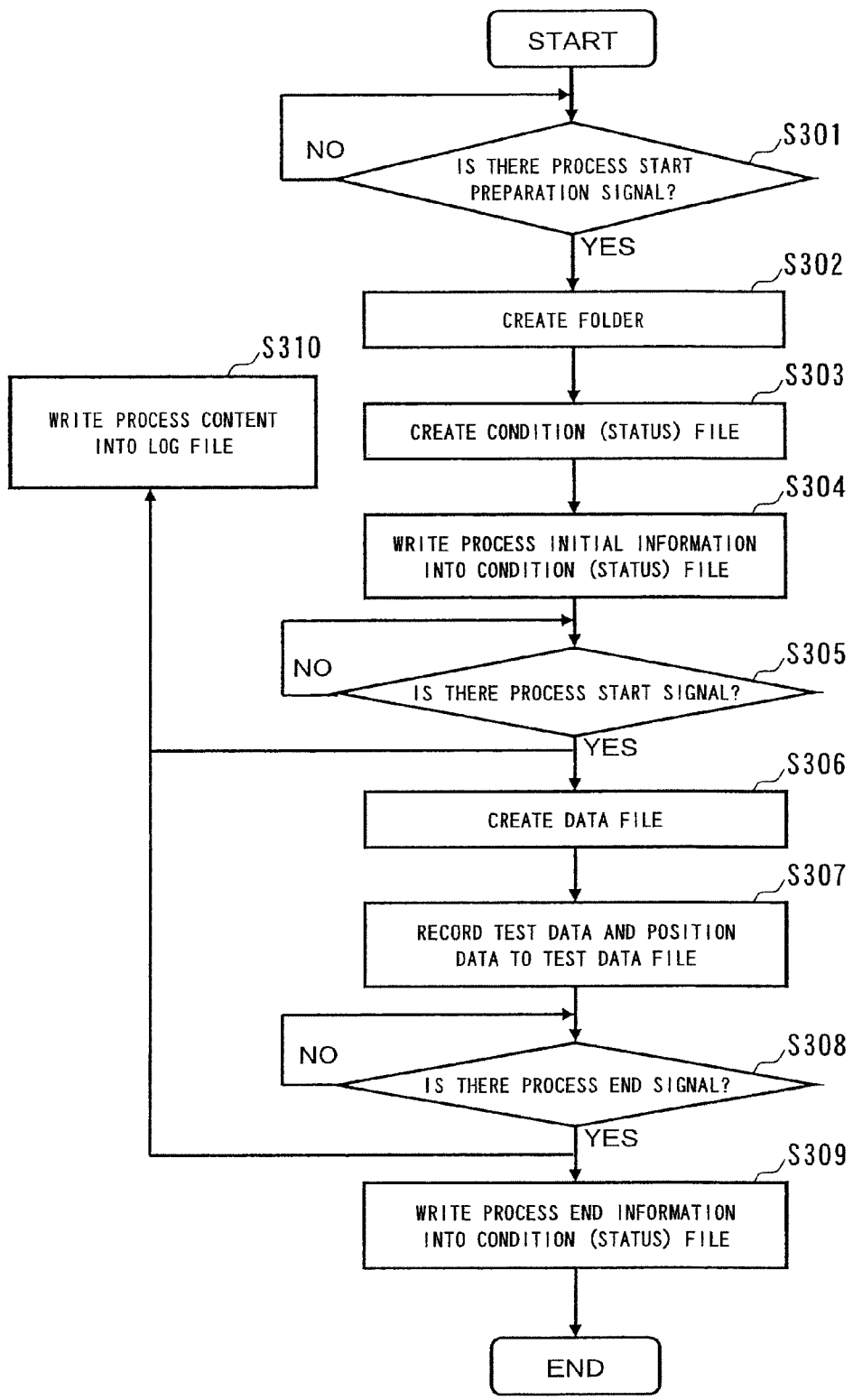
FIG. 49 is a flowchart showing a data storing sequence according to the first embodiment.

As shown in FIG. 49, the procedures for ultrasonic data storing in the first example are fairly similar to the procedures for the ultrasonic data storing in FIG. 45. The difference resides in that a log file is created from the operating start time of the data storing program, and in the event that the data storing preparation is completed, or a process start preparation signal, process start signal or process end signal is received from the drive control mechanism, the processing content and receiving time are written into a log file.

S301 through S305 in FIG. 49 have the same procedures as S101 through S105 in FIG. 45. In this first example, when the data storing mechanism 304 receives the process start signal from the drive control device 303 (S305), the processing content and receiving time are written into a log file (S310).

S306 through S308 also have the same procedures as S106 through S108 in FIG. 45. In this first example, when the data storing mechanism 304 receives the process end signal from the drive control device 303 (S305), the processing content and receiving time is written into a log file (S310).

Similar to the case in FIG. 45, finally, the data storing mechanism 304 writes the process end information into a condition file and ends the process (S309).

Further, in the case of an error occurring in the AD converting unit or digital signal input/output unit (DIO) provided on the data storing mechanism 304, the time of the error occurring and the error location is immediately written into the log file.

With this first example, in a case of a trouble occurring in the stored data, the information relating to the trouble is recorded into the log file, and by checking the log file by the tester, it is confirmed whether or not the flaw was occurring during data storage. Thus, the tester can check afterwards as to whether the data is obtained with a correct flow for performing data storing, and test data and test results can be traced.

Second Example

Next, a second example of the ultrasonic inspecting device relating to the present invention will be described with reference to FIG. 50 through FIG. 53.

Figure 46:
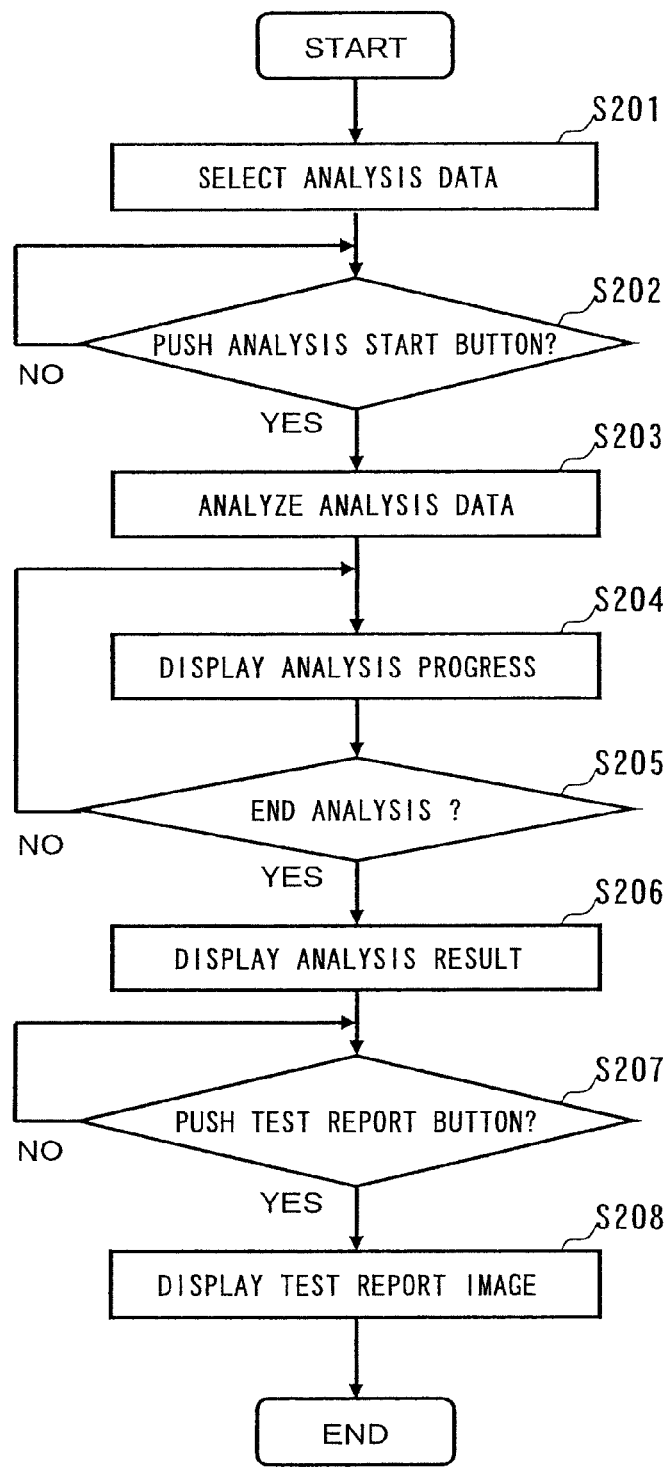
FIG. 46 is a flowchart showing an analysis processing sequence.

With the second example, at the end of the procedures of the data storing and the data analysis in the flowcharts in FIG. 45 and FIG. 46, an electronic signature of the tester is added to each file such as the condition file, data file and the like.

Alternatively, data tampering-prevention processing is performed on each file at the end of the procedures of the data storing and the data analysis in the flowcharts in FIG. 45 and FIG. 46.

Figure 50:
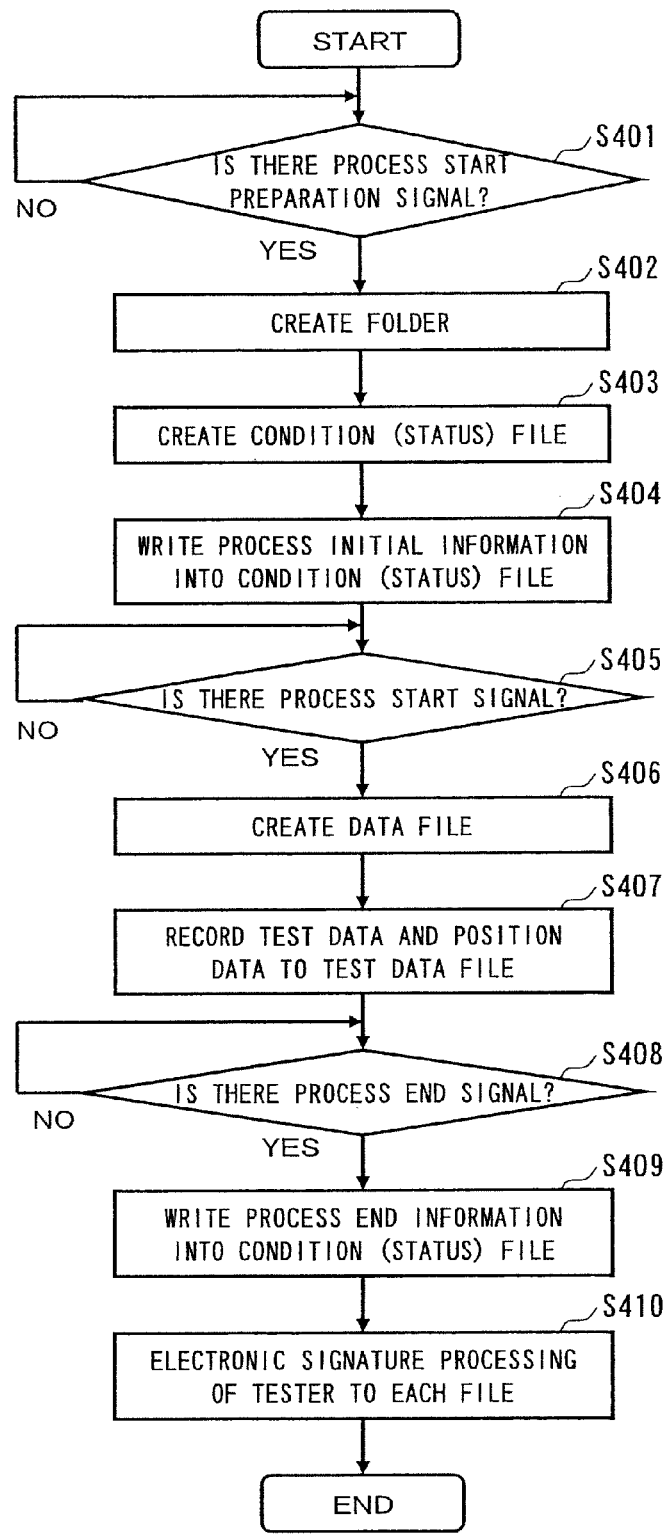
FIG. 50 is a flowchart showing a data storing sequence according to a second embodiment of the ultrasonic inspecting device according to the present invention.

S401 through S409 in FIG. 50 have the same procedures as S101 through S109 in FIG. 45. In this second example, after the data storing mechanism 304 writes the process end information in the condition file (S409), an electronic signature of the tester is added in each data file (S410).

Figure 51:
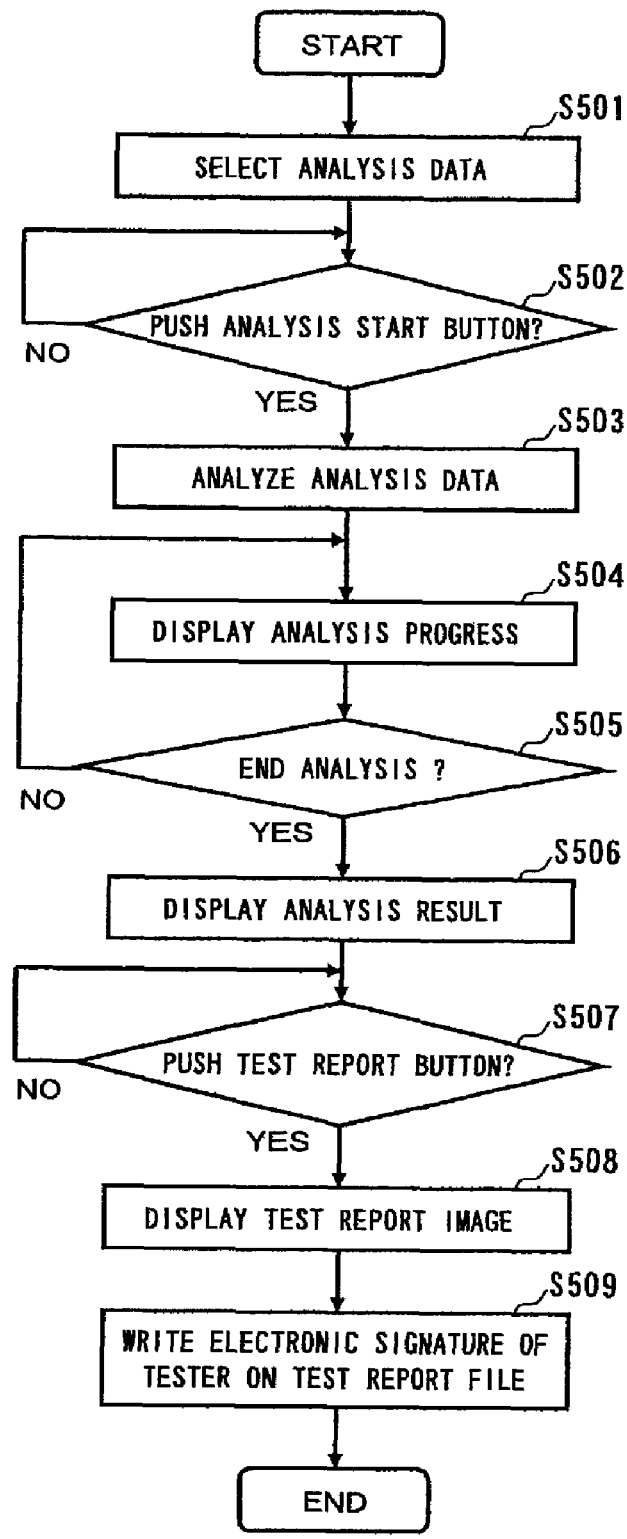
FIG. 51 is a flowchart showing an analysis processing sequence according to the second embodiment.

S501 through S508 in FIG. 51 also have the same procedures as S201 through S208 in FIG. 46. In this second example, after the test report screen 314 is created and displayed (S508), an electronic signature of the tester is added in the test report (S509).

Figure 52:
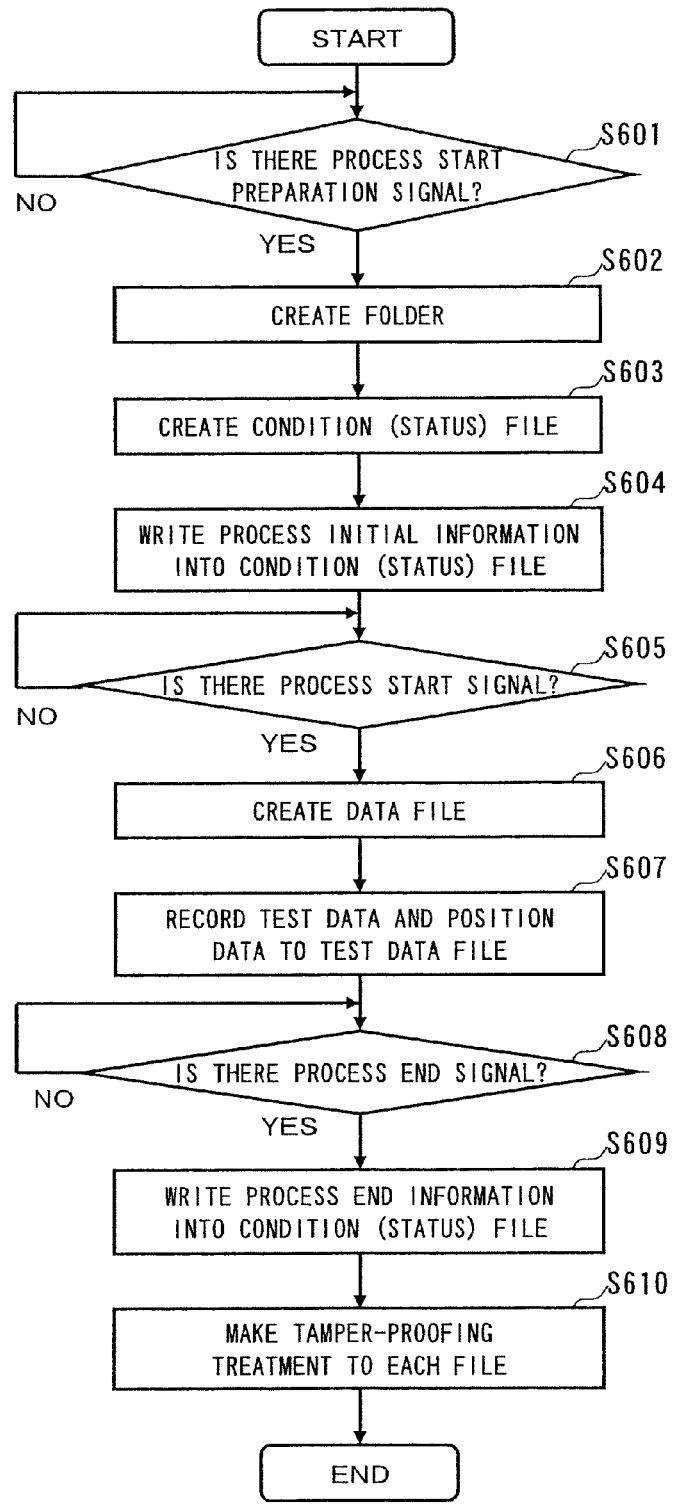
FIG. 52 is a flowchart showing another example of a data storing sequence according to the second embodiment.

Furthermore, S601 through S609 in FIG. 52 also have the same procedures as S101 through S109 in FIG. 45. In the second example, after the data storing mechanism 304 writes the process end information in the condition file (S609), a function for tamper-proofing is added in each data file (S610).

Figure 53:
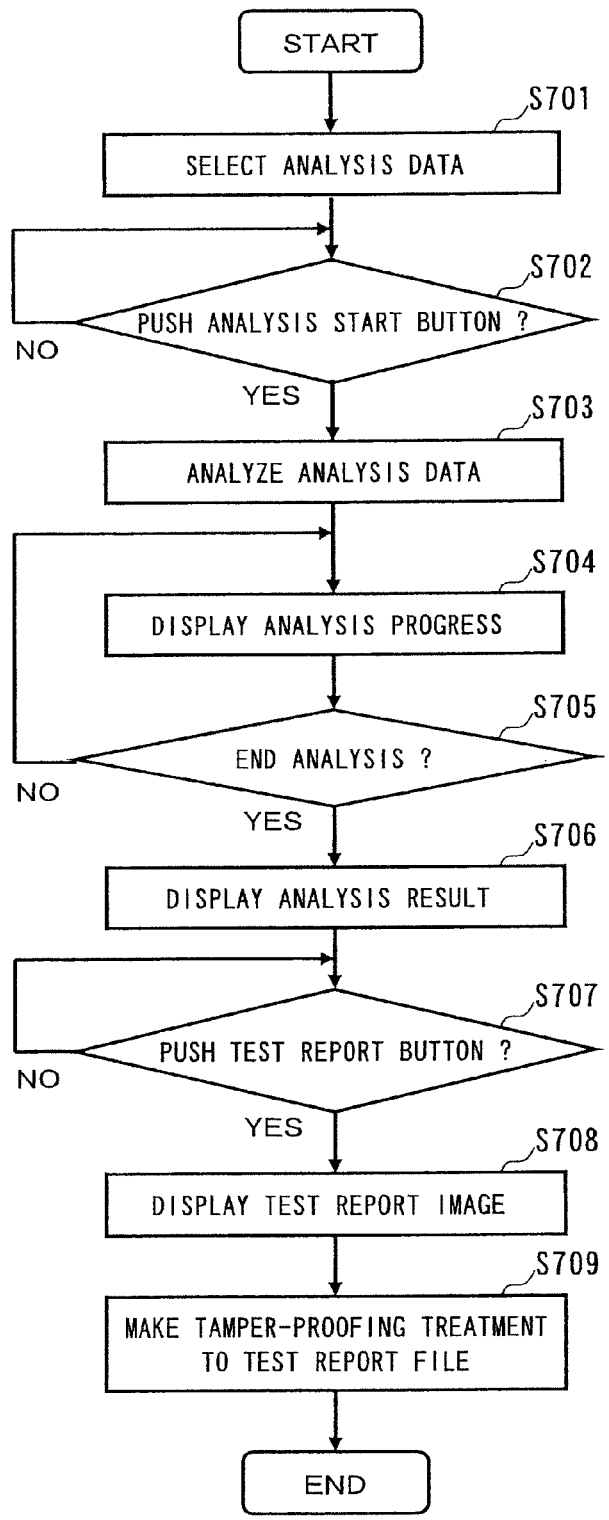
FIG. 53 is a flowchart showing another example of an analysis processing sequence according to the second embodiment.

S701 through S708 in FIG. 53 also have the same procedures as S201 through S208 in FIG. 46. In the second example, after the test report screen 314 is created and displayed (S708), a function for tamper-proofing is added in the test report (S709).

With this second example, by electronically signing an electronic file of the test report, a test report with electronic data can be created, which has the same meaning as a signature on a printed test report.

As methods for electronic signature, methods using public encryption technology wherein each tester has their own public key can be used, or biometric methods which digitally read and confirm fingerprints or irises, voiceprints, palm prints, vein shapes, DNA and the like, or methods using confirmation keys or IC cards which each tester holds and inserts into a USB or RC232C port instead of an actual signature, can also be used.

It should be noted that the electronic signature can be used with test data, not only for test reports.

By using public encryption technology or electronic watermark technology for the test data or test reports as a technology to prevent data tampering, cases of data-tampering can be easily discovered.

Further, in the event that electronic watermarks for preventing tampering of the test data is used on both the test data and the test report, by using a specific electronic watermark for each test, not only can the existence or absence of data tampering be found, but also, the test data and test reports can be correctly correlated in a sure manner.

According to the second example of this embodiment, traceability of the test data and test results can be obtained with a high degree of reliability.

Hereinafter, embodiments of the surface testing device and surface testing method relating to the laser maintenance apparatus, and particularly, to the laser inspecting device and method mentioned hereinbefore, of the present invention will be described with reference to the drawings.

Figure 60:
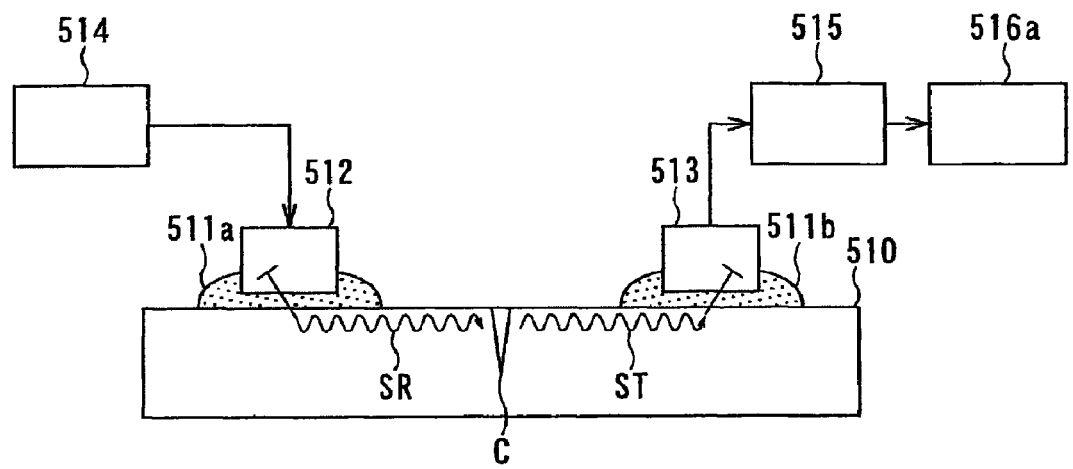
FIG. 60 is a conceptual diagram illustrating a first embodiment of a surface testing device according to the present invention.

FIG. 60 is a conceptual diagram illustrating a first embodiment of a surface testing device according to the present invention.

The surface testing device according to the present embodiment comprises a generation ultrasonic probe 512 and a detection ultrasonic probe 513 with couplants 511a and 511b being interposed to an object 510 to be tested or inspected and bringing the couplants 511a and 511b into contact with the object 510.

The surface testing device also comprises a transmitter 514 to be connected to the generation ultrasonic probe 512, and a receiver 515 is connected to the detection ultrasonic probe 513. The receiver 515 provides the received ultrasonic signal to a flaw-evaluating device 516a to transmit a signal having a predetermined frequency f and convert this signal into a surface wave SR at the generation ultrasonic probe 512 to transmit this wave to the object 510 to be tested.

The surface wave SR generated to the object 510 propagates the surface of the subject 510, and if the surface thereof includes a flaw C, the surface wave SR becomes a generation wave ST which is attenuated by the flaw C, and the detection ultrasonic probe 513 to receives this generation wave ST.

This detection signal is received at a receiver 515, calculated and processed at a flaw-evaluating device 516a, thereby calculating the presence of the flaw C and the depth thereof.

The present embodiment utilizes that the penetration depth of the surface wave SR varies depending on a frequency f and estimates a flaw depth from the attenuation ratio for each frequency of the generation wave ST generated the flaw C of the surface layer portion of the object 510 to be tested.

Figure 61:
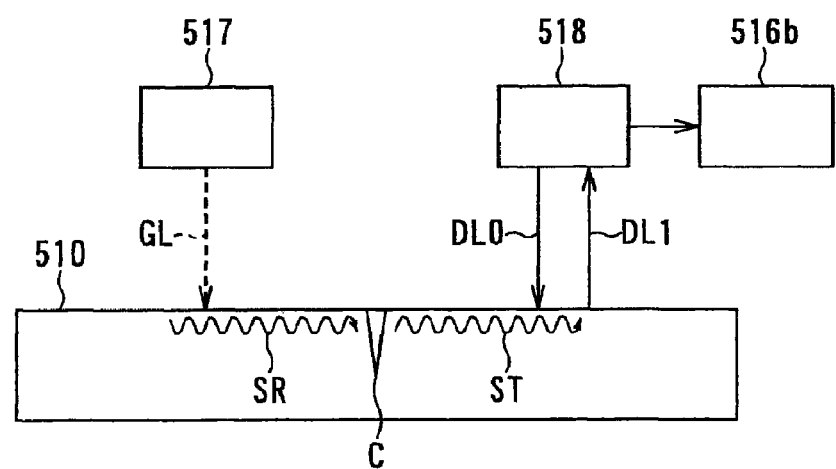
FIG. 61 is a conceptual diagram illustrating a second embodiment of a surface testing device according to the present invention.

However, the surface testing device is not restricted to this example, and as shown in FIG. 61, for example, the surface testing device may comprise an ultrasonic generation laser device 517, an ultrasonic detection laser device 518, and a flaw-evaluating device 516b.

The ultrasonic generation laser device 517 is for irradiating laser light GL modulated in a pulse shape at the object 510. The ultrasonic detection laser device 518 is for receiving detection laser reflection light DLI obtained as variation information by the surface layer portion evaporating or expanding thermally when the laser light GL is irradiated at the object 510, the distortion thereof generating an ultrasonic wave, the surface wave SR serving as the generated ultrasonic wave generating the flaw C, upon this reaching a detection position as a generation wave ST while vibrating, and irradiated detection laser light DLD changing in frequency, phase, and reflection direction due to this vibration. The flaw-evaluating device 516b is for calculating and processing the presence of the flaw C and the depth thereof of the object 510 based on the information from this ultrasonic detection laser device 518.

Thus, the employment of a laser ultrasonic wave is useful for the generation and detection of a wideband ultrasonic wave.

Incidentally, processing and procedures for estimating the depth of the flaw C generated in the object 510 to be tested are built in the flaw-evaluating devices 516a and 516b shown in FIG. 60 and FIG. 61.

Figure 62:
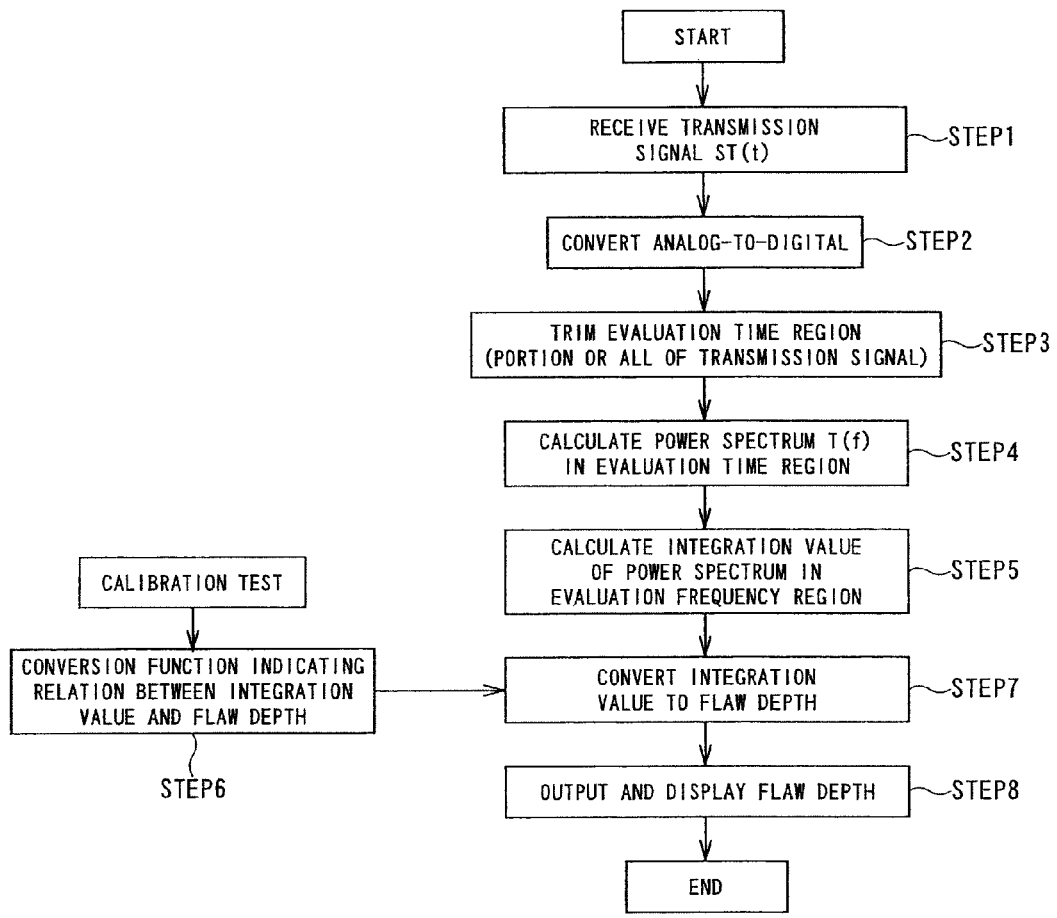
FIG. 62 is a flowchart illustrating a first embodiment of a surface testing method according to the present invention.

FIG. 62 is a block diagram illustrating the first embodiment of a surface testing method according to the present invention which is a processing sequence for estimating the depth of the flaw C generated in the object 510.

In a case that the flaw C exists in the object 510 to be tested, the surface testing method according to this embodiment receives a generation signal which was generated through the object and attenuated (step 1), converts this detection signal into digital signal from analog signal (step 2), and following conversion to a digital signal, performs trimming of an evaluation time region (step 3).

Figure 66:
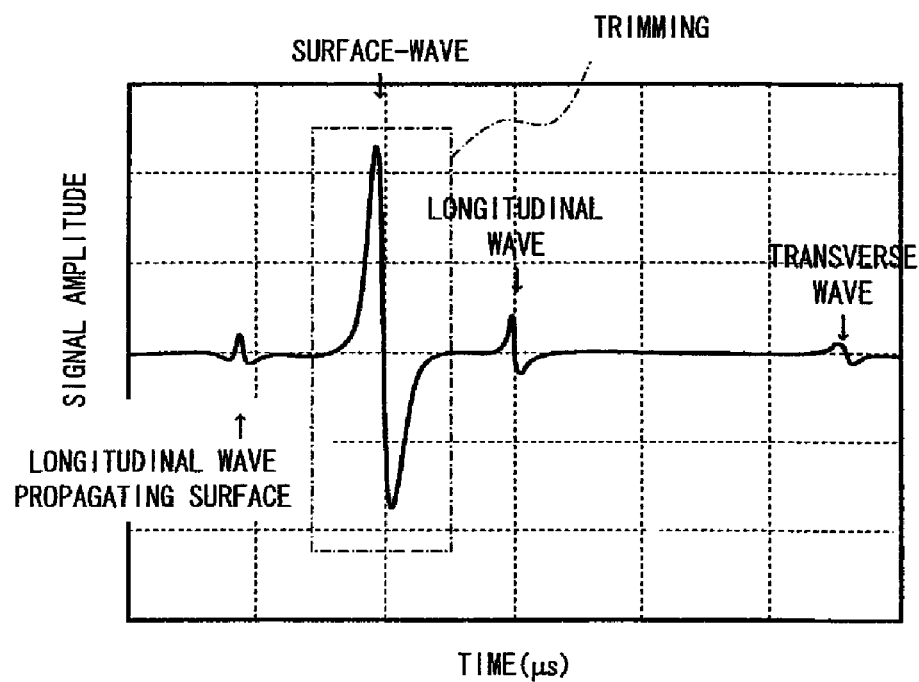
FIG. 66 is a diagram illustrating a trimming as a region to be evaluated, of the waveforms of a surface wave to be applied to a surface testing method according to the present invention.

This trimming is, for example, as shown in FIG. 66, the peak value of a surface wave, or of amplitude waveforms in a predetermined time zone, e.g., an evaluation object such as a longitudinal wave.

When a particular region serving as a survey object is trimmed (step 3), a power spectrum T(f) in the time region to be evaluated is calculated (step 4), and calculates an integration value I of the power spectrum in the evaluation frequency region is then calculated (step 5).

This integration value I is not the power spectrum T(f) generating a flaw in a discrete frequency, but an integration value in the frequency band specified as an object to be evaluated.

Providing that the minimum frequency in the specified frequency band is $f_L$, and the maximum frequency thereof is $f_H$, the integration value I can be obtained from the following Expression 4.

$$I = \int_{f_L}^{f_H} T(f) df \quad \text{[Expression 4]}$$

In consideration of a digital value, a digital integration value J in the entire frequency band employs the following expression as a performance index.

$$J = \sum_{f=f_L}^{f_H} T(f) \quad \text{[Expression 5]}$$

Further, as described above, the integration value I in the specified frequency band and the digital integration value J may be normalized with the power spectrum R(f) of the surface wave SR of the sound portion, the following normalized integration value $I_{norm}$ and the following normalized digital integration value $J_{norm}$ may be employed as an evaluation index. Otherwise, the following integration value $I_{norm-1}$ in the specific frequency region normalized by another technique, and the following normalized digital integration value $J_{norm-1}$ may be employed as an evaluation index.

$$I_{norm} = \frac{\int_{f_L}^{f_H} T(f) df}{\int_{f_L}^{f_H} R(f) df} \quad \text{[Expression 6]}$$

$$J_{norm} = \frac{\sum_{f=f_L}^{f_H} T(f)}{\sum_{f=f_L}^{f_H} R(f)}$$

$$I_{norm-1} = \int_{f_L}^{f_H} \frac{T(f)}{R(f)} df \quad \text{[Expression 7]}$$

$$J_{norm-1} = \sum_{f=f_L}^{f_H} \frac{T(f)}{R(f)}$$

Further, when the integration value I of the power spectrum is calculated (step 5), a conversion relation diagram between the EIV and a flaw depth is created by a specimen or the like beforehand (step 6), and the EIV I in the conversion relation diagram between the integration value and a flaw depth is plotted so as to calculate the conversion value between the integration value and a flaw depth (step 7).

Subsequently, the depth of the flaw C generated at the object 510 to be tested is displayed on a display or the like (step 8).

Thus, this embodiment integrates the power spectrum in the frequency region to be evaluated, collates this integration value I with the conversion relation diagram between the integration value and a flaw depth which has been created beforehand, and estimates the depth of the flaw C of the subject 510 to be tested, whereby the depth of the flaw can be correctly estimated without receiving influence of noise.

Figure 63:
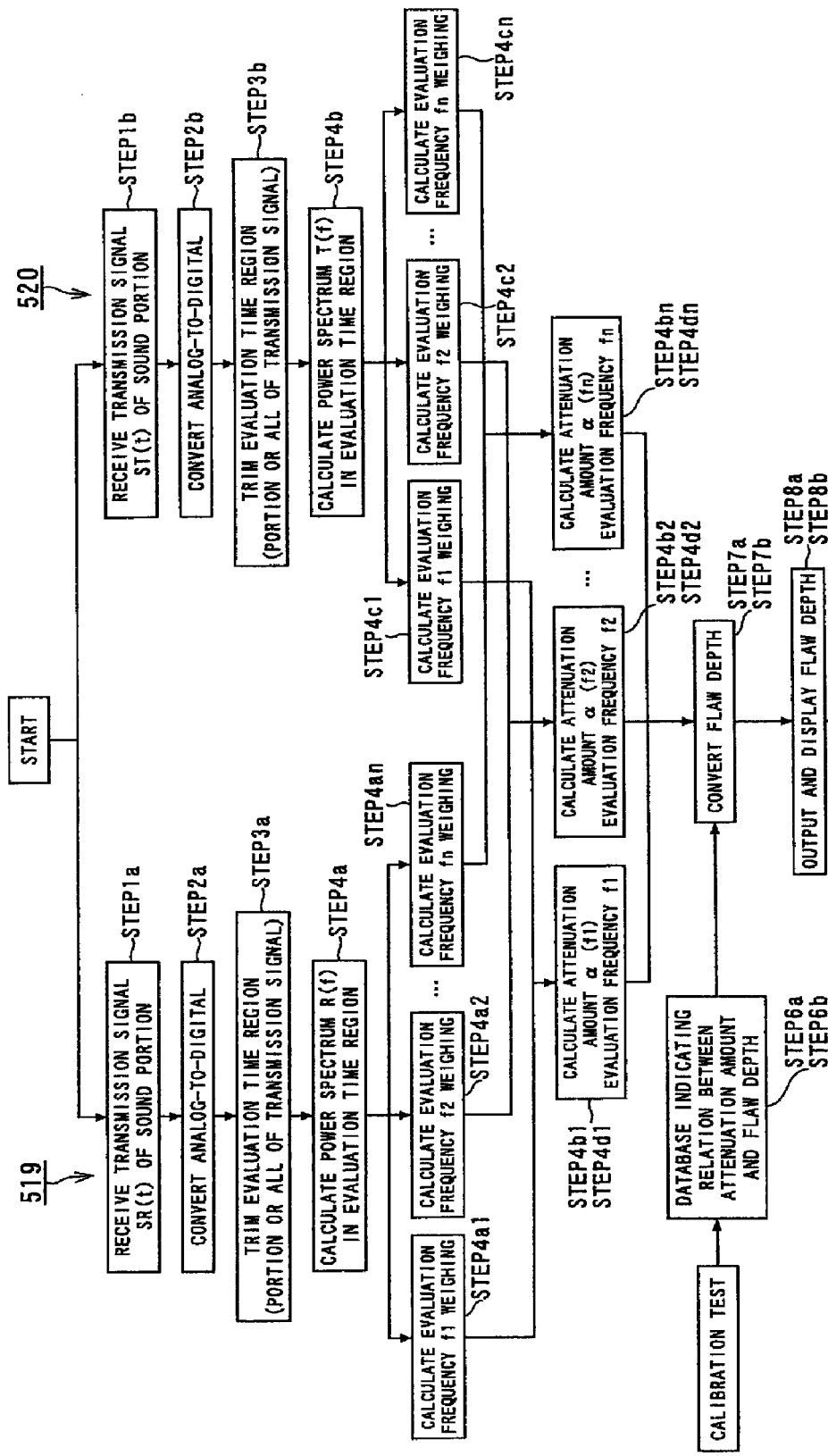
FIG. 63 is a flow chart illustrating a second embodiment of a surface testing method according to the present invention.

FIG. 63 is a flow diagram illustrating a second embodiment of a surface testing method according to the present invention which is a processing sequence for estimating the depth of the flaw C of the object 510 which is built in the flaw-evaluating devices 16a and 16b shown in FIG. 60 and FIG. 61.

When obtaining the performance-index of the region to be evaluated, the surface testing method according to the present embodiment multiplies the power spectrum (f) of the generation signal in each frequency f by a weighting function W(f) for weighting the frequency band in the region to be evaluated (enlarging frequency fluctuation distribution in vividly), represents the normalized generation power spectrum E(f) as $$E(f)=W(f) \times T(f) \quad \text{[Expression 8]}$$

to employ this expression as a performance-index, and applies this weighting function W(f) to both the power spectrum R(f) of the passage wave passing through the sound portion of the subject 510 and the power spectrum T(f) of the generation wave generating the flawed portion.

Herein, as one example of the weighting function W(f), an inverse function of the power spectrum R(f) of the passage wave in the sound portion of the subject 510 is applied.

The normalized passage power spectrum E(f) at this time can be represented as $$E(f) = \frac{T(f)}{R(f)} \quad \text{[Expression 9]}$$

Further, the weighting function W(f) can be applied through substitution as follows.

$$W(f)=f^n \quad \text{[Expression 10]}$$

Thus, upon the weighting function W(f) being substituted with the $f^n$ of the frequency f, the change in the specific frequency to be evaluated becomes markedly clear, and accordingly, the evaluation (performance)-index becomes more clear.

In this embodiment, "n" can be determined arbitrarily (not including zero), but in a case of desiring to focus attention on a high-frequency region for improving the detection sensitivity of a fine flaw, a number satisfying $n \geq 1$ should be employed.

In a case that a dominant attenuation factor in the propagation route can be identified as transition in a material or diffusion due to grains, the attenuation due to the transition is generally in proportion to the frequency f, and further, the attenuation due to grain boundary diffusion preferably may employ n=2 or n=4 of physical models which are in proportion to the frequency f.

When applying such a weighting function W(f), the present embodiment first calculates the power spectrum R(f) of the time region to be evaluated which is a survey identifying object in the sound portion 519 of the subject 510 (step 4a), of the calculated power spectrum R(f), multiplies the evaluation frequencies $f_1, f_2, ---, f_n$ by the weighting function, performs the weighting calculation of the frequencies $f_1, f_2$, and so on through the frequency $f_n$ to be evaluated (steps 4$a_1$, 4$a_2$, ---, 4$a_n$), and calculates the amount of attenuation $\alpha(f_1)$, $\alpha(f_2)$, ---, $\alpha(f_n)$ of the frequencies $f_1, f_2, ---, f_n$ to be evaluated (steps 4$b_1$, 4$b_2$, ---, 4$b_n$).

Upon the amount of attenuation $\alpha(f_1), \alpha(f_2), ---, \alpha(f_n)$ of the frequencies $f_1, f_2, ---, f_n$ to be evaluated being calculated (steps 4$b_1$, 4$b_2$, ---, 4$b_n$), the present embodiment creates the database for conversion between the amount of attenuation and a flaw depth using a specimen or the like beforehand (step 6a), collates this database with the amount of attenuation $\alpha(f_1), \alpha(f_2), ---, \alpha(f_n)$ of the frequencies $f_1, f_2, ---, f_n$ to be evaluated, thereby calculating the conversion value of a flaw depth (step 7a).

Subsequently, the depth of the flaw C generated at the subject 510 to be tested is displayed on a display or the like (step 8a).

Furthermore, this embodiment calculates the power spectrum T(f) even as to the flawed portion 520 of the subject 510 in the same way as described above (step 4b), performs the weighting calculation of the frequencies $f_1, f_2, ---, f_n$ to be evaluated (steps 4$c_1$, 4$c_2$, ---, 4$c_n$), and further calculates the amount of attenuation $\alpha(f_1), \alpha(f_2), ---, \alpha(f_n)$ of the frequencies $f_1, f_2, ---, f_n$ to be evaluated (steps 4$d_1$, 4$d_2$, ---, 4$d_n$), collates the database which has been created beforehand with the amount of attenuation $\alpha(f_1), \alpha(f_2), ---, \alpha(f_n)$ of the frequencies $f_1, f_2, ---, f_n$ to be evaluated to calculate the flaw depth conversion value, and displays this data information (step 7b and step 8b).

Note that the other steps are the same as the steps in the first embodiment, so the same reference numerals or the subscripts "a" and "b" of the same reference numerals are simply given here, and redundant description will be omitted.

Thus, regarding both the sound portion 519 and the flawed portion 520 of the subject 510 to be tested, the present embodiment performs the weighting calculation of the evaluation frequencies $f_1, f_2, ---, f_n$ (steps 4$a_1$, 4$a_2$, ---, 4$a_n$), calculates the amount of attenuation $\alpha(f_1), \alpha(f_2), ---, \alpha(f_n)$ of the frequencies $f_1, f_2, ---, f_n$ to be evaluated (steps 4$b_1$, 4$b_2$, ---, 4$b_n$), collates the database which has been created beforehand with the calculated amount of attenuation $\alpha(f_1), \alpha(f_2), ---, \alpha(f_n)$ to calculate the flaw depth conversion value (steps 7a and 7b), so that even if the flaw C of the object 510 is fine, the object 510 can be detected with high precision according to this embodiment.

Figure 64:
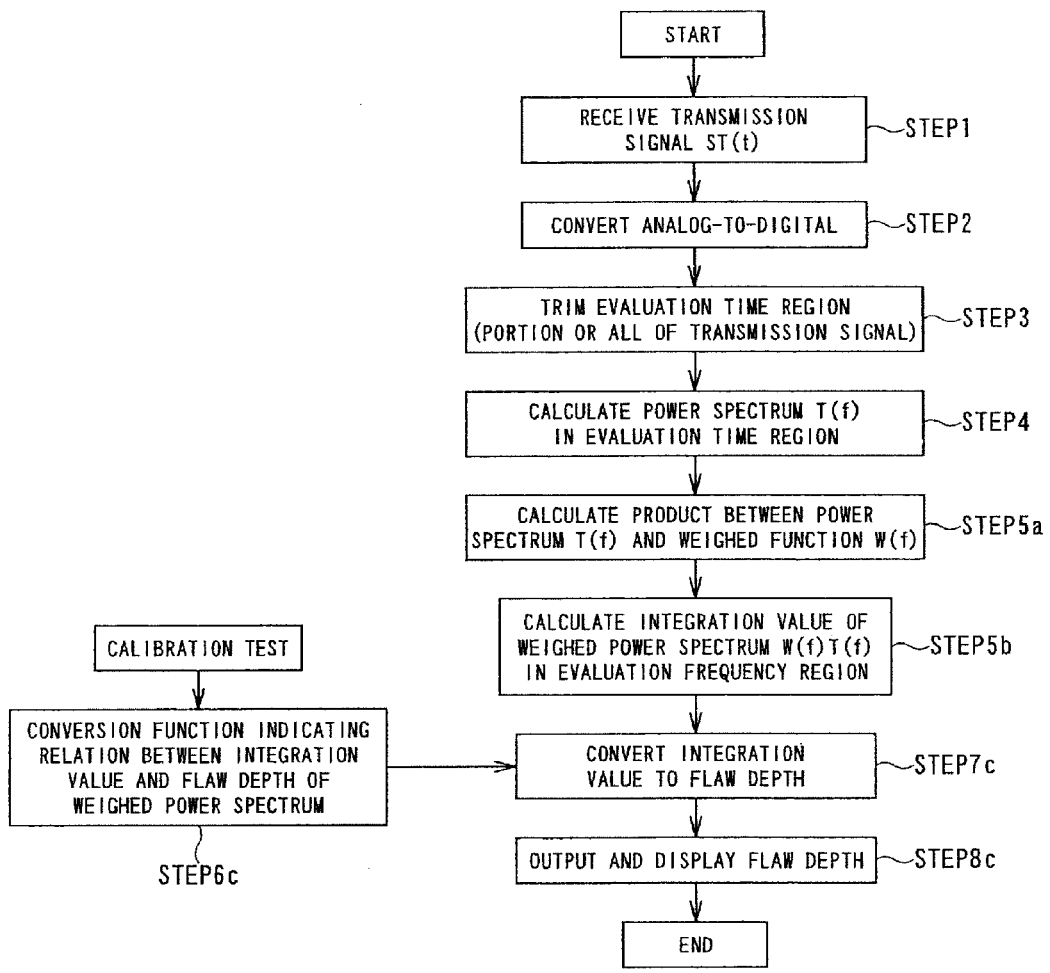
FIG. 64 is a flowchart illustrating a third embodiment of a surface testing method according to the present invention.

FIG. 64 is a flow diagram illustrating a third embodiment of a surface testing method according to the present invention, which is a processing sequence for estimating the depth of the flaw C of the object 510 built in the flaw-evaluating devices 516a and 516b shown in FIG. 60 and FIG. 61.

The surface testing method according to this embodiment, after calculating the power spectrum T(f) of the time region to be evaluated (step 4), calculates the product between the calculated power spectrum T(f) and the weighting function W(f) (step 5a), further calculates the integration value of the weighting power spectrum W(f)×T(f) in the frequency region to be evaluated (step 5b), collates the conversion function indicating the relation between the integration value and a flaw depth of the weighting power spectrum which has been created beforehand with the integration value of the above weighting power spectrum W(f)×T(f) (step 6c), obtains the conversion value between the integration value and a flaw depth (step 7c), and displays the flaw depth from the obtained conversion value between the integration value and a flaw depth (step 8c).

Here, the integration value I of the weighting power spectrum W(f)×T(f) in step 5b can be obtained as a performance-index with the following Expression.

$$I = \int_{f_L}^{f_H} W(f) \times T(f) df \qquad \text{[Expression 11]}$$

Furthermore, in consideration of a digital value, a digital integration value J in the entire frequency band can be obtained with the following expression as a performance-index.

$$I = \sum_{f=f_L}^{f_H} W(f) \times T(f) \qquad \text{[Expression 12]}$$

Further, as described above, the integration value in the specified frequency band and the digital integration value J may be normalized with the power spectrum R(f) of the surface wave SR of the sound portion 519, the following normalized integration value $I_{norm}$ and the following normalized digital integration value $J_{norm}$ may be employed as a performance-index. Otherwise, the following integration value $I_{norm-1}$ in the specific frequency region normalized by another technique, and the following normalized digital integration value $J_{norm-1}$ may be employed as a performance-index.

$$I_{norm} = \frac{\int_{f_L}^{f_H} W(f) \times T(f) df}{\int_{f_L}^{f_H} W(f) \times R(f) df} \qquad \text{[Expression 13]}$$

$$J_{norm} = \frac{\sum_{f=f_L}^{f_H} W(f) \times T(f)}{\sum_{f=f_L}^{f_H} W(f) \times R(f)}$$

$$I_{norm-1} = \int_{f_L}^{f_H} \frac{W(f) \times T(f)}{W(f) \times R(f)} df \qquad \text{[Expression 14]}$$

$$J_{norm-1} = \sum_{f=f_L}^{f_H} \frac{W(f) \times T(f)}{W(f) \times R(f)}$$

When normalizing the integration value in the specified frequency band and the digital integration value J with the power spectrum T(f) of the generation signal generating the flawed portion 520 of the subject 510 to be tested, the following normalized integration value $I_{momentum}$ of the generation wave generating the flawed portion 20 and the following normalized digital integration Value $J_{momentum}$ may be employed as a performance-index, or these values may be further normalized with the R(f) or the integration value thereof, and the normalized values may be employed as a performance-index.

$$I_{momentum} = \frac{\int_{f_L}^{f_H} W(f) \times T(f) df}{\int_{f_L}^{f_H} T(f) df}$$ [Expression 15]

$$J_{momentum} = \frac{\sum_{f_L}^{f_H} W(f) \times T(f)}{\sum_{f_L}^{f_H} T(f)}$$

Incidentally, the other steps are the same as the steps in the first embodiment, so that the same reference numerals or the subscripts "a", "b", and "c" of the same reference numerals are simply appended herein, and the redundant description will be omitted herein.

In this embodiment, the power spectrum T(f) of the time region to be evaluated is calculated (step 4), the product between the calculated power spectrum T(f) and the weighting function W(f) is also calculated (step 5a), the integration value of the weighting power spectrum W(f)×T(f) in the evaluation frequency region is calculated (step 5b), and the flaw depth of the subject 510 to be tested is converted and estimated (step 6c and step 7c), to thereby estimate the depth of a flaw correctly without receiving influence of noise.

Figure 65:
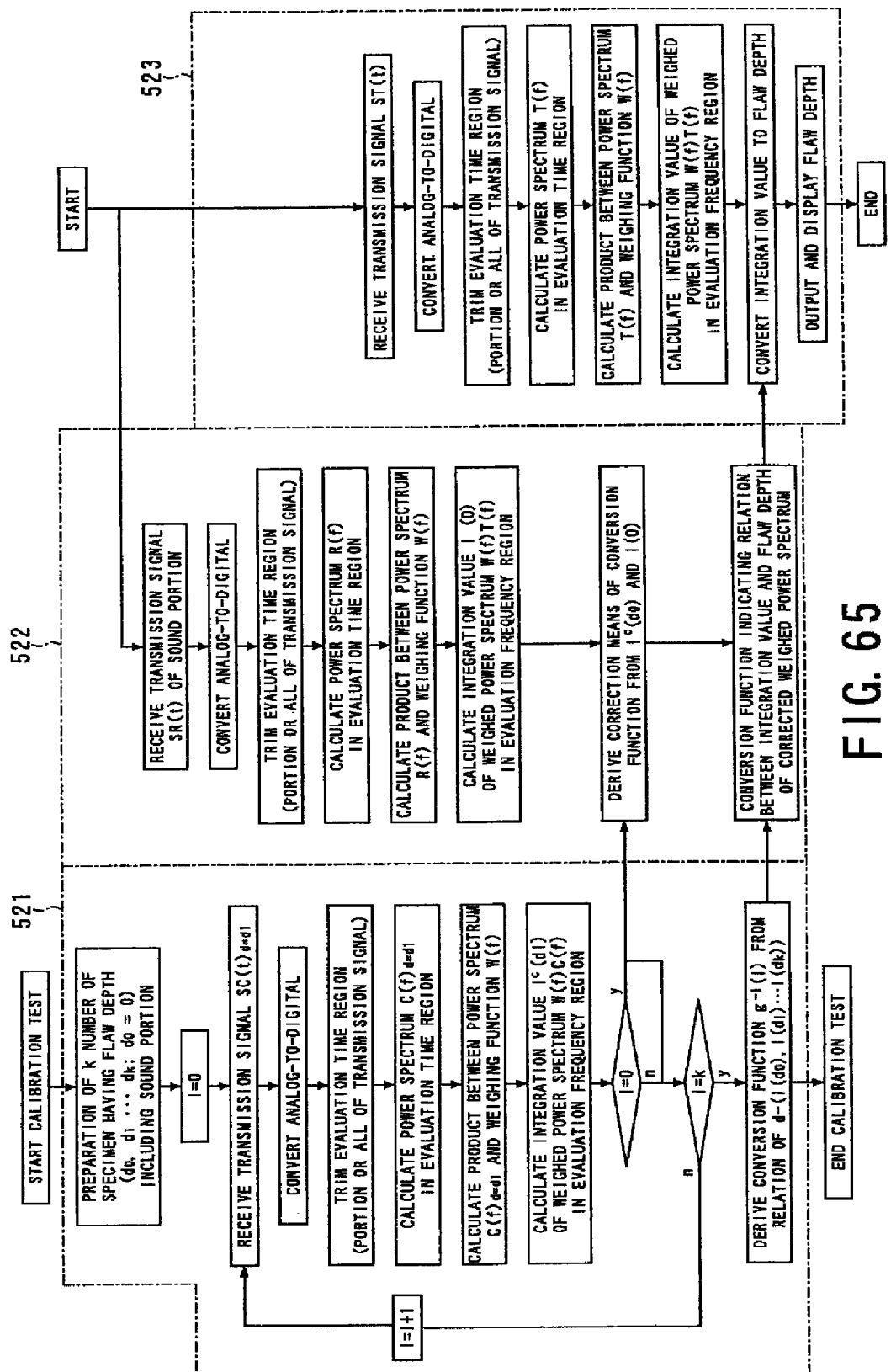
FIG. 65 is a flow chart illustrating a fourth embodiment of a surface testing method according to the present invention.

FIG. 65 is a block diagram illustrating a fourth embodiment of a surface testing method according to the present invention which is a processing sequence for estimating the depth of the flaw C of the subject 510 to be tested built-in the flaw-evaluating devices 516a and 516b shown in FIG. 60 and FIG. 61.

In the surface testing method according to this embodiment, the entire process is classified into three processes of a calibration specimen flaw depth calculation section 521, a real machine sound portion data information collection section 522, and a real machine flaw depth calculation section 523, and a conversion function $g^{-1}(I)$ is derived between a performance-index and a flaw depth at the calibration specimen flaw depth calculation section 521. Furthermore, the conversion value between the integration value and a flaw depth is obtained on the basis of this derived conversion function $g^{-1}(I)$ between a performance-index and a flaw depth, the conversion function indicating the relation between the integration value of the weighting power spectrum derived and corrected at the real machine sound portion data information collection section 522 and a flaw depth, and the integration value I of the weighting power spectrum W(f)×T(f) in the evaluation frequency region of the real machine flaw depth calculation section 523, and the depth of a real machine flaw is then estimated.

The processing sequences at the calibration specimen flaw depth calculation section 521, real machine sound portion data information collection section 522, and real machine flaw depth calculation section 523 are the same as the steps 1 through 8c mentioned with respect to the first embodiment through the third embodiment, and accordingly, the redundant description is omitted herein.

However, the calibration specimen flaw depth calculation section 521 derives the conversion function $g^{-1}(I)$ between a performance-index and a flaw depth in accordance with the following processing sequence.

First, the calibration specimen flaw depth calculation section 521 prepares a calibration specimen including a sound portion (flaw depth do=0), and at least two or more flaws having different known depths $d_1, d_2, ---, d_n$. Here, the flaw length has a sufficient flaw length as compared with the width of a surface wave beam to be employed, and also, the maximum depth $d_n$ is deeper than the maximum depth to be tested at a real testing process.

Further, the calibration specimen preferably has not only the above flaws but also the same surface state and same ultrasonic properties (sound velocity and attenuation properties and the like) as the object 510 to be tested, which is actually tested as equivalent as possible. In the event that the current state of the subject 510 cannot be identified, the surface state and ultrasonic properties (sound velocity and attenuation properties and the like) may be simulated as similar as possible based on the data at the time of manufacture.

In such calibration specimen, the generation surface wave as to the respective flaw depths $d_1, d_2, ---, d_n$ is measured, and the calculated values in the first to third embodiments are applied to this result, and an integration value $I_c(d)$ serving as a calibration performance-index or a digital integration value $J^c(d)$ (hereinafter, represented with $I^c(d)$ for facilitating description) is calculated.

Figure 67:
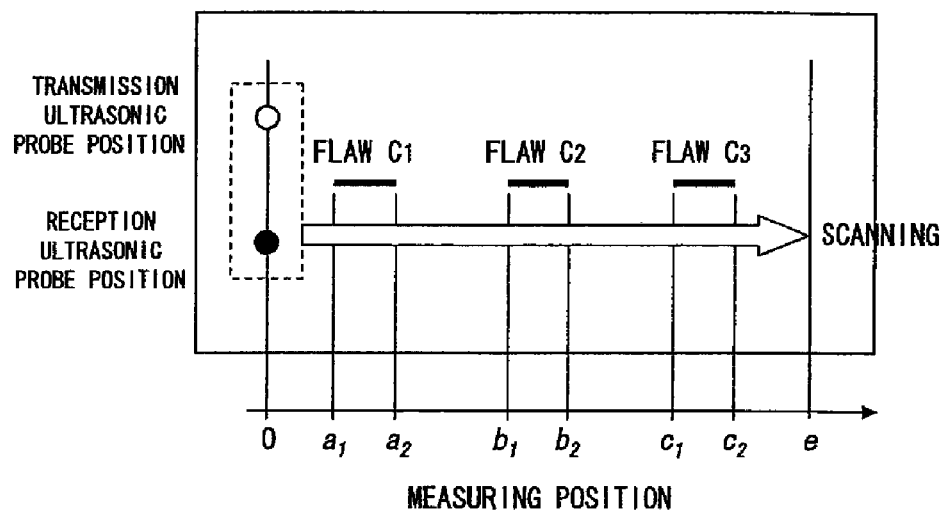
FIG. 67 is a diagram illustrating the position of a flaw to be detected during scanning of a test object using a generation ultrasonic probe and a reception ultrasonic probe with a surface testing device according to the present invention.
Figure 68:
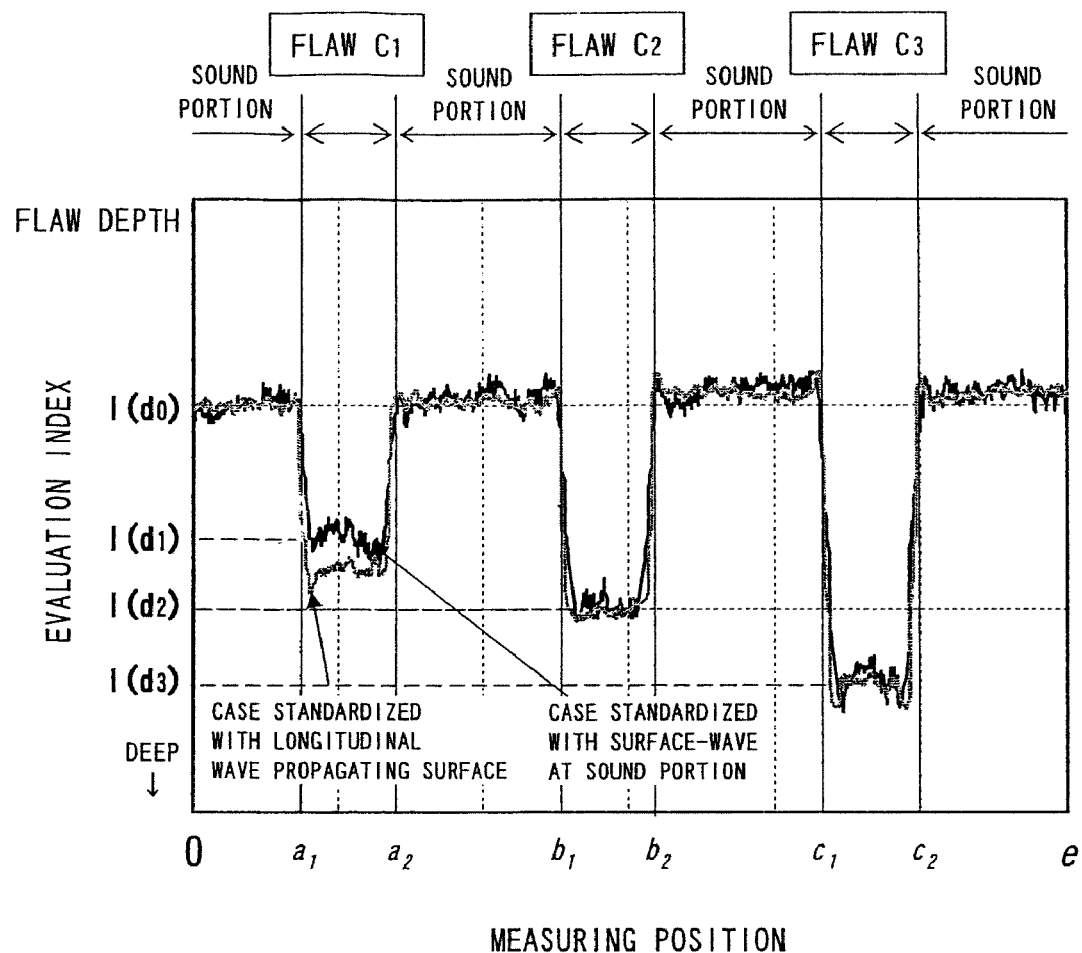
FIG. 68 is a diagram illustrating, of the evaluation index value of a surface wave when the surface wave propagates a sound portion and a flawed portion of a test object, the evaluation index value of the flawed portion when assuming that the sound portion is zero with a surface testing device according to the present invention.

That is, as shown in FIG. 67, when the generation ultrasonic probe 512 and the detection ultrasonic probe 513 detect flawed portions $C_1, C_2$, and $C_3$ during the scanning of the object 510 to be tested, the EIV of the detected flawed portions $C_1, C_2$, and $C_3$ and the EIV of sound portions are represented as shown in FIG. 68.

Further, FIG. 68 is a diagram, in which the horizontal axis represents a measuring position and the vertical axis represents the EIV, illustrating the evaluation index value of the flawed portions when assuming that the flaw depth of the sound portion is zero.

Thus, herein, in the present embodiment, the flaw depths d1, d2 and so on of the flawed portions C1, C2, and C3 are calculated as a performance-index on the basis of the flaw depth zero (0) of the sound portion in the object 510.

The relation between the obtained integration value $I^c(d)$ and the known flaw depth d is subjected to fitting in a function form, and the conversion function $g^{-1}(I)$ between a performance-index and a flaw depth is obtained from the result g(d) thereof.

Furthermore, the measurement conditions such as sensitivity at the time of an actual testing need to be identical to those at the time of a calibration test, but in the case of changing them unavoidably, it is necessary to adopt the following procedures.

First, at the time of the real testing, the generation surface wave of a sound portion is measured at a portion which can be assured to include no flaw, and the calculated values in the first to third embodiments are applied to this result so as to calculate the performance-index I (0) of zero (0). This is then compared with the zero (0) data $I^c$ (0) at a calibration specimen, and recalibration of the conversion function $g^{-1}$ (I) between a performance-index and a flaw depth is performed.

A method for recalibration introduces $I=g(d)-(I^c(0)-I(0))$ or $\beta=I(0)/I^c(0)$ [Expression 16] depending on the difference between the calibration conditions and the actual measurement conditions, and when assuming that $I=\beta \cdot g(d)$ [Expression 17], the inverse function $g^{-1}(I)$ thereof or $J^{-1}(I)$ is obtained.

Thus, when estimating a real machine flaw depth, the present embodiment calculates a flaw depth based on the respective conversion functions derived at the three classified calibration specimen flaw depth calculation section 521, real machine sound portion data information collection section 522, and real machine flaw depth calculation section 523, and the integration value of the weighting power spectrum W(f)×

T(f), and estimates the flaw depth, whereby the depth of a flaw can be correctly estimated without receiving influence of noise.

Furthermore, preferred embodiments of the surface inspecting device relating to the laser maintenance apparatus of the present invention will be described hereunder with reference to the accompanying drawings.

First Embodiment

Figure 69:
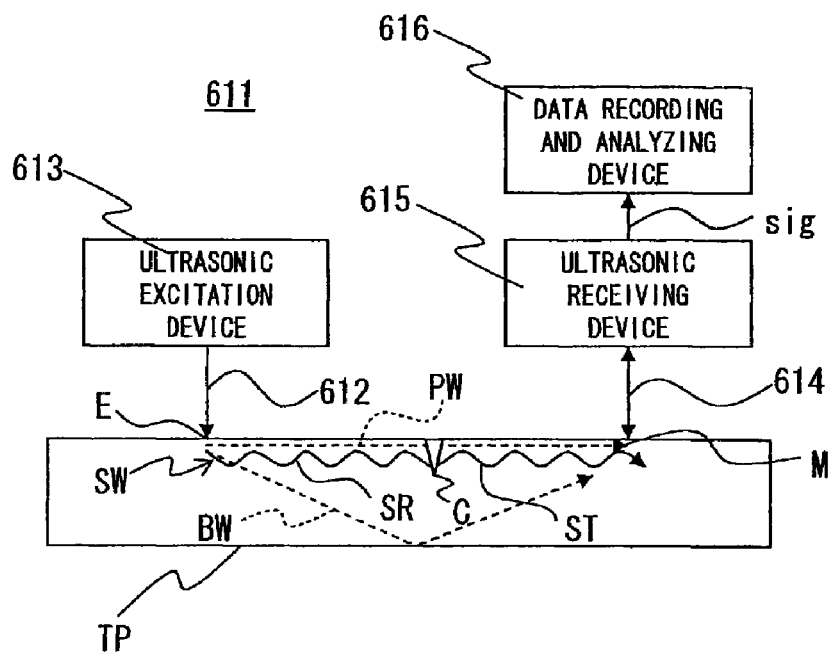
FIG. 69 is a schematic view illustrating the configuration of a first embodiment of a surface inspecting device according to the present invention.

FIG. 69 is a schematic view illustrating the configuration of a first embodiment of a surface inspecting device 611 according to the present invention. This surface inspecting device 611 comprises an ultrasonic exciting device 613 for irradiating laser light 612 in a pulse shape to a predetermined generation point E of a body TP to be inspected so as to excite an ultrasonic wave, an ultrasonic detection device 615 for irradiating laser light 614 to a detection point M spaced by a known distance from the generation point E, and receiving an ultrasonic wave by receiving the reflection light thereof, and a data recording and analyzing device 616 serving as one example of correcting means for inputting and recording the output signal sig from this ultrasonic detection device 615, and detecting the presence, position, and depth of a flaw C of a surface opening of the object TP.

In the surface inspecting device 611 of this laser ultrasonic method, ultrasonic waves having various types of modes are generated such as a longitudinal wave PW propagating the surface layer of the object TP, a bulk wave BW, and the like other than a surface SW (SR, ST). Further, the surface wave SW includes a surface wave SR to be inputted to the flaw C and a generation surface wave ST generating the flaw C.

Figure 70:
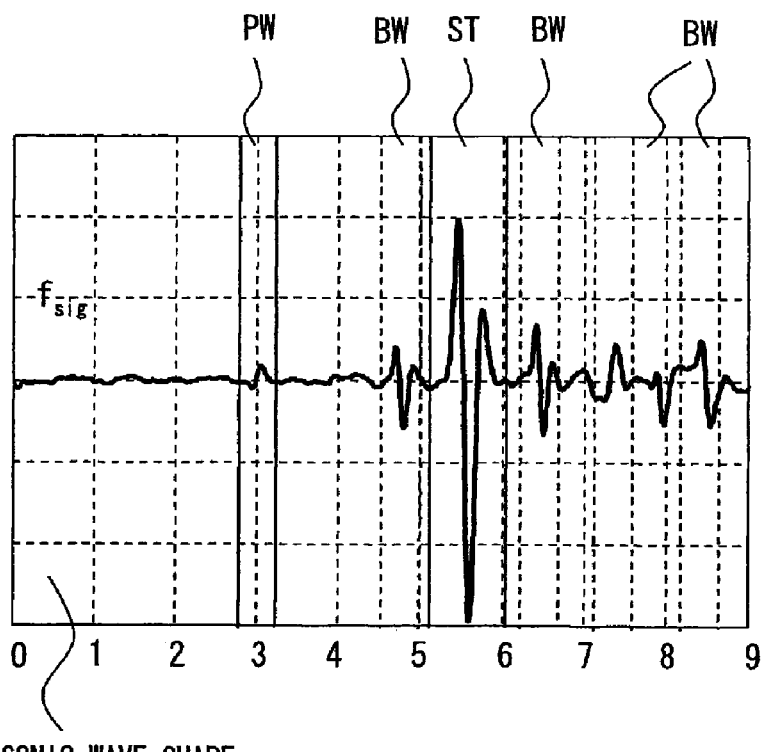
FIG. 70 is a waveform chart illustrating one example of various types of mode ultrasonic waveform to be recorded by the data recording and analyzing device shown in FIG. 69.

FIG. 70 illustrates one example of an ultrasonic waveform to be inputted to the data recording and analyzing device 616. The velocity of the ultrasonic wave excited at the generation point E has been known beforehand, so that the data recording and analyzing device 616 measures and records the output signal sig from the ultrasonic detection device 615 as shown in FIG. 70 in a measurement time having a predetermined time width centered on a predetermined detection point in time since the laser light 612 has been irradiated at the generation point E until it reaches the detection point M, and analyzes the output signal sig, thereby obtaining the presence, position, and depth of the flaw C.

In the case of obtaining the depth of the flaw C, the data recording and analyzing device 616 obtains this depth based on the amount of change (amount of attenuation) such as the amplitude and frequency components of the generation surface wave ST, but employs a longitudinal wave PW and a volume wave BW other than the generation surface wave SW as the correction waves of the generation surface wave ST.

That is, the correcting means of the data recording and analyzing device 616 employs the volume wave BW propagating another route as a correction wave $f_{correct}$ of the generation surface wave ST in the case where the inspecting region of the body TP to be inspected has always a constant shape. For example, peak-to-peak values regarding the amplitudes of the generation surface wave ST and the volume wave BW are each calculated, the ratio (STP-P/BWP-P) between the peak-to-peak (STP-P) of the amplitude of the generation surface wave ST and the peak-to-peak (BWP-P) of the amplitude of the volume wave BW is obtained as a performance-index value, and the depth of this flaw C is obtained by applying this performance-index value to a calibration curve (or conversion data table), in which the corresponding relation between this performance-index value and the depth of the flaw C has been obtained beforehand.

Furthermore, the correcting means of the data recording and analyzing device 16 may obtain the depth of the flaw C by obtaining the root mean square (RMS) of each of the generation surface wave ST and the volume wave BW, obtaining the ratio (ST-RMS/BW-RMS) between the RMS of this generation surface wave ST and the RMS of the volume wave BW as a performance-index value, and applying this performance-index value to a calibration curve or the like wherein the corresponding relation between the performance-index value and the depth of the flaw C has been obtained beforehand.

Further, the ratio (ST-T/BW-T) between the values integrated with a region between an arbitrary minimal frequency $f_L$ and a maximal frequency $f_H$ as shown in the following Expression (18-1 may be employed as this performance-index value $I_{correct}$ by subjecting each of the generation surface wave ST and the volume wave BW to FFT to obtain a power spectrum T.

As shown in the following Expression (18-2), the value obtained by multiplying the power spectrum T ($f_{correct}$) by an arbitrary weighting function w(f), and integrating the result thereof may be employed as the $I_{correct}$. Of course, in the other methods other than those mentioned above, methods for calculating the performance-index value from the correction waveform $f_{correct}$ are available. Furthermore, a method other than division can be conceived as a correcting method as to the generation surface wave ST.

[Expression 18]

$$I_{correct} = \int_{fL}^{fH} T(f_{correct}) df \qquad (1)$$

$$I_{correct} = \int_{fL}^{fH} w(f) \cdot T(f_{correct}) df \qquad (2)$$

Consequently, according to this data recording and analyzing device 616, the volume wave BW to be employed for correction of the generation surface wave ST is measured at the same time as the generation surface wave ST, so that this waveform is a waveform in which the surface state of the body TP to be inspected and non-stability of measurement by the data recording and analyzing device 616 are reflected. Accordingly, just the amount of a measurement error may be cancelled by performing normalization with these signals.

Second Embodiment

In the case that the inspected region of the body TP includes a non-constant shape, in the case that the ultrasonic wave of the other mode does not arrive within the measurement period of the data recording and analyzing device 616, or in the case that the attenuation is too great to employ the surface wave, the longitudinal (vertical) wave PW propagating the surface can be employed. It is needless to say that even in the case that the inspected region of the body TP has a constant shape, the longitudinal wave PW can be employed. Here, the longitudinal wave PW and the surface wave SW use the same propagation route, so that in the case of an occurrence of a crack over the propagation route, the generation waveform changes as with the surface wave SW. However, the amount of change of the generation wave is different from the case of the surface wave SW.

Accordingly, the performance-index value obtained by the surface wave SW generating the flaw C is corrected by dividing this value with the performance value obtained by the longitudinal wave PW propagating the surface layer, thereby creating a new performance-index.

Figure 71:
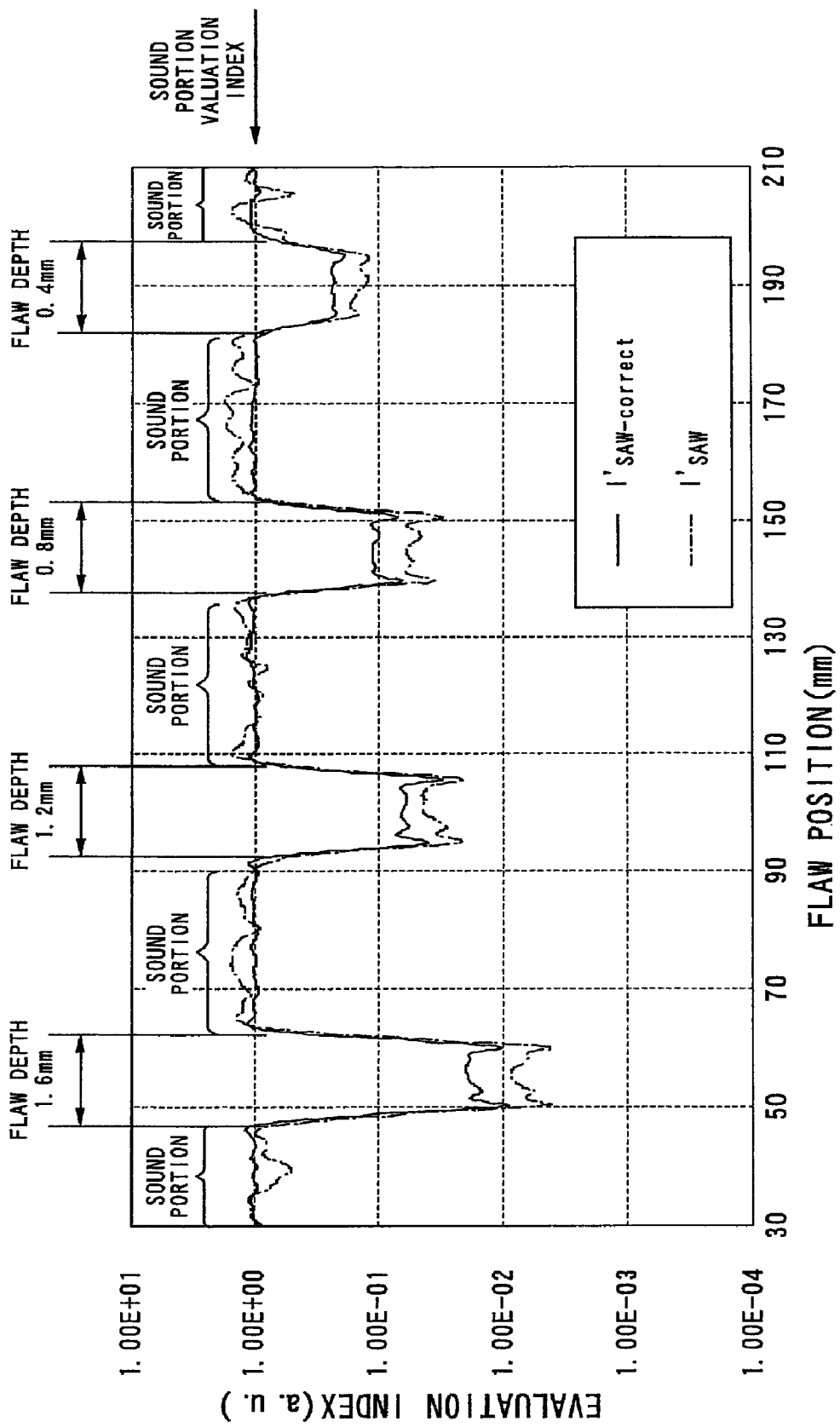
FIG. 71 is a diagram comparing the performance-index of a flaw depth in a case in which a surface wave is corrected with another ultrasonic wave other than the surface wave, and the evaluation index value of a flaw depth in a case in which the surface wave is not corrected.

FIG. 71 illustrates one example of the surface-wave analysis result at the time of the surface wave SW generating to a sound portion (no flaw C), and the flaw C of depths 0.4 mm, 0.8 mm, 1.2 mm, and 1.6 mm, for example. A performance-index I'$_{SAW}$ without correction shown in FIG. 71 is calculated by applying Expression (18-2) to the surface wave SW to obtain a performance-index I$_{SAW}$ with correction, and dividing the calculated result by the performance-index I$_{SAW}$. On the other hand, a performance-index I'$_{SAW\text{-}correct}$ with correction shown in FIG. 71 is calculated by further dividing the obtained performance-index I$_{SAW}$ by the performance-index I$_{correct}$, after the dividing thereof by the performance-index I$_{SAW}$ of the sound portion.

Figure 72:
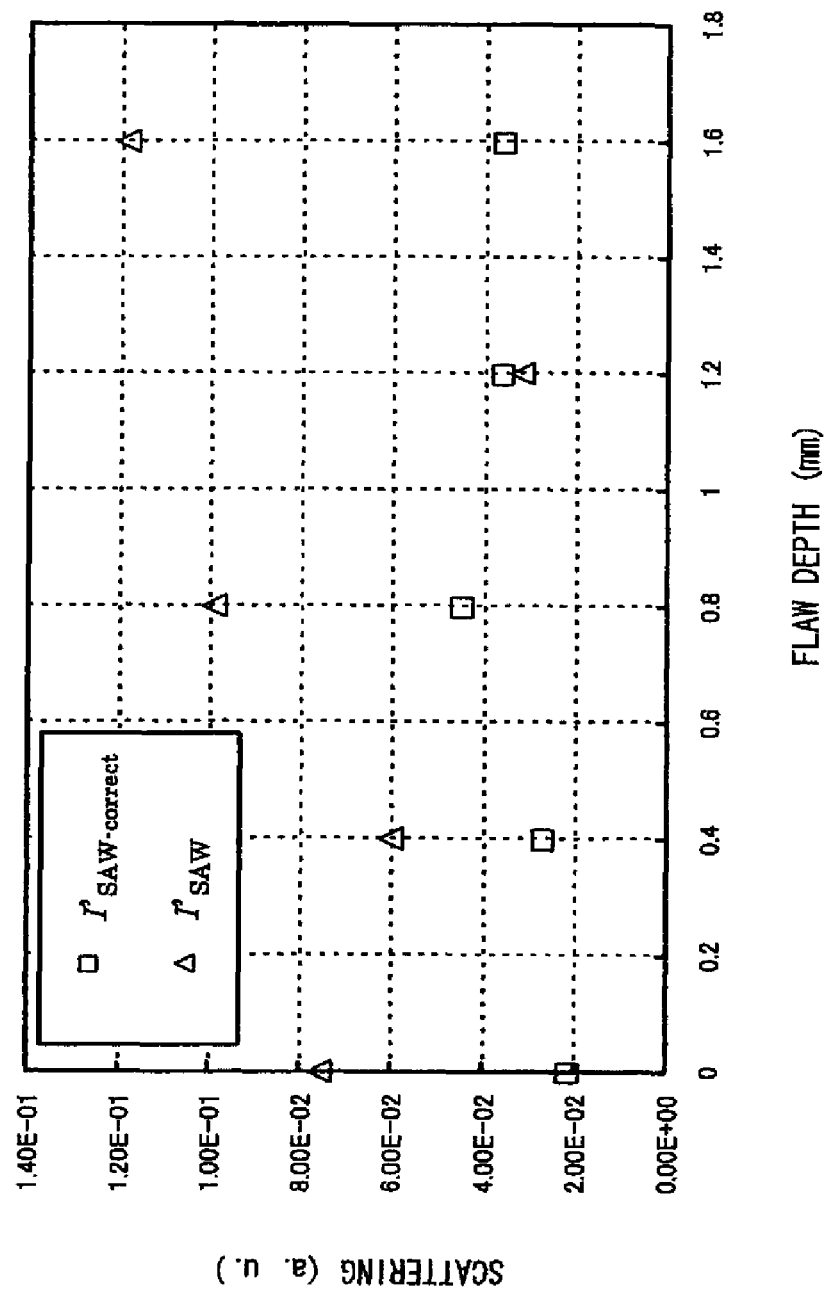
FIG. 72 is a diagram comparing the deviation of the evaluation index value in each flaw depth in a case in which the surface wave is corrected, and the deviation of the evaluation index value each flaw depth in a case in which the surface wave is not corrected.

FIG. 72 is a graph comparing the irregularities of the performance-index values at the respective depths of the flaw C. It can be understood that the irregularities of the performance-index I'$_{SAW\text{-}correct}$ subjected to correction are greatly reduced as compared with the performance-index I'$_{SAW}$ without correction. Thus, the calculated performance-index becomes a performance-index which cancels out the measurement error factors such as the irregularities of the surface state, whereby flaw detection precision with higher precision can be provided. Here, the ultrasonic wave of the other mode propagating the same route as the surface wave SW other than the longitudinal wave PW can be employed, as a matter of course. Moreover, the ultrasonic wave of the other mode propagating a different route from the surface wave SW but affected by the flaw C in the same way can be of course employed.

Further, the performance-index value may be increased by multiplying the performance-index values between the longitudinal wave PW and the volume wave BW, and thus, even in the case that the respective performance-index values of the volume wave BW and the longitudinal wave PW are small and the amount of change is small, the amount of change of these longitudinal wave PW and the volume wave BW can be measured. Thus, measurement precision can be improved.

Third Embodiment

With the above second embodiment, the performance-index I$_{correct}$ is calculated as to another correction ultrasonic wave f$_{correct}$ propagating the same route as the surface wave SW, and correction is then performed by dividing the surface wave SW. However, this correction is sometimes performed with another ultrasonic wave, or another technique can be employed in some cases. On the other hand, there may cause a case in which the amount of change of the generation surface wave ST at the time of generating to the flaw C is small, or a case in which the amount of change for each depth of the flaw C to be measured is too small to capture this amount.

Accordingly, the amount of change due to the flaw C obtained by the performance-index I$_{correct}$ and the amount of change due to the flaw C obtained by the performance-index of the surface wave SW are doubly obtained by integrating the ISAW by the calculated performance-index I$_{correct}$. Thus, the amount of change which is difficult to be measured can be grasped.

Further, the ultrasonic wave to be employed as the performance-index I$_{correct}$ does not have the same route as the surface wave SW, but in the same way, the ultrasonic wave of another mode which affects the influence of the flaw C can be employed. In addition, the performance-index I$_{correct}$ to be employed is not restricted to one, and rather, multiple ultrasonic waves can be employed as long as the ultrasonic waves are affected by the influence of the flaw C, and these performance-index values can be integrated with the performance-index I$_{SAW}$ of the surface wave SW.

Fourth Embodiment

Figure 73:
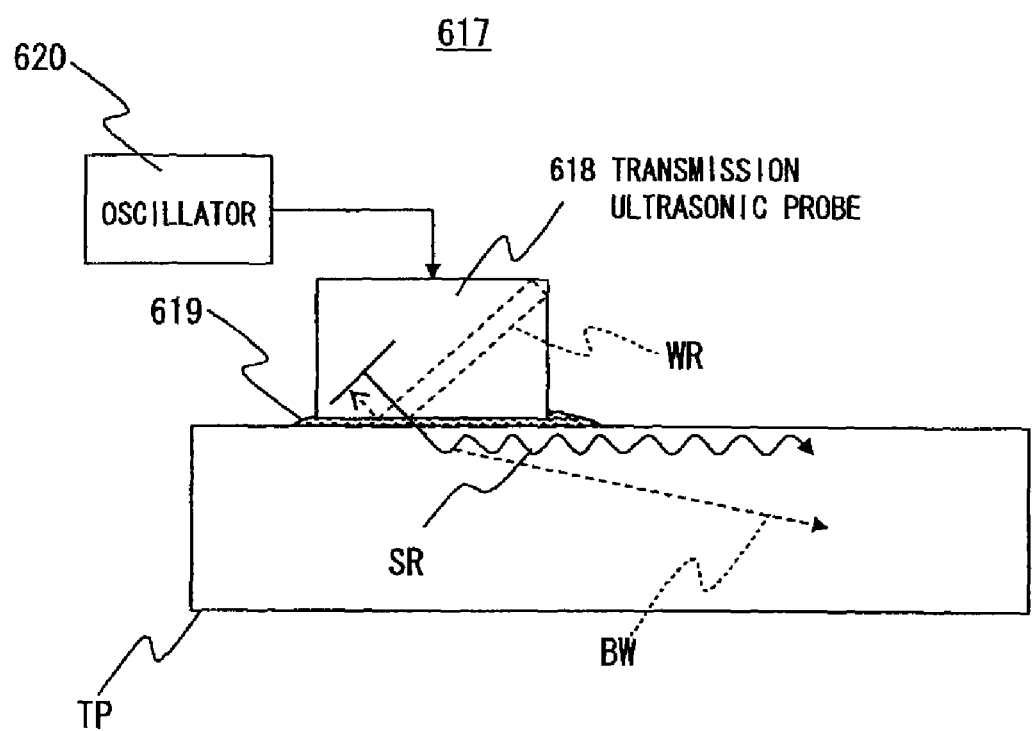
FIG. 73 is a schematic view illustrating the configuration of another embodiment of a surface inspecting device according to the present invention.
Figure 74:
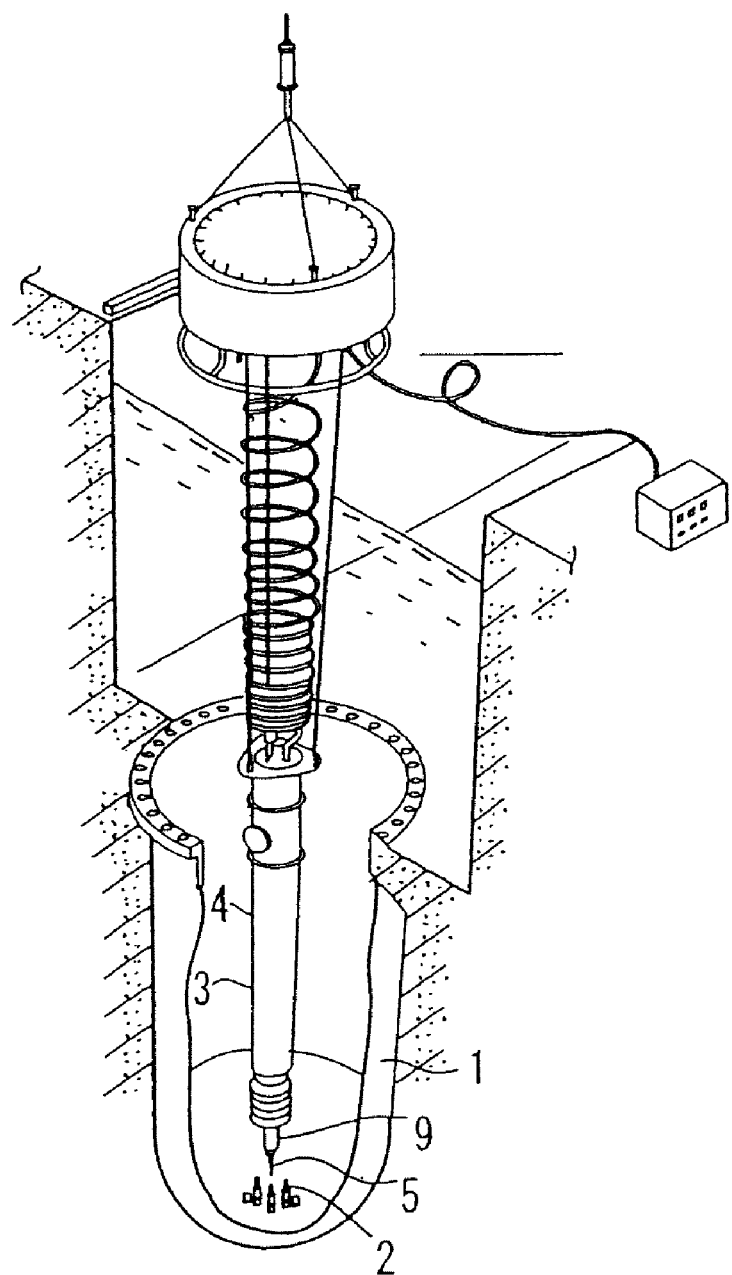
FIG. 74 is an overall configuration diagram of a conventional nondestructive testing device of bottom-mounted instrumentation tubes.
Figure 75:
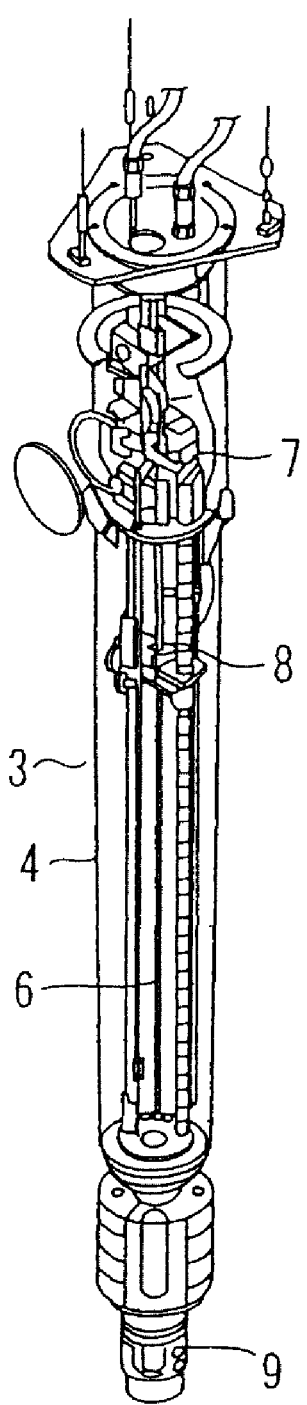
FIG. 75 is a perspective view illustrating the overall configuration of the nondestructive testing device shown in FIG. 74.
Figure 76:
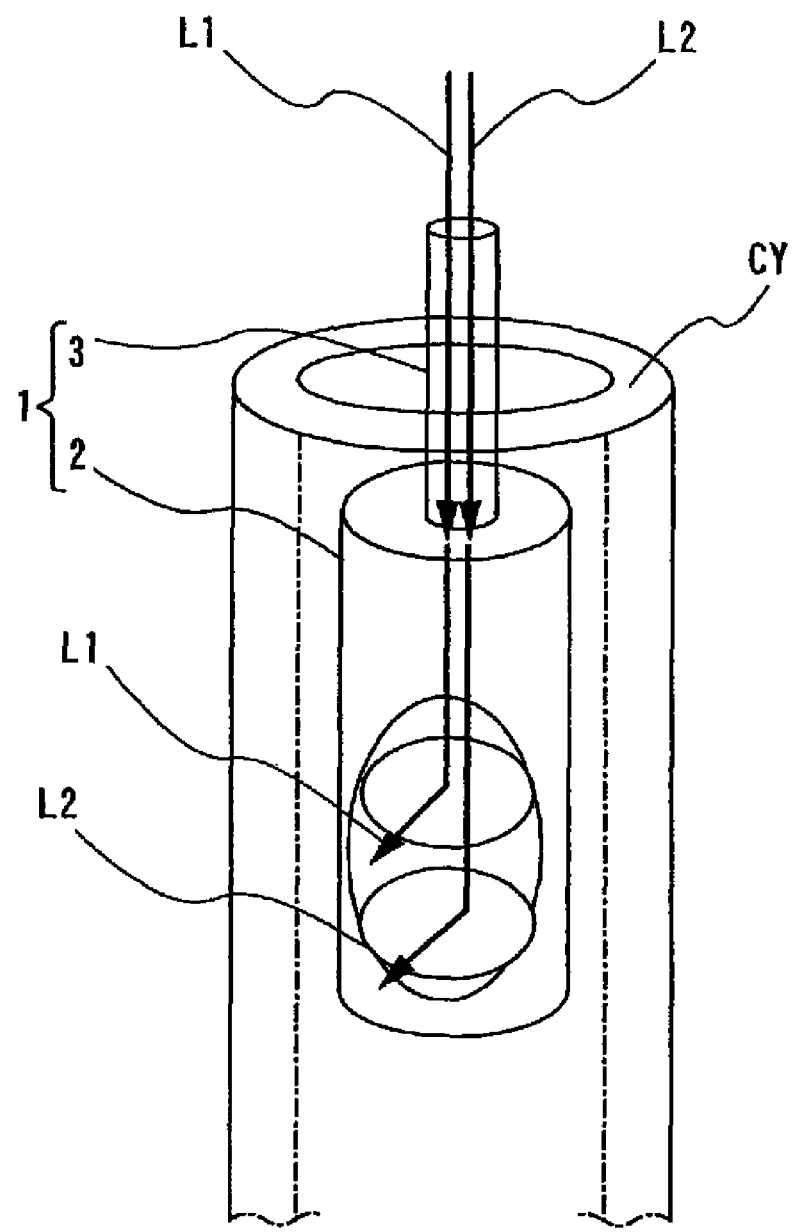
FIG. 76 is a diagram illustrating an example of the configuration of a laser ultrasonic inspecting irradiation head for tubular structures.
Figure 77:
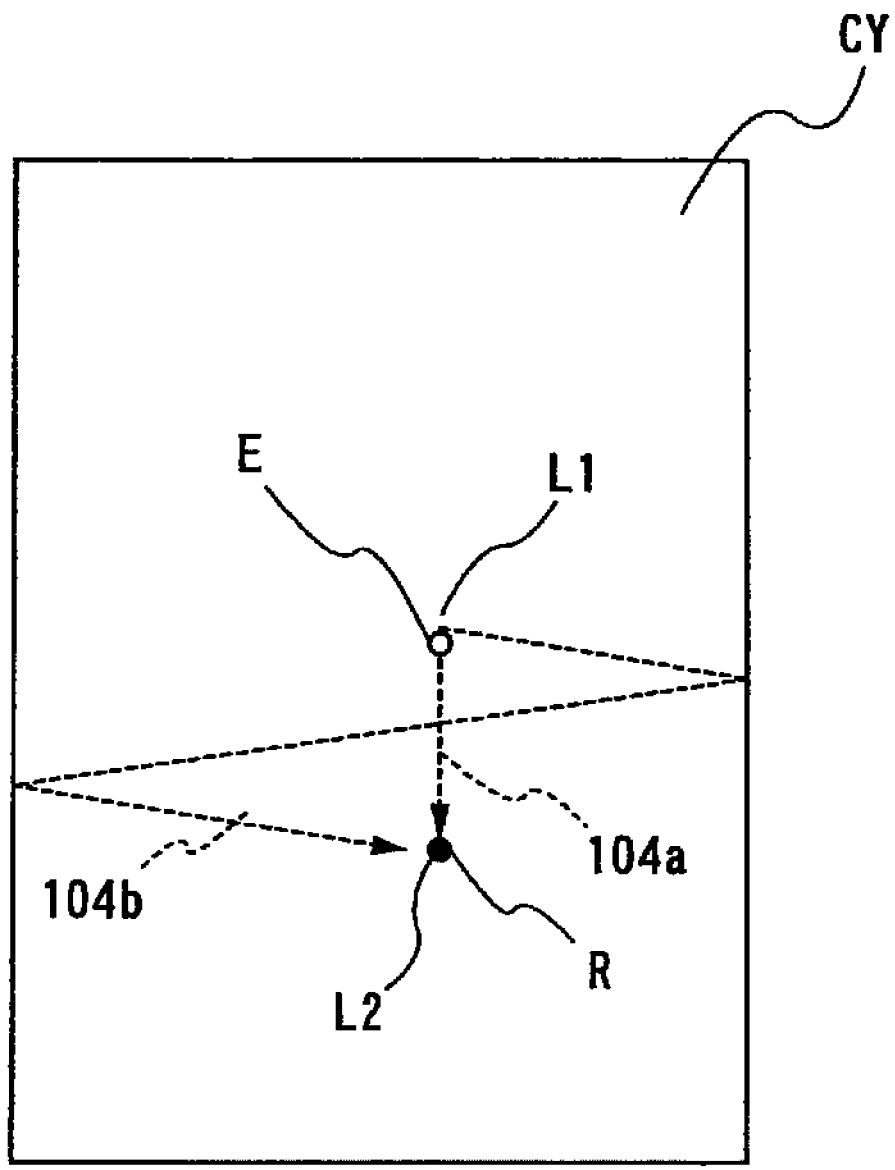
FIG. 77 is a diagram showing the behavior of generating ultrasound with a conventional laser irradiation head.
Figure 78:
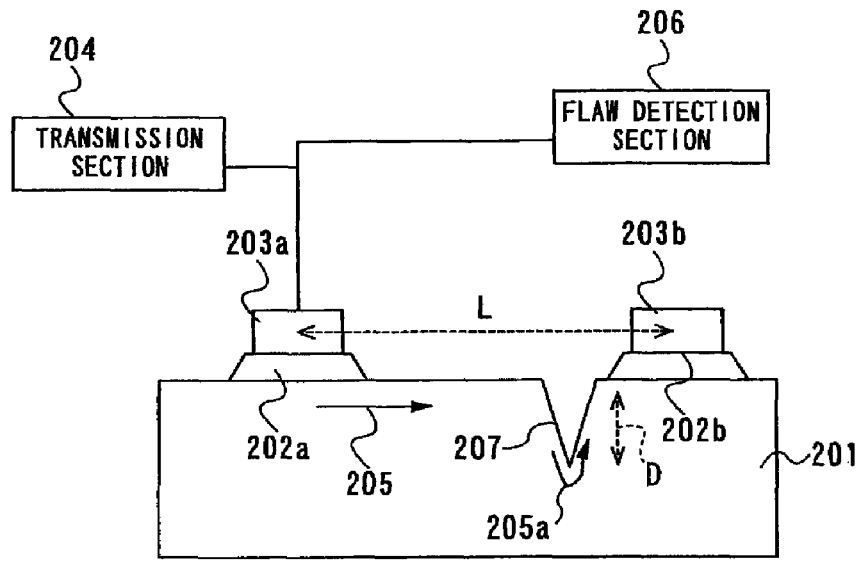
FIG. 78 is a functional block diagram of a conventional first ultrasonic inspecting device.
Figure 79:
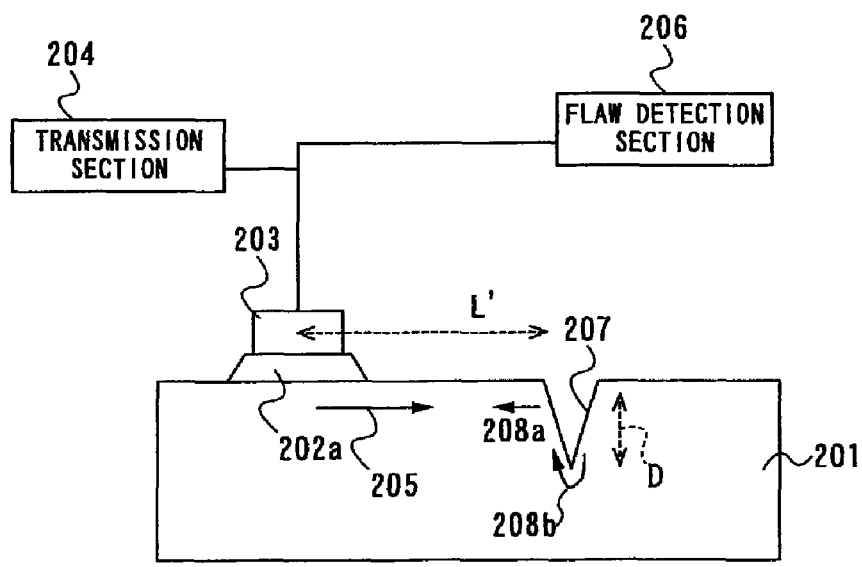
FIG. 79 is a functional block diagram of a conventional second ultrasonic inspecting device.

FIG. 73 is a schematic view illustrating the principal configurations of a fourth embodiment of a surface inspecting device 617 according to the present invention. In this surface inspecting device 617, the ultrasonic exciting device 613 shown in FIG. 69 is substituted with a generation ultrasonic probe 618 formed of a piezoelectric device.

The ultrasonic probe 618, which is disposed in a state abutting on the surface of the body TP to be inspected via a couplant 619, is for receiving the voltage of a predetermined frequency from an oscillator 620, converting the voltage into an ultrasonic wave having a predetermined frequency, and generating this wave to the body TP to be inspected.

Even in this surface inspecting device 617, the ultrasonic wave generated from the ultrasonic probe 618 is subjected to mode conversion at the wedge and the surface to be inspected, and propagates the surface of the body TP as the surface wave SW. On the other hand, as shown in FIG. 73, an ultrasonic wave WR reflecting in the wedge, and other ultrasonic waves other than the surface wave SW are oscillated. The ultrasonic wave WR reflecting in the wedge also has an ultrasonic waveform in proportion to the strength to press against the surface of the body TP of the ultrasonic probe 618, so that the ultrasonic waveform can be subjected to correction processing with the performance-index I$_{correct}$ which subjected the waveform of the surface wave SW to the above correction processing.

What is claimed is:
1. A laser ultrasonic detection device comprising:
   a laser oscillating device including a seed laser oscillating element for oscillating seed laser light irradiated on a surface of an object to be measured from which an ultrasonic signal is detected and an optical amplifier for amplifying an oscillating light of the seed laser oscillating element in the form of pulses;
   an optical interference device for extracting an ultrasonic signal from a signal light of the laser light reflected and scattered from a measurement object surface;
   a signal processing device for processing an output signal of the optical interference device; and
   a condition detecting device for detecting a condition of the laser oscillating device;
   an optical fiber for transferring the laser light irradiated on a measurement object from the laser oscillation device;
   an end face reflecting detector for detecting a back-scattering and back-reflection light from the optical fiber; and
   a control device for controlling an incident position of the laser light to the optical fiber from the incident state at a time when an incident light result of the laser light detected by the end face reflecting detector is out of a preliminarily set allowable range,
   wherein the condition detecting device displays and records the incident state of the laser light detected by the end face reflecting detector, and when the incident state result of the laser light detected by the end face reflecting detector does not return within the allowable range even in driving of the control device, it is determined that some abnormality exists in a transferring path of the laser light.
2. The laser ultrasonic detection device according to claim 1, wherein the condition detecting device detects at least one of an oscillating condition of the seed laser oscillating device and a condition of the laser light oscillated in pulses from the optical amplifier.

3. The laser ultrasonic detection device according to claim 1, wherein the optical amplifier includes a coolant supplying device for supplying coolant to and cooling a pumping optical source which pumps an optical amplification medium contained in the optical amplifier, the condition detecting device executes at least one of an operation for detecting the condition of the coolant supplied from the coolant supplying device or an operation for controlling the condition of the coolant.

4. The laser ultrasonic detection device according to claim 1, further comprising:
- an image sensor for detecting an input end face of the optical fiber;
- an image processing device for analyzing an incident state of the laser light of the optical fiber from detecting results from the image sensor; and
- a control device for controlling the incident state of the laser light of the optical fiber from the incident state results of the laser light which is detected by the image processing device,
- wherein the condition detecting device displays and records the incident state of the laser light which is detected by the image processing device.

5. The laser ultrasonic detection device according to claim 1, further comprising:
- a pulse power source for driving a pumping optical source which pumps the optical amplification medium contained in the optical amplifier,
- wherein the condition detecting device executes at least one of an operation for detecting the oscillating condition of the pulse power source and an operation for controlling the oscillating condition.

6. The laser ultrasonic detection device according to claim 1, further comprising:
- a data storing device for storing the output signal of the condition detecting device or a portion or all of the feature amounts, and a communication device for performing transferring of a readout of a portion or all of the signal accumulated in the data storing device, or for transferring the control signal.

7. The laser ultrasonic detection device according to claim 1, wherein the optical interference device includes a Fabry-Perot interferometer having an incident light amount detector for detecting the incident light amount and an output light amount detector for detecting an output light amount and for extracting an ultrasonic signal from a signal light of the laser light reflected and scattered from a measurement object surface, and the condition detecting device is for displaying and recording at least one of the output signal of the incident light amount detector and the output signal of the output light amount detector synchronous with the ultrasonic signal of the signal processing device.

* * * * *